United States Patent
Li et al.

(10) Patent No.: US 12,398,150 B2
(45) Date of Patent: Aug. 26, 2025

(54) ORGANIC ELECTROLUMINESCENT MATERIAL AND DEVICE THEREOF

(71) Applicant: BEIJING SUMMER SPROUT TECHNOLOGY CO., LTD., Beijing (CN)

(72) Inventors: Feng Li, Beijing (CN); Yang Wang, Beijing (CN); Jianfei Yao, Beijing (CN); Junfei Wang, Beijing (CN); Gang Yang, Beijing (CN); Chi Yuen Raymond Kwong, Beijing (CN); Chuanjun Xia, Beijing (CN)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 781 days.

(21) Appl. No.: 17/547,871

(22) Filed: Dec. 10, 2021

(65) Prior Publication Data

US 2022/0213116 A1  Jul. 7, 2022

(30) Foreign Application Priority Data

Dec. 11, 2020  (CN) .......................... 202011436454.5

(51) Int. Cl.
*C07D 493/00* (2006.01)
*C07D 495/00* (2006.01)
(Continued)

(52) U.S. Cl.
CPC ......... *C07D 493/00* (2013.01); *C07D 495/00* (2013.01); *C07F 7/0812* (2013.01);
(Continued)

(58) Field of Classification Search
CPC .. C07D 251/24; H10K 85/342; H10K 85/654; H10K 85/6574; H10K 85/6576; H10K 85/346
See application file for complete search history.

(56) References Cited

U.S. PATENT DOCUMENTS 5,703,436 A  12/1997  Forrest et al.
5,707,745 A  1/1998  Forrest et al.
(Continued)

FOREIGN PATENT DOCUMENTS

CN  108884086 A  11/2018
CN  110268036 A  9/2019
(Continued)

OTHER PUBLICATIONS

Computer-generated English-language translation of WO-2021221475-A1.*
(Continued)

*Primary Examiner* — Vu A Nguyen
(74) *Attorney, Agent, or Firm* — ArentFox Schiff LLP; Joseph M. Maraia; Marlo Schepper Grolnic

(57) ABSTRACT

Provided are an organic electroluminescent material and device. The organic electroluminescent material is a compound having a structure of Formula 1. Those novel compounds are applicable to electroluminescent devices and can provide better device performance, such as an increase in device lifetime. Further provided are an electroluminescent device containing the compound and a compound composition containing the compound.

26 Claims, 2 Drawing Sheets

(51) Int. Cl.
*C07F 7/08* (2006.01)
*C07F 7/30* (2006.01)
*C07F 15/00* (2006.01)
*H10K 50/11* (2023.01)
*H10K 50/16* (2023.01)
*H10K 85/30* (2023.01)
*H10K 85/40* (2023.01)
*H10K 85/60* (2023.01)
*H10K 101/00* (2023.01)
*H10K 101/10* (2023.01)
*H10K 101/30* (2023.01)
*H10K 101/40* (2023.01)

(52) U.S. Cl.
CPC ............ *C07F 7/30* (2013.01); *C07F 15/0033* (2013.01); *C07F 15/0086* (2013.01); *H10K 85/342* (2023.02); *H10K 85/346* (2023.02); *H10K 85/40* (2023.02); *H10K 85/622* (2023.02); *H10K 85/626* (2023.02); *H10K 85/654* (2023.02); *H10K 85/6574* (2023.02); *H10K 85/6576* (2023.02); *H10K 50/11* (2023.02); *H10K 50/16* (2023.02); *H10K 2101/10* (2023.02); *H10K 2101/30* (2023.02); *H10K 2101/40* (2023.02); *H10K 2101/90* (2023.02)

(56) References Cited

U.S. PATENT DOCUMENTS

| | | | |
|---|---|---|---|
| 5,844,363 A | 12/1998 | Gu et al. | |
| 6,097,147 A | 8/2000 | Baldo et al. | |
| 6,303,238 B1 * | 10/2001 | Thompson | C07D 487/22 428/917 |
| 7,279,704 B2 | 10/2007 | Walters et al. | |
| 7,968,146 B2 | 6/2011 | Wagner et al. | |
| 2003/0230980 A1 | 12/2003 | Forrest et al. | |
| 2004/0174116 A1 | 9/2004 | Lu et al. | |
| 2014/0158992 A1 | 6/2014 | Kia et al. | |
| 2015/0207082 A1 | 7/2015 | Dyatkin et al. | |
| 2015/0249221 A1 | 9/2015 | Zeng et al. | |
| 2015/0349273 A1 | 12/2015 | Hung et al. | |
| 2016/0028021 A1 | 1/2016 | Zeng et al. | |
| 2016/0093808 A1 | 3/2016 | Adamovich et al. | |
| 2016/0197285 A1 | 7/2016 | Zeng et al. | |
| 2016/0233429 A1 | 8/2016 | Xia et al. | |
| 2016/0233436 A1 | 8/2016 | Zeng et al. | |
| 2016/0359122 A1 | 12/2016 | Boudreault et al. | |
| 2017/0054087 A1 | 2/2017 | Zeng et al. | |
| 2018/0301639 A1 | 10/2018 | Zeng et al. | |
| 2018/0337348 A1 * | 11/2018 | Jung | H10K 85/626 |
| 2019/0372012 A1 | 12/2019 | Cho et al. | |
| 2020/0203631 A1 | 6/2020 | Gao et al. | |
| 2020/0231581 A1 | 7/2020 | Chae et al. | |
| 2020/0251666 A1 * | 8/2020 | Cai | C07F 15/0033 |
| 2021/0257554 A1 | 8/2021 | Zeng et al. | |

FOREIGN PATENT DOCUMENTS

| | | | | |
|---|---|---|---|---|
| CN | 112759578 A | | 5/2021 | |
| EP | 3415512 B1 | | 4/2021 | |
| JP | 2017107992 A | | 6/2017 | |
| JP | 2019513131 A | | 5/2019 | |
| JP | 2020066622 A | | 4/2020 | |
| JP | 2020125289 A | | 8/2020 | |
| JP | 2022534887 A | | 8/2022 | |
| KR | 10-2018-0055698 A | | 5/2018 | |
| KR | 20180061075 A | | 6/2018 | |
| KR | 20180068869 A | * | 6/2018 | ............ C09K 11/06 |
| KR | 10-2021-0133891 A | | 11/2021 | |
| WO | 2018093080 A1 | | 5/2018 | |
| WO | 2019164218 A1 | | 8/2019 | |
| WO | 2019231226 A1 | | 12/2019 | |
| WO | 2019232120 A1 | | 12/2019 | |
| WO | WO-2021221475 A1 | * | 11/2021 | ............ H10K 50/11 |

OTHER PUBLICATIONS

Computer-generated English-language translation of KR-20180068869-A.*
First Office Action in Chinese Application No. 202011436454.5 dated Nov. 2, 2023 [with English translation], 10 pages.
Search Report in Chinese Application No. 202011436454.5 dated Oct. 31, 2023 [with English translation], 5 pages.
Official Communication in German Application No. 102021132671.0 dated Oct. 19, 2023 [with English translation], 11 pages.
Request for the Submission of an Opinion in Korean Application No. 10-2021-0176271 dated Feb. 20, 2024 [with English translation], 28 pages.
Tang et al., "Organic electroluminescent diodes," Appl. Phys. Lett. 51(12), pp. 913-915, DOI:10.1063/1.98799 (1987).
Joyama et al., "Highly efficient organic light-emitting diodes from delayed fluorescence," Nature 492, pp. 234-240, DOI:10.1038/nature 11687 (Dec. 2012).
Notice of Reasons for Refusal in JP Application No. 2021-201157, dated Nov. 18, 2022 (with English machine translation), 11 pgs.

* cited by examiner

ORGANIC ELECTROLUMINESCENT MATERIAL AND DEVICE THEREOF

CROSS-REFERENCE TO RELATED APPLICATION(S)

This application claims priority to Chinese Patent Application No. CN 202011436454.5 filed on Dec. 11, 2020, the disclosure of which is incorporated herein by reference in its entirety.

TECHNICAL FIELD

The present disclosure relates to compounds for organic electronic devices such as organic light-emitting devices. In particular, the present disclosure relates to a compound having a structure of Formula 1, an organic electroluminescent device containing the compound and a compound composition containing the compound.

BACKGROUND

Organic electronic devices include, but are not limited to, the following types: organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This device laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since the OLED is a self-emitting solid state device, it offers tremendous potential for display and lighting applications. In addition, the inherent properties of organic materials, such as their flexibility, may make them well suited for particular applications such as fabrication on flexible substrates.

The OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of the fluorescent OLED is only 25%. This limitation hindered the commercialization of OLED. In 1997, Forrest and Thompson reported phosphorescent OLED, which uses triplet emission from heavy metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. A small molecule refers to any organic or organometallic material that is not a polymer. The molecular weight of the small molecule can be large as long as it has well defined structure. Dendrimers with well-defined structures are considered as small molecules. Polymer OLEDs include conjugated polymers and non-conjugated polymers with pendant emitting groups. Small molecule OLED can become the polymer OLED if post polymerization occurred during the fabrication process.

There are various methods for OLED fabrication. Small molecule OLEDs are generally fabricated by vacuum thermal evaporation. Polymer OLEDs are fabricated by solution process such as spin-coating, inkjet printing, and slit printing. If the material can be dissolved or dispersed in a solvent, the small molecule OLED can also be produced by solution process.

The emitting color of the OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent device still suffers from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime. Triazine-based organic semiconductor materials are widely used in OLEDs due to their excellent photoelectric performance, redox performance and stability.

JP2017107992A has disclosed an organic compound having the following general structural formula:

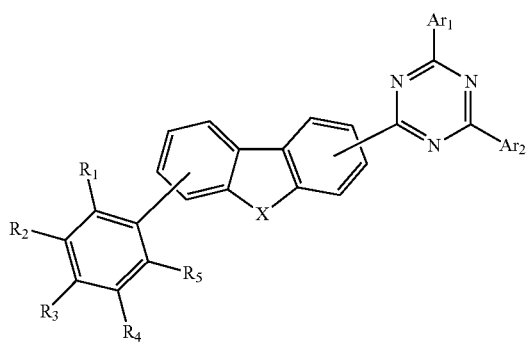

and an organic light-emitting device containing the compound, wherein X is oxygen or sulfur, and $R_1$ to $R_5$ are each independently selected from hydrogen, alkyl, cyano or fluorine. A specific structure disclosed is

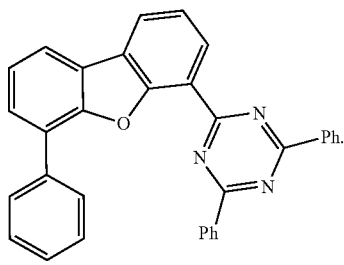 [SMILES: c1ccc(-c2nc(-c3ccccc3)nc(-c3cccc4c3oc3c(-c5ccccc5)cccc34)n2)cc1]

This application has neither studied nor paid attention to an effect of $R_1$ to $R_5$ being aryl on device performance.

KR20180068869A has disclosed an organic optoelectronic device, the light-emitting layer of which contains two kinds of host, one of the host has a general structural formula of

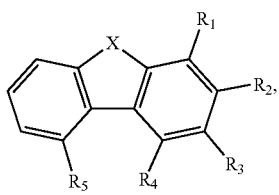

wherein $R_1$ to $R_4$ are each independently selected from hydrogen, $C_{6-60}$ aryl or a $C_{2-60}$ heterocyclic group or have a structure of Formula

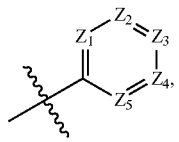

wherein $Z_1$ to $Z_5$ are each independently N or $CR_6$, and $R_6$ is selected from hydrogen, substituted or unsubstituted $C_{6-60}$ aryl or substituted or unsubstituted $C_{2-60}$ heteroaryl; $R_5$ is a $C_{2-60}$ heterocyclic group or has a structure of Formula

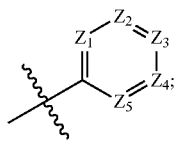

and at least one of $R_1$ to $R_5$ has a structure of Formula

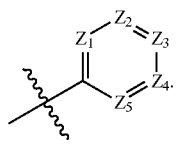

This application has disclosed the following compounds among specific structures:

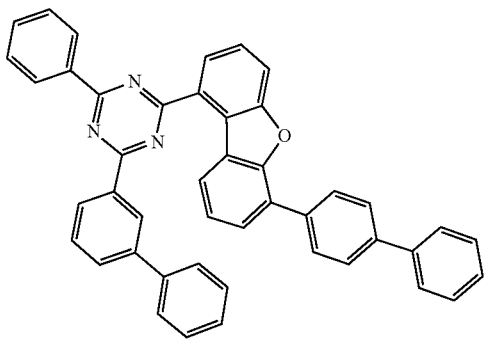

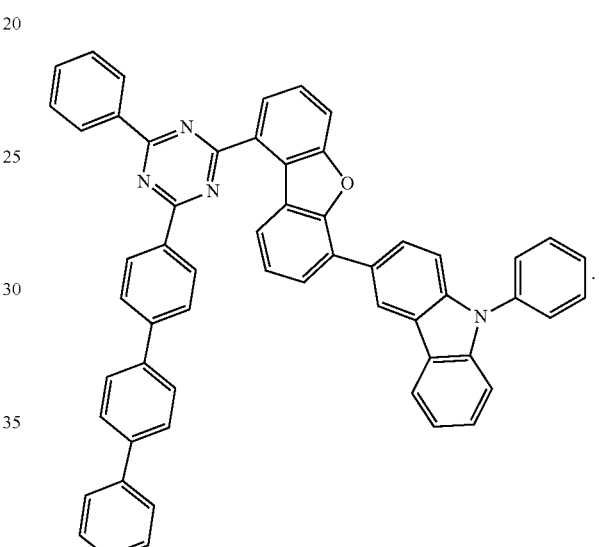

This application has neither studied nor paid attention to an effect of a 4-biphenyl group joined to a triazine ring and a biphenyl group at position 6 of dibenzofuran on device performance.

CN110268036A has disclosed an organic optoelectronic device, the light-emitting layer of which contains a compound having a structure represented by the following general formula:

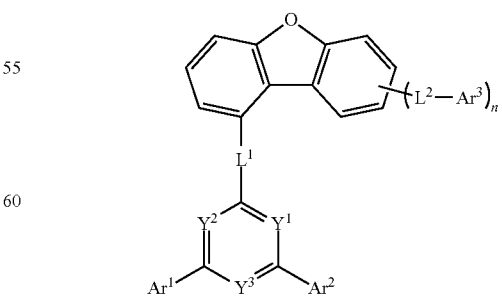

and further disclosed that the compound has a structure represented by

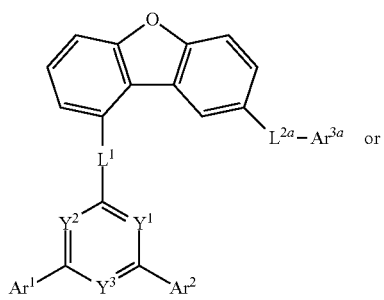

or

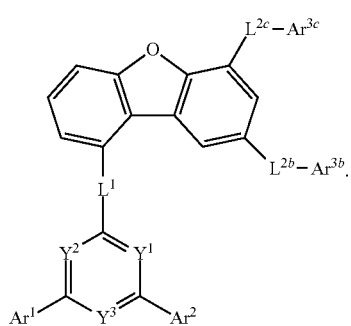

This application has disclosed the

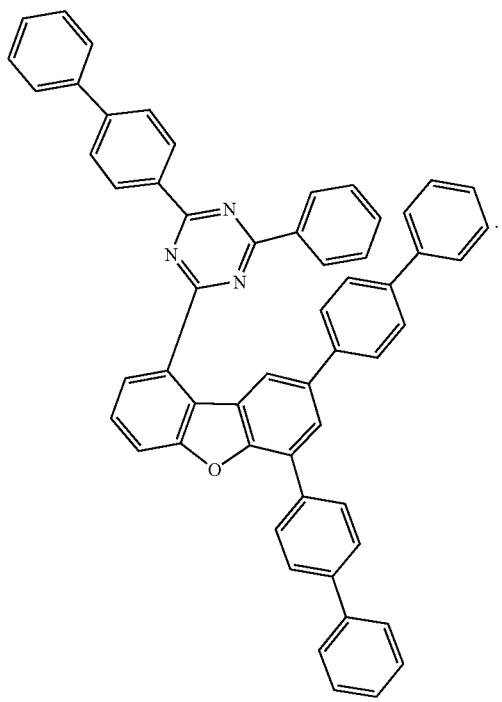 [SMILES: c1ccc(-c2ccc(-c3cc(-c4ccc(-c5ccccc5)cc4)c4oc5cccc(-c6nc(-c7ccccc7)nc(-c7ccc(-c8ccccc8)cc7)n6)c5c4c3)cc2)cc1]

following compound among specific structures: This application has paid attention to such compounds with a substitution at position 8 of dibenzofuran or with substitutions at position 6 and position 8 of dibenzofuran and has neither studied nor paid attention to an effect of no substitution at position 8 of dibenzofuran on device performance.

KR20180061075A has disclosed an organic compound having the following general structural formula:

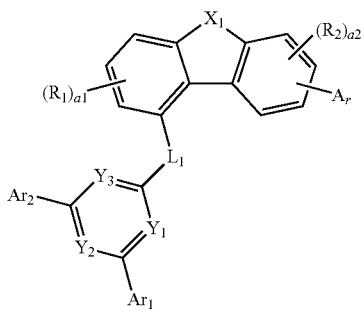

and an organic light-emitting device containing the compound, wherein X is O or S, A is

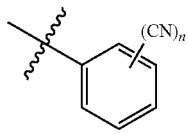

or $C_{6-60}$ aryl substituted with at least one

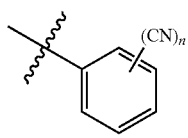

or $C_{2-60}$ heteroaryl containing 1 to 3 heteroatoms selected from N, O or S. This application has disclosed the following compounds among specific structures:

 and

This application has neither disclosed a compound containing a substituent with no cyano substitution on a dibenzo five-membered heterocycle nor studied and paid attention to an effect of aryl with no cyano substitution on the dibenzo five-membered heterocycle on device performance.

CN108884086A has disclosed an organic compound having the following general structural formula:

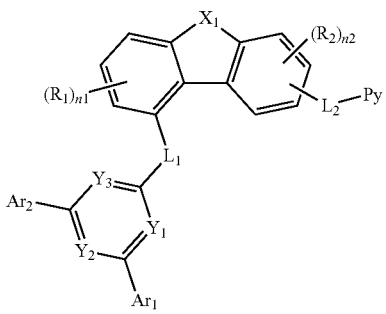

and an organic light-emitting device containing the compound, where Py is substituted or unsubstituted $C_{4-60}$ heteroaryl containing one N atom, and $Ar_1$ and $Ar_2$ are each independently selected from substituted or unsubstituted $C_{6-60}$ aryl or substituted or unsubstituted $C_{2-60}$ heteroaryl containing 1 to 3 heteroatoms selected from N, O or S. This application has further disclosed that the compound has the following general structure:

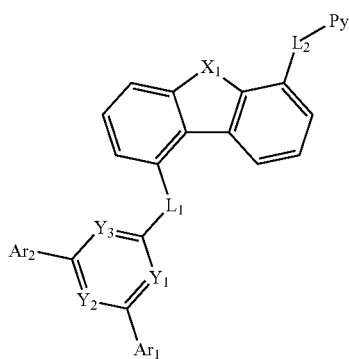

or

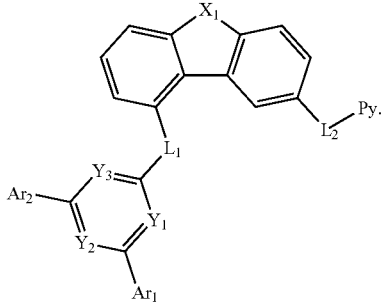

This application has disclosed the following compounds

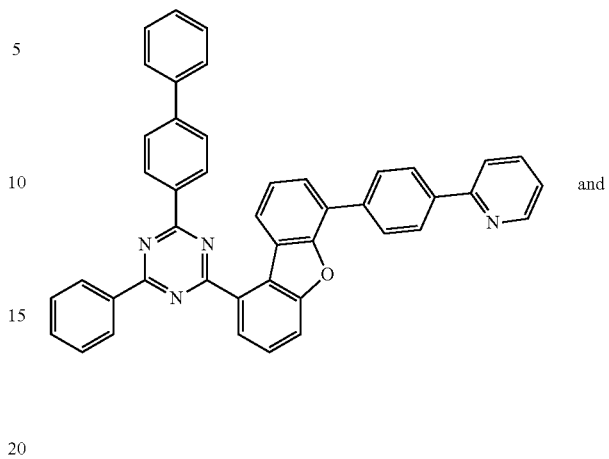

and

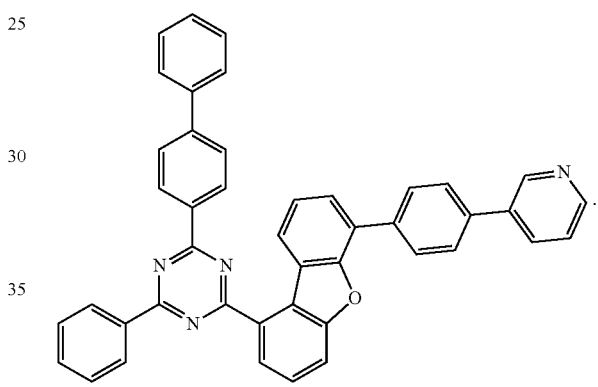

among specific structures: This application has neither disclosed nor studied a compound whose substituent on a dibenzo five-membered heterocycle is heteroaryl without N and an effect thereof on device performance.

WO2019164218A1 has disclosed an organic compound having the following general structural formula:

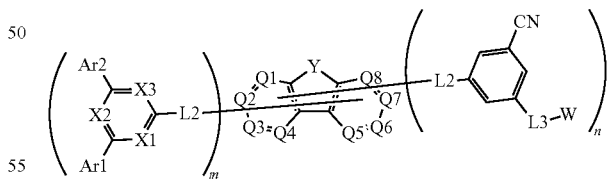

and an organic light-emitting device containing the compound, wherein W, $Ar_1$ and $Ar_2$ are identical to or different from each other and are each independently selected from substituted or unsubstituted aryl or a substituted or unsubstituted heterocyclic group; and $L_1$ to $L_3$ are identical to or different from each other and are each independently selected from a direct bond, substituted or unsubstituted arylene or substituted or unsubstituted heteroarylene. The following compounds among specific structures are disclosed:

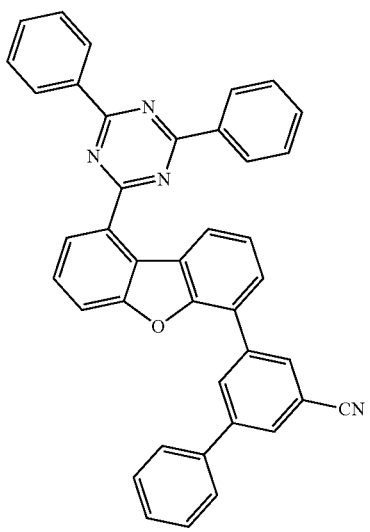

and

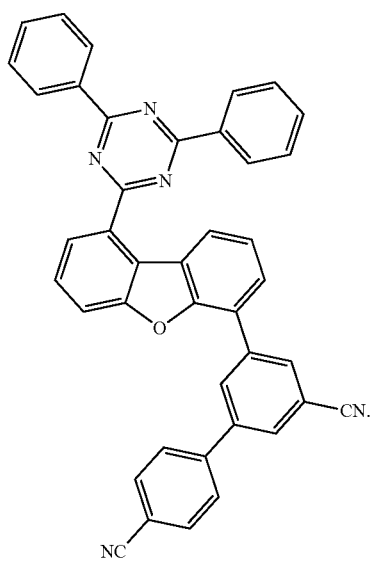

This application has neither disclosed a compound containing a substituent with no cyano substitution on a dibenzo five-membered heterocycle nor studied and paid attention to an effect of aryl with no cyano substitution on the dibenzo five-membered heterocycle on device performance.

WO2019231226A1 has disclosed an organic electronic device, the light-emitting layer of which contains two kinds of host, one of the host material has the following general structural formula:

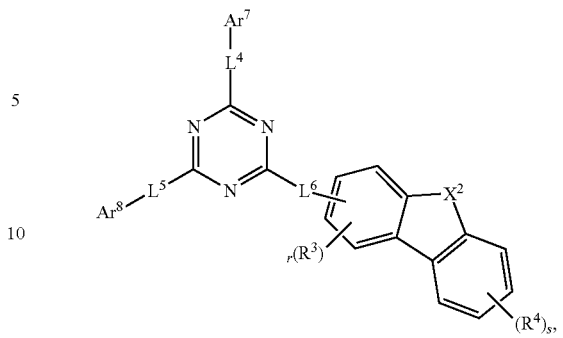

wherein $X^2$ is N-$L^7$-$Ar^9$, O, S or CR'R". This application has further disclosed that the host material has the following general formula:

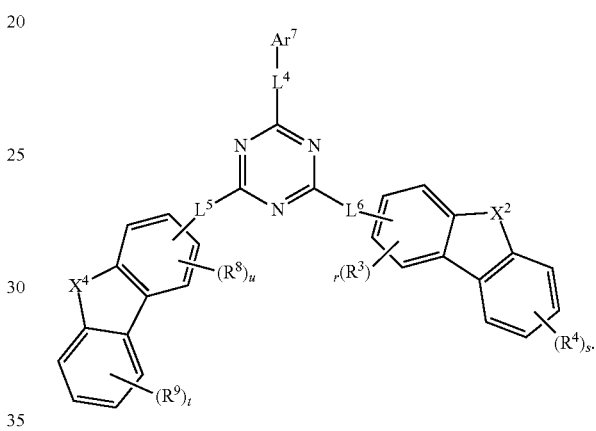

The following compound among specific structures is disclosed:

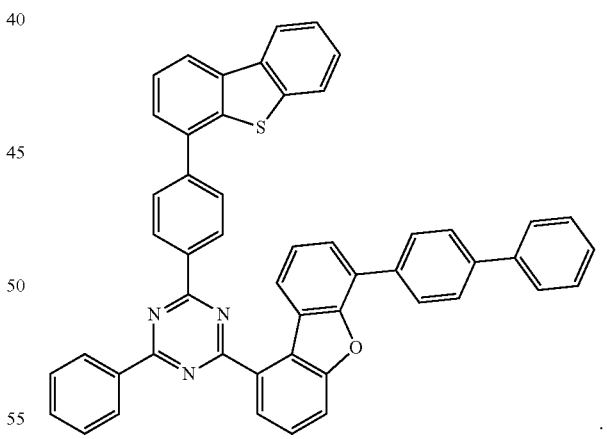

This application has neither studied nor paid attention to an effect of a compound containing an aryl group at position 6 of a dibenzo five-membered heterocycle and, meanwhile, containing a triazine substituent having (hetero)aryl with a non-fused ring heteroaryl substitution at position 1 of the dibenzo five-membered heterocycle on device performance.

SUMMARY

The present disclosure aims to provide a series of compounds each having a structure of Formula 1 to solve at least part of the preceding problems. Those novel compounds are applicable to organic electroluminescent devices and can provide better device performance such as an improved device lifetime.

An embodiment of the present disclosure provides a compound having a structure of Formula 1:

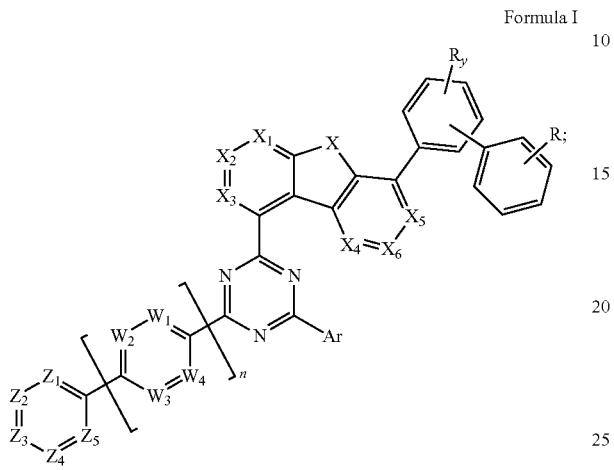

Formula I wherein
X is selected from O, S or Se;
n is selected from 1, 2, 3, 4 or 5;
$X_1$ to $X_5$ are, at each occurrence identically or differently, selected from $CR_x$ or N;
$X_6$ is CH or CD;
$W_1$ to $W_4$ are, at each occurrence identically or differently, selected from $CR_x$ or N;
$Z_1$ to $Z_5$ are, at each occurrence identically or differently, selected from $CR_z$ or N;
Ar is selected from substituted or unsubstituted aryl having 6 to 30 carbon atoms;
R and $R_y$ represent, at each occurrence identically or differently, mono-substitution, multiple substitutions or non-substitution;
$R_x$, $R_w$ and $R_z$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

$R_y$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

R is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, an acyl group, a carbonyl group, a carboxylic acid group, an ester group, an isocyano group, a hydroxyl group, a sulfanyl group, a sulfinyl group, a sulfonyl group, a phosphino group and combinations thereof; and adjacent substituents R, $R_y$ and $R_w$ can be optionally joined to form a ring.

Another embodiment of the present disclosure provides an organic electroluminescent device. The organic electroluminescent device includes an anode, a cathode and an organic layer disposed between the anode and the cathode, wherein the organic layer contains the compound in the preceding embodiment.

Another embodiment of the present disclosure further provides a compound composition. The compound composition contains the compound in the preceding embodiment.

The present disclosure provides a series of compounds each having a structure of Formula 1. Those novel compounds are applicable to organic electroluminescent devices and can provide better device performance such as an improved device lifetime.

DETAILED DESCRIPTION

Figure 1:
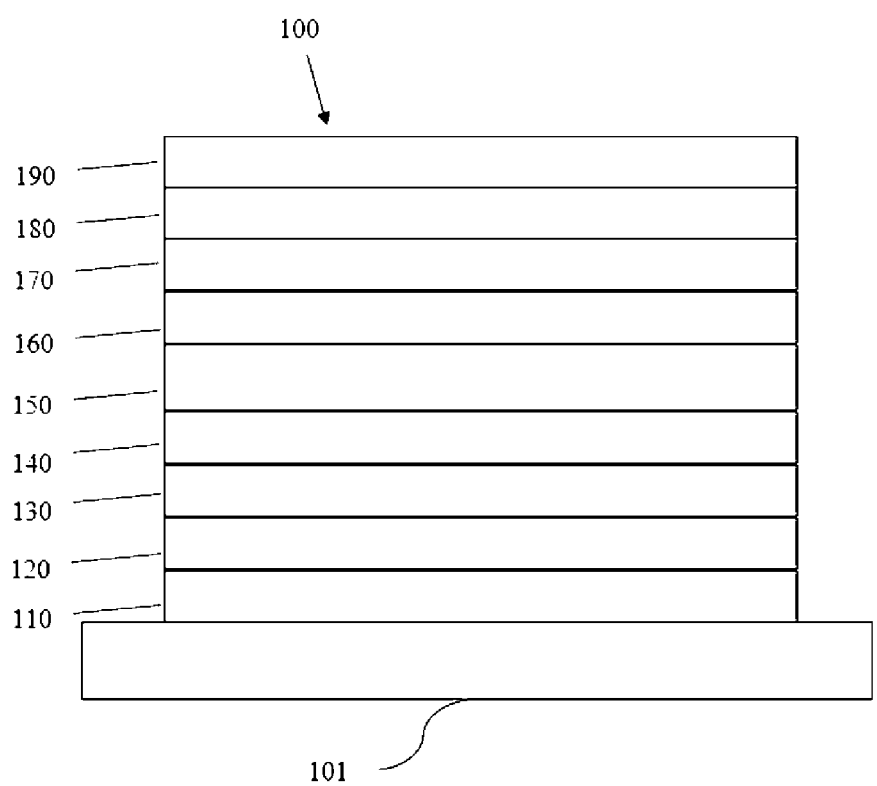
FIG. 1 is a schematic diagram of an organic light-emitting apparatus that may include a compound and a compound composition disclosed herein.

OLEDs can be fabricated on various types of substrates such as glass, plastic, and metal foil. FIG. 1 schematically shows an organic light emitting device 100 without limitation. The figures are not necessarily drawn to scale. Some of the layers in the figures can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, the contents of which are incorporated by reference herein in its entirety.

More examples for each of these layers are available. For example, a flexible and transparent substrate-anode combination is disclosed in U.S. Pat. No. 5,844,363, which is incorporated by reference herein in its entirety. An example of a p-doped hole transport layer is m-MTDATA doped with F4-TCNQ at a molar ratio of 50:1, as disclosed in U.S. Patent Application Publication No. 2003/0230980, which is incorporated by reference herein in its entirety. Examples of host materials are disclosed in U.S. Pat. No. 6,303,238 to Thompson et al., which is incorporated by reference herein in its entirety. An example of an n-doped electron transport layer is BPhen doped with Li at a molar ratio of 1:1, as disclosed in U.S. Patent Application Publication No. 2003/0230980, which is incorporated by reference herein in its entirety. U.S. Pat. Nos. 5,703,436 and 5,707,745, which are incorporated by reference herein in their entireties, disclose examples of cathodes including composite cathodes having a thin layer of metal such as Mg:Ag with an overlying transparent, electrically-conductive, sputter-deposited ITO layer. The theory and use of blocking layers are described in more detail in U.S. Pat. No. 6,097,147 and U.S. Patent Application Publication No. 2003/0230980, which are incorporated by reference herein in their entireties. Examples of injection layers are provided in U.S. Patent Application Publication No. 2004/0174116, which is incorporated by reference herein in its entirety. A description of protective layers may be found in U.S. Patent Application Publication No. 2004/0174116, which is incorporated by reference herein in its entirety.

The layered structure described above is provided by way of non-limiting examples. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have two layers of different emitting materials to achieve desired emission spectrum.

In one embodiment, an OLED may be described as having an "organic layer" disposed between a cathode and an anode. This organic layer may comprise a single layer or multiple layers.

Figure 2:
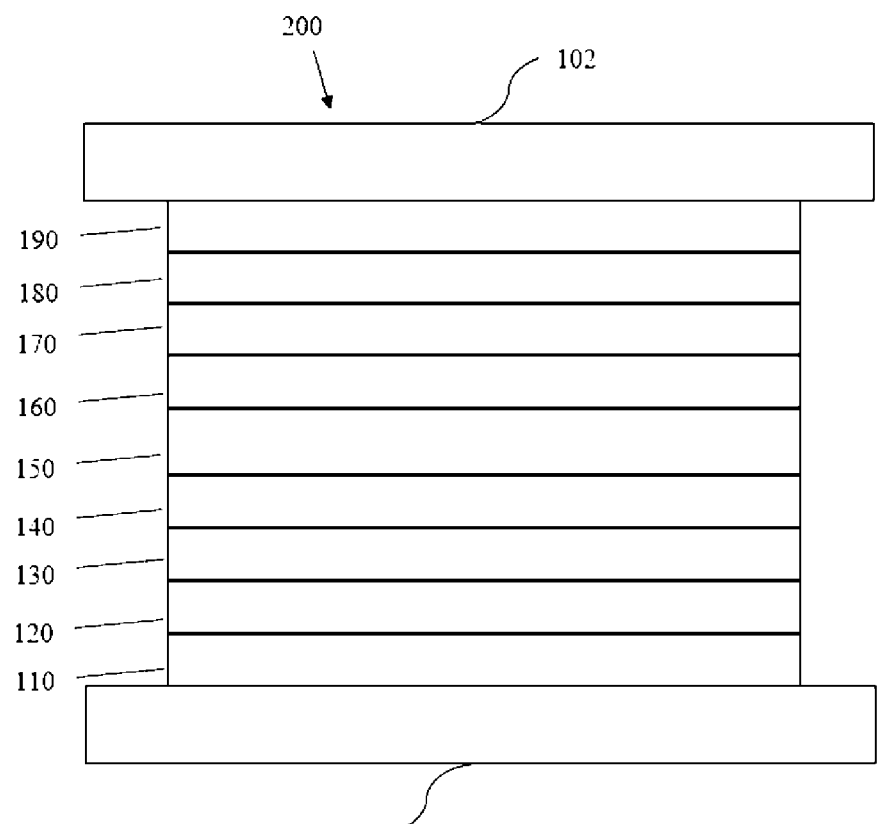
FIG. 2 is a schematic diagram of another organic light-emitting apparatus that may include a compound and a compound composition disclosed herein.

An OLED can be encapsulated by a barrier layer. FIG. 2 schematically shows an organic light emitting device 200 without limitation. FIG. 2 differs from FIG. 1 in that the organic light emitting device include a barrier layer 102, which is above the cathode 190, to protect it from harmful species from the environment such as moisture and oxygen. Any material that can provide the barrier function can be used as the barrier layer such as glass or organic-inorganic hybrid layers. The barrier layer should be placed directly or indirectly outside of the OLED device. Multilayer thin film encapsulation was described in U.S. Pat. No. 7,968,146, which is incorporated by reference herein in its entirety.

Devices fabricated in accordance with embodiments of the present disclosure can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from the substrate. There may be other layers between the first and second layers, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing (RISC) rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap (AES-T). Organic, non-metal containing, donor-acceptor luminescent materials may be able to achieve this. The emission in these materials is generally characterized as a donor-acceptor charge-transfer (CT) type emission. The spatial separation of the HOMO and LUMO in these donor-acceptor type compounds generally results in small AES-T. These states may involve CT states. Generally, donor-acceptor luminescent materials are constructed by connecting an electron donor moiety such as amino- or carbazole-derivatives and an electron acceptor moiety such as N-containing six-membered aromatic rings.

Definition of Terms of Substituents

Halogen or halide—as used herein includes fluorine, chlorine, bromine, and iodine.

Alkyl—as used herein includes both straight and branched chain alkyl groups. Alkyl may be alkyl having 1 to 20 carbon atoms, preferably alkyl having 1 to 12 carbon atoms, and more preferably alkyl having 1 to 6 carbon atoms. Examples of alkyl groups include a methyl group, an ethyl group, a propyl group, an isopropyl group, a n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, and a 3-methylpentyl group. Of the above, preferred are a methyl group, an ethyl group, a propyl group, an isopropyl group, a n-butyl group, an s-butyl group, an isobutyl group, a t-butyl group, an n-pentyl group, a neopentyl group, and an n-hexyl group. Additionally, the alkyl group may be optionally substituted.

Cycloalkyl—as used herein includes cyclic alkyl groups. The cycloalkyl groups may be those having 3 to 20 ring carbon atoms, preferably those having 4 to 10 carbon atoms. Examples of cycloalkyl include cyclobutyl, cyclopentyl, cyclohexyl, 4-methylcyclohexyl, 4,4-dimethylcylcohexyl, 1-adamantyl, 2-adamantyl, 1-norbornyl, 2-norbornyl, and the like. Of the above, preferred are cyclopentyl, cyclohexyl, 4-methylcyclohexyl, and 4,4-dimethylcylcohexyl. Additionally, the cycloalkyl group may be optionally substituted.

Heteroalkyl—as used herein, includes a group formed by replacing one or more carbons in an alkyl chain with a hetero-atom(s) selected from the group consisting of a nitrogen atom, an oxygen atom, a sulfur atom, a selenium atom, a phosphorus atom, a silicon atom, a germanium atom, and a boron atom. Heteroalkyl may be those having 1 to 20 carbon atoms, preferably those having 1 to 10 carbon atoms, and more preferably those having 1 to 6 carbon atoms. Examples of heteroalkyl include methoxymethyl, ethoxymethyl, ethoxyethyl, methylthiomethyl, ethylthiomethyl, ethylthioethyl, methoxymethoxymethyl, ethoxymethoxymethyl, ethoxyethoxyethyl, hydroxymethyl, hydroxyethyl, hydroxypropyl, mercaptomethyl, mercaptoethyl, mercaptopropyl, aminomethyl, aminoethyl, aminopropyl, dimethylaminomethyl, trimethylsilyl, dimethylethylsilyl, dimethylisopropylsilyl, t-butyldimethylsilyl, triethylsilyl, triisopropylsilyl, trimethylsilylmethyl, trimethylsilylethyl, and trimethylsilylisopropyl. Additionally, the heteroalkyl group may be optionally substituted.

Alkenyl—as used herein includes straight chain, branched chain, and cyclic alkene groups. Alkenyl may be those having 2 to 20 carbon atoms, preferably those having 2 to 10 carbon atoms. Examples of alkenyl include vinyl, 1-propenyl group, 1-butenyl, 2-butenyl, 3-butenyl, 1,3-butandienyl, 1-methylvinyl, styryl, 2,2-diphenylvinyl, 1,2-diphenylvinyl, 1-methylallyl, 1,1-dimethylallyl, 2-methylallyl, 1-phenylallyl, 2-phenylallyl, 3-phenylallyl, 3,3-diphenylallyl, 1,2-dimethylallyl, 1-phenyl-1-butenyl, 3-phenyl-1-butenyl, cyclopentenyl, cyclopentadienyl, cyclohexenyl, cycloheptenyl, cycloheptatrienyl, cyclooctenyl, cyclooctatetraenyl, and norbornenyl. Additionally, the alkenyl group may be optionally substituted.

Alkynyl—as used herein includes straight chain alkynyl groups. Alkynyl may be those having 2 to 20 carbon atoms, preferably those having 2 to 10 carbon atoms. Examples of alkynyl groups include ethynyl, propynyl, propargyl, 1-butynyl, 2-butynyl, 3-butynyl, 1-pentynyl, 2-pentynyl, 3,3-dimethyl-1-butynyl, 3-ethyl-3-methyl-1-pentynyl, 3,3-diisopropyl-1-pentynyl, phenylethynyl, phenylpropynyl, etc. Of the above, preferred are ethynyl, propynyl, propargyl, 1-butynyl, 2-butynyl, 3-butynyl, 1-pentynyl, and phenylethynyl. Additionally, the alkynyl group may be optionally substituted.

Aryl or an aromatic group—as used herein includes non-condensed and condensed systems. Aryl may be those having 6 to 30 carbon atoms, preferably those having 6 to 20 carbon atoms, and more preferably those having 6 to 12 carbon atoms. Examples of aryl groups include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Examples of non-condensed aryl groups include phenyl, biphenyl-2-yl, biphenyl-3-yl, biphenyl-4-yl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-(2-phenylpropyl)phenyl, 4'-methylbiphenylyl, 4"-t-butyl-p-terphenyl-4-yl, o-cumenyl, m-cumenyl, p-cumenyl, 2,3-xylyl, 3,4-xylyl, 2,5-xylyl, mesityl, and m-quarterphenyl. Additionally, the aryl group may be optionally substituted.

Heterocyclic groups or heterocycle—as used herein include non-aromatic cyclic groups. Non-aromatic heterocyclic groups includes saturated heterocyclic groups having 3 to 20 ring atoms and unsaturated non-aromatic heterocyclic groups having 3 to 20 ring atoms, where at least one ring atom is selected from the group consisting of a nitrogen atom, an oxygen atom, a sulfur atom, a selenium atom, a silicon atom, a phosphorus atom, a germanium atom, and a boron atom. Preferred non-aromatic heterocyclic groups are those having 3 to 7 ring atoms, each of which includes at least one hetero-atom such as nitrogen, oxygen, silicon, or sulfur. Examples of non-aromatic heterocyclic groups include oxiranyl, oxetanyl, tetrahydrofuranyl, tetrahydropyranyl, dioxolanyl, dioxanyl, aziridinyl, dihydropyrrolyl, tetrahydropyrrolyl, piperidinyl, oxazolidinyl, morpholinyl, piperazinyl, oxepinyl, thiepinyl, azepinyl, and tetrahydrosilolyl. Additionally, the heterocyclic group may be optionally substituted.

Heteroaryl—as used herein, includes non-condensed and condensed hetero-aromatic groups having 1 to 5 hetero-atoms, where at least one hetero-atom is selected from the group consisting of a nitrogen atom, an oxygen atom, a sulfur atom, a selenium atom, a silicon atom, a phosphorus atom, a germanium atom, and a boron atom. A heteroaromatic group is also referred to as heteroaryl. Heteroaryl may be those having 3 to 30 carbon atoms, preferably those having 3 to 20 carbon atoms, and more preferably those having 3 to 12 carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridoindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof.

Additionally, the heteroaryl group may be optionally substituted.

Alkoxy—as used herein, is represented by —O-alkyl, —O-cycloalkyl, —O-heteroalkyl, or —O-heterocyclic group. Examples and preferred examples of alkyl, cycloalkyl, heteroalkyl, and heterocyclic groups are the same as those described above. Alkoxy groups may be those having 1 to 20 carbon atoms, preferably those having 1 to 6 carbon atoms. Examples of alkoxy groups include methoxy, ethoxy, propoxy, butoxy, pentyloxy, hexyloxy, cyclopropyloxy, cyclobutyloxy, cyclopentyloxy, cyclohexyloxy, tetrahydrofuranyloxy, tetrahydropyranyloxy, methoxypropyloxy, ethoxyethyloxy, methoxymethyloxy, and ethoxymethyloxy. Additionally, the alkoxy group may be optionally substituted.

Aryloxy—as used herein, is represented by —O-aryl or —O-heteroaryl. Examples and preferred examples of aryl and heteroaryl are the same as those described above. Aryloxy groups may be those having 6 to 30 carbon atoms, preferably those having 6 to 20 carbon atoms. Examples of aryloxy groups include phenoxy and biphenyloxy. Additionally, the aryloxy group may be optionally substituted.

Arylalkyl—as used herein, contemplates alkyl substituted with an aryl group. Arylalkyl may be those having 7 to 30 carbon atoms, preferably those having 7 to 20 carbon atoms, and more preferably those having 7 to 13 carbon atoms. Examples of arylalkyl groups include benzyl, 1-phenylethyl, 2-phenylethyl, 1-phenylisopropyl, 2-phenylisopropyl, phenyl-t-butyl, alpha-naphthylmethyl, 1-alpha-naphthylethyl, 2-alpha-naphthylethyl, 1-alpha-naphthylisopropyl, 2-alpha-naphthylisopropyl, beta-naphthylmethyl, 1-beta-naphthylethyl, 2-beta-naphthylethyl, 1-beta-naphthylisopropyl, 2-beta-naphthylisopropyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, and 1-chloro-2-phenylisopropyl. Of the above, preferred are benzyl, p-cyanobenzyl, m-cyanobenzyl, o-cyanobenzyl, 1-phenylethyl, 2-phenylethyl, 1-phenylisopropyl, and 2-phenylisopropyl. Additionally, the arylalkyl group may be optionally substituted.

Alkylsilyl—as used herein, contemplates a silyl group substituted with an alkyl group. Alkylsilyl groups may be those having 3 to 20 carbon atoms, preferably those having 3 to 10 carbon atoms. Examples of alkylsilyl groups include trimethylsilyl, triethylsilyl, methyldiethylsilyl, ethyldimethylsilyl, tripropylsilyl, tributylsilyl, triisopropylsilyl, methyldiisopropylsilyl, dimethylisopropylsilyl, tri-t-butylsilyl, triisobutylsilyl, dimethyl t-butylsilyl, and methyldi-t-butylsilyl. Additionally, the alkylsilyl group may be optionally substituted.

Arylsilyl—as used herein, contemplates a silyl group substituted with an aryl group. Arylsilyl groups may be those having 6 to 30 carbon atoms, preferably those having 8 to 20 carbon atoms. Examples of arylsilyl groups include triphenylsilyl, phenyldibiphenylylsilyl, diphenylbiphenylsilyl, phenyldiethylsilyl, diphenylethylsilyl, phenyldimethylsilyl, diphenylmethylsilyl, phenyldiisopropylsilyl, diphenylisopropylsilyl, diphenylbutylsilyl, diphenylisobutylsilyl, diphenyl t-butylsilyl. Additionally, the arylsilyl group may be optionally substituted.

The term "aza" in azadibenzofuran, azadibenzothiophene, etc. means that one or more of C—H groups in the respective aromatic fragment are replaced by a nitrogen atom. For example, azatriphenylene encompasses dibenzo[f,h]quinoxaline, dibenzo[f,h]quinoline and other analogs with two or more nitrogens in the ring system. One of ordinary skill in the art can readily envision other nitrogen analogs of the aza-derivatives described above, and all such analogs are intended to be encompassed by the terms as set forth herein.

In the present disclosure, unless otherwise defined, when any term of the group consisting of substituted alkyl, substituted cycloalkyl, substituted heteroalkyl, substituted heterocyclic group, substituted arylalkyl, substituted alkoxy, substituted aryloxy, substituted alkenyl, substituted alkynyl, substituted aryl, substituted heteroaryl, substituted alkylsilyl, substituted arylsilyl, substituted amino, substituted acyl, substituted carbonyl, a substituted carboxylic acid group, a substituted ester group, substituted sulfinyl, substituted sulfonyl, and substituted phosphino is used, it means that any group of alkyl, cycloalkyl, heteroalkyl, heterocyclic group, arylalkyl, alkoxy, aryloxy, alkenyl, alkynyl, aryl, heteroaryl, alkylsilyl, arylsilyl, amino, acyl, carbonyl, a carboxylic acid group, an ester group, sulfinyl, sulfonyl, and phosphino may be substituted with one or more moieties selected from the group consisting of deuterium, halogen, unsubstituted alkyl having 1 to 20 carbon atoms, unsubstituted cycloalkyl having 3 to 20 ring carbon atoms, unsubstituted heteroalkyl having 1 to 20 carbon atoms, an unsubstituted heterocyclic group having 3 to 20 ring atoms, unsubstituted arylalkyl having 7 to 30 carbon atoms, unsubstituted alkoxy having 1 to 20 carbon atoms, unsubstituted aryloxy having 6 to 30 carbon atoms, unsubstituted alkenyl having 2 to 20 carbon atoms, unsubstituted alkynyl having 2 to 20 carbon atoms, unsubstituted aryl having 6 to 30 carbon atoms, unsubstituted heteroaryl having 3 to 30 carbon atoms, unsubstituted alkylsilyl having 3 to 20 carbon atoms, unsubstituted arylsilyl group having 6 to 20 carbon atoms, unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or an attached fragment are considered to be equivalent.

In the compounds mentioned in the present disclosure, hydrogen atoms may be partially or fully replaced by deuterium. Other atoms such as carbon and nitrogen may also be replaced by their other stable isotopes. The replacement by other stable isotopes in the compounds may be preferred due to its enhancements of device efficiency and stability.

In the compounds mentioned in the present disclosure, multiple substitution refers to a range that includes a di-substitution, up to the maximum available substitution. When substitution in the compounds mentioned in the present disclosure represents multiple substitution (including di-, tri-, and tetra-substitutions etc.), that means the substituent may exist at a plurality of available substitution positions on its linking structure, the substituents present at a plurality of available substitution positions may have the same structure or different structures.

In the compounds mentioned in the present disclosure, adjacent substituents in the compounds cannot be joined to form a ring unless otherwise explicitly defined, for example, adjacent substituents can be optionally joined to form a ring. In the compounds mentioned in the present disclosure, the expression that adjacent substituents can be optionally joined to form a ring includes a case where adjacent substituents may be joined to form a ring and a case where adjacent substituents are not joined to form a ring. When adjacent substituents can be optionally joined to form a ring, the ring formed may be monocyclic or polycyclic, as well as alicyclic, heteroalicyclic, aromatic, or heteroaromatic. In such expression, adjacent substituents may refer to substituents bonded to the same atom, substituents bonded to carbon atoms which are directly bonded to each other, or substituents bonded to carbon atoms which are more distant from each other. Preferably, adjacent substituents refer to substituents bonded to the same carbon atom and substituents bonded to carbon atoms which are directly bonded to each other.

The expression that adjacent substituents can be optionally joined to form a ring is also intended to mean that two substituents bonded to the same carbon atom are joined to each other via a chemical bond to form a ring, which can be exemplified by the following formula:

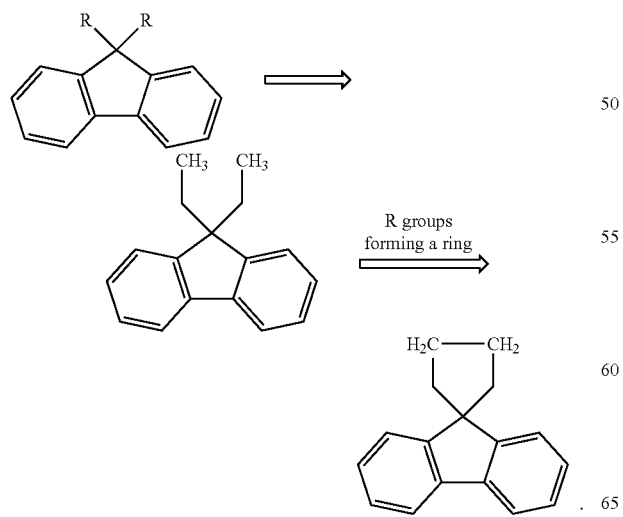

The expression that adjacent substituents can be optionally joined to form a ring is also intended to mean that two substituents bonded to carbon atoms which are directly bonded to each other are joined to each other via a chemical bond to form a ring, which can be exemplified by the following formula:

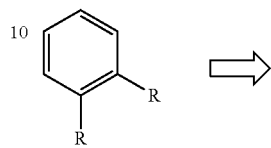

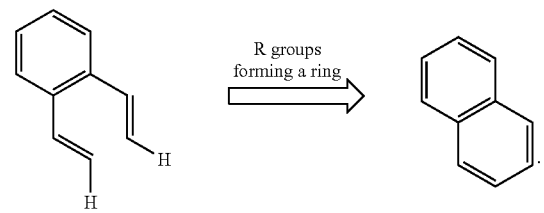

Furthermore, the expression that adjacent substituents can be optionally joined to form a ring is also intended to mean that, in the case where one of the two substituents bonded to carbon atoms which are directly bonded to each other represents hydrogen, the second substituent is bonded at a position at which the hydrogen atom is bonded, thereby forming a ring. This is exemplified by the following formula:

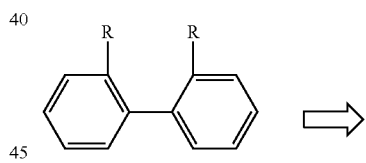

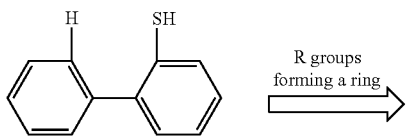

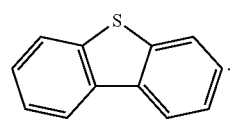

An embodiment of the present disclosure provides a compound having a structure of Formula 1:

Formula I

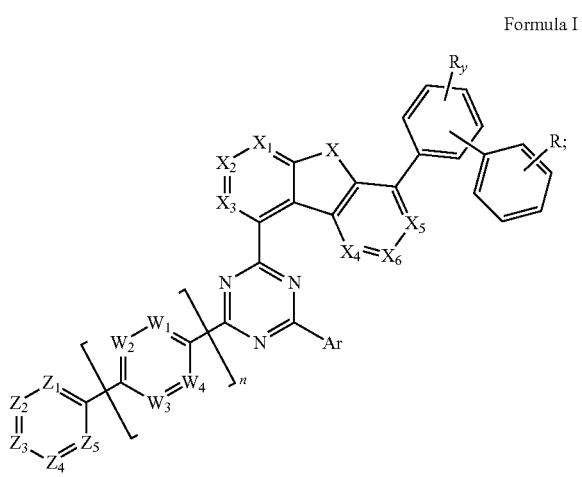

wherein
X is selected from O, S or Se;
n is selected from 1, 2, 3, 4 or 5;
$X_1$ to $X_5$ are, at each occurrence identically or differently, selected from $CR_x$ or N;
$X_6$ is CH or CD;
$W_1$ to $W_4$ are, at each occurrence identically or differently, selected from $CR_w$ or N; $Z_1$ to $Z_5$ are, at each occurrence identically or differently, selected from $CR_z$ or N;
Ar is selected from substituted or unsubstituted aryl having 6 to 30 carbon atoms;
R and $R_y$ represent, at each occurrence identically or differently, mono-substitution, multiple substitutions or non-substitution;
$R_x$, $R_w$ and $R_z$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;
$R_y$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;
R is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, an acyl group, a carbonyl group, a carboxylic acid group, an ester group, an isocyano group, a hydroxyl group, a sulfanyl group, a sulfinyl group, a sulfonyl group, a phosphino group and combinations thereof; and
adjacent substituents R, $R_y$ and $R_w$ can be optionally joined to form a ring.

In this embodiment, the expression that "adjacent substituents R, $R_y$ and $R_w$ can be optionally joined to form a ring" is intended to mean that any one or more of groups of adjacent substituents, such as two substituents R, two substituents $R_y$ and two substituents $R_w$, can be joined to form a ring. Obviously, it is possible that none of these substituents are joined to form a ring.

According to an embodiment of the present disclosure, wherein, X is selected from O or S.

According to an embodiment of the present disclosure, wherein, X is O.

According to an embodiment of the present disclosure, wherein, at least one of $X_1$ to $X_5$ is N.

According to an embodiment of the present disclosure, wherein, $X_1$ to $X_5$ are, at each occurrence identically or differently, selected from $CR_x$, wherein $R_x$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms and substituted or unsubstituted arylsilyl having 6 to 20 carbon atoms.

According to an embodiment of the present disclosure, wherein, $R_x$ is, at each occurrence identically or differently, selected from the group consisting of: hydrogen, deuterium, fluorine, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms and combinations thereof.

According to an embodiment of the present disclosure, wherein, at least one of $W_1$ to $W_4$ is N.

According to an embodiment of the present disclosure, wherein, $W_1$ to $W_4$ are, at each occurrence identically or differently, selected from $CR_w$, wherein $R_w$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted alkenyl having 2 to 20 carbon atoms, substituted or unsubstituted arylalkyl having 7 to 30 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms and substituted or unsubstituted arylsilyl having 6 to 20 carbon atoms.

According to an embodiment of the present disclosure, wherein, $R_w$ is, at each occurrence identically or differently, selected from the group consisting of: hydrogen, deuterium, fluorine, substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms and combinations thereof.

According to an embodiment of the present disclosure, wherein, at least one of $Z_1$ to $Z_5$ is N.

According to an embodiment of the present disclosure, wherein, $Z_1$ to $Z_5$ are, at each occurrence identically or differently, selected from $CR_z$, wherein $R_z$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms and substituted or unsubstituted arylsilyl having 6 to 20 carbon atoms.

According to an embodiment of the present disclosure, wherein, $R_z$ is, at each occurrence identically or differently, selected from the group consisting of: hydrogen, deuterium, fluorine, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms and combinations thereof.

According to an embodiment of the present disclosure, wherein, R and $R_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms and substituted or unsubstituted arylsilyl having 6 to 20 carbon atoms.

According to an embodiment of the present disclosure, wherein, R and $R_y$ are, at each occurrence identically or differently, selected from the group consisting of: hydrogen, deuterium, fluorine, substituted or unsubstituted alkyl having 1 to 20 carbon atoms, substituted or unsubstituted alkenyl having 2 to 20 carbon atoms, substituted or unsubstituted cycloalkyl having 3 to 20 ring carbon atoms, substituted or unsubstituted aryl having 6 to 30 carbon atoms and combinations thereof.

According to an embodiment of the present disclosure, wherein, $R_x$ and $R_z$ are, at each occurrence identically or differently, selected from hydrogen, deuterium, fluorine, substituted or unsubstituted phenyl, substituted or unsubstituted naphthyl, substituted or unsubstituted biphenyl or a combination thereof.

According to an embodiment of the present disclosure, wherein, $R_y$, $R_w$ and R are, at each occurrence identically or differently, selected from hydrogen, deuterium, fluorine, substituted or unsubstituted vinyl, substituted or unsubstituted phenyl, substituted or unsubstituted naphthyl, substituted or unsubstituted biphenyl, substituted or unsubstituted terphenyl, substituted or unsubstituted phenanthryl or a combination thereof.

According to an embodiment of the present disclosure, wherein, Ar is selected from substituted or unsubstituted aryl having 6 to 20 carbon atoms.

According to an embodiment of the present disclosure, wherein, Ar is selected from substituted or unsubstituted phenyl, substituted or unsubstituted naphthyl, substituted or unsubstituted biphenyl, substituted or unsubstituted terphenyl, substituted or unsubstituted triphenylenyl or a combination thereof; optionally, hydrogen in the above groups can be partially or fully deuterated.

According to an embodiment of the present disclosure, wherein, Ar is selected from phenyl, naphthyl, biphenyl, terphenyl, triphenylenyl or a combination thereof; optionally, hydrogen in the above groups can be partially or fully deuterated.

According to an embodiment of the present disclosure, wherein, n is selected from 1, 2 or 3.

According to an embodiment of the present disclosure, wherein, n is selected from 1 or 2.

According to an embodiment of the present disclosure, wherein, the compound is selected from the group consisting of Compound A-1 to Compound A-497, wherein the specific structures of Compound A-1 to Compound A-497 are referred to claim 8.

According to an embodiment of the present disclosure, wherein, the compound is selected from the group consisting of Compound A-1 to Compound A-526, wherein the specific structures of Compound A-1 to Compound A-526 are referred to claim 8.

An embodiment of the present disclosure provides an organic electroluminescent device. The organic electroluminescent device includes an anode, a cathode and an organic layer disposed between the anode and the cathode, wherein the organic layer contains the compound in any one of the preceding embodiments.

According to an embodiment of the present disclosure, wherein, in the organic electroluminescent device, the organic layer is a light-emitting layer, the compound is a host compound, and the light-emitting layer contains at least a first metal complex.

According to an embodiment of the present disclosure, wherein, in the organic electroluminescent device, the organic layer is an electron transporting layer and the compound is an electron transporting compound.

According to an embodiment of the present disclosure, wherein, in the organic electroluminescent device, the first metal complex has a structure represented by Formula 2:

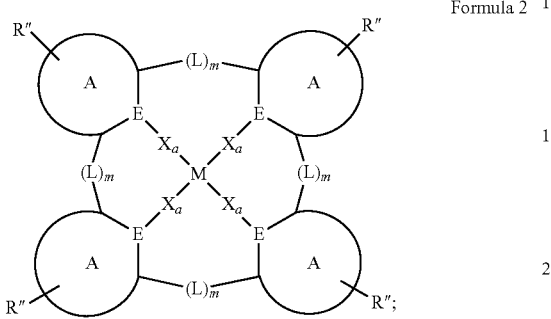

Formula 2 wherein
the metal M is, at each occurrence identically or differently, selected from the group consisting of Cu, Ag, Au, Ru, Rh, Pd, Os, Ir and Pt;
A is, at each occurrence identically or differently, selected from a substituted or unsubstituted aromatic ring having 5 to 30 ring atoms, a substituted or unsubstituted heteroaromatic ring having 5 to 30 ring atoms or a combination thereof;
L is, at each occurrence identically or differently, selected from the group consisting of: a single bond, BR', CR'R', NR', O, SiR'R', PR', S, GeR'R', Se, substituted or unsubstituted vinylene, ethynylene, substituted or unsubstituted arylene having 5 to 30 carbon atoms, substituted or unsubstituted heteroarylene having 5 to 30 carbon atoms and combinations thereof; when two R' are present at the same time, the two R' are identical or different;
m is, at each occurrence identically or differently, selected from 0 or 1; when m=0, the rings A are not joined to each other;
E is, at each occurrence identically or differently, selected from C or N;
$X_a$ is, at each occurrence identically or differently, selected from a single bond, O or S;
R" represents mono-substitution, multiple substitutions or non-substitution;
R' and R" are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof; and adjacent substituents R', R" can be optionally joined to form a ring.

In this embodiment, the expression that "adjacent substituents R', R" can be optionally joined to form a ring" is intended to mean that any one or more of groups of adjacent substituents, such as two substituents R', two substituents R" and substituents R' and R", can be joined to form a ring. Obviously, it is possible that none of these substituents are joined to form a ring.

In this embodiment, when m is 0, it means that the corresponding L does not exist. For example, when one m is 0, Formula 2 is

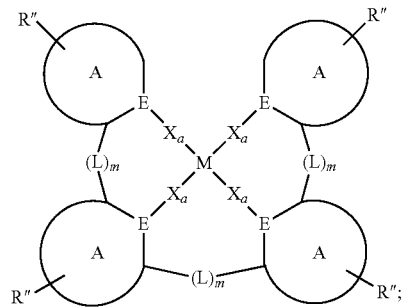

when two m are 0, Formula 2 is

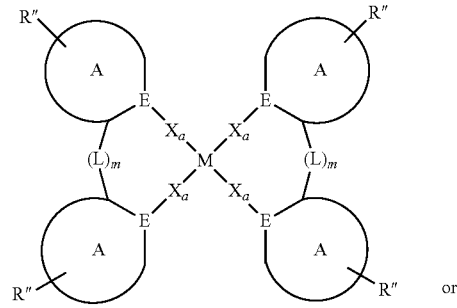

or

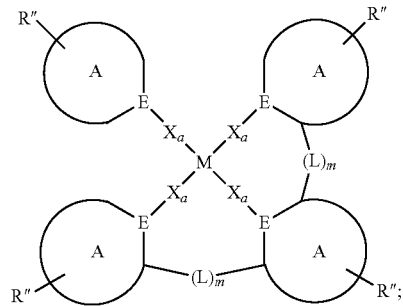

when three m is 0, Formula 2 is

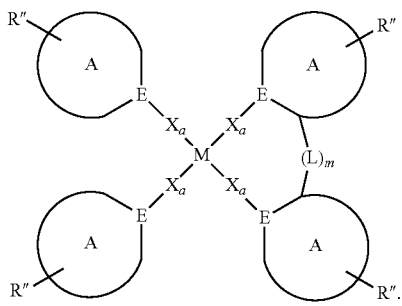

According to an embodiment of the present disclosure, wherein, in Formula 2, at least one A is selected from a substituted or unsubstituted heteroaromatic ring having 5 to 30 ring atoms.

According to an embodiment of the present disclosure, wherein, in Formula 2, at least one A is selected from substituted or unsubstituted benzimidazole, benzoxazole or benzothiazole and is coordinated to M through a dashed line of

According to an embodiment of the present disclosure, wherein, in Formula 2, at least one A is selected from a substituted or unsubstituted heteroaromatic ring having 5 to 30 ring atoms.

According to an embodiment of the present disclosure, wherein, in Formula 2, at least one A is selected from substituted or unsubstituted pyridine and is coordinated to M through N of pyridine.

According to an embodiment of the present disclosure, wherein, in Formula 2, at least one m, at least two m or at least three m are not 0.

According to an embodiment of the present disclosure, wherein, in Formula 2, L is a single bond.

According to an embodiment of the present disclosure, wherein, in Formula 2, at least one $X_a$ is O or S.

According to an embodiment of the present disclosure, wherein, in Formula 2, at least one $X_a$ is O.

According to an embodiment of the present disclosure, wherein, the first metal complex has a general formula of $M(L_a)_f(L_b)_g(L_c)_h$, wherein $L_a$ has a structure represented by Formula 3:

Formula 3

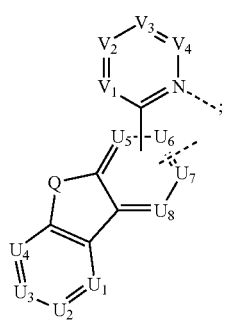

wherein
the metal M is, at each occurrence identically or differently, selected from the group consisting of Cu, Ag, Au, Ru, Rh, Pd, Os, Ir and Pt;
$L_a$, $L_b$ and $L_c$ are a first ligand, a second ligand and a third ligand coordinated to the metal M, respectively; $L_a$, $L_b$ and $L_c$ can be optionally joined to form a multidentate ligand; for example, any two of $L_a$, $L_b$ and $L_c$ may be joined to form a tetradentate ligand; in another example, $L_a$, $L_b$ and $L_c$ may be joined to each other to form a hexadentate ligand; in another example, none of $L_a$, $L_b$ and $L_c$ are joined so that the multidentate ligand is not formed; f is selected from 0, 1, 2 or 3, g is selected from 0, 1, 2 or 3, and his selected from 0, 1 or 2;
when f is 2 or 3, a plurality of $L_a$ are identical or different; when g is 2 or 3, a plurality of $L_b$ are identical or different; when h is 2, two $L_c$ are identical or different;
Q is, at each occurrence identically or differently, selected from the group consisting of O, S, Se, $NR_q$, $CR_uR_u$ and $SiR_uR_u$; when two $R_q$ are present at the same time, the two $R_q$ are identical or different;
$U_1$ to $U_8$ are, at each occurrence identically or differently, selected from C, $CR_u$ or N; at least one of $U_5$ to $U_8$ is C and joined to

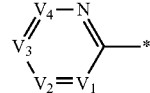

in Formula 3, wherein "*" represents a joining position;
$U_5$, $U_6$, $U_7$ or $U_8$ is joined to the metal M by a metal-carbon bond or a metal-nitrogen bond;
$V_1$ to $V_4$ are, at each occurrence identically or differently, selected from $CR_v$ or N;
$R_q$, $R_u$ and $R_v$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof;
adjacent substituents $R_q$, $R_u$ and $R_v$ can be optionally joined to form a ring;
$L_b$ and $L_c$ are, at each occurrence identically or differently, selected from a structure represented by any one of the group consisting of the following:

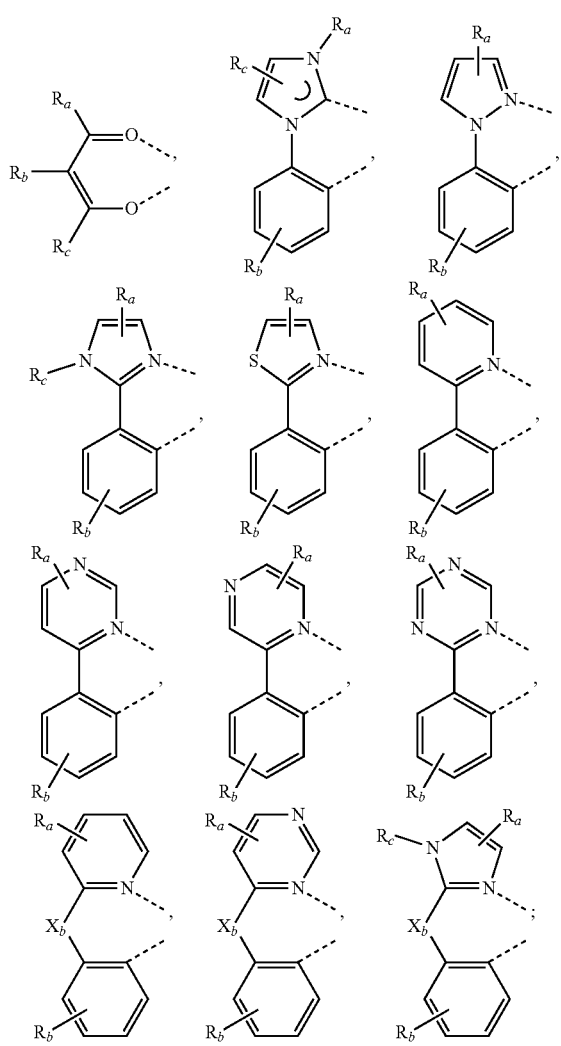

wherein

R$_a$, R$_b$ and R$_c$ represent, at each occurrence identically or differently, mono-substitution, multiple substitutions or non-substitution;

X$_b$ is, at each occurrence identically or differently, selected from the group consisting of: O, S, Se, NR$_{N1}$ and CR$_{C1}$R$_{C2}$;

R$_a$, R$_b$, R$_c$, R$_{N1}$, R$_{C1}$ and R$_{C2}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof; and adjacent substituents R$_a$, R$_b$, R$_{N1}$, R$_{C1}$ and R$_{C2}$ can be optionally joined to form a ring.

Herein, the expression that "adjacent substituents R$_q$, R$_u$ and R$_v$ can be optionally joined to form a ring" is intended to mean that any one or more of groups of adjacent substituents, such as two substituents R$_q$, two substituents R$_u$, two substituents R$_v$, substituents R$_u$ and R$_v$ and substituents R$_u$ and R$_q$, can be joined to form a ring. Obviously, it is possible that none of these substituents are joined to form a ring.

In this embodiment, the expression that "adjacent substituents R$_a$, R$_b$, R$_{N1}$, R$_{C1}$ and R$_{C2}$ can be optionally joined to form a ring" is intended to mean that any one or more of groups of adjacent substituents, such as two substituents R$_a$, two substituents R$_b$, two substituents substituents R$_a$ and R$_b$, substituents R$_a$ and R$_c$, substituents R$_b$ and R$_c$, substituents R$_a$ and R$_{N1}$, substituents R$_b$ and R$_{N1}$, substituents R$_a$ and R$_{C1}$, substituents R$_a$ and R$_{C2}$, substituents R$_b$ and R$_{C1}$, substituents R$_b$ and R$_{C2}$ and substituents R$_{C1}$ and R$_{C2}$, can be joined to form a ring. Obviously, it is possible that none of these substituents are joined to form a ring.

According to an embodiment of the present disclosure, wherein, at least one of V$_1$ to V$_4$ is N, for example, at least one or two of V$_1$ to V$_4$ are N.

According to an embodiment of the present disclosure, wherein, at least one of U$_1$ to U$_8$ is N, for example, at least one or two of U$_1$ to U$_8$ are N.

According to another embodiment of the present disclosure, the ligand L$_a$ has a structure represented by Formula 3a:

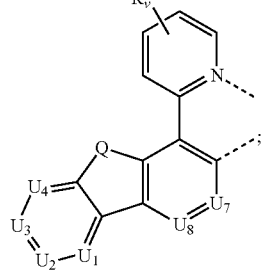

Formula 3a wherein

Q is, at each occurrence identically or differently, selected from the group consisting of O, S, Se, NR$_q$, CR$_q$R$_q$ and SiR$_q$R$_q$; when two R$_q$ are present at the same time, the two R$_q$ may be identical or different;

U$_1$ to U$_4$, U$_7$ and U$_8$ are, at each occurrence identically or differently, selected from CR$_u$ or N;

R$_v$ represents, at each occurrence identically or differently, mono-substitution, multiple substitutions or non-substitution;

R$_q$, R$_u$ and R$_v$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof; and adjacent substituents $R_q$, $R_u$ and $R_v$ can be optionally joined to form a ring.

According to another embodiment of the present disclosure, the ligand $L_a$ is, at each occurrence identically or differently, selected from any one of the following structures:

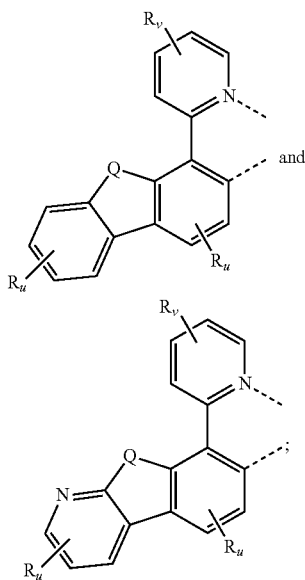

and wherein

Q is, at each occurrence identically or differently, selected from the group consisting of O, S, Se, $NR_q$, $CR_qR_q$ and $SiR_qR_q$; when two $R_q$ are present at the same time, the two $R_q$ may be identical or different;

$R_u$ and $R_v$ represent, at each occurrence identically or differently, mono-substitution, multiple substitutions or non-substitution;

$R_q$, $R_u$ and $R_v$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof; and adjacent substituents $R_q$, $R_u$ and $R_v$ can be optionally joined to form a ring.

According to another embodiment of the present disclosure, the first metal complex has a structure represented by Formula 4:

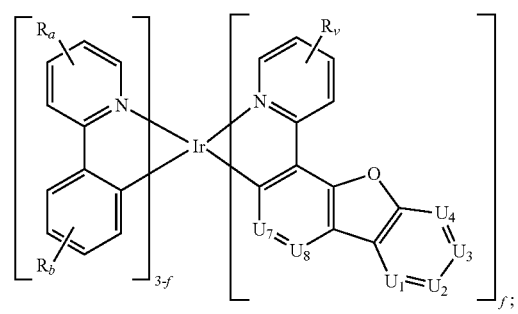

Formula 4 wherein f is 0, 1, 2 or 3; when f is 2 or 3, a plurality of $L_a$ are identical or different; when f is 0 or 1, a plurality of $L_b$ are identical or different;

$U_4$ is, at each occurrence identically or differently, selected from $CR_u$ or N;

$U_1$ to $U_3$, $U_7$ and $U_8$ are, at each occurrence identically or differently, selected from $CR_u$;

$R_a$, $R_b$ and $R_v$ represent, at each occurrence identically or differently, mono-substitution, multiple substitutions or non-substitution;

$R_a$, $R_b$, $R_u$ and $R_v$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof; and adjacent substituents $R_a$, $R_b$, $R_u$ and $R_v$ can be optionally joined to form a ring.

In this embodiment, the expression that "adjacent substituents $R_a$, $R_b$, $R_u$ and $R_v$ can be optionally joined to form a ring" is intended to mean that any one or more of groups of adjacent substituents, such as two substituents $R_a$, two substituents $R_b$, two substituents $R_u$, two substituents $R_v$, and two substituents $R_a$ and $R_b$, can be joined to form a ring. Obviously, it is possible that none of these substituents are joined to form a ring.

According to an embodiment of the present disclosure, wherein, in Formula 3a and Formula 4, at least one of $U_1$ to $U_8$ is selected from $CR_u$ and $R_u$ is cyano.

According to an embodiment of the present disclosure, wherein, in Formula 3a and Formula 4, at least one of $U_2$ to $U_4$ is selected from $CR_u$ and $R_u$ is cyano.

According to an embodiment of the present disclosure, wherein, in Formula 3a and Formula 4, $U_3$ or $U_4$ is selected from $CR_u$ and $R_u$ is cyano.

According to an embodiment of the present disclosure, wherein, in Formula 3a and Formula 4, one of $U_2$ to $U_4$ is selected from $CR_u$ and $R_u$ is cyano; and another one of $U_1$ to $U_4$ is selected from substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms or substituted or unsubstituted heteroaryl having 3 to 30 carbon atoms.

According to an embodiment of the present disclosure, wherein, in Formula 3a and Formula 4, $U_4$ is $CR_u$ and $R_u$ is substituted or unsubstituted phenyl; and $U_3$ is $CR_u$ and $R_u$ is cyano.

According to an embodiment of the present disclosure, wherein, in Formula 3a and Formula 4, $U_3$ is $CR_u$ and $R_u$ is substituted or unsubstituted phenyl; and $U_4$ is $CR_u$ and $R_u$ is cyano.

According to an embodiment of the present disclosure, wherein, in Formula 3a and Formula 4, $U_3$ is $CR_u$ and $R_u$ is substituted or unsubstituted alkyl having 1 to 10 carbon atoms; and $U_4$ is $CR_u$ and $R_u$ is cyano.

According to an embodiment of the present disclosure, wherein, in Formula 3a and Formula 4, at least one of $U_1$ to $U_8$ is selected from $CR_u$ and $R_u$ is fluorine.

According to an embodiment of the present disclosure, wherein, in Formula 3a and Formula 4, $U_3$ is selected from $CR_u$ and $R_u$ is fluorine; and $U_1$ is selected from $CR_u$ and $R_u$ is substituted or unsubstituted aryl having 6 to 30 carbon atoms or substituted or unsubstituted heteroaryl having 3 to 30 carbon atoms.

According to an embodiment of the present disclosure, wherein, $R_u$ and $R_v$ are, at each occurrence identically or differently, selected from the group consisting of: hydrogen, deuterium, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms and combinations thereof.

According to an embodiment of the present disclosure, wherein, at least one of $R_u$ is selected from substituted or unsubstituted alkyl having 1 to 20 carbon atoms or substituted or unsubstituted cycloalkyl having 3 to 20 ring carbon atoms.

According to an embodiment of the present disclosure, wherein, at least one $R_u$ is fluorine.

According to an embodiment of the present disclosure, wherein, at least one $R_u$ is cyano.

According to an embodiment of the present disclosure, wherein, there are at least two $R_u$, one of which is fluorine and the other one of which is selected from substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms or substituted or unsubstituted heteroaryl having 3 to 30 carbon atoms.

According to an embodiment of the present disclosure, wherein, there are at least two $R_u$, one of which is cyano and the other one of which is selected from substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms or substituted or unsubstituted heteroaryl having 3 to 30 carbon atoms.

According to an embodiment of the present disclosure, wherein, $L_a$ is, at each occurrence identically or differently, selected from the group consisting of: $L_{a1-1}$ to $L_{a1-114}$, $L_{a2-1}$ to $L_{a2-83}$, $L_{a3-1}$ to $L_{a3-73}$ and $L_{a4-1}$ to $L_{a4-82}$, wherein the specific structures of $L_{a1-1}$ to $L_{a1-114}$, $L_{a2-1}$ to $L_{a2-83}$, $L_{a3-1}$ to $L_{a3-73}$ and $L_{a4-1}$ to $L_{a4-82}$ are referred to claim 17.

According to an embodiment of the present disclosure, wherein, $L_b$ is, at each occurrence identically or differently, selected from the group consisting of $L_{b1}$ to $L_{b227}$, wherein the specific structures of $L_{b1}$ to $L_{b227}$ are referred to claim 18.

According to an embodiment of the present disclosure, wherein, $L_c$ is, at each occurrence identically or differently, selected from the group consisting of $L_{b1}$ to $L_{b227}$, wherein the specific structures of $L_{b1}$ to $L_{b227}$ are referred to claim 18.

According to an embodiment of the present disclosure, wherein, the first metal complex has a general formula of $Ir(L_a)_2L_b$ or $IrL_a(L_b)_2$, wherein $L_a$ is, at each occurrence identically or differently, selected from the group consisting of: $L_{a1-1}$ to $L_{a1-114}$, $L_{a2-1}$ to $L_{a2-83}$, $L_{a3-1}$ to $L_{a3-73}$ and $L_{a4-1}$ to $L_{a4-82}$ and $L_b$ is, at each occurrence identically or differently, selected from the group consisting of $L_{b1}$ to $L_{b227}$, wherein the specific structures of $L_{a1-1}$ to $L_{a1-114}$, $L_{a2-1}$ to $L_{a2-83}$, $L_{a3-1}$ to $L_{a3-73}$ and $L_{a4-1}$ to $L_{a4-82}$ are referred to claim 17 and the specific structures of $L_{b1}$ to $L_{b227}$ are referred to claim 18.

According to an embodiment of the present disclosure, wherein, the first metal complex has a general formula of $Ir(L_b)_3$ or $Ir(L_b)_2L_c$ or $IrL_b(L_c)_2$, wherein $L_b$ is, at each occurrence identically or differently, selected from the group consisting of $L_{b1}$ to $L_{b227}$ and $L_c$ is, at each occurrence identically or differently, selected from the group consisting of $L_{b1}$ to $L_{b227}$, wherein the specific structures of $L_{b1}$ to $L_{b227}$ are referred to claim 18.

According to an embodiment of the present disclosure, wherein, the first metal complex is selected from the group consisting of: GD1-1 to GD1-87, GD2-1 to GD2-84, GD3-1 to GD3-75, GD4-1 to GD4-86, GD5-1 to GD5-85, GD6-1 to GD6-46 and GD7-1 to GD7-28, wherein the specific structures of GD1-1 to GD1-87, GD2-1 to GD2-84, GD3-1 to GD3-75, GD4-1 to GD4-86, GD5-1 to GD5-85, GD6-1 to GD6-46 and GD7-1 to GD7-28 are referred to claim 19.

According to an embodiment of the present disclosure, wherein, in the organic electroluminescent device, the light-emitting layer further contains a second host compound, wherein the second host compound comprises at least one chemical group selected from the group consisting of: benzene, pyridine, pyrimidine, triazine, carbazole, azacarbazole, indolocarbazole, dibenzothiophene, aza-dibenzothiophene, dibenzofuran, azadibenzofuran, dibenzoselenophene, triphenylene, azatriphenylene, fluorene, silafluorene, naphthalene, quinoline, isoquinoline, quinazoline, quinoxaline, phenanthrene, azaphenanthrene and combinations thereof.

According to an embodiment of the present disclosure, wherein, in the organic electroluminescent device, the light-emitting layer further contains a second host compound, wherein the second host compound comprises at least one chemical group selected from the group consisting of: benzene, carbazole, indolocarbazole, fluorene, silafluorene and combinations thereof.

According to an embodiment of the present disclosure, wherein, in the organic electroluminescent device, the second host compound has a structure represented by Formula 5:

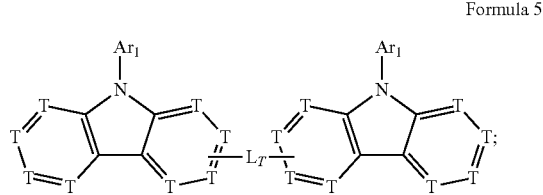

Formula 5 wherein $L_T$ is, at each occurrence identically or differently, selected from a single bond, substituted or unsubstituted alkylene having 1 to 20 carbon atoms, substituted or unsubstituted cycloalkylene having 3 to 20 carbon atoms, substituted or unsubstituted arylene having 6 to 20 carbon atoms, substituted or unsubstituted heteroarylene having 3 to 20 carbon atoms or a combination thereof;

T is, at each occurrence identically or differently, selected from C, $CR_t$ or N;

$R_t$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof;

$Ar_1$ is, at each occurrence identically or differently, selected from substituted or unsubstituted aryl having 6 to 30 carbon atoms, substituted or unsubstituted heteroaryl having 3 to 30 carbon atoms or a combination thereof; and adjacent substituents $R_t$ can be optionally joined to form a ring.

Herein, the expression that "adjacent substituents $R_t$ can be optionally joined to form a ring" is intended to mean that any one or more of groups of adjacent substituents $R_t$ can be joined to form a ring. Obviously, it is possible that none of these substituents are joined to form a ring.

According to an embodiment of the present disclosure, wherein, in the organic electroluminescent device, the second host compound has a structure represented by Formula 6:

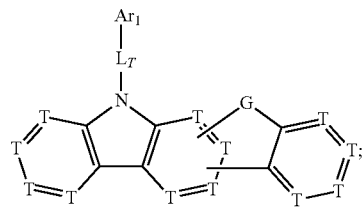

Formula 6 wherein

G is, at each occurrence identically or differently, selected from $C(R_g)_2$, $NR_g$, O or S;

T is, at each occurrence identically or differently, selected from C, $CR_t$ or N;

$L_T$ is, at each occurrence identically or differently, selected from a single bond, substituted or unsubstituted alkylene having 1 to 20 carbon atoms, substituted or unsubstituted cycloalkylene having 3 to 20 carbon atoms, substituted or unsubstituted arylene having 6 to 20 carbon atoms, substituted or unsubstituted heteroarylene having 3 to 20 carbon atoms or a combination thereof;

$R_t$ and $R_g$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof;

$Ar_1$ is, at each occurrence identically or differently, selected from substituted or unsubstituted aryl having 6 to 30 carbon atoms, substituted or unsubstituted heteroaryl having 3 to 30 carbon atoms or a combination thereof; and adjacent substituents $R_t$, $R_g$ can be optionally joined to form a ring.

Herein, the expression that "adjacent substituents $R_t$, $R_g$ can be optionally joined to form a ring" is intended to mean that any one or more of groups of adjacent substituents $R_t$ and adjacent substituents $R_t$ and $R_g$ can be joined to form a ring. Obviously, it is possible that none of these substituents are joined to form a ring.

According to an embodiment of the present disclosure, wherein, in the organic electroluminescent device, the second host compound has a structure represented by one of Formulas 5-a to 5-j:

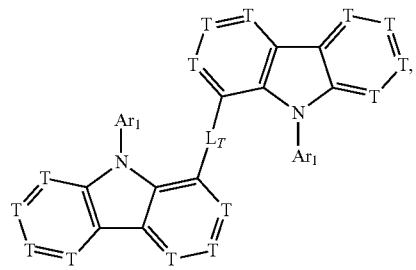

Formula 5-a

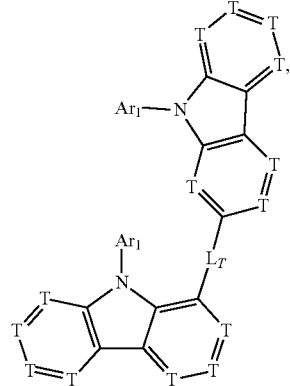

Formula 5-b

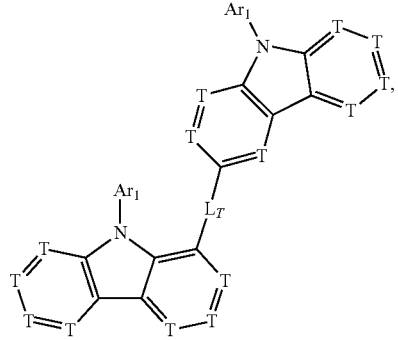

Formula 5-c

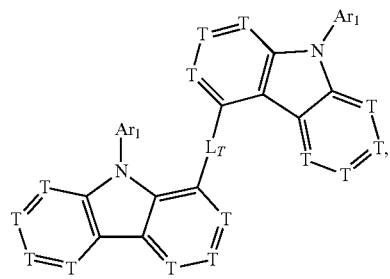

Formula 5-d

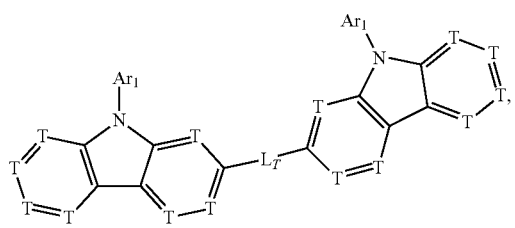

Formula 5-e

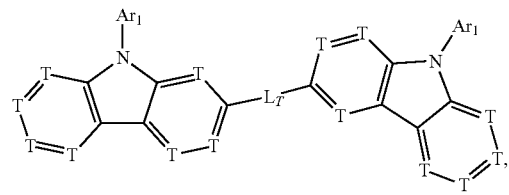

Formula 5-f

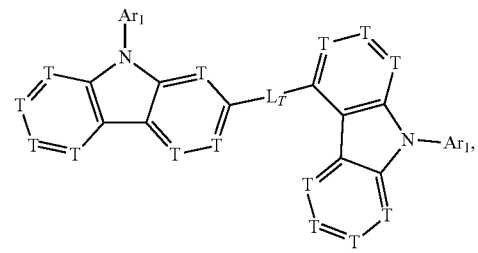

Formula 5-g

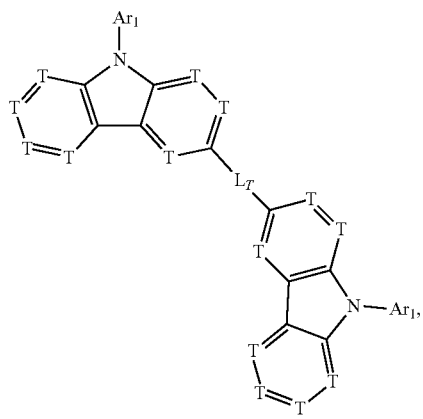

Formula 5-h

-continued

Formula 5-i

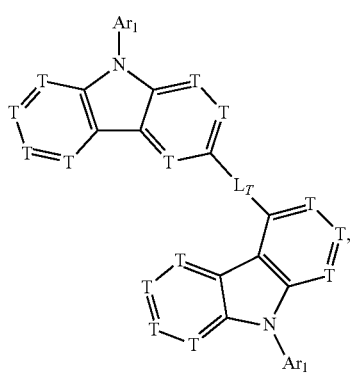

Formula 5-j

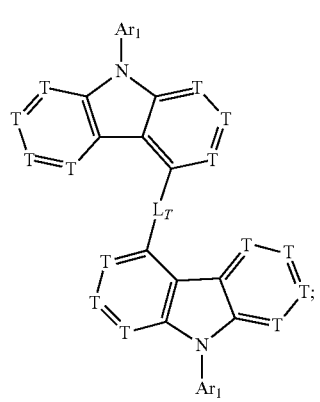

wherein $L_T$ is, at each occurrence identically or differently, selected from a single bond, substituted or unsubstituted alkylene having 1 to 20 carbon atoms, substituted or unsubstituted cycloalkylene having 3 to 20 carbon atoms, substituted or unsubstituted arylene having 6 to 20 carbon atoms, substituted or unsubstituted heteroarylene having 3 to 20 carbon atoms or a combination thereof;

T is, at each occurrence identically or differently, selected from $CR_t$ or N;

$R_t$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof;

$Ar_t$ is, at each occurrence identically or differently, selected from substituted or unsubstituted aryl having 6 to 30 carbon atoms, substituted or unsubstituted heteroaryl having 3 to 30 carbon atoms or a combination thereof; and adjacent substituents $R_t$ can be optionally joined to form a ring.

According to an embodiment of the present disclosure, wherein, in the organic electroluminescent device, the second host compound has a structure represented by one of Formulas 6-a to 6-f:

Formula 6-a

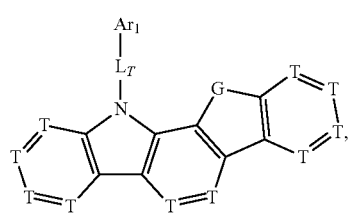

Formula 6-b

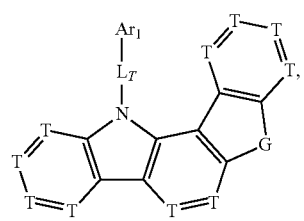

Formula 6-c

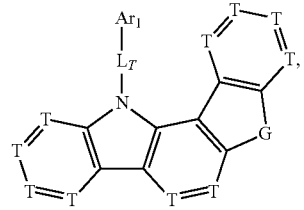

Formula 6-d

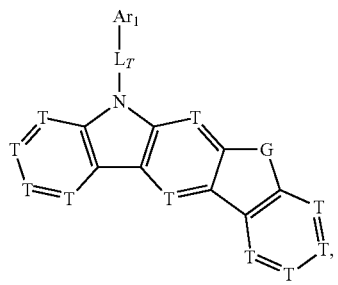

Formula 6-e

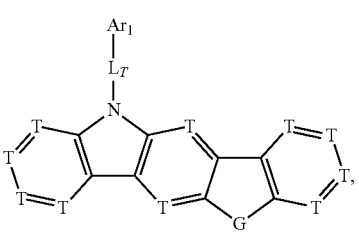

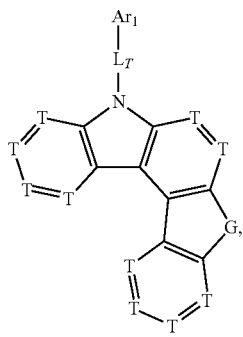

-continued

Formula 6-f

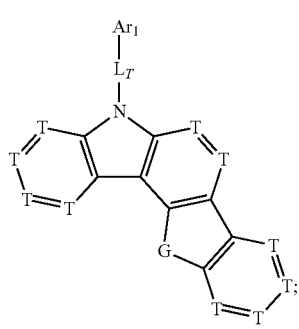

wherein

G is, at each occurrence identically or differently, selected from $C(R_g)_2$, $NR_g$, O or S;

T is, at each occurrence identically or differently, selected from $CR_t$ or N;

$L_T$ is, at each occurrence identically or differently, selected from a single bond, substituted or unsubstituted alkylene having 1 to 20 carbon atoms, substituted or unsubstituted cycloalkylene having 3 to 20 carbon atoms, substituted or unsubstituted arylene having 6 to 20 carbon atoms, substituted or unsubstituted heteroarylene having 3 to 20 carbon atoms or a combination thereof;

$R_t$ and $R_g$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof;

$Ar_t$ is, at each occurrence identically or differently, selected from substituted or unsubstituted aryl having 6 to 30 carbon atoms, substituted or unsubstituted heteroaryl having 3 to 30 carbon atoms or a combination thereof; and adjacent substituents $R_t$, $R_g$ can be optionally joined to form a ring.

According to an embodiment of the present disclosure, wherein, at least one of all T is selected from N, for example, one or two of all T are N.

An embodiment of the present disclosure further provides a compound composition. The compound composition contains the compound in any one of the preceding embodiments.

Combination with Other Materials

The materials described in the present disclosure for a particular layer in an organic light emitting device can be used in combination with various other materials present in the device. The combinations of these materials are described in more detail in U.S. Pat. App. No. 20160359122 at paragraphs 0132-0161, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, compounds disclosed herein may be used in combination with a wide variety of hosts, emissive dopants, transporting layers, blocking layers, injection layers, electrodes and other layers that may be present. The combination of these materials is described in detail in paragraphs 0080-0101 of U.S. Pat. App. No. 20150349273, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

In the embodiments of material synthesis, all reactions were performed under nitrogen protection unless otherwise stated. All reaction solvents were anhydrous and used as received from commercial sources. Synthetic products were structurally confirmed and tested for properties using one or more conventional equipment in the art (including, but not limited to, nuclear magnetic resonance instrument produced by BRUKER, liquid chromatograph produced by SHIMADZU, liquid chromatograph-mass spectrometry produced by SHIMADZU, gas chromatograph-mass spectrometry produced by SHIMADZU, differential Scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this patent.

Material Synthesis Example

The method for preparing a compound in the present disclosure is not limited herein. Typically, the following compounds are used as examples without limitations, and synthesis routes and preparation methods thereof are described below.

Synthesis Example 1: Synthesis of Compound A-1

Step 1: Synthesis of Intermediate C

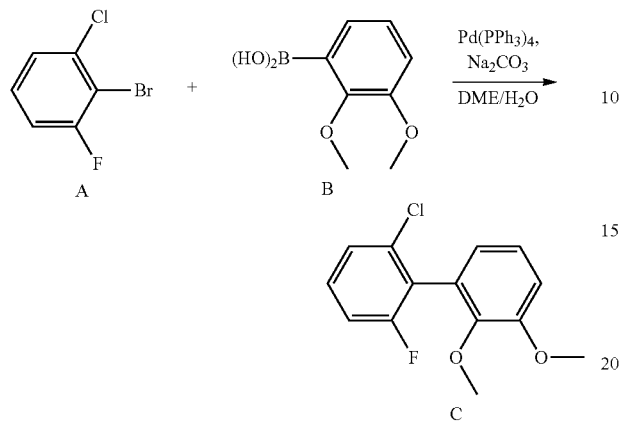

In a three-necked round-bottom flask, A (24.4 g, 116.5 mmol), B (23.3 g, 128.2 mmol), Pd(PPh$_3$)$_4$ (2.69 g, 2.33 mmol) and Na$_2$CO$_3$ (24.7 g, 223.0 mmol) were added to ethylene glycol dimethyl ether (400 mL) and H$_2$O (200 mL) and heated to reflux overnight under nitrogen protection. After the reaction was finished, heating was stopped and the system was cooled to room temperature. The system stood still to separate layers, an aqueous phase was extracted with DCM several times, and organic phases were combined, dried over anhydrous Na$_2$SO$_4$, filtered and concentrated under reduced pressure. The crude product was purified through column chromatography (PE:DCM=2:1) to obtain Intermediate C (30.7 g, 115.1 mmol) as a white solid with a yield of 98.8%.

Step 2: Synthesis of Intermediate D

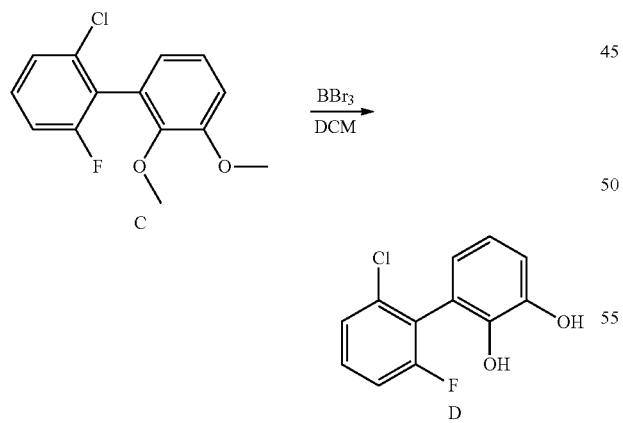

In a single-necked round-bottom flask, C (30.7 g, 115.1 mmol) was dissolved in DCM (300 mL) and BBr$_3$ (109.6 g, 437.4 mmol) was slowly added dropwise to the system at 0° C. After dropwise addition, the system was gradually warmed to room temperature and reacted overnight. After the reaction was finished, the reaction solution was slowly poured into water and extracted several times. The organic phases were combined, dried over anhydrous Na$_2$SO$_4$, filtered and concentrated under reduced pressure. The crude product was purified through column chromatography (PE:EA=4:1) to obtain Intermediate D (26.8 g, 112.3 mmol) as a white solid with a yield of 97.6%.

Step 3: Synthesis of Intermediate E

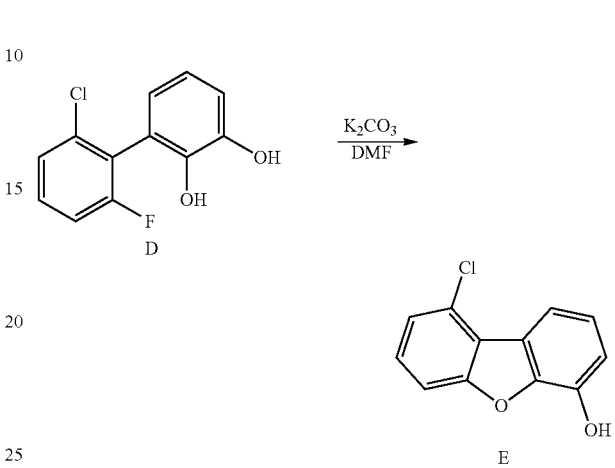

In a three-necked round-bottom flask, D (26.8 g, 112.3 mmol) and K$_2$CO$_3$ (38.8 g, 138.21 mmol) were added to DMF (360 mL) and heated to 140° C. and reacted overnight under nitrogen protection. After the reaction was finished, heating was stopped, the system was cooled to room temperature, and the reaction solution was poured into a large amount of water and extracted with DCM several times. The organic phases were combined, dried over anhydrous Na$_2$SO$_4$, filtered and concentrated under reduced pressure. The crude product was purified through column chromatography (PE:EA=5:1) to obtain Intermediate E (22.6 g, 103.4 mmol) as a white solid with a yield of 92.0%.

Step 4: Synthesis of Intermediate F

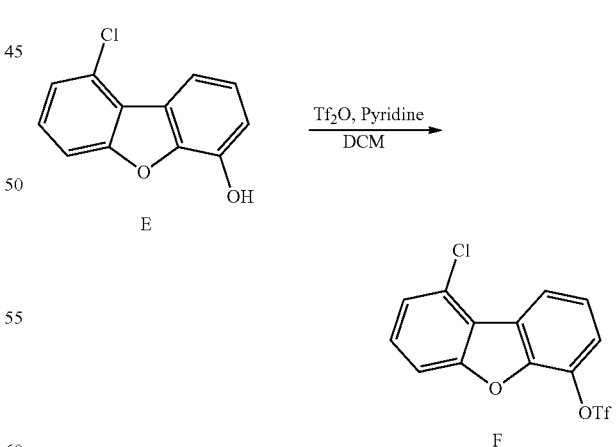

In a single-necked round-bottom flask, E (22.6 g, 103.4 mmol) and pyridine (17.8 g, 224.6 mmol) were dissolved in DCM (400 mL) and trifluoromethanesulfonic anhydride (38.0 g, 134.8 mmol) was slowly added dropwise to the system at 0° C. After dropwise addition, the system was gradually warmed to room temperature and reacted overnight. After the reaction was finished, the reaction solution was poured into water and extracted several times. The organic phases were combined, dried over anhydrous Na$_2$SO$_4$, filtered and concentrated under reduced pressure. The crude product was purified through column chromatography (PE:DCM=30:1) to obtain Intermediate F (23.6 g, 67.3 mmol) as a white solid with a yield of 65.1%.

Step 5: Synthesis of Intermediate G

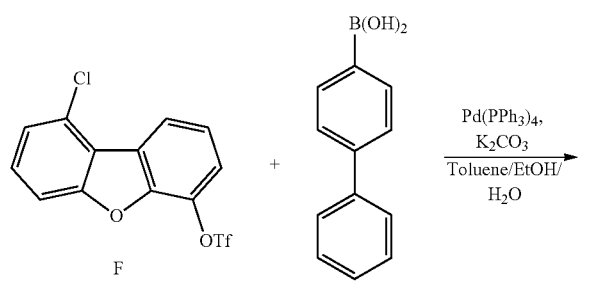

In a three-necked round-bottom flask, F (11.4 g, 32.5 mmol), 4-biphenylboronic acid (7.72 g, 39.0 mmol), Pd(PPh$_3$)$_4$ (0.75 g, 0.65 mmol) and K$_2$CO$_3$ (9.0 g, 65.0 mmol) were added to toluene (140 mL), EtOH (35 mL) and H$_2$O (35 mL) and heated to reflux overnight under nitrogen protection. After the reaction was finished, heating was stopped and the system was cooled to room temperature. The system stood still to separate layers, an aqueous phase was extracted with DCM several times, and organic phases were combined, dried over anhydrous Na$_2$SO$_4$, filtered and concentrated under reduced pressure. The crude product was purified through column chromatography (PE:DCM=40:1-45:1) to obtain Intermediate G (9.6 g, 27.06 mmol) as a white solid with a yield of 83.3%.

Step 6: Synthesis of Intermediate H

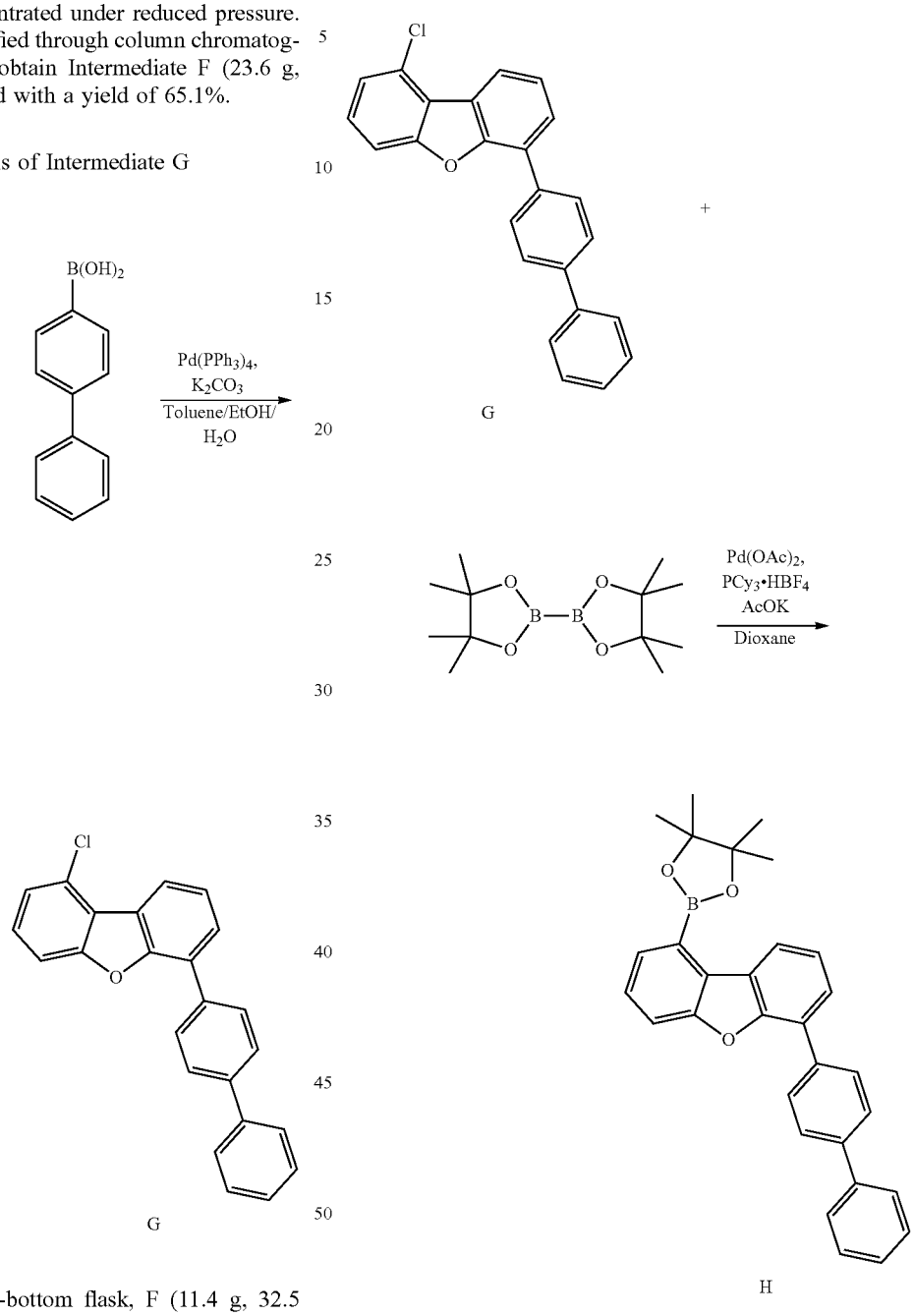

In a three-necked round-bottom flask, G (9.6 g, 27.06 mmol), bis(pinacolato)diboron (10.3 g, 40.58 mmol), Pd(OAc)$_2$ (0.18 g, 0.81 mmol), tricyclohexylphosphine tetrafluoroborate (PCy$_3$·HBF$_4$) (0.60 g, 1.62 mmol) and AcOK (5.3 g, 54.12 mmol) were added to 1,4-dioxane (110 mL) and heated to reflux overnight under nitrogen protection. After the reaction was finished, heating was stopped and the system was cooled to room temperature. The reaction solution was filtered through Celite. The filtrate was concentrated under reduced pressure. The crude product was purified through column chromatography (PE:DCM=4:1→2:1) to obtain Intermediate H (8.5 g, 19.04 mmol) as a pale yellow solid with a yield of 70.4%.

Step 7: Synthesis of Compound A-1

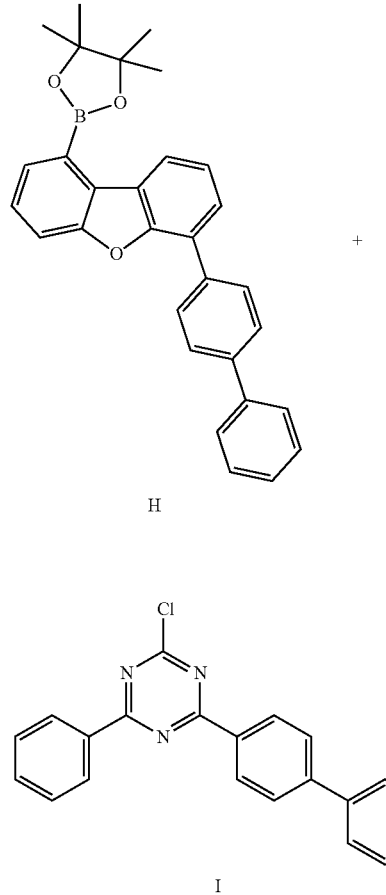

In a three-necked round-bottom flask, H (4.0 g, 8.96 mmol), I (3.08 g, 8.96 mmol), Pd(PPh$_3$)$_4$ (0.31 g, 0.27 mmol) and K$_2$CO$_3$ (2.48 g, 17.92 mmol) were added to toluene (40 mL), EtOH (10 mL) and H$_2$O (10 mL) and heated to reflux overnight under nitrogen protection. After the reaction was finished, heating was stopped, the system was cooled to room temperature and filtered through suction under reduced pressure, and the obtained solid was washed with water and methanol in sequence. The solid was recrystallized from toluene/acetonitrile to obtain a white solid (4.8 g, 7.65 mmol) with a yield of 85.3%. The product was confirmed as the target product A-1 with a molecular weight of 627.2.

Synthesis Example 2: Synthesis of Compound A-19

Step 1: Synthesis of Compound A-19

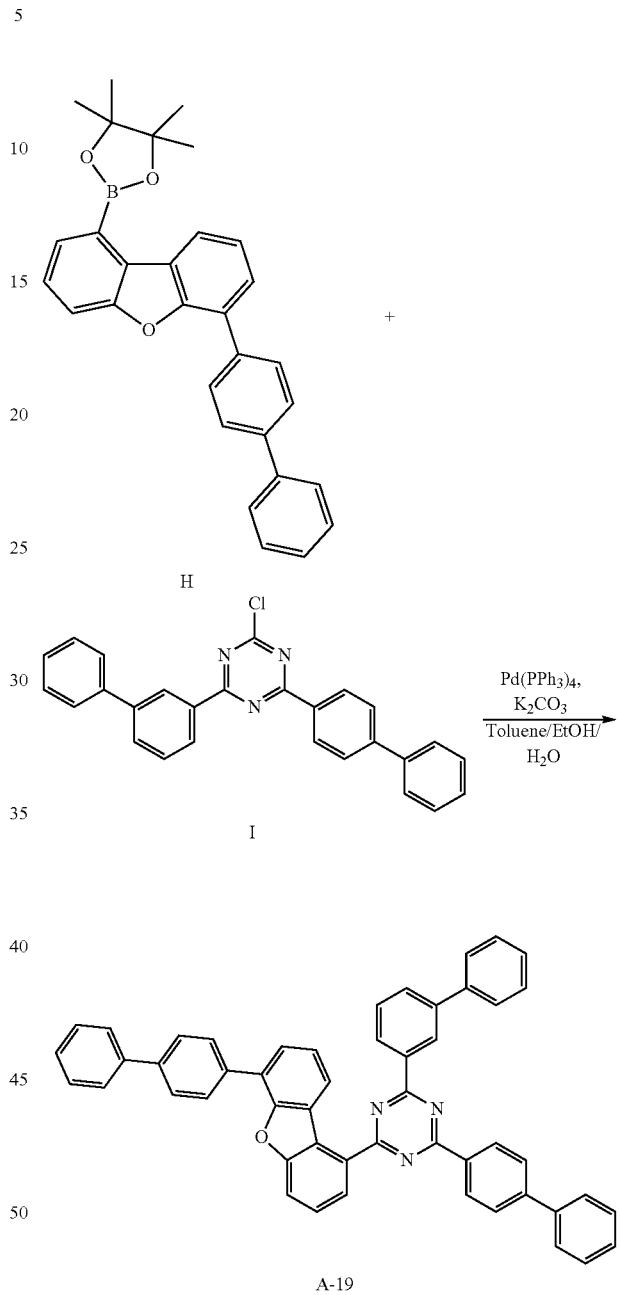

In a three-necked round-bottom flask, H (3.36 g, 7.53 mmol), J (3.16 g, 7.53 mmol), Pd(PPh$_3$)$_4$ (0.26 g, 0.226 mmol) and K$_2$CO$_3$ (2.08 g, 15.06 mmol) were added to toluene (36 mL), EtOH (9 mL) and H$_2$O (9 mL) and heated to reflux overnight under nitrogen protection. After the reaction was finished, heating was stopped, the system was cooled to room temperature and filtered through suction under reduced pressure, and the obtained solid was washed with water and methanol in sequence. The solid was recrystallized from toluene to obtain a white solid (4.3 g, 6.11 mmol) with a yield of 81.1%. The product was confirmed as the target product A-19 with a molecular weight of 703.3.

Synthesis Example 3: Synthesis of Compound A-27

Step 1: Synthesis of Intermediate K

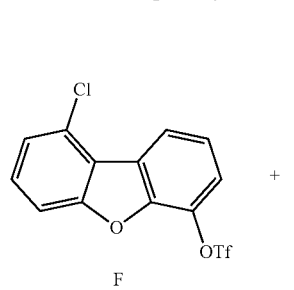

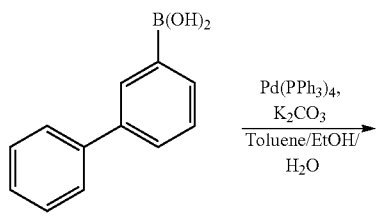

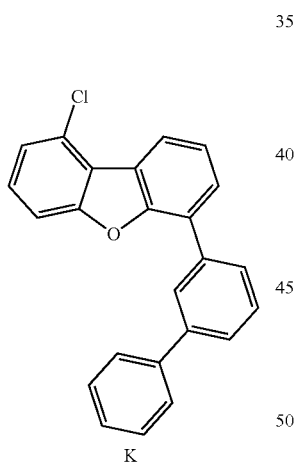

In a three-necked round-bottom flask, F (6.6 g, 18.82 mmol), 3-biphenylboronic acid (4.47 g, 22.57 mmol), Pd(PPh$_3$)$_4$ (0.653 g, 0.56 mmol) and K$_2$CO$_3$ (5.19 g, 37.61 mmol) were added to toluene (64 mL), EtOH (16 mL) and H$_2$O (16 mL) and heated to reflux overnight under nitrogen protection. After the reaction was finished, heating was stopped and the system was cooled to room temperature. The system stood still to separate layers, an aqueous phase was extracted with DCM several times, and organic phases were combined, dried over anhydrous Na$_2$SO$_4$, filtered and concentrated under reduced pressure. The crude product was purified through column chromatography (PE:DCM=100:1-40:1) to obtain Intermediate K (6.0 g, 16.91 mmol) as a white solid with a yield of 89.8%.

Step 2: Synthesis of Intermediate L

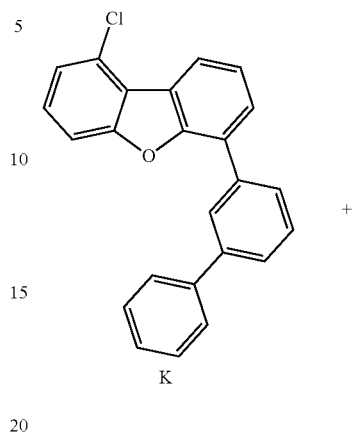

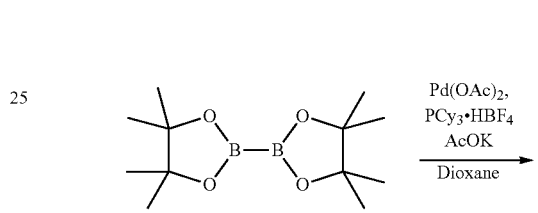

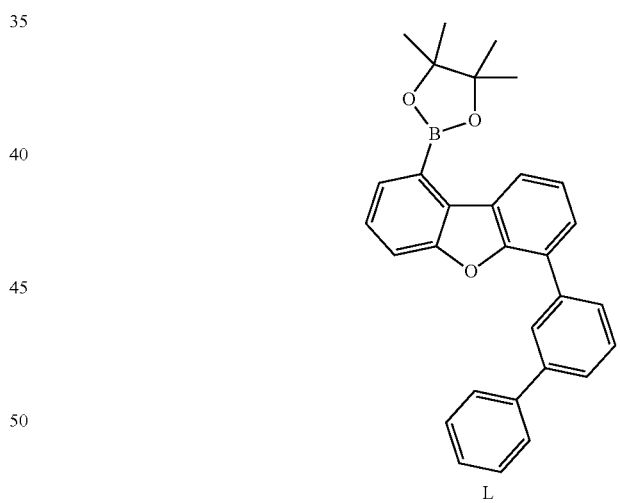

In a three-necked round-bottom flask, K (6.0 g, 16.91 mmol), bis(pinacolato)diboron (7.73 g, 30.44 mmol), Pd(OAc)$_2$ (0.19 g, 0.85 mmol), tricyclohexylphosphine tetrafluoroborate (PCy$_3$·HBF$_4$) (0.623 g, 1.69 mmol) and AcOK (3.32 g, 33.83 mmol) were added to 1,4-dioxane (85 mL) and heated to reflux overnight under nitrogen protection. After the reaction was finished, heating was stopped and the system was cooled to room temperature. The reaction solution was filtered through Celite. The filtrate was concentrated under reduced pressure. The crude product was purified through column chromatography (PE:DCM=8:1-4:1) to obtain Intermediate L (4.8 g, 10.75 mmol) as a white solid with a yield of 63.6%.

Step 3: Synthesis of Compound A-27

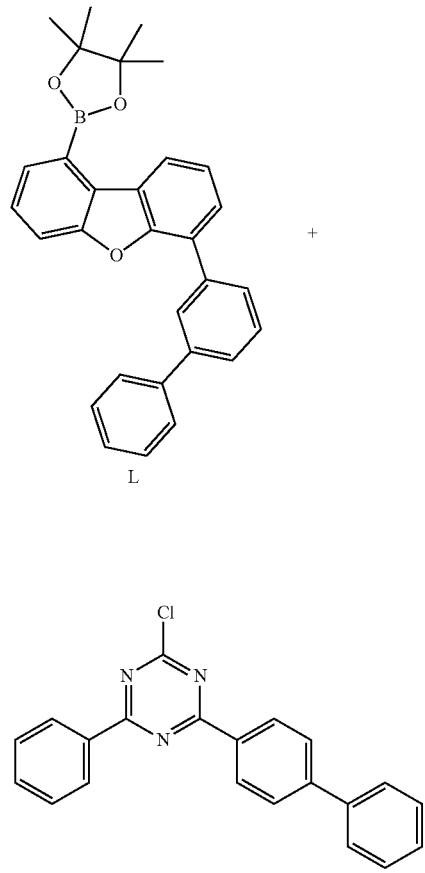

Synthesis Example 4: Synthesis of Compound A-45

Step 1: Synthesis of Compound A-45

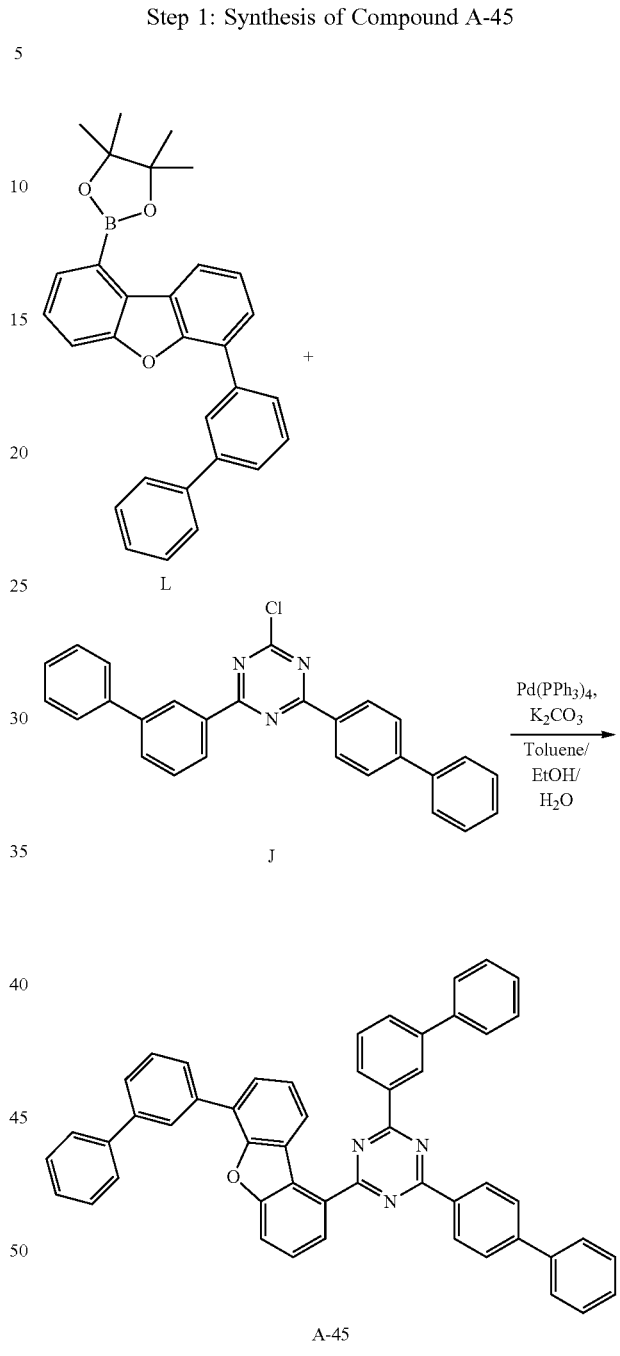

In a three-necked round-bottom flask, L (3.3 g, 7.4 mmol), I (2.54 g, 7.4 mmol), Pd(PPh$_3$)$_4$ (0.256 g, 0.20 mmol) and K$_2$CO$_3$ (2.04 g, 14.8 mmol) were added to toluene (32 mL), EtOH (8 mL) and H$_2$O (8 mL) and heated to reflux overnight under nitrogen protection. After the reaction was finished, heating was stopped, the system was cooled to room temperature and filtered through suction under reduced pressure, and the obtained solid was washed with water and methanol in sequence. The solid was recrystallized from toluene/acetonitrile to obtain a white solid (3.0 g, 4.8 mmol) with a yield of 64.9%. The product was confirmed as the target product A-27 with a molecular weight of 627.2.

In a three-necked round-bottom flask, L (3.3 g, 7.4 mmol), J (3.1 g, 7.4 mmol), Pd(PPh$_3$)$_4$ (0.257 g, 0.22 mmol) and K$_2$CO$_3$ (2.0 g, 14.8 mmol) were added to toluene (32 mL), EtOH (8 mL) and H$_2$O (8 mL) and heated to reflux overnight under nitrogen protection. After the reaction was finished, heating was stopped, the system was cooled to room temperature and filtered through suction under reduced pressure, and the obtained solid was washed with water and ethanol in sequence. The solid was recrystallized from toluene/acetonitrile to obtain a white solid (4.1 g, 5.8 mmol) with a yield of 78.8%. The product was confirmed as the target product A-45 with a molecular weight of 703.3.

Synthesis Example 5: Synthesis of Compound A-3

Step 1: Synthesis of Intermediate M

Step 2: Synthesis of Intermediate N

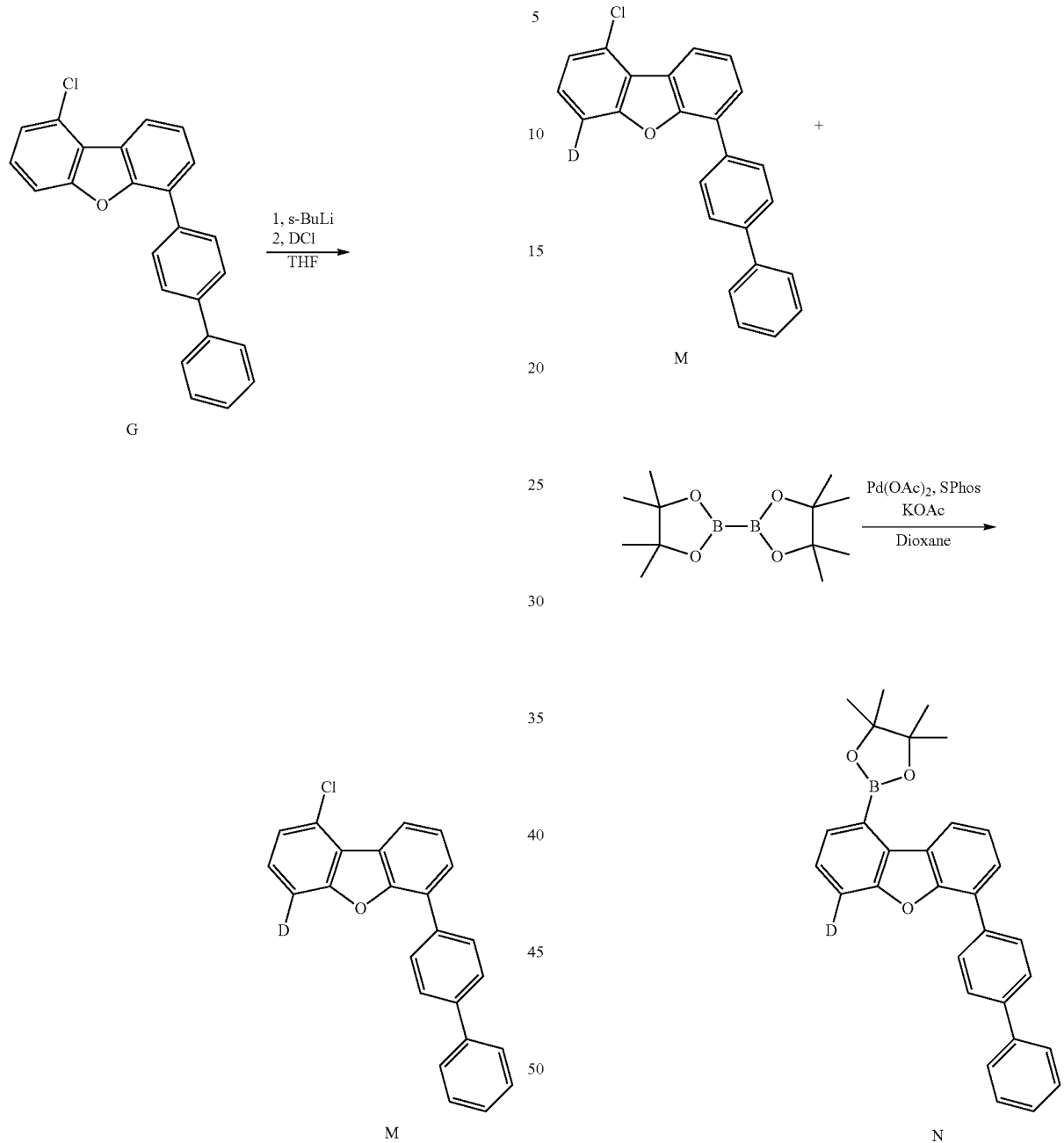

In a three-necked round-bottom flask, G (2.5 g, 7.06 mmol) was dissolved in THF (80 mL) and sec-butyl lithium (1 M, 8.5 mmol) was slowly added dropwise to the system at −78° C. under nitrogen protection. After dropwise addition, the system was reacted for 1 h at a low temperature. A solution (1 mL) of deuterium chloride (20%) in deuterium water was added and the system was slowly warmed to room temperature and reacted overnight. After the reaction was finished, the solvent was removed through rotary evaporation under reduced pressure, and the solid was recrystallized from ethanol to obtain Intermediate M (2 g, 5.63 mmol) as a white solid with a yield of 80%.

In a three-necked round-bottom flask, M (4.4 g, 12.4 mmol), bis(pinacolato)diboron (4.72 g, 18.6 mmol), Pd(OAc)$_2$ (56 mg, 0.25 mmol), 2-dicyclohexylphosphino-2',6'-dimethoxybiphenyl(SPhos) (204 mg, 0.5 mmol) and KOAc (3.65 g, 37.2 mmol) were added to 1,4-dioxane (125 mL) and heated to reflux overnight under nitrogen protection. Heating was stopped, the system was cooled to room temperature and filtered through Celite, and the filtrate was concentrated under reduced pressure. The crude product was purified through column chromatography (PE:DCM=2:1) to obtain Intermediate N (2.2 g, 4.9 mmol) as a white solid with a yield of 40%.

Step 3: Synthesis of Compound A-3

Synthesis Example 6: Synthesis of Compound A-2

Step 1: Synthesis of Compound A-2

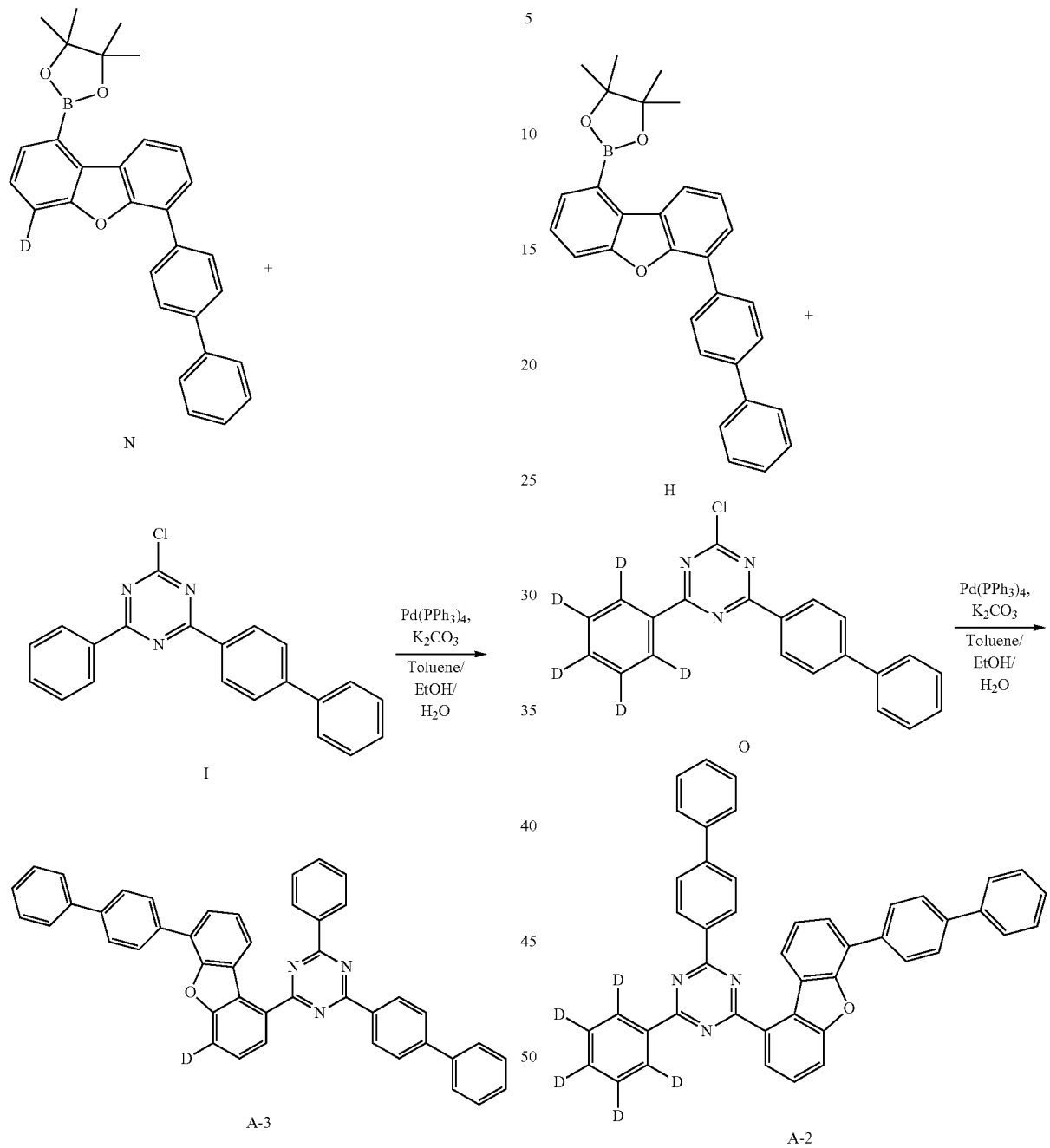

In a three-necked round-bottom flask, N (2.2 g, 4.9 mmol), I (1.69 g, 4.9 mmol), Pd(PPh$_3$)$_4$ (114 mg, 0.1 mmol) and K$_2$CO$_3$ (1.36 g, 9.8 mmol) were added to toluene (40 mL), EtOH (5 mL) and H$_2$O (5 mL) and heated to reflux overnight under nitrogen protection. After the reaction was finished, heating was stopped, the system was cooled to room temperature and filtered through suction under reduced pressure, and the obtained solid was washed with water and methanol in sequence. The solid was recrystallized from toluene/acetonitrile to obtain a white solid (2.8 g, 4.46 mmol) with a yield of 91%. The product was confirmed as the target product A-3 with a molecular weight of 628.2.

In a three-necked round-bottom flask, H (2.95 g, 6.6 mmol), O (2.3 g, 6.6 mmol), Pd(PPh$_3$)$_4$ (0.15 g, 0.13 mmol) and K$_2$CO$_3$ (1.82 g, 13.2 mmol) were added to toluene (40 mL), EtOH (10 mL) and H$_2$O (10 mL) and heated to reflux overnight under nitrogen protection. After the reaction was finished, heating was stopped, the system was cooled to room temperature and filtered through suction under reduced pressure, and the obtained solid was washed with water and methanol in sequence. The solid was recrystallized from toluene/acetonitrile to obtain a white solid (3.0 g, 4.74 mmol) with a yield of 71.8%. The product was confirmed as the target product A-2 with a molecular weight of 632.3.

Synthesis Example 7: Synthesis of Compound A-5

Step 1: Synthesis of Compound A-5

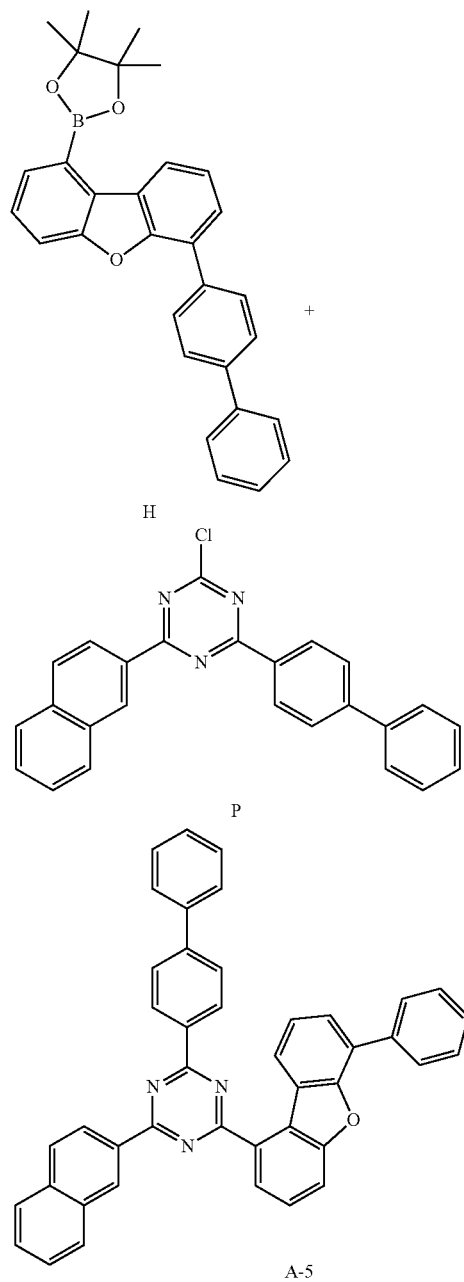

Synthesis Example 8: Synthesis of Compound A-20

Step 1: Synthesis of Compound A-20

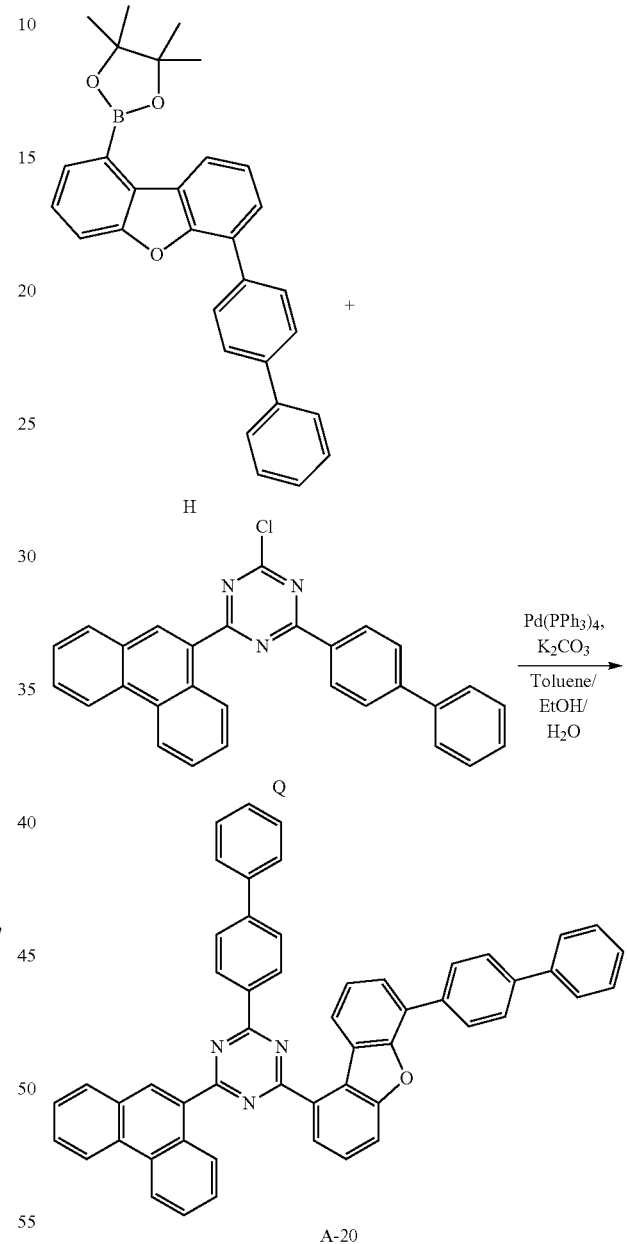

In a three-necked round-bottom flask, H (4.3 g, 9.6 mmol), P (3.8 g, 9.6 mmol), Pd(PPh$_3$)$_4$ (0.22 g, 0.19 mmol) and K$_2$CO$_3$ (2.6 g, 19.2 mmol) were added to toluene (32 mL), EtOH (8 mL) and H$_2$O (8 mL) and heated to reflux overnight under nitrogen protection. After the reaction was finished, heating was stopped, the system was cooled to room temperature and filtered through suction under reduced pressure, and the obtained solid was washed with water and methanol in sequence. The solid was recrystallized from toluene/acetonitrile to obtain a white solid (5.2 g, 7.67 mmol) with a yield of 79.9%. The product was confirmed as the target product A-5 with a molecular weight of 677.2.

In a three-necked round-bottom flask, H (3.69 g, 8.27 mmol), Q (3.67 g, 8.27 mmol), Pd(PPh$_3$)$_4$ (0.29 g, 0.25 mmol) and K$_2$CO$_3$ (2.29 g, 16.54 mmol) were added to toluene (40 mL), EtOH (10 mL) and H$_2$O (10 mL) and heated to reflux overnight under nitrogen protection. After the reaction was finished, heating was stopped, the system was cooled to room temperature and filtered through suction under reduced pressure, and the obtained solid was washed with water and methanol in sequence. The solid was recrystallized from toluene to obtain a white solid (5.4 g, 7.42 mmol) with a yield of 89.7%. The product was confirmed as the target product A-20 with a molecular weight of 727.3.

Synthesis Example 9: Synthesis of Compound A-105

Step 1: Synthesis of Intermediate S

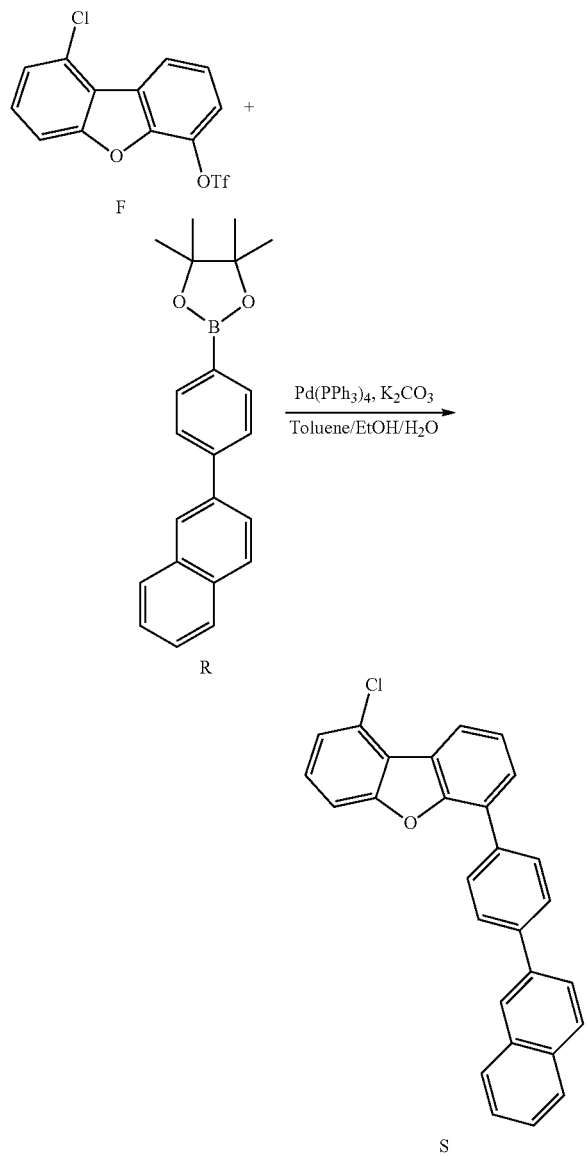

In a three-necked round-bottom flask, F (23.9 g, 71.6 mmol), R (26.0 g, 78.7 mmol), Pd(PPh$_3$)$_4$ (1.65 g, 1.4 mmol) and K$_2$CO$_3$ (19.8 g, 143.2 mmol) were added to toluene (240 mL), EtOH (60 mL) and H$_2$O (60 mL) and heated to reflux overnight under nitrogen protection. After the reaction was finished, heating was stopped and the system was cooled to room temperature. The system stood still to separate layers, an aqueous phase was extracted with DCM several times, and organic phases were combined, dried over anhydrous Na$_2$SO$_4$, filtered and concentrated under reduced pressure. The crude product was purified through column chromatography (PE:DCM=40:1→15:1) to obtain Intermediate S (21.0 g, 51.8 mmol) as a white solid with a yield of 72.3%.

Step 2: Synthesis of Intermediate T

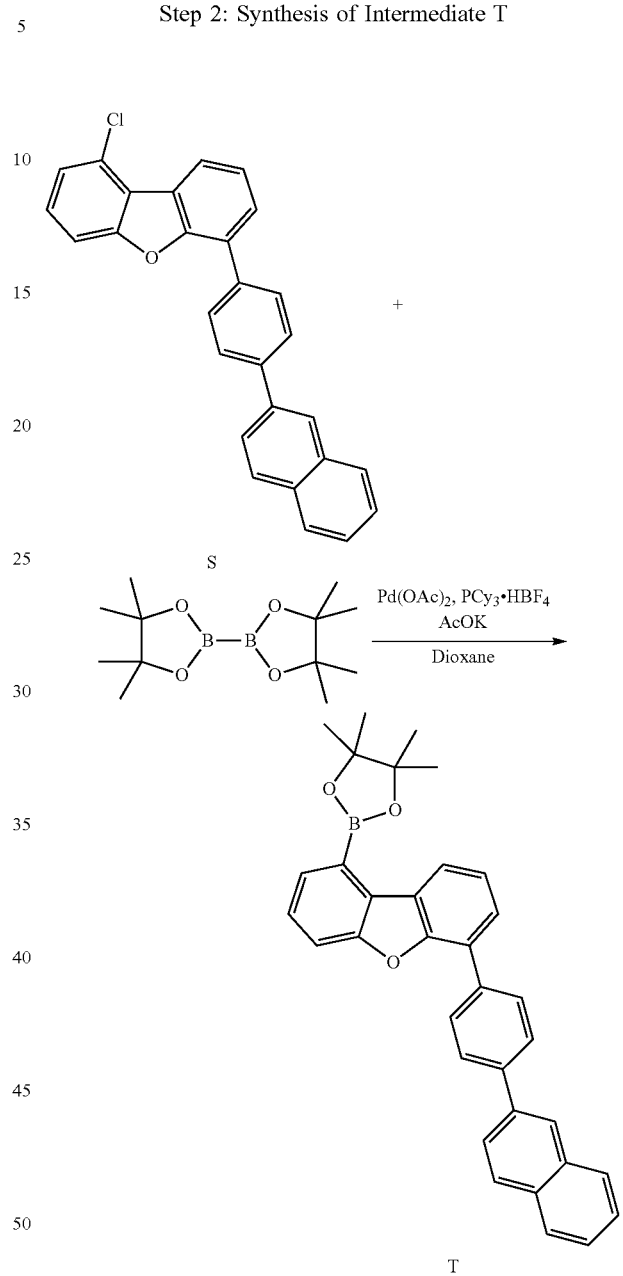

In a three-necked round-bottom flask, S (6.1 g, 15.0 mmol), bis(pinacolato)diboron (6.86 g, 27.0 mmol), Pd(OAc)$_2$ (0.17 g, 0.75 mmol), tricyclohexylphosphine tetrafluoroborate (PCy$_3$·HBF$_4$) (0.55 g, 1.5 mmol) and AcOK (2.9 g, 30.0 mmol) were added to 1,4-dioxane (75 mL) and heated to reflux overnight under nitrogen protection. After the reaction was finished, heating was stopped and the system was cooled to room temperature. The reaction solution was filtered through Celite. The filtrate was concentrated under reduced pressure. The crude product was purified through column chromatography (PE:DCM=5:1-4:1) to obtain Intermediate T (4.1 g, 8.26 mmol) as a white solid with a yield of 55.1%.

Step 3: Synthesis of Compound A-105

Synthesis Example 10: Synthesis of Compound A-526

Step 1: Synthesis of Intermediate V

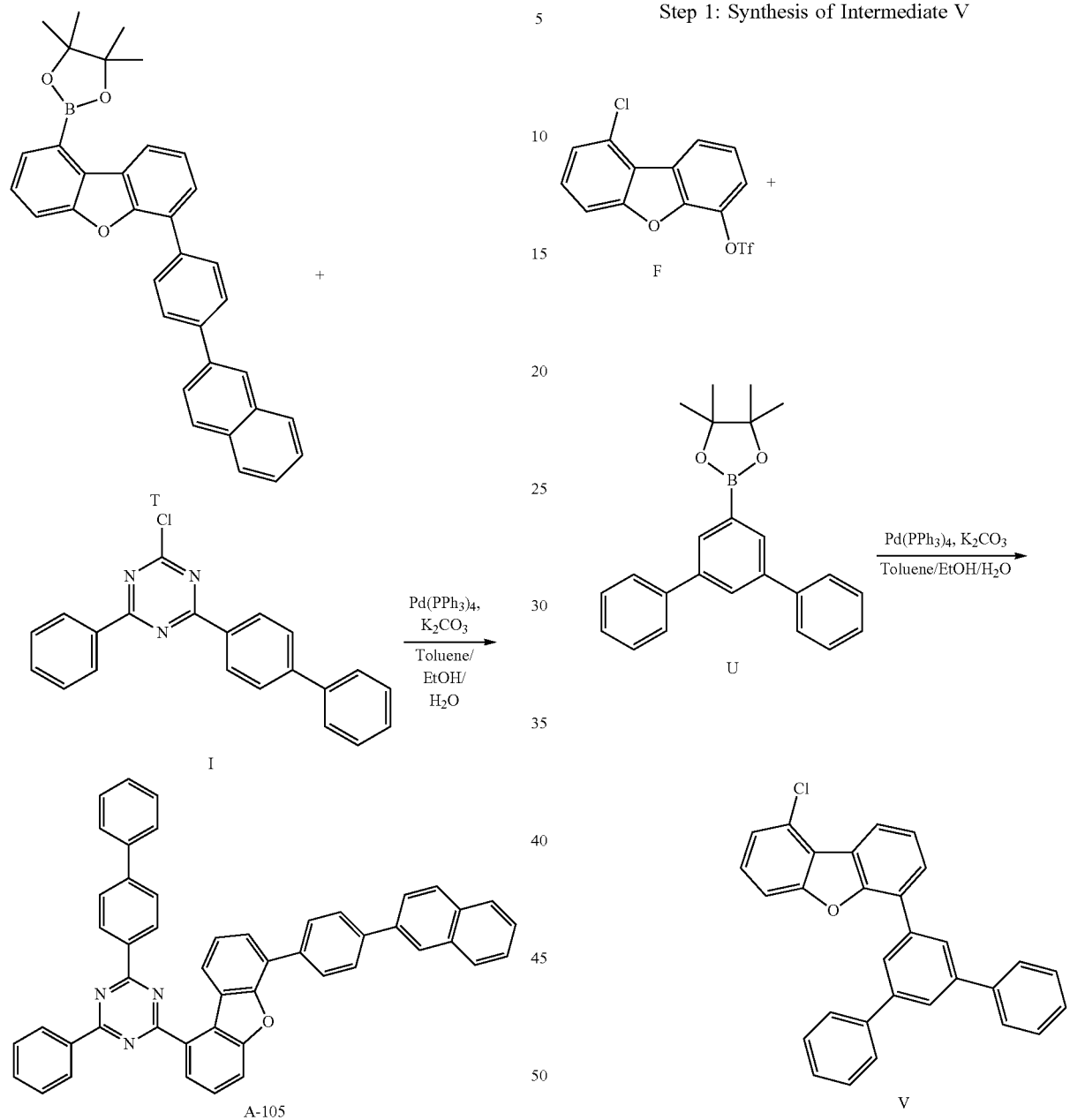

In a three-necked round-bottom flask, T (4.1 g, 8.26 mmol), I (2.8 g, 8.26 mmol), Pd(PPh₃)₄ (0.29 g, 0.25 mmol) and K₂CO₃ (2.3 g, 16.54 mmol) were added to toluene (28 mL), EtOH (7 mL) and H₂O (7 mL) and heated to reflux overnight under nitrogen protection. After the reaction was finished, heating was stopped, the system was cooled to room temperature and filtered through suction under reduced pressure, and the obtained solid was washed with water and methanol in sequence. The solid was recrystallized from toluene/acetonitrile to obtain a white solid (4.0 g, 5.9 mmol) with a yield of 71.4%. The product was confirmed as the target product A-105 with a molecular weight of 677.2.

In a three-necked round-bottom flask, F (6.9 g, 19.65 mmol), U (7.0 g, 19.65 mmol), Pd(PPh₃)₄ (0.68 g, 0.59 mmol) and K₂CO₃ (5.43 g, 36.3 mmol) were added to toluene (80 mL), EtOH (20 mL) and H₂O (20 mL) and heated to reflux overnight under nitrogen protection. After the reaction was finished, heating was stopped and the system was cooled to room temperature. The system stood still to separate layers, an aqueous phase was extracted with DCM several times, and organic phases were combined, dried over anhydrous Na₂SO₄, filtered and concentrated under reduced pressure. The crude product was purified through column chromatography (PE:DCM=40:1→15:1) to obtain Intermediate V (7.8 g, 18.1 mmol) as a white solid with a yield of 92.1%.

Step 2: Synthesis of Intermediate W

Step 3: Synthesis of Compound A-526

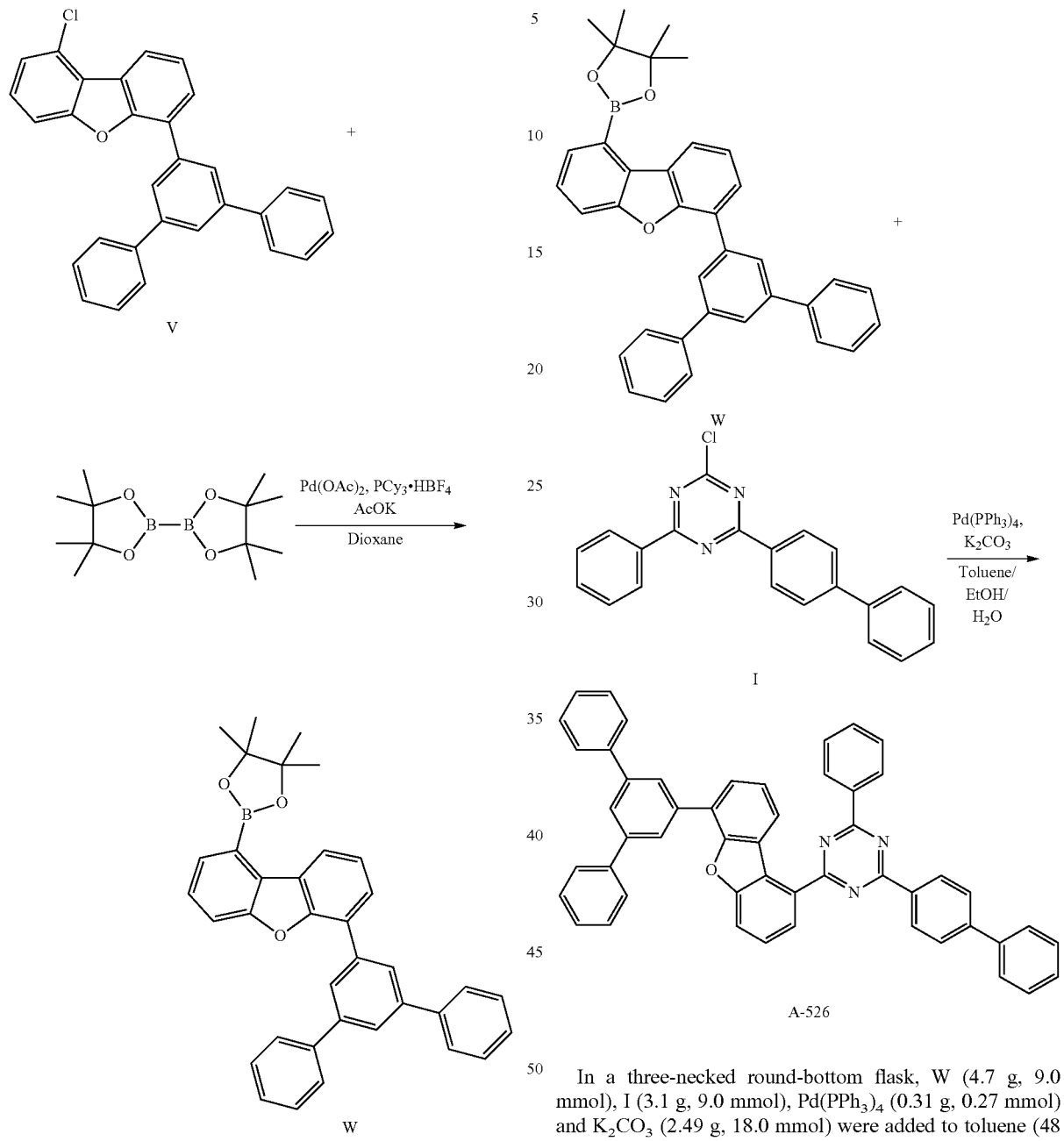

In a three-necked round-bottom flask, V (7.8 g, 18.1 mmol), bis(pinacolato)diboron (8.27 g, 32.6 mmol), Pd(OAc)₂ (0.16 g, 0.72 mmol), tricyclohexylphosphine tetrafluoroborate (PCy₃·HBF₄) (0.53 g, 1.45 mmol) and KOAc (3.55 g, 36.2 mmol) were added to 1,4-dioxane (80 mL) and heated to reflux overnight under nitrogen protection. After the reaction was finished, heating was stopped and the system was cooled to room temperature. The reaction solution was filtered through Celite. The filtrate was concentrated under reduced pressure. The crude product was purified through column chromatography (PE:DCM=4:1→2:1) to obtain Intermediate W (5.7 g, 10.9 mmol) as a pale yellow solid with a yield of 60.3%.

In a three-necked round-bottom flask, W (4.7 g, 9.0 mmol), I (3.1 g, 9.0 mmol), Pd(PPh₃)₄ (0.31 g, 0.27 mmol) and K₂CO₃ (2.49 g, 18.0 mmol) were added to toluene (48 mL), EtOH (12 mL) and H₂O (12 mL) and heated to reflux overnight under nitrogen protection. After the reaction was finished, heating was stopped, the system was cooled to room temperature and filtered through suction under reduced pressure, and the obtained solid was washed with water and methanol in sequence. The solid was recrystallized from toluene/acetonitrile to obtain a white solid (5.2 g, 7.39 mmol) with a yield of 82.1%. The product was confirmed as the target product A-526 with a molecular weight of 703.3. Those skilled in the art will appreciate that the above preparation methods are merely exemplary. Those skilled in the art can obtain other compound structures of the present disclosure through the modifications of the preparation methods.

Device Example

Device Example 1

First, a glass substrate having an Indium Tin Oxide (ITO) anode with a thickness of 80 nm was cleaned and then treated with oxygen plasma and UV ozone. After the treatment, the substrate was dried in a glovebox to remove moisture. Then, the substrate was mounted on a substrate holder and placed in a vacuum chamber. Organic layers specified below were sequentially deposited through vacuum thermal evaporation on the ITO anode at a rate of 0.2 to 2 Angstroms per second and a vacuum degree of about $10^{-8}$ torr. Compound HI was used as a hole injection layer (HIL). Compound HT was used as a hole transporting layer (HTL). Compound H1 was used as an electron blocking layer (EBL). Compound GD4-59 was doped in Compound H1 and Compound A-1 of the present disclosure, all of which were co-deposited for use as an emissive layer (EML). Compound H2 was used as a hole blocking layer (HBL). On the HBL, Compound ET and 8-hydroxyquinolinolato-lithium (Liq) were co-deposited for use as an electron transporting layer (ETL). Finally, 8-hydroxyquinolinolato-lithium (Liq) was deposited as an electron injection layer with a thickness of 1 nm and Al was deposited as a cathode with a thickness of 120 nm. The device was transferred back to the glovebox and encapsulated with a glass lid and a moisture getter to complete the device.

Device Example 2

Device Example 2 was prepared by the same method as Device Example 1, except that in the EML, Compound A-1 was replaced with Compound A-19.

Device Example 3

Device Example 3 was prepared by the same method as Device Example 1, except that in the EML, Compound A-1 was replaced with Compound A-27.

Device Example 4

Device Example 4 was prepared by the same method as Device Example 1, except that in the EML, Compound A-1 was replaced with Compound A-45.

Device Example 5

Device Example 5 was prepared by the same method as Device Example 1, except that in the EML, Compound GD4-59 was replaced with Compound GD2-81 and H1:A-1:GD2-81=56:38:6.

Device Example 6

Device Example 6 was prepared by the same method as Device Example 1, except that in the EML, Compound GD4-59 was replaced with Compound GD2-82 and H1:A-1:GD2-82=56:38:6.

Device Example 7

Device Example 7 was prepared by the same method as Device Example 1, except that in the EML, Compound GD4-59 was replaced with Compound GD2-18 and H1:A-1:GD2-18=56:38:6.

Device Example 8

Device Example 8 was prepared by the same method as Device Example 1, except that in the EML, Compound GD4-59 was replaced with Compound GD2-83 and H1:A-1:GD2-83=56:38:6.

Device Example 9

Device Example 9 was prepared by the same method as Device Example 1, except that in the EML, Compound GD4-59 was replaced with Compound GD2-84 and H1:A-1:GD2-84=56:38:6.

Device Example 10

Device Example 10 was prepared by the same method as Device Example 1, except that in the EML, Compound A-1 was replaced with Compound A-526.

Device Comparative Example 1

Device Comparative Example 1 was prepared by the same method as Device Example 1, except that in the EML, Compound A-1 was replaced with Compound C-1.

Device Comparative Example 2

Device Comparative Example 2 was prepared by the same method as Device Example 1, except that in the EML, Compound A-1 was replaced with Compound C-2.

Device Comparative Example 3

Device Comparative Example 3 was prepared by the same method as Device Example 1, except that in the EML, Compound A-1 was replaced with Compound C-3.

Device Comparative Example 4

Device Comparative Example 4 was prepared by the same method as Device Example 1, except that in the EML, Compound A-1 was replaced with Compound C-4.

Device Comparative Example 5

Device Comparative Example 5 was prepared by the same method as Device Example 1, except that in the EML, Compound A-1 was replaced with Compound C-5.

Device Comparative Example 6

Device Comparative Example 6 was prepared by the same method as Device Example 1, except that in the EML, Compound A-1 was replaced with Compound C-6.

Device Comparative Example 7

Device Comparative Example 7 was prepared by the same method as Device Example 1, except that in the EML, Compound A-1 was replaced with Compound C-7.

Device Comparative Example 8

Device Comparative Example 8 was prepared by the same method as Device Example 1, except that in the EML, Compound A-1 was replaced with Compound C-8.

Detailed structures and thicknesses of layers of the devices are shown in the following table. Layers using more than one material were obtained by doping different compounds at their weight ratio as recorded.

TABLE 1

Device structures in Examples 1 to 10 and Comparative Examples 1 to 8

| Device ID | HIL | HTL | EBL | EML | HBL | ETL |
|---|---|---|---|---|---|---|
| Example 1 | Compound HI (100 Å) | Compound HT (350 Å) | Compound H1 (50 Å) | Compound H-1:Compound A-1:Compound GD4-59 (64:28:8) (400 Å) | Compound H2 (50 Å) | Compound ET:Liq (40:60) (350 Å) |
| Example 2 | Compound HI (100 Å) | Compound HT (350 Å) | Compound H1 (50 Å) | Compound H1:Compound A-19:Compound GD4-59 (64:28:8) (400 Å) | Compound H2 (50 Å) | Compound ET:Liq (40:60) (350 Å) |
| Example 3 | Compound HI (100 Å) | Compound HT (350 Å) | Compound H1 (50 Å) | Compound H1:Compound A-27:Compound GD4-59 (64:28:8) (400 Å) | Compound H2 (50 Å) | Compound ET:Liq (40:60) (350 Å) |
| Example 4 | Compound HI (100 Å) | Compound HT (350 Å) | Compound H1 (50 Å) | Compound H1:Compound A-45:Compound GD4-59 (64:28:8) (400 Å) | Compound H2 (50 Å) | Compound ET:Liq (40:60) (350 Å) |
| Example 5 | Compound HI (100 Å) | Compound HT (350 Å) | Compound H1 (50 Å) | Compound H1:Compound A-1:Compound GD2-81 (56:38:6) (400 Å) | Compound H2 (50 Å) | Compound ET:Liq (40:60) (350 Å) |
| Example 6 | Compound HI (100 Å) | Compound HT (350 Å) | Compound H1 (50 Å) | Compound H1:Compound A-1:Compound GD2-82 (56:38:6) (400 Å) | Compound H2 (50 Å) | Compound ET:Liq (40:60) (350 Å) |
| Example 7 | Compound HI (100 Å) | Compound HT (350 Å) | Compound H1 (50 Å) | Compound H1:Compound A-1:Compound GD2-18 (56:38:6) (400 Å) | Compound H2 (50 Å) | Compound ET:Liq (40:60) (350 Å) |
| Example 8 | Compound HI (100 Å) | Compound HT (350 Å) | Compound H1 (50 Å) | Compound H1:Compound A-1:Compound GD2-83 (56:38:6) (400 Å) | Compound H2 (50 Å) | Compound ET:Liq (40:60) (350 Å) |
| Example 9 | Compound HI (100 Å) | Compound HT (350 Å) | Compound H1 (50 Å) | Compound H1:Compound A-1:Compound GD2-84 (56:38:6) (400 Å) | Compound H2 (50 Å) | Compound ET:Liq (40:60) (350 Å) |
| Example 10 | Compound HI (100 Å) | Compound HT (350 Å) | Compound H1 (50 Å) | Compound H1:Compound A-526:Compound GD4-59 (64:28:8) (400 Å) | Compound H2 (50 Å) | Compound ET:Liq (40:60) (350 Å) |
| Comparative Example 1 | Compound HI (100 Å) | Compound HT (350 Å) | Compound H1 (50 Å) | Compound H1:Compound C-1:Compound GD4-59 (64:28:8) (400 Å) | Compound H2 (50 Å) | Compound ET:Liq (40:60) (350 Å) |
| Comparative Example 2 | Compound HI (100 Å) | Compound HT (350 Å) | Compound H1 (50 Å) | Compound H1:Compound C-2:Compound GD4-59 (64:28:8) (400 Å) | Compound H2 (50 Å) | Compound ET:Liq (40:60) (350 Å) |

TABLE 1-continued

Device structures in Examples 1 to 10 and Comparative Examples 1 to 8

| Device ID | HIL | HTL | EBL | EML | HBL | ETL |
|---|---|---|---|---|---|---|
| Comparative Example 3 | Compound HI (100 Å) | Compound HT (350 Å) | Compound H1 (50 Å) | Compound H1:Compound C-3:Compound GD4-59 (64:28:8) (400 Å) | Compound H2 (50 Å) | Compound ET:Liq (40:60) (350 Å) |
| Comparative Example 4 | Compound HI (100 Å) | Compound HT (350 Å) | Compound H1 (50 Å) | Compound H1:Compound C-4:Compound GD4-59 (64:28:8) (400 Å) | Compound H2 (50 Å) | Compound ET:Liq (40:60) (350 Å) |
| Comparative Example 5 | Compound HI (100 Å) | Compound HT (350 Å) | Compound H1 (50 Å) | Compound H1:Compound C-5:Compound GD4-59 (64:28:8) (400 Å) | Compound H2 (50 Å) | Compound ET:Liq (40:60) (350 Å) |
| Comparative Example 6 | Compound HI (100 Å) | Compound HT (350 Å) | Compound H1 (50 Å) | Compound H1:Compound C-6:Compound GD4-59 (64:28:8) (400 Å) | Compound H2 (50 Å) | Compound ET:Liq (40:60) (350 Å) |
| Comparative Example 7 | Compound HI (100 Å) | Compound HT (350 Å) | Compound H1 (50 Å) | Compound H1:Compound C-7:Compound GD4-59 (64:28:8) (400 Å) | Compound H2 (50 Å) | Compound ET:Liq (40:60) (350 Å) |
| Comparative Example 8 | Compound HI (100 Å) | Compound HT (350 Å) | Compound H1 (50 Å) | Compound H1:Compound C-8:Compound GD4-59 (64:28:8) (400 Å) | Compound H2 (50 Å) | Compound ET:Liq (40:60) (350 Å) |

The structures of the materials used in the devices are shown as follows:

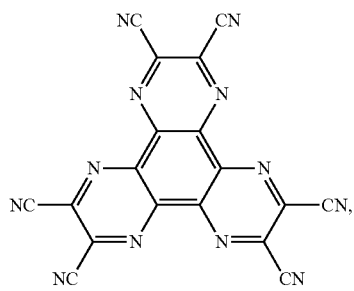

HI

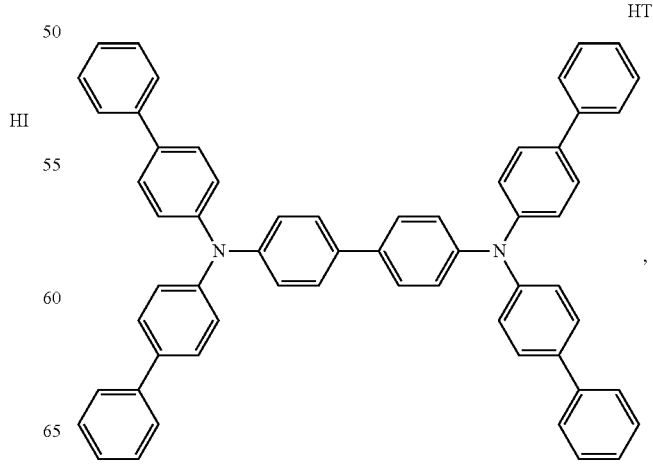

HT

-continued

H1
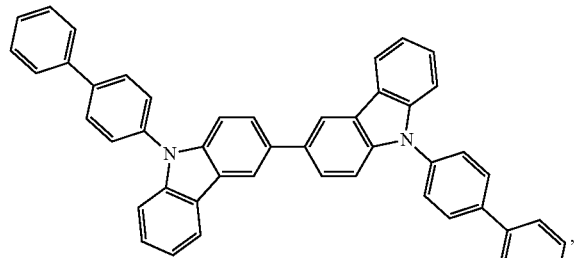
H2
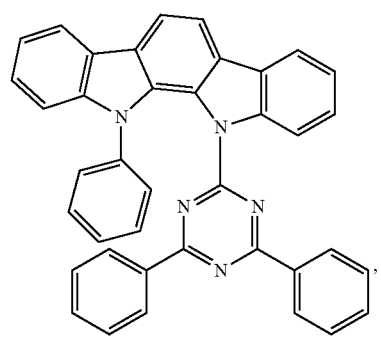
A-1
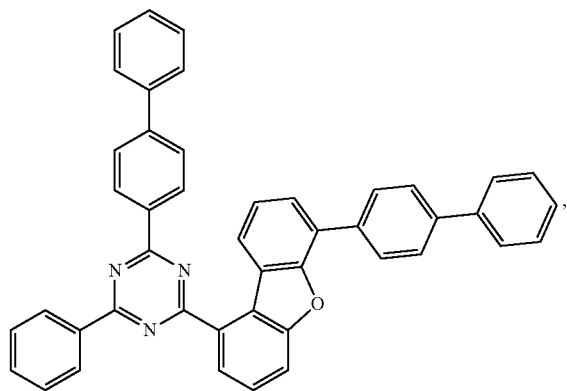
A-19
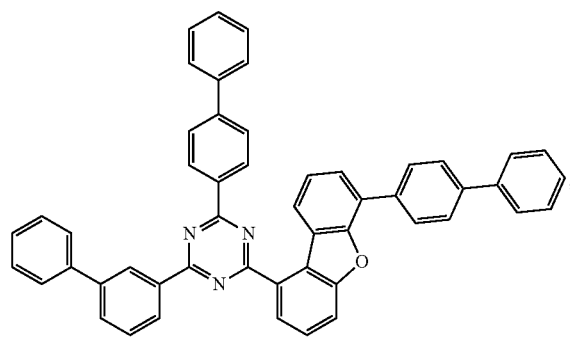
A-27
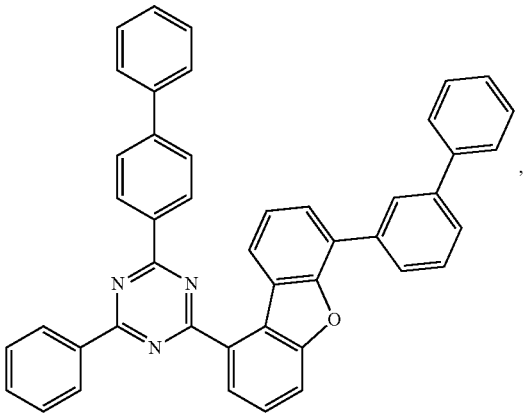
A-45
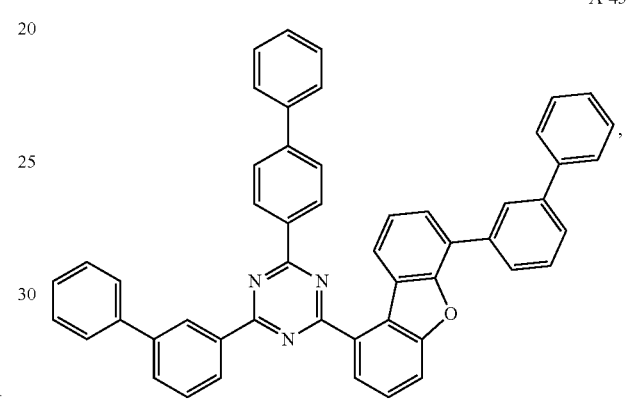
A-526
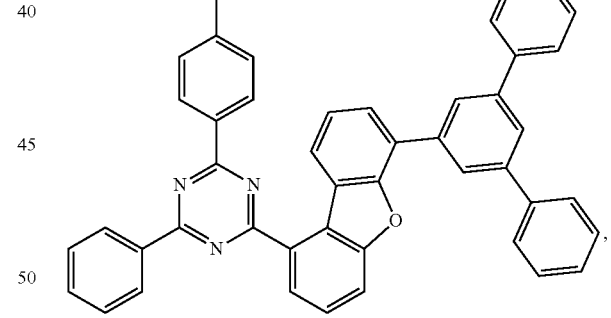
C-1
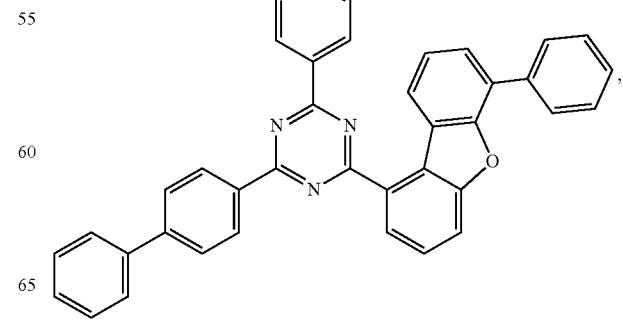

-continued
C-2
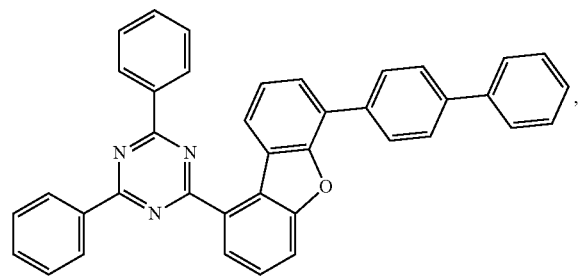
C-3
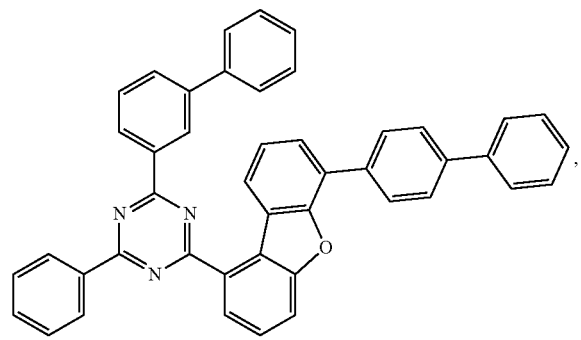
C-4
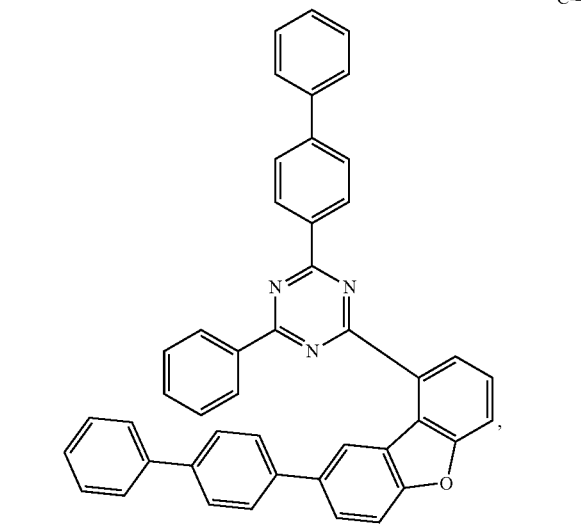
C-5
C-6
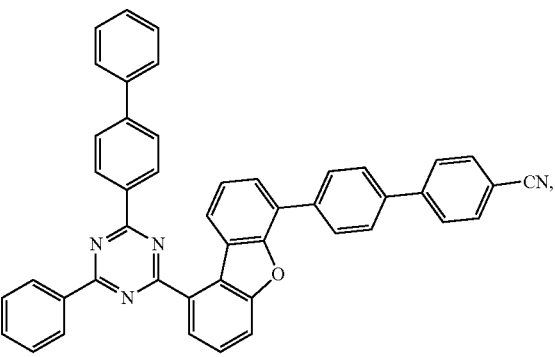
C-7
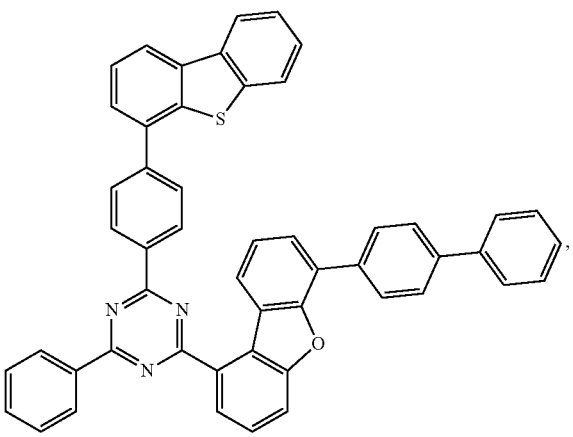
C-8
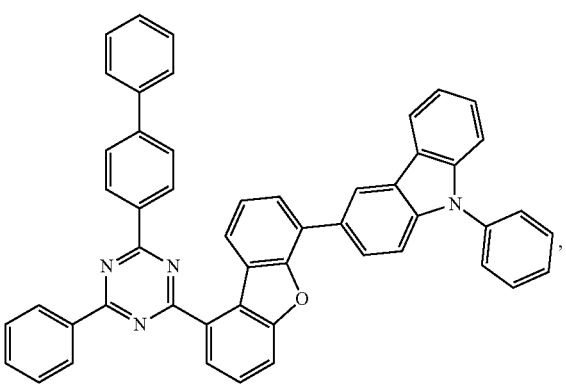
GD4-59
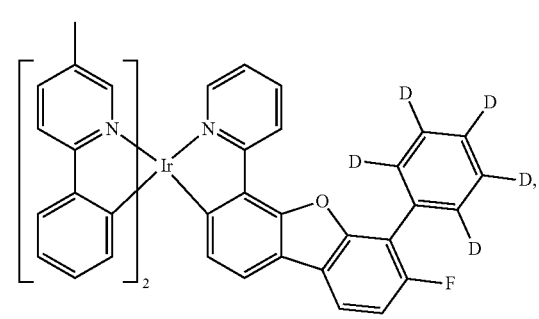

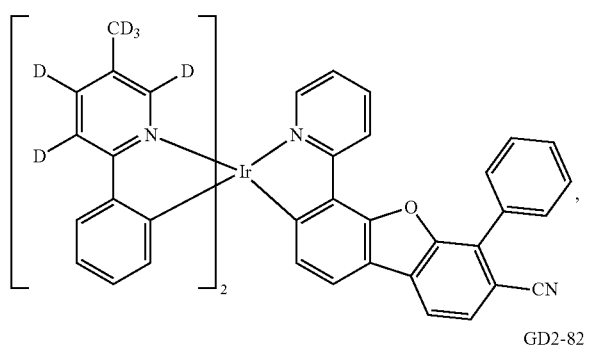

GD2-81

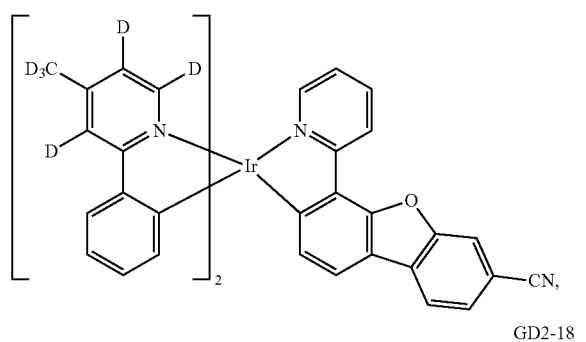

GD2-82

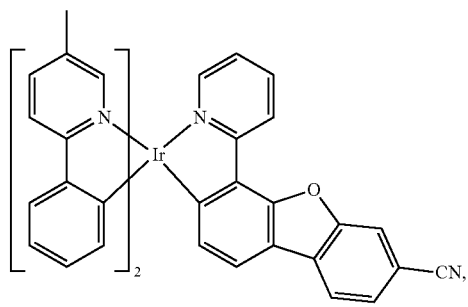

GD2-18

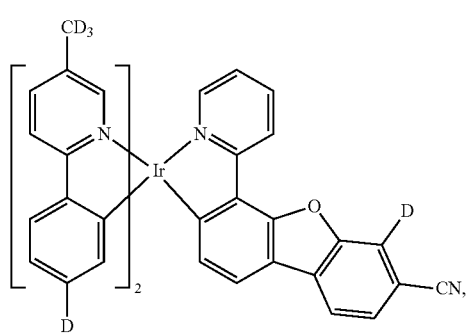

GD2-83

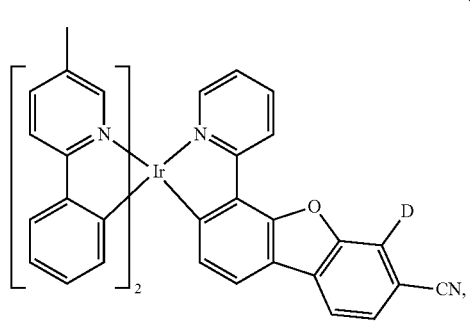

GD2-84

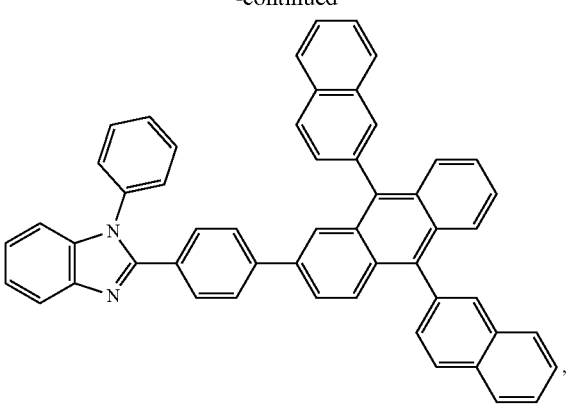

ET

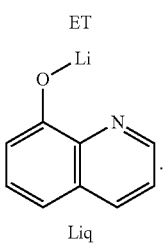

Liq

Table 2 shows CIE data and current efficiency measured at a constant current of 15 mA/cm$^2$ and a device lifetime (LT95) measured at a constant current of 80 mA/cm$^2$.

TABLE 2

Device data of Examples 1 to 10 and Comparative Examples 1 to 8

| Device ID | EML | CIE (x, y) | Current Efficiency (cd/A) | Lifetime LT95 (hrs) |
|---|---|---|---|---|
| Example 1 | H1:A-1:GD4-59 (64:28:8) | (0.355, 0.620) | 85 | 63.7 |
| Example 2 | H1:A-19:GD4-59 (64:28:8) | (0.356, 0.619) | 85 | 65.0 |
| Example 3 | H1:A-27:GD4-59 (64:28:8) | (0.353, 0.621) | 86 | 65.5 |
| Example 4 | H1:A-45:GD4-59 (64:28:8) | (0.355, 0.620) | 85 | 77.0 |
| Example 5 | H1:A-1:GD2-81 (56:38:6) | (0.349, 0.629) | 94 | 54.8 |
| Example 6 | H1:A-1:GD2-82 (56:38:6) | (0.350, 0.627) | 91 | 70.5 |
| Example 7 | H1:A-1:GD2-18 (56:38:6) | (0.348, 0.628) | 93 | 56.2 |
| Example 8 | H1:A-1:GD2-83 (56:38:6) | (0.347, 0.629) | 93 | 73.8 |
| Example 9 | H1:A-1:GD2-84 (56:38:6) | (0.346, 0.630) | 94 | 53.8 |
| Example 10 | H1:A-526:GD4-59 (64:28:8) | (0.357, 0.618) | 85 | 63.9 |
| Comparative Example 1 | H1:C-1:GD4-59 (64:28:8) | (0.355, 0.620) | 85 | 48.3 |
| Comparative Example 2 | H1:C-2:GD4-59 (64:28:8) | (0.352, 0.622) | 87 | 44.0 |
| Comparative Example 3 | H1:C-3:GD4-59 (64:28:8) | (0.354, 0.621) | 87 | 45.2 |
| Comparative Example 4 | H1:C-4:GD4-59 (64:28:8) | (0.351, 0.623) | 86 | 47.6 |
| Comparative Example 5 | H1:C-5:GD4-59 (64:28:8) | (0.358, 0.618) | 83 | 2.2 |
| Comparative Example 6 | H1:C-6:GD4-59 (64:28:8) | (0.360, 0.617) | 77 | 35.2 |
| Comparative Example 7 | H1:C-7:GD4-59 (64:28:8) | (0.359, 0.617) | 84 | 53.5 |

TABLE 2-continued

Device data of Examples 1 to 10 and
Comparative Examples 1 to 8

| Device ID | EML | CIE (x, y) | Current Efficiency (cd/A) | Lifetime LT95 (hrs) |
|---|---|---|---|---|
| Comparative Example 8 | H1:C-8:GD4-59 (64:28:8) | (0.356, 0.620) | 86 | 45.7 |

Discussion

In Example 1 to Example 4, Example 10 and Comparative Example 1, a phosphorescent dopant GD4-59 was doped in Compounds A-1, A-19, A-27, A-45 and A-526 of the present disclosure and Compound C-1 that is not provided in the present disclosure. Compared with Comparative Example 1, Example 1 to Example 4, Example 10 have substantially the same current efficiency and device lifetimes that are increased by 31.9%, 34.6%, 35.6%, 59.4% and 32.3%, respectively. This shows that when applied to electroluminescent devices, the compound having an aryl substitution with a phenyl substitution at position 6 of a dibenzo five-membered heterocycle in the present disclosure has a longer device lifetime than the compound with merely a phenyl substitution at position 6.

In Example 1 to Example 4, Example 10 and Comparative Example 2, the phosphorescent dopant GD4-59 was doped in Compounds A-1, A-19, A-27, A-45 and A-526 of the present disclosure and Compound C-2 that is not provided in the present disclosure. Compared with Comparative Example 2, Example 1 to Example 4, Example 10 have substantially the same current efficiency and device lifetimes that are increased by 44.8%, 47.7%, 48.9%, 75.0% and 45.2%, respectively. This shows that when applied to electroluminescent devices, the compound with a bi(hetero)aryl substitution on triazine in the present disclosure has a longer device lifetime than the compound with a single aryl substitution on triazine.

In Example 1 to Example 4, Example 10 and Comparative Example 3, the phosphorescent dopant GD4-59 was doped in Compounds A-1, A-19, A-27, A-45 and A-526 of the present disclosure and Compound C-3 that is not provided in the present disclosure. Compared with Comparative Example 3, Example 1 to Example 4, Example 10 have substantially the same current efficiency and device lifetimes that are increased by 40.9%, 43.8%, 44.9%, 70.4% and 41.4%, respectively. This shows that when applied to electroluminescent devices, the compound with a bi(hetero)aryl substitution joined at a para-position of triazine in the present disclosure has a longer device lifetime than the compound with a bi(hetero)aryl substitution joined at a meta-position of triazine.

In Example 1 to Example 4, Example 10 and Comparative Example 4, the phosphorescent dopant GD4-59 was doped in Compounds A-1, A-19, A-27, A-45 and A-526 of the present disclosure and Compound C-4 that is not provided in the present disclosure. Compared with Comparative Example 4, Example 1 to Example 4, Example 10 have substantially the same current efficiency and device lifetimes that are increased by 33.8%, 36.6%, 37.6%, 61.8% and 34.2%, respectively. When applied to electroluminescent devices, the compound having the bi(hetero)aryl substitution at position 6 of the dibenzo five-membered heterocycle in the present disclosure has the longer device lifetime than the compound having the bi(hetero)aryl substitution at position 8 of the dibenzo five-membered heterocycle.

In Example 1 to Example 4, Example 10 and Comparative Example 5, the phosphorescent dopant GD4-59 was doped in Compounds A-1, A-19, A-27, A-45 and A-526 of the present disclosure and Compound C-5 that is not provided in the present disclosure. Compared with Comparative Example 5, Example 1 to Example 4, Example 10 all have improved current efficiency and device lifetimes that are increased by 28.9 times, 29.5 times, 29.8 times, 35 times and 29 times, respectively. This shows that when applied to electroluminescent devices, the compound having a (hetero)aryl substitution with a phenyl substitution at position 6 of the dibenzo five-membered heterocycle in the present disclosure has the longer device lifetime than the compound having a (hetero)aryl substitution with a heteroaryl substitution at position 6 of the dibenzo five-membered heterocycle.

In Example 1 to Example 4, Example 10 and Comparative Example 6, the phosphorescent dopant GD4-59 was doped in Compounds A-1, A-19, A-27, A-45 and A-526 of the present disclosure and Compound C-6 that is not provided in the present disclosure. Compared with Comparative Example 6, Example 1 to Example 4, Example 10 all have improved current efficiency and device lifetimes that are increased by 81.0%, 84.7%, 86.1%, 118.8% and 81.5%, respectively. This shows that when applied to electroluminescent devices, the compound of the present disclosure with a non-cyano substituted phenyl substituted (hetero)aryl has the longer device lifetime than the compound with a cyano substituted phenyl substituted (hetero)aryl.

In Example 1 to Example 4, Example 10 and Comparative Example 7, the phosphorescent dopant GD4-59 was doped in Compounds A-1, A-19, A-27, A-45 and A-526 of the present disclosure and Compound C-7 that is not provided in the present disclosure. Compared with Comparative Example 7, Example 1 to Example 4, Example 10 have substantially the same current efficiency and device lifetimes that are increased by 19.1%, 21.5%, 22.4%, 43.9% and 19.4%, respectively. This shows that when applied to electroluminescent devices, the compound having a terminal six-membered (hetero)aryl substitution on (hetero)aryl on triazine in the present disclosure has the longer device lifetime than the compound having a terminal fused ring heteroaryl substitution on (hetero)aryl on triazine.

In Example 1 to Example 4, Example 10 and Comparative Example 8, the phosphorescent dopant GD4-59 was doped in Compounds A-1, A-19, A-27, A-45 and A-526 of the present disclosure and Compound C-8 that is not provided in the present disclosure. Compared with Comparative Example 8, Example 1 to Example 4, Example 10 have substantially the same current efficiency and device lifetimes that are increased by 39.4%, 42.2%, 43.3%, 68.5% and 39.8%, respectively. This shows that when applied to electroluminescent devices, the compound having a (hetero)aryl substitution with a phenyl substitution at position 6 of the dibenzo five-membered heterocycle in the present disclosure has the longer device lifetime than the compound having a fused ring (hetero)aryl substitution at position 6 of the dibenzo five-membered heterocycle.

In Example 5 to Example 9, different phosphorescent dopants were doped in Compound A-1 of the present disclosure and the devices all exhibit higher current efficiency and longer lifetimes. This shows that the compound of the present disclosure can be combined with a wide range of phosphorescent dopants and obtain excellent device performance.

In summary, when used as host materials in a light-emitting layer, the compounds of the present disclosure improve the ability of a material to balance electron transport and hole transport. Compared with compounds that are not provided in the present disclosure and used as the host materials in the light-emitting layer, the compounds of the present disclosure improve device performance, where the devices all have substantially the same or improved current efficiency and significantly improved lifetimes compared with comparative examples. The compounds of the present disclosure are of great help to the industry.

Device Example 11

First, a glass substrate having an Indium Tin Oxide (ITO) anode with a thickness of 80 nm was cleaned and then treated with oxygen plasma and UV ozone. After the treatment, the substrate was dried in a glovebox to remove moisture. Then, the substrate was mounted on a substrate holder and placed in a vacuum chamber. Organic layers specified below were sequentially deposited through vacuum thermal evaporation on the ITO anode at a rate of 0.2 to 2 Angstroms per second and a vacuum degree of about $10^{-8}$ torr. Compound HI was used as a hole injection layer (HIL). Compound HT was used as a hole transporting layer (HTL). Compound EB was used as an electron blocking layer (EBL). Compound BD was doped in Compound H3, which were co-deposited for use as an emissive layer (EML). Compound HB was used as a hole blocking layer (HBL). On the HBL, Compound A-1 and 8-hydroxyquinolinolato-lithium (Liq) were co-deposited for use as an electron transporting layer (ETL). Finally, 8-hydroxyquinolinolato-lithium (Liq) was deposited as an electron injection layer with a thickness of 1 nm and Al was deposited as a cathode with a thickness of 120 nm. The device was transferred back to the glovebox and encapsulated with a glass lid to complete the device.

Device Comparative Example 9

Device Comparative Example 9 was prepared by the same method as Device Example 11, except that in the ETL, Compound A-1 was replaced with Compound ET.

Detailed structures and thicknesses of layers of the devices are shown in the following table. Layer using more than one material were obtained by doping different compounds at their weight ratio as recorded.

The structures of the new materials used in the devices are shown as follows:

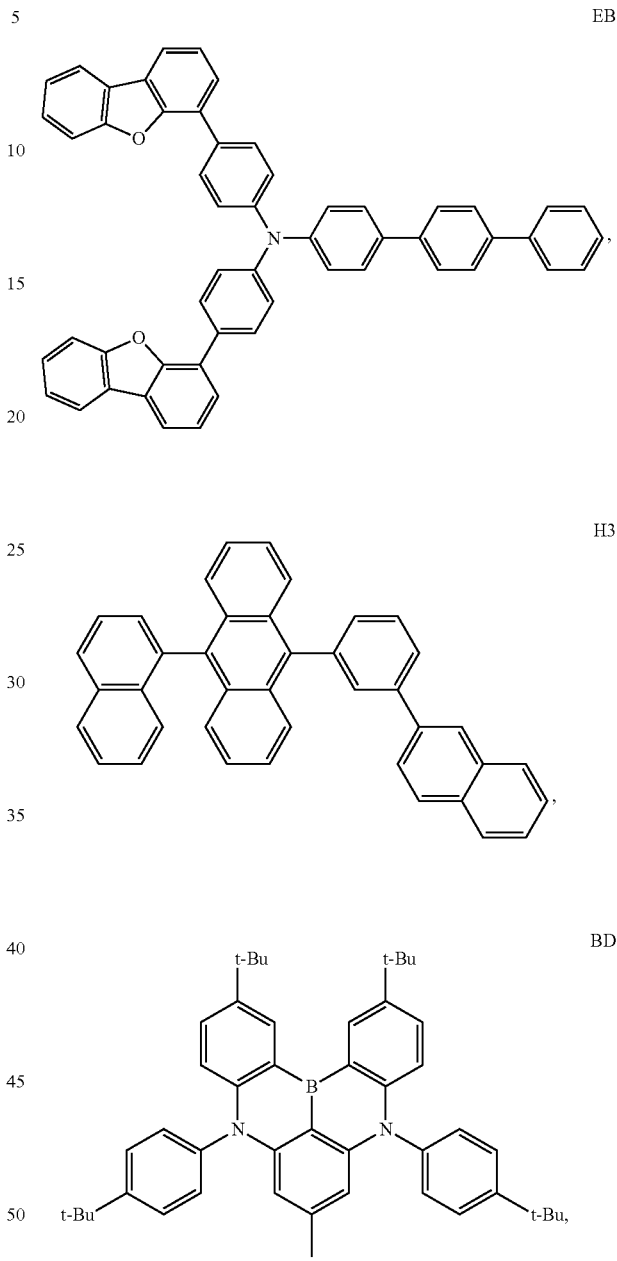

TABLE 3

| Device structures in Example 11 and Comparative Example 9 | | | | | | |
|---|---|---|---|---|---|---|
| Device ID | HIL | HTL | EBL | EML | HBL | ETL |
| Example 11 | Compound HI (100 Å) | Compound HT (1220 Å) | Compound EB (50 Å) | Compound H3:Compound BD (98:2) (250 Å) | Compound HB (50 Å) | Compound A-1:Liq (40:60) (300 Å) |
| Comparative Example 9 | Compound HI (100 Å) | Compound HT (1220 Å) | Compound EB (50 Å) | Compound H3:Compound BD (98:2) (250 Å) | Compound HB (50 Å) | Compound A-1:Liq (40:60) (300 Å) |

-continued

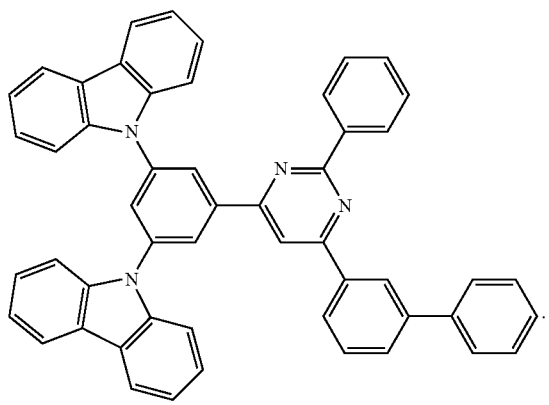

HB

Table 4 shows CIE data, driving voltage (V) and external quantum efficiency (EQE) measured at a constant current of 15 mA/cm$^2$ and a device lifetime (LT95) measured at a constant current of 80 mA/cm$^2$.

TABLE 4

Device data of Example 11 and Comparative Example 9

| Device ID | ETL | CIE (x, y) | Driving Voltage (V) | EQE (%) | Lifetime LT95 (hrs) |
| --- | --- | --- | --- | --- | --- |
| Example 11 | A-1:Liq (40:60) | (0.133, 0.079) | 4.42 | 9.04 | 62.0 |
| Comparative Example 9 | ET:Liq (40:60) | (0.133, 0.079) | 4.51 | 8.83 | 62.7 |

Discussion

Compound A-1 of the present disclosure and Compound ET that is not provided in the present disclosure are used as electron transporting materials in Example 11 and Comparative Example 9, respectively. Compared with Comparative Example 9, Example 11 has substantially the same lifetime, improved EQE and reduced driving voltage. It is to be noted that Compound ET is a commercial electron transporting material at present. It can be seen that the compound of the present disclosure is also an excellent electron transporting material.

It should be understood that various embodiments described herein are merely examples and not intended to limit the scope of the present disclosure. Therefore, it is apparent to those skilled in the art that the present disclosure as claimed may include variations from specific embodiments and preferred embodiments described herein. Many of materials and structures described herein may be substituted with other materials and structures without departing from the spirit of the present disclosure. It should be understood that various theories as to why the present disclosure works are not intended to be limitative.

What is claimed is:

1. A compound having a following structure:

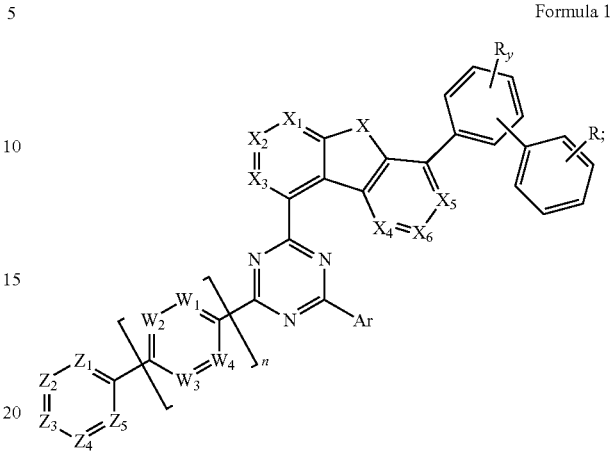

Formula 1 wherein

X is selected from O, S or Se;

n is selected from 1, 2, 3, 4 or 5;

$X_1$ to $X_5$ are, at each occurrence identically or differently, selected from $CR_x$ or N;

$X_6$ is CH or CD;

$W_1$ to $W_4$ are, at each occurrence identically or differently, selected from $CR_w$ or N;

$Z_1$ to $Z_5$ are, at each occurrence identically or differently, selected from $CR_z$ or N;

Ar is selected from substituted or unsubstituted biphenyl-3-yl;

R and $R_y$ represent, at each occurrence identically or differently, mono-substitution, multiple substitutions or non-substitution;

$R_x$, $R_w$ and $R_z$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

$R_y$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, a carbonyl group, a carboxylic acid group, an ester group, a cyano group, an isocyano group, a hydroxyl group, a sulfanyl group, a sulfinyl group, a sulfonyl group, a phosphino group and combinations thereof;

R is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, an acyl group, a carbonyl group, a carboxylic acid group, an ester group, an isocyano group, a hydroxyl group, a sulfanyl group, a sulfinyl group, a sulfonyl group, a phosphino group and combinations thereof; and adjacent substituents R, $R_y$ and $R_w$ can be optionally joined to form a ring.

2. The compound according to claim 1, wherein X is selected from O or S.

3. The compound according to claim 1, wherein $X_1$ to $X_5$ are, at each occurrence identically or differently, selected from $CR_x$ and/or $Z_1$ to $Z_5$ are, at each occurrence identically or differently, selected from $CR_z$, wherein $R_x$ and $R_z$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms and substituted or unsubstituted arylsilyl having 6 to 20 carbon atoms.

4. The compound according to claim 1, wherein $W_1$ to $W_4$ are, at each occurrence identically or differently, selected from $CR_w$, wherein $R_w$, R and $R_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted alkenyl having 2 to 20 carbon atoms, substituted or unsubstituted arylalkyl having 7 to 30 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms and substituted or unsubstituted arylsilyl having 6 to 20 carbon atoms.

5. The compound according to claim 1, wherein at least one of $X_1$ to $X_5$ is N and/or at least one of $W_1$ to $W_4$ is N and/or at least one of $Z_1$ to $Z_5$ is N.

6. The compound according to claim 1, wherein n is selected from 1, 2 or 3.

7. The compound according to claim 1, wherein the compound is selected from the group consisting of the following compounds:

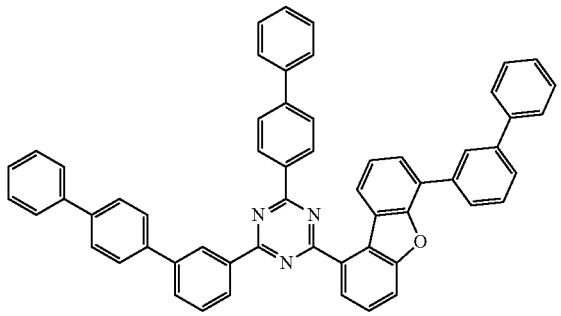

A-49

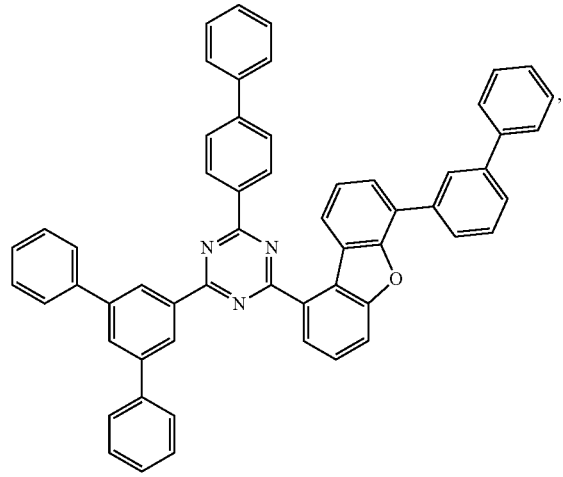

A-51

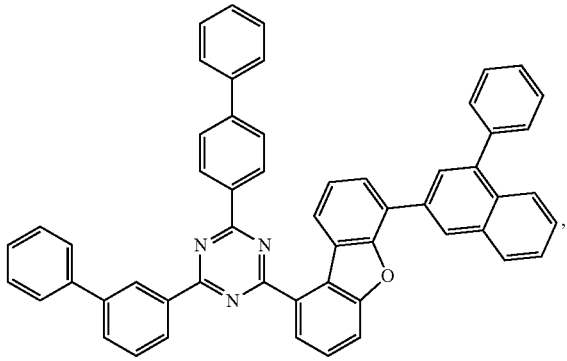

A-175

A-179
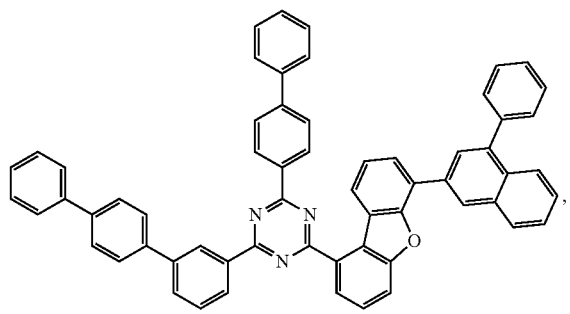
A-181
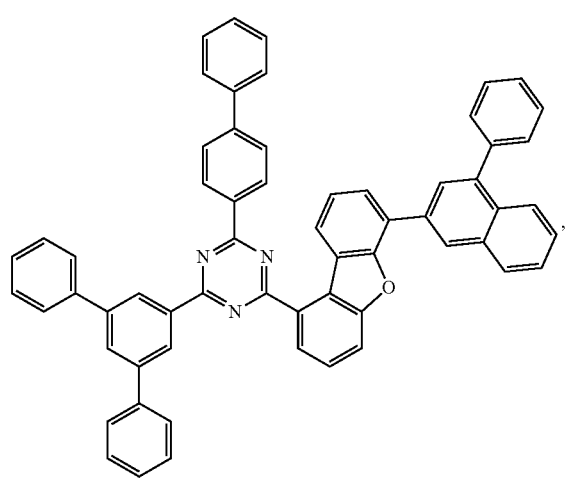
A-201
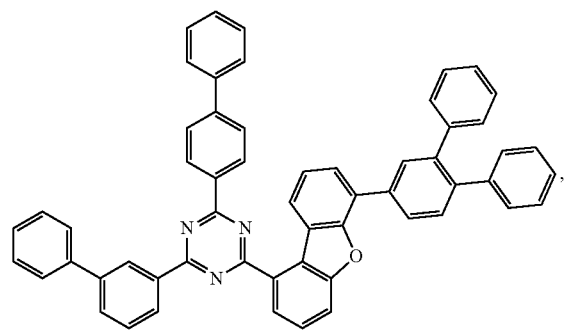
A-205
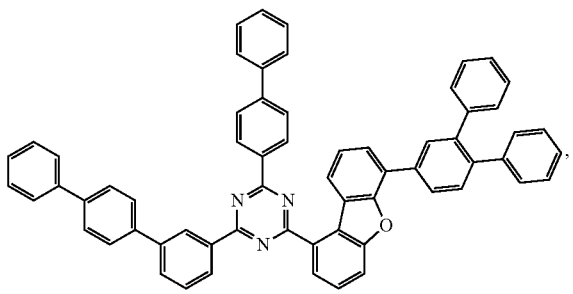
A-207
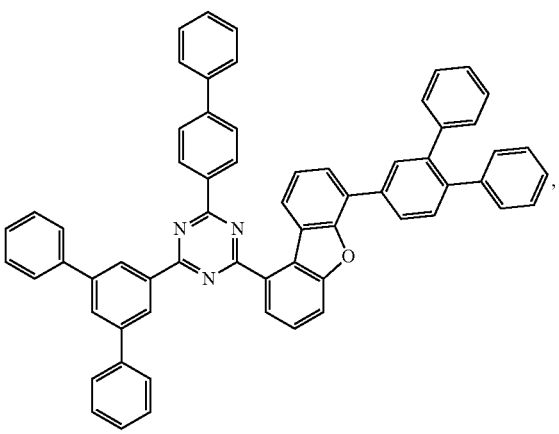
A-279
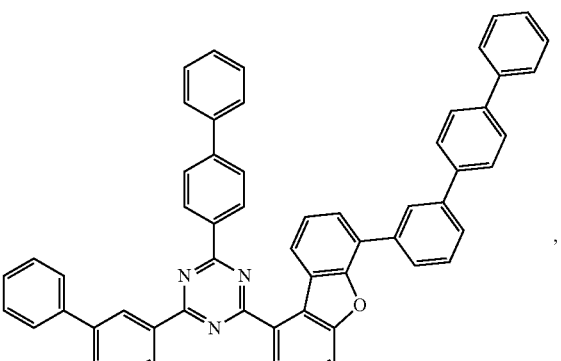
A-283
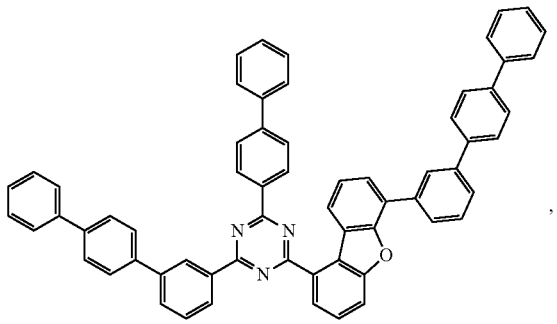

-continued
A-285
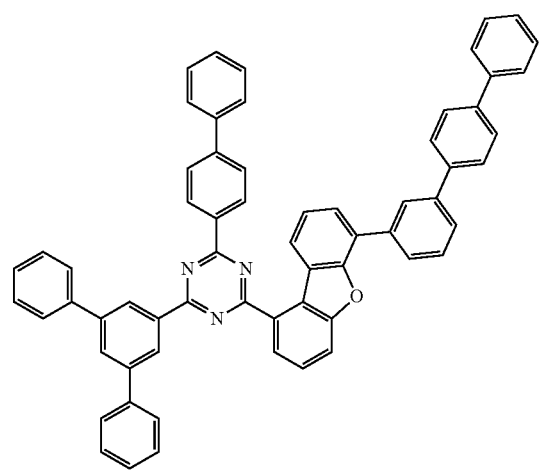
A-331
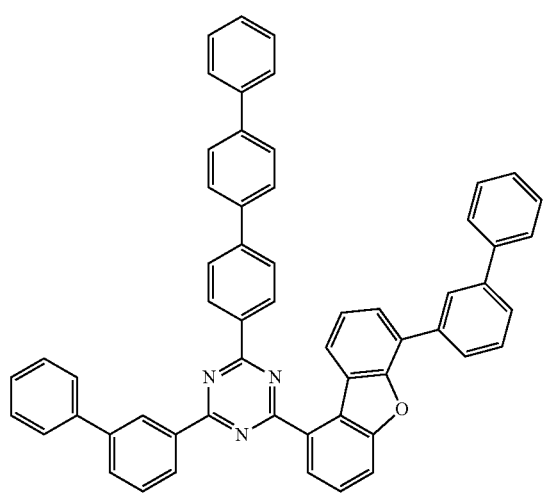
A-335
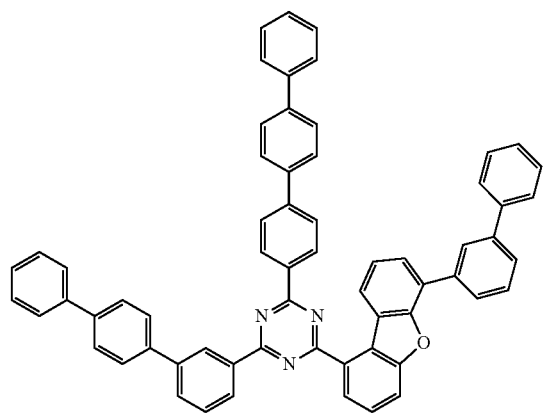
-continued
A-337
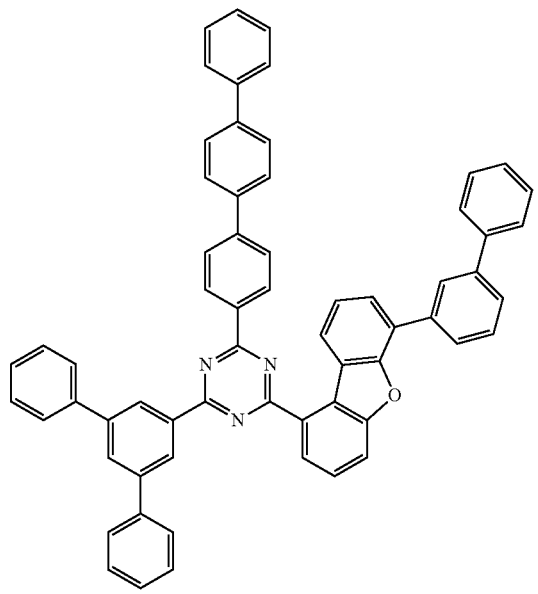
A-383
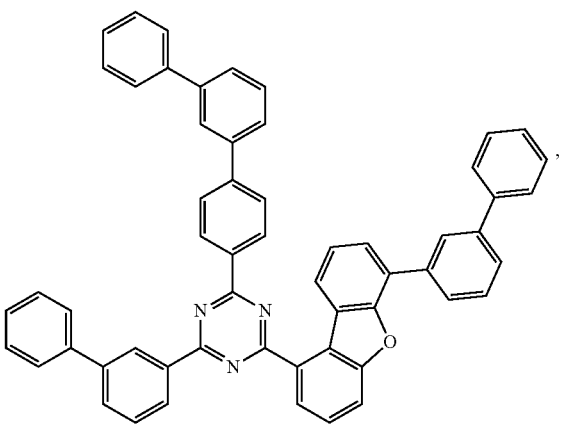
A-387
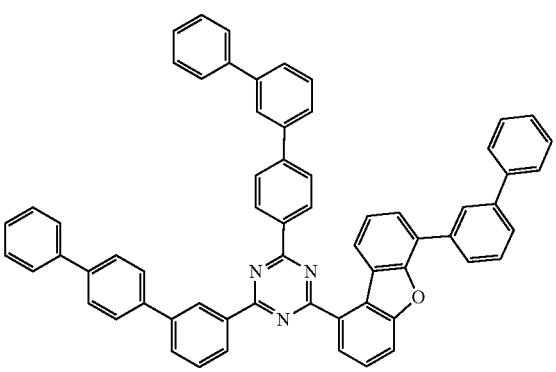

A-389

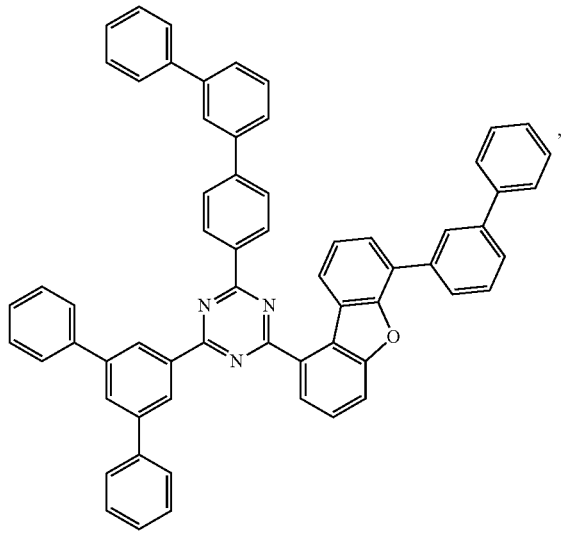

A-490

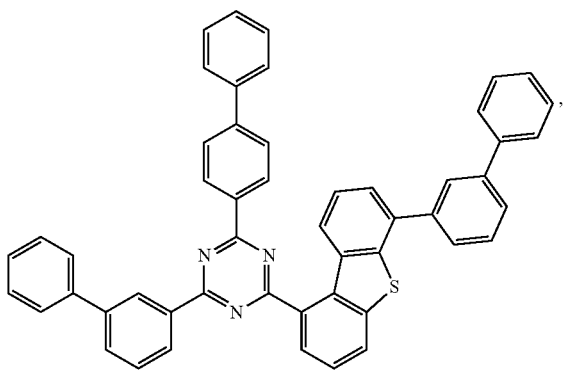

A-494

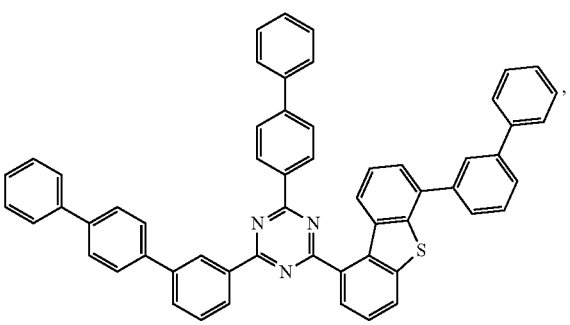

A-496

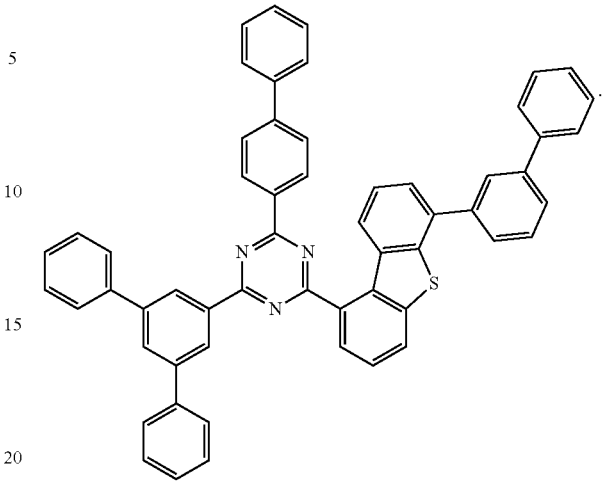

8. An organic electroluminescent device, comprising an anode, a cathode and an organic layer disposed between the anode and the cathode, wherein the organic layer contains the compound according to claim 1.

9. The organic electroluminescent device according to claim 8, wherein the organic layer is a light-emitting layer, the compound is a host compound, and the light-emitting layer contains at least a first metal complex.

10. The organic electroluminescent device according to claim 9, wherein the first metal complex has a structure represented by Formula 2:

Formula 2

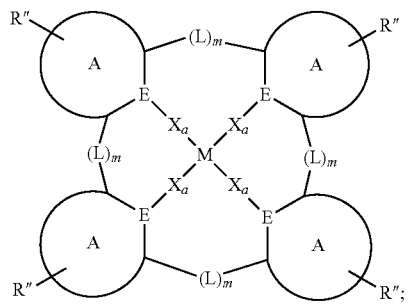

wherein
the metal M is, at each occurrence identically or differently, selected from the group consisting of Cu, Ag, Au, Ru, Rh, Pd, Os, Ir and Pt;
A is, at each occurrence identically or differently, selected from a substituted or unsubstituted aromatic ring having 5 to 30 ring atoms, a substituted or unsubstituted heteroaromatic ring having 5 to 30 ring atoms or a combination thereof;
L is, at each occurrence identically or differently, selected from the group consisting of: a single bond, BR', CR'R', NR', O, SiR'R', PR', S, GeR'R', Se, substituted or unsubstituted vinylene, ethynylene, substituted or unsubstituted arylene having 5 to 30 carbon atoms, substituted or unsubstituted heteroarylene having 5 to 30 carbon atoms and combinations thereof; when two R' are present at the same time, the two R' are identical or different;

m is, at each occurrence identically or differently, selected from 0 or 1; when m=0, the rings A are not joined to each other;

E is, at each occurrence identically or differently, selected from C or N;

$X_a$ is, at each occurrence identically or differently, selected from a single bond, O or S;

R" represents mono-substitution, multiple substitutions or non-substitution;

R' and R" are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof; and adjacent substituents R', R" can be optionally joined to form a ring.

11. The organic electroluminescent device according to claim 9, wherein the first metal complex has a general formula of $M(L_a)_f(L_b)_g(L_c)_h$, wherein $L_a$ has a structure represented by Formula 3:

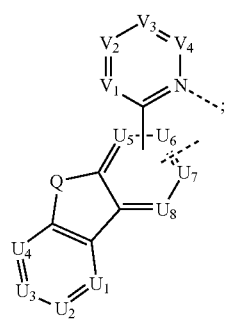

Formula 3 wherein the metal M is, at each occurrence identically or differently, selected from the group consisting of Cu, Ag, Au, Ru, Rh, Pd, Os, Ir and Pt;

$L_a$, $L_b$ and $L_c$ are a first ligand, a second ligand and a third ligand coordinated to the metal M, respectively; $L_a$, $L_b$ and $L_c$ can be optionally joined to form a multidentate ligand;

f is selected from 0, 1, 2 or 3, g is selected from 0, 1, 2 or 3, and h is selected from 0, 1 or 2;

when f is 2 or 3, a plurality of $L_a$ are identical or different; when g is 2 or 3, a plurality of $L_b$ are identical or different; when h is 2, two $L_c$ are identical or different;

Q is, at each occurrence identically or differently, selected from the group consisting of O, S, Se, $NR_q$, $CR_qR_q$ and $SiR_qR_q$; when two $R_q$ are present at the same time, the two $R_q$ are identical or different;

$U_1$ to $U_8$ are, at each occurrence identically or differently, selected from C, $CR_u$ or N;

$U_5$, $U_6$, $U_7$ or $U_8$ is joined to the metal M by a metal-carbon bond or a metal-nitrogen bond;

$V_1$ to $V_4$ are, at each occurrence identically or differently, selected from $CR_v$ or N;

$R_q$, $R_u$ and $R_v$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof;

adjacent substituents $R_q$, $R_u$ and $R_v$ can be optionally joined to form a ring;

$L_b$ and $L_c$ are, at each occurrence identically or differently, selected from a structure represented by any one of the group consisting of the following:

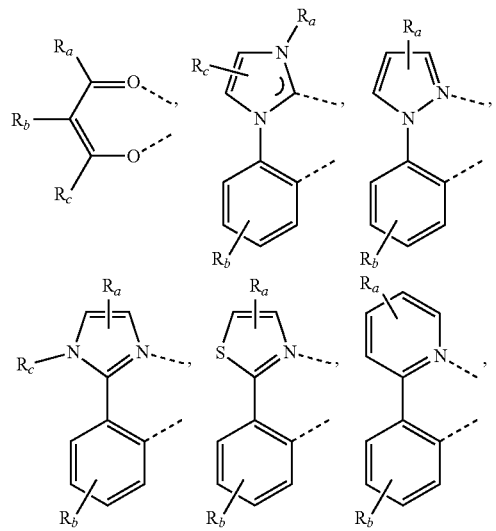

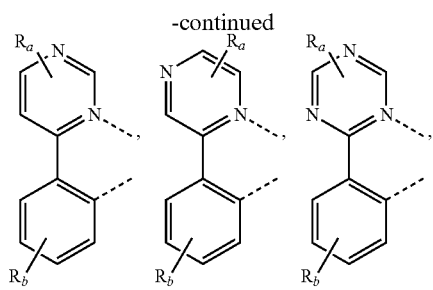

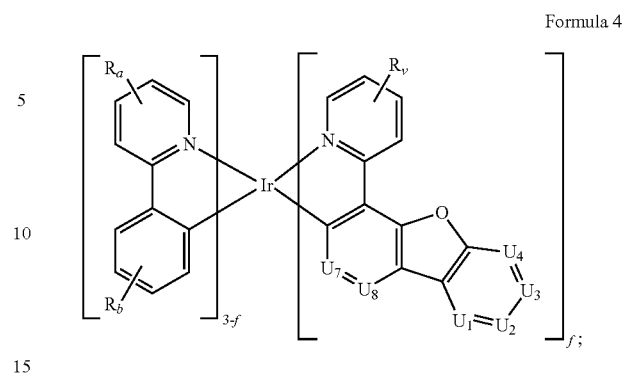

Formula 4

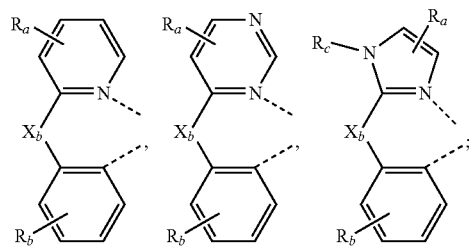

wherein $R_a$, $R_b$ and $R_c$ represent, at each occurrence identically or differently, mono-substitution, multiple substitutions or non-substitution;

$X_b$ is, at each occurrence identically or differently, selected from the group consisting of: O, S, Se, $NR_{N1}$ and $CR_{C1}R_{C2}$;

$R_a$, $R_b$, $R_c$, $R_{N1}$, $R_{C1}$ and $R_{C2}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof; and adjacent substituents $R_a$, $R_b$, $R_c$, $R_{N1}$, $R_{C1}$ and $R_{C2}$ can be optionally joined to form a ring.

12. The organic electroluminescent device according to claim 11, wherein the first metal complex has a structure represented by Formula 4:

wherein f is 0, 1, 2 or 3; when f is 2 or 3, a plurality of $L_a$ are identical or different; when f is 0 or 1, a plurality of $L_b$ are identical or different;

$U_4$ is, at each occurrence identically or differently, selected from $CR_u$ or N;

$U_1$ to $U_3$, $U_7$ and $U_8$ are, at each occurrence identically or differently, selected from $CR_u$;

$R_a$, $R_b$ and $R_v$ represent, at each occurrence identically or differently, mono-substitution, multiple substitutions or non-substitution;

$R_a$, $R_b$, $R_u$ and $R_v$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof; and adjacent substituents $R_a$, $R_b$, $R_u$ and $R_v$ can be optionally joined to form a ring.

13. The organic electroluminescent device according to claim 11, wherein at least one of $R_u$ is selected from substituted or unsubstituted alkyl having 1 to 20 carbon atoms or substituted or unsubstituted cycloalkyl having 3 to 20 ring carbon atoms.

14. The organic electroluminescent device according to claim 11, wherein at least one $R_u$ is fluorine or cyano.

15. The organic electroluminescent device according to claim 11, wherein there are at least $R_u$, one of which is fluorine or cyano and the other one of which is selected from substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms or substituted or unsubstituted heteroaryl having 3 to 30 carbon atoms.
16. The organic electroluminescent device according to claim 11, wherein $L_a$ is selected from the group consisting of the following:
$L_{a1-1}$
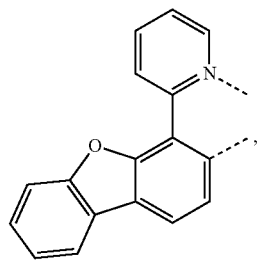
$L_{a1-2}$
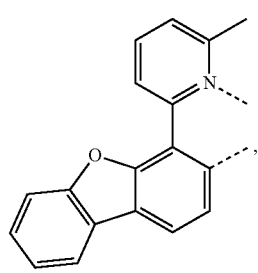
$L_{a1-3}$
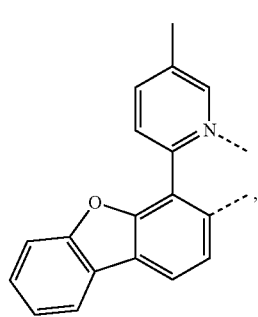
$L_{a1-4}$
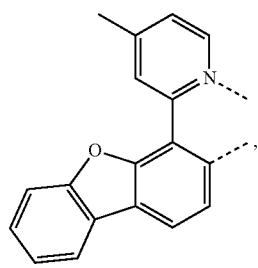
$L_{a1-5}$
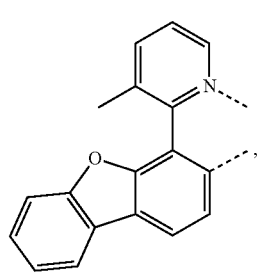
-continued
$L_{a1-6}$
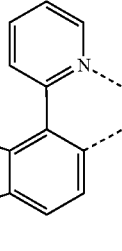
$L_{a1-7}$
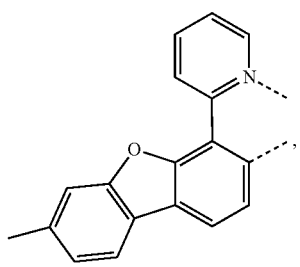
$L_{a1-8}$
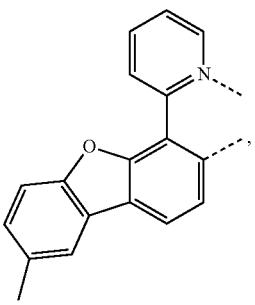
$L_{a1-9}$
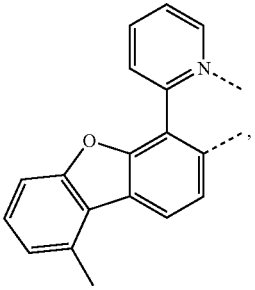
$L_{a1-10}$
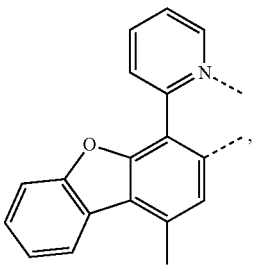

L_{a1-11} 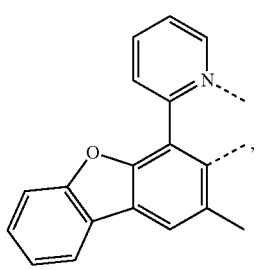
L_{a1-12} 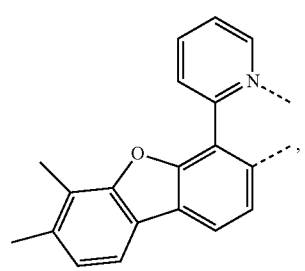
L_{a1-13} 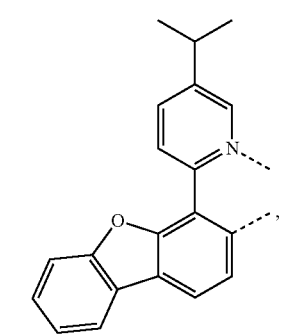
L_{a1-14} 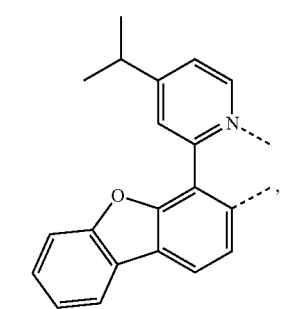
L_{a1-15} 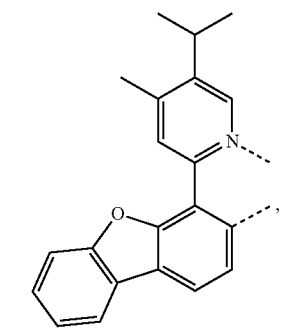
L_{a1-16} 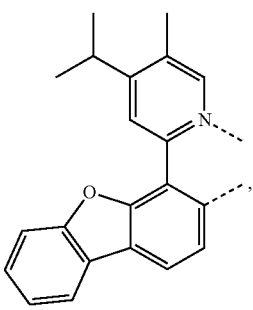
L_{a1-17} 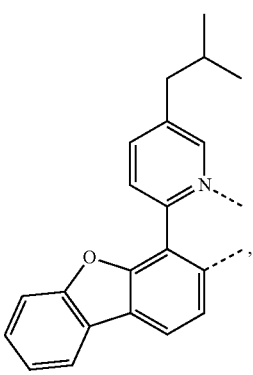
L_{a1-18} 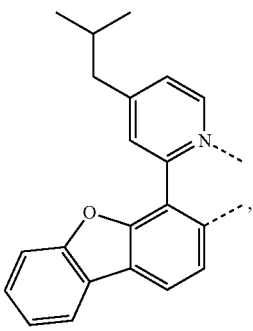
L_{a1-19} 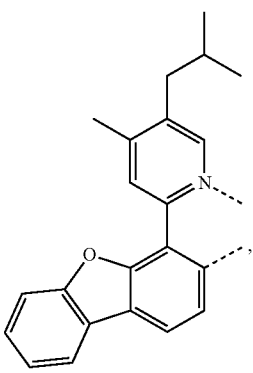

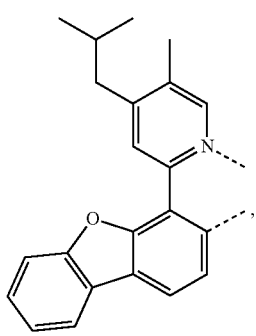 $L_{a1-20}$
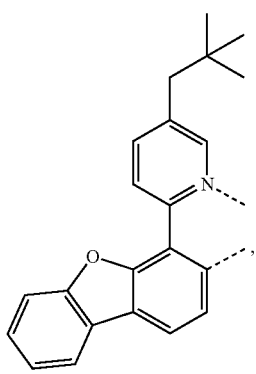 $L_{a1-21}$
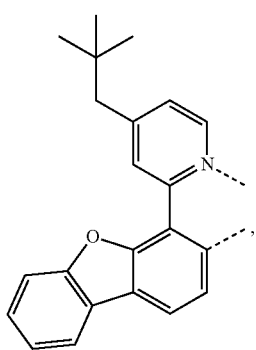 $L_{a1-22}$
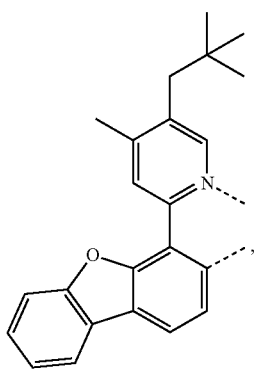 $L_{a1-23}$
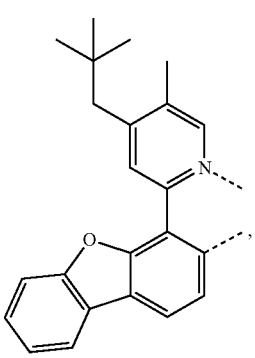 $L_{a1-24}$
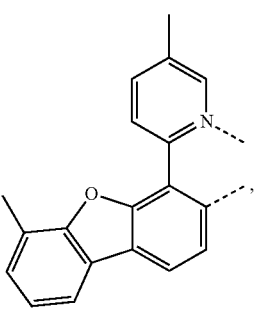 $L_{a1-25}$
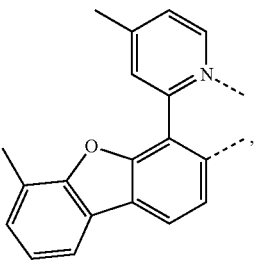 $L_{a1-26}$
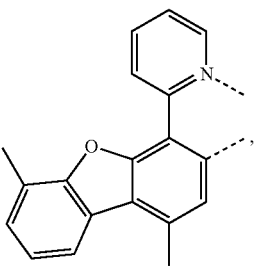 $L_{a1-27}$
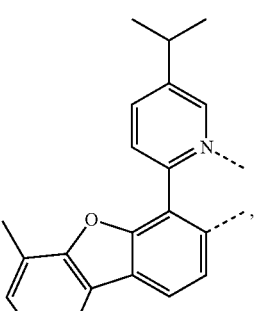 $L_{a1-28}$ L<sub>a1-29</sub>
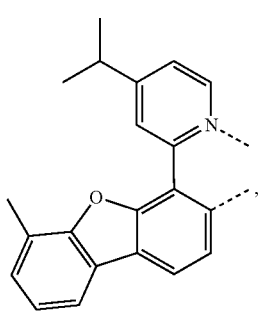
L<sub>a1-30</sub>
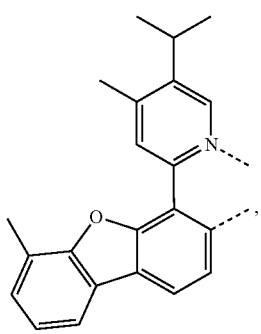
L<sub>a1-31</sub>
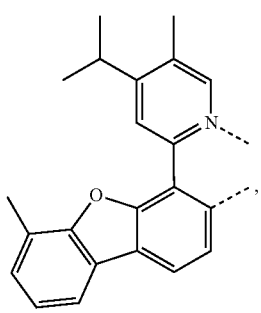
L<sub>a1-32</sub>
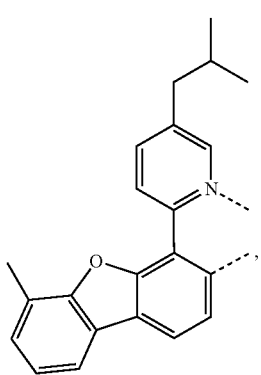
L<sub>a1-33</sub>
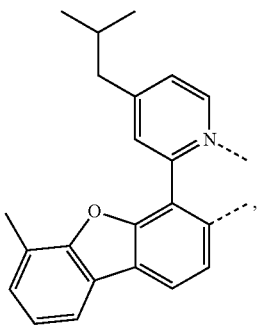
L<sub>a1-34</sub>
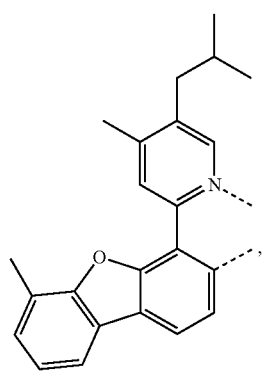
L<sub>a1-35</sub>
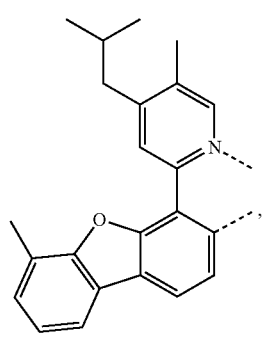
L<sub>a1-36</sub>
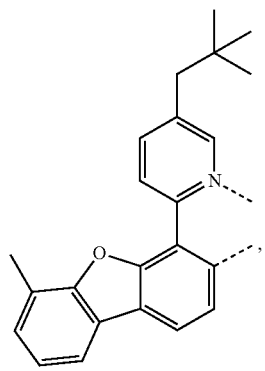

L_{a1-37}
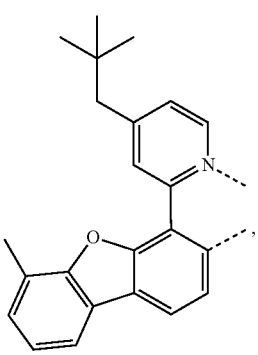
L_{a1-38}
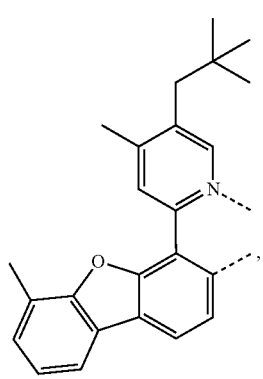
L_{a1-39}
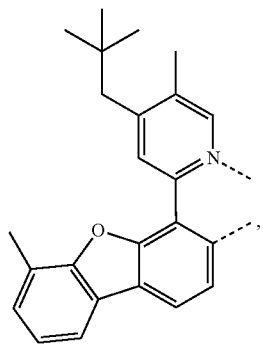
L_{a1-40}
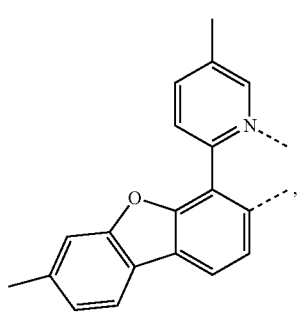
L_{a1-41}
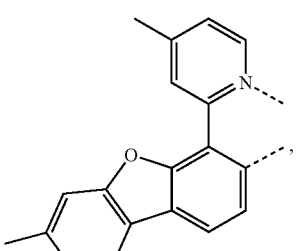
L_{a1-42}
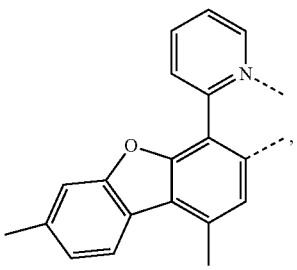
L_{a1-43}
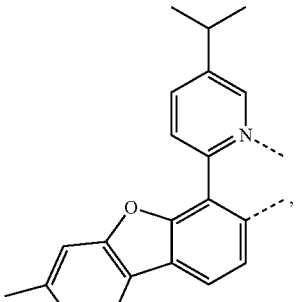
L_{a1-44}
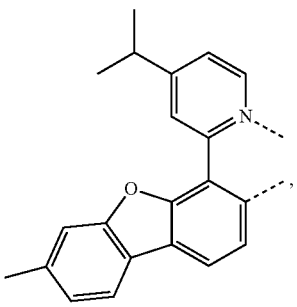
L_{a1-45}
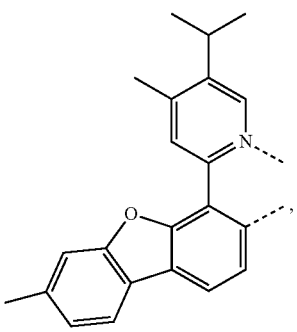

-continued
L<sub>a1-46</sub>
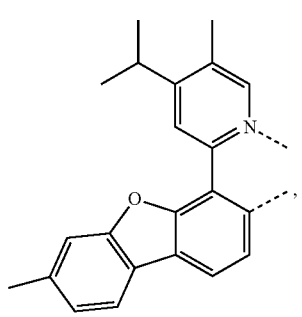
L<sub>a1-47</sub>
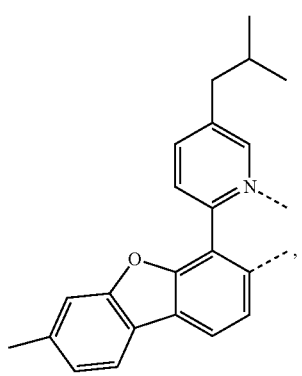
L<sub>a1-48</sub>
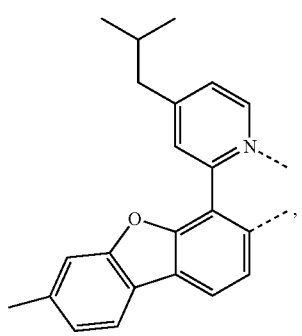
L<sub>a1-49</sub>
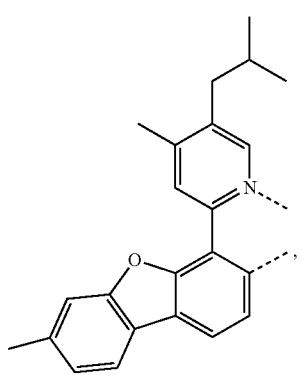
L<sub>a1-50</sub>
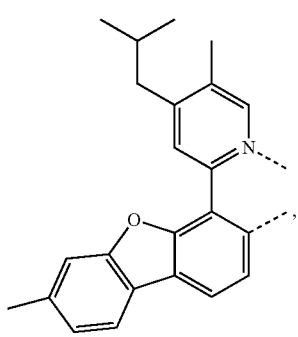
L<sub>a1-51</sub>
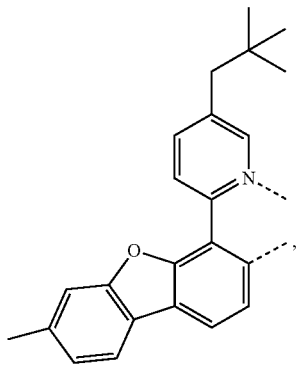
L<sub>a1-52</sub>
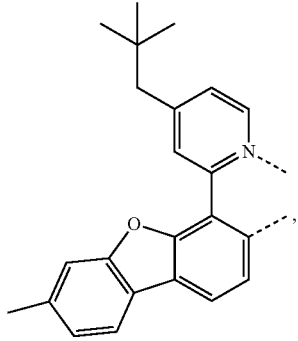
L<sub>a1-53</sub>
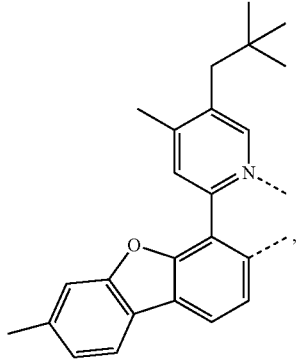

L_{a1-54}
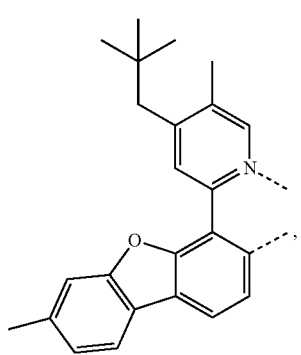
L_{a1-55}
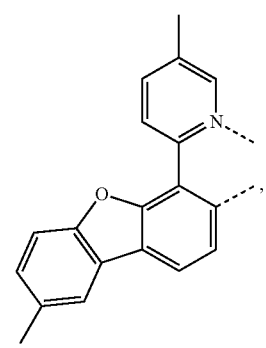
L_{a1-56}
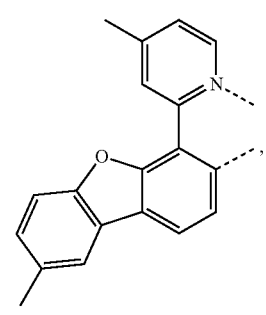
L_{a1-57}
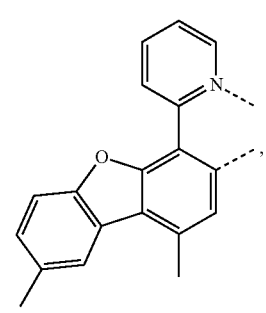
L_{a1-58}
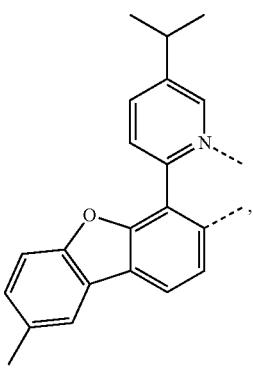
L_{a1-59}
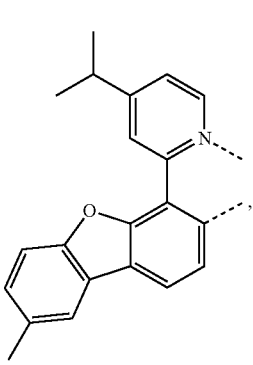
L_{a1-60}
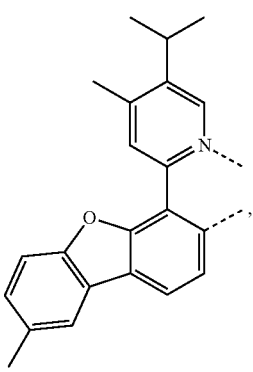
L_{a1-61}
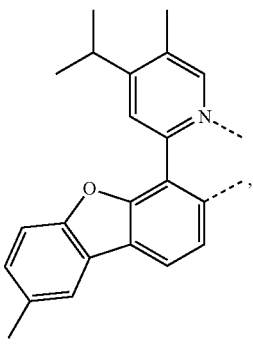

L<sub>a1-62</sub> 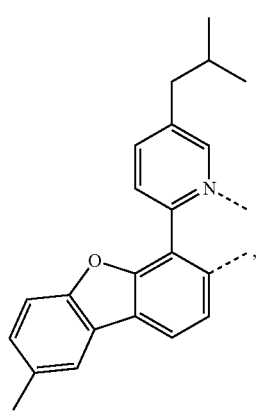
L<sub>a1-63</sub> 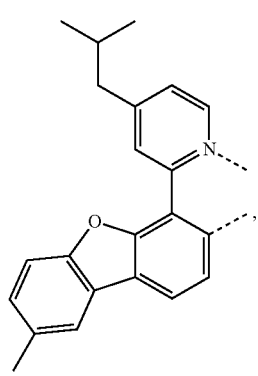
L<sub>a1-64</sub> 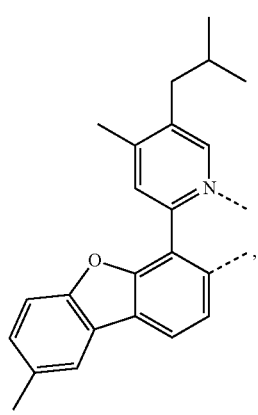
L<sub>a1-65</sub> 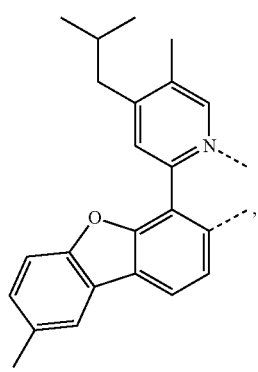
L<sub>a1-66</sub> 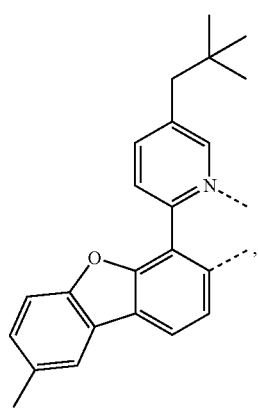
L<sub>a1-67</sub> 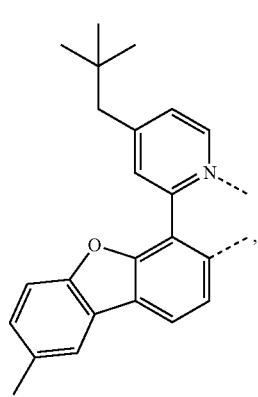
L<sub>a1-68</sub> 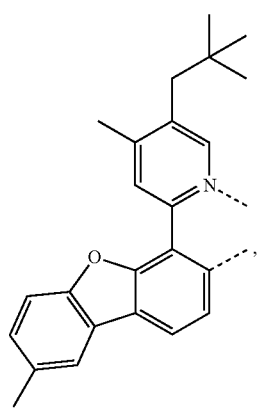
L<sub>a1-69</sub> 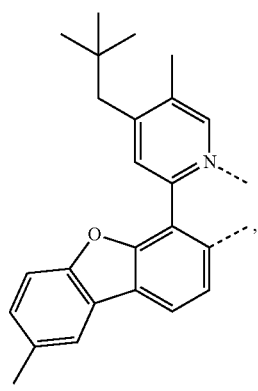

L<sub>a1-70</sub>
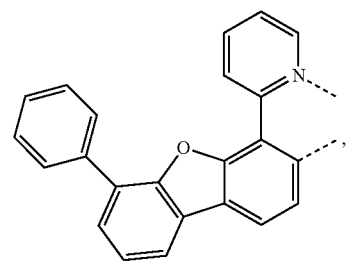
L<sub>a1-71</sub>
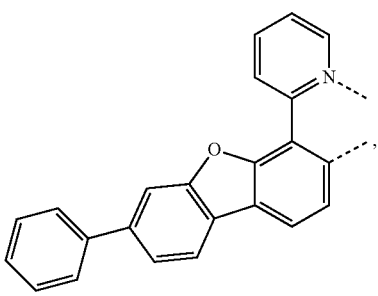
L<sub>a1-72</sub>
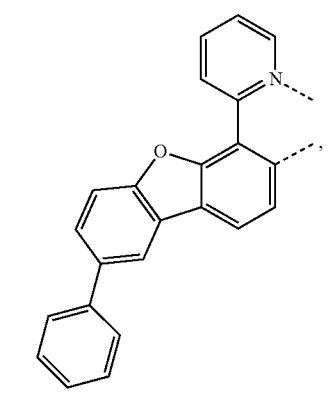
L<sub>a1-73</sub>
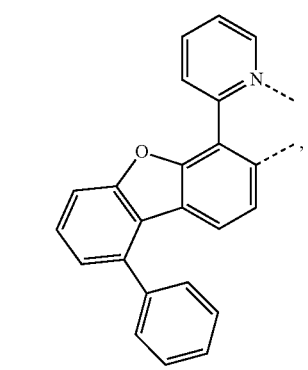
L<sub>a1-74</sub>
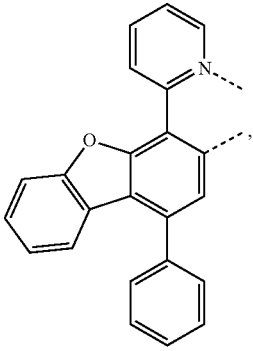
L<sub>a1-75</sub>
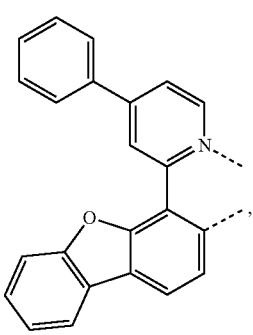
L<sub>a1-76</sub>
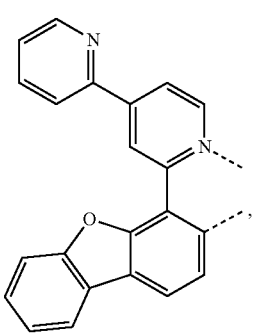
L<sub>a1-77</sub>
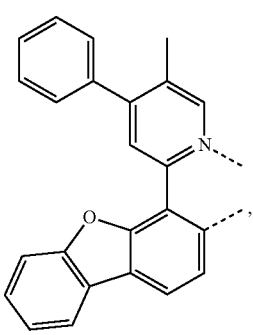

L<sub>a1-78</sub>
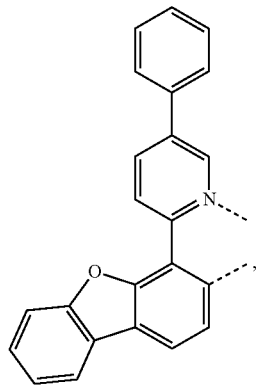
L<sub>a1-79</sub>
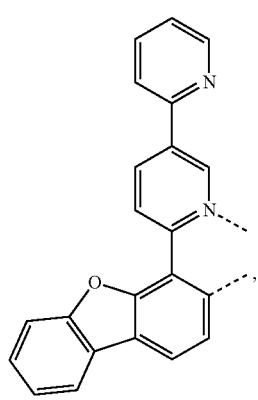
L<sub>a1-80</sub>
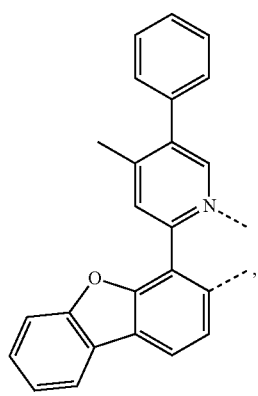
L<sub>a1-81</sub>
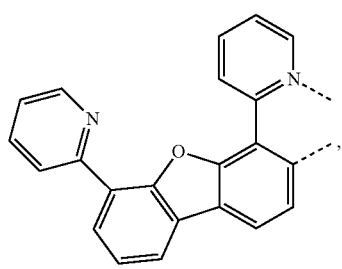
L<sub>a1-82</sub>
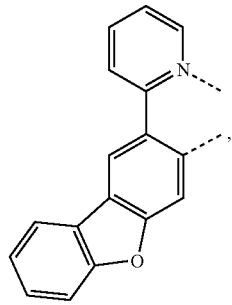
L<sub>a1-83</sub>
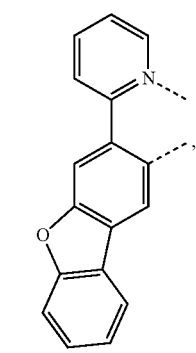
L<sub>a1-84</sub>
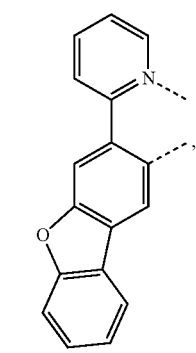
L<sub>a1-85</sub>
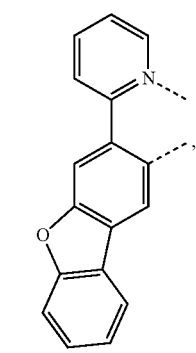
L<sub>a1-86</sub>
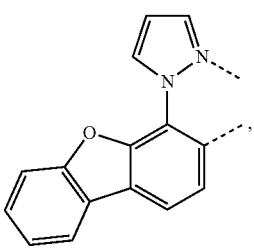

L<sub>a1-87</sub>
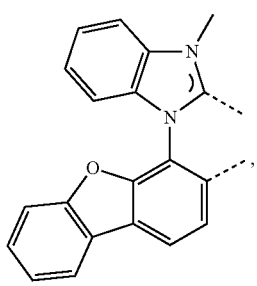
L<sub>a1-88</sub>
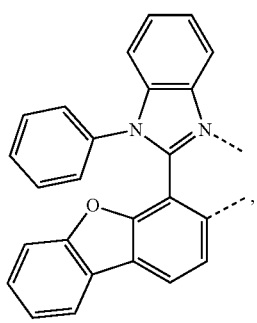
L<sub>a1-89</sub>
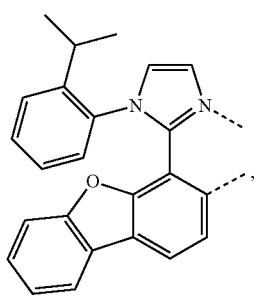
L<sub>a1-90</sub>
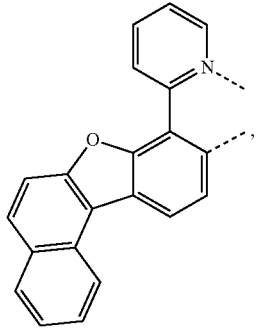
L<sub>a1-91</sub>
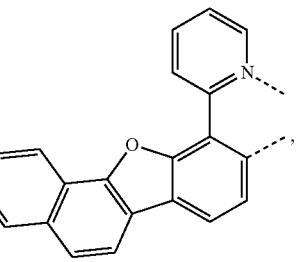
L<sub>a1-92</sub>
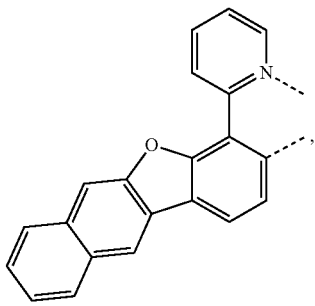
L<sub>a1-93</sub>
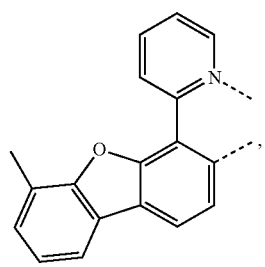
L<sub>a1-94</sub>
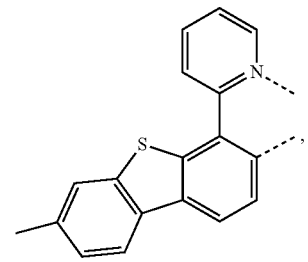
L<sub>a1-95</sub>
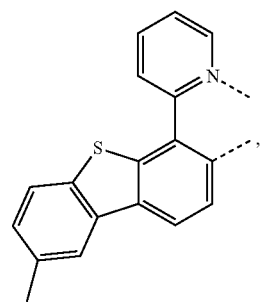
L<sub>a1-96</sub>
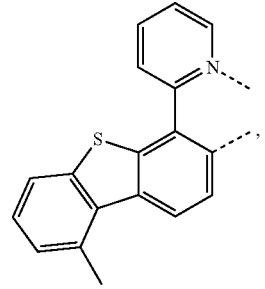

117
-continued
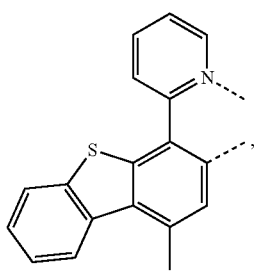
L_{a1-97}
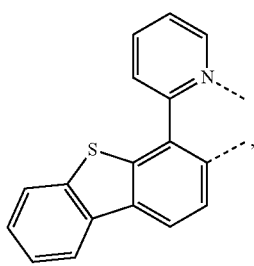
L_{a1-98}
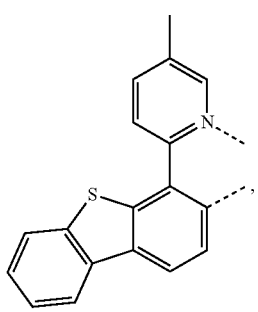
L_{a1-99}
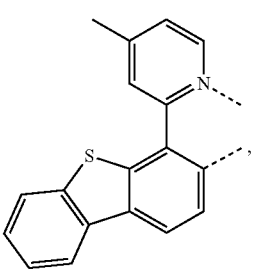
L_{a1-100}
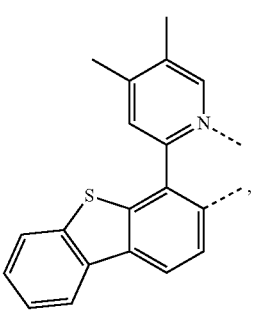
L_{a1-101}
118
-continued
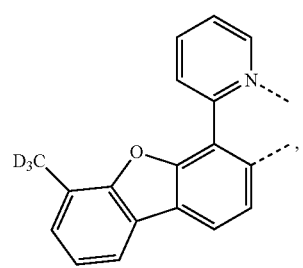
L_{a1-102}
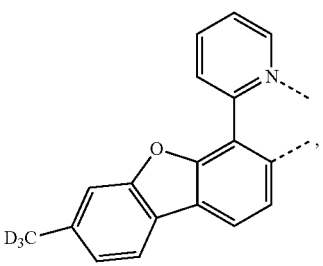
L_{a1-103}
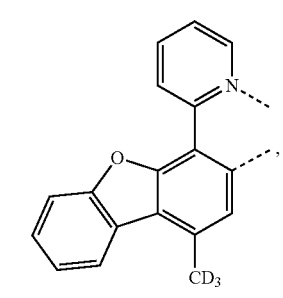
L_{a1-104}
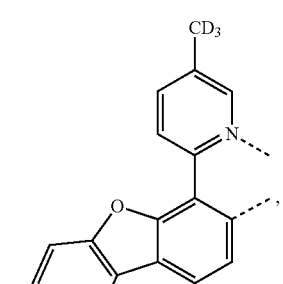
L_{a1-105}
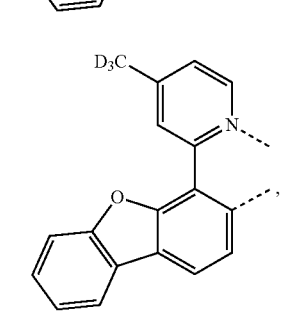
L_{a1-106}

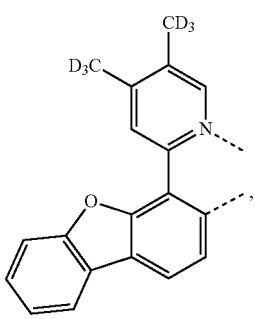
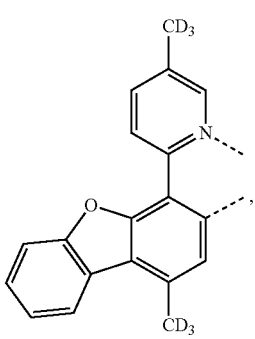
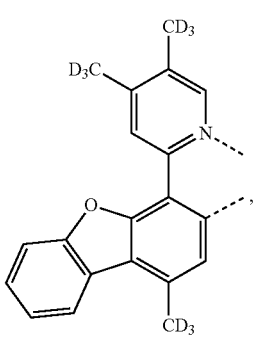
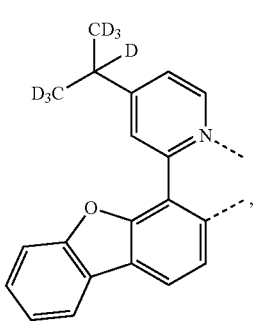
L<sub>a1-107</sub>
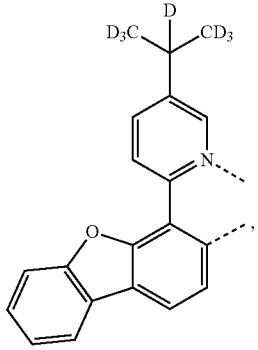
L<sub>a1-108</sub>
L<sub>a1-109</sub>
L<sub>a1-110</sub>
L<sub>a1-111</sub>
L<sub>a1-112</sub>
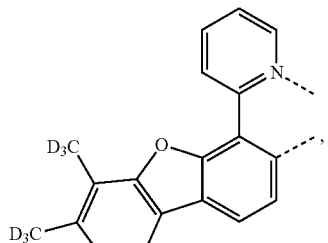
L<sub>a1-113</sub>
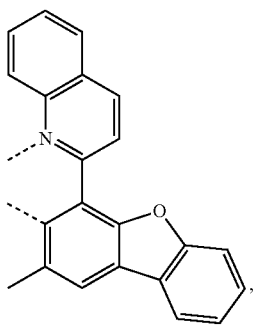
L<sub>a1-114</sub>
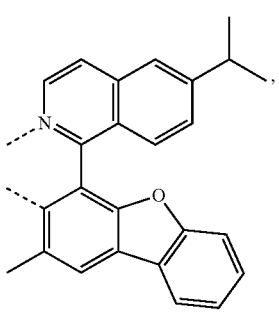
L<sub>a2-1</sub>
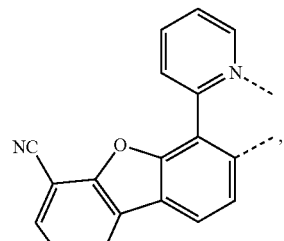

-continued
L<sub>a2-2</sub>
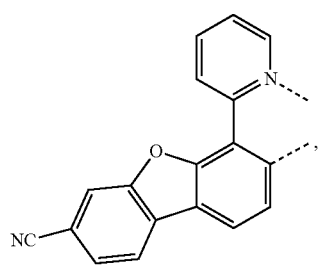
L<sub>a2-3</sub>
L<sub>a2-4</sub>
L<sub>a2-5</sub>
L<sub>a2-6</sub>
L<sub>a2-7</sub>
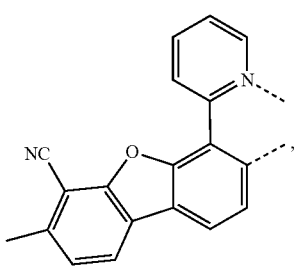
L<sub>a2-8</sub>
L<sub>a2-9</sub>
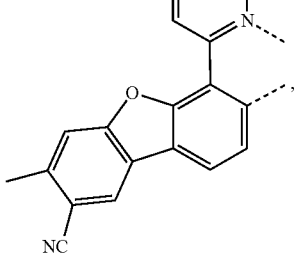
L<sub>a2-10</sub>
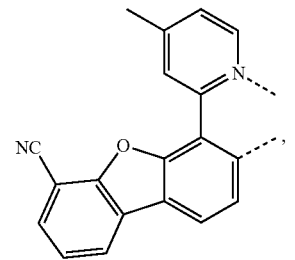
L<sub>a2-11</sub>
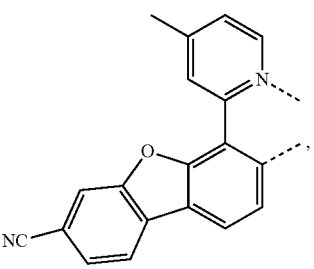
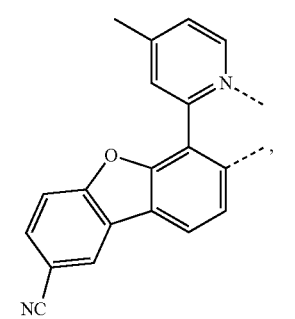

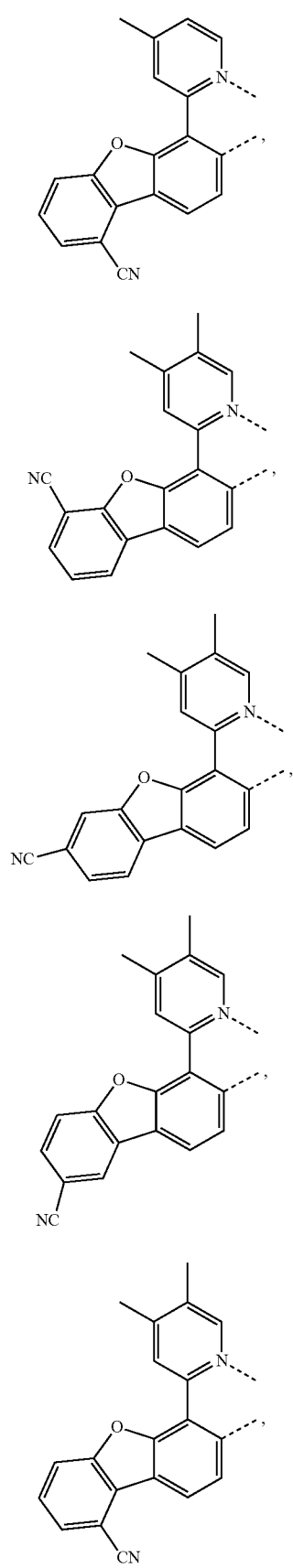
L<sub>a2-12</sub>
L<sub>a2-13</sub>
L<sub>a2-14</sub>
L<sub>a2-15</sub>
L<sub>a2-16</sub>
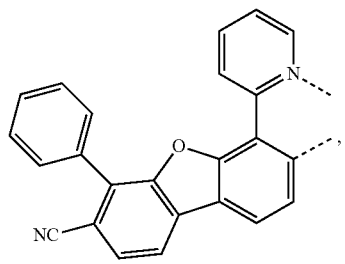
L<sub>a2-17</sub>
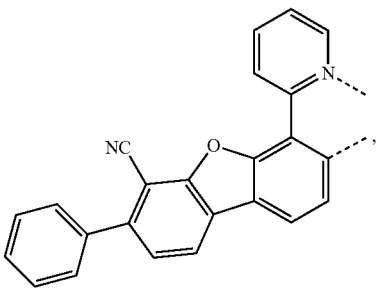
L<sub>a2-18</sub>
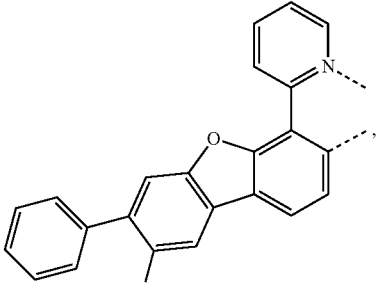
L<sub>a2-19</sub>
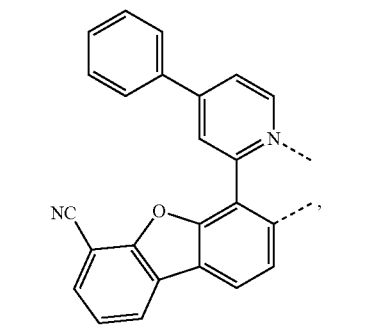
L<sub>a2-20</sub>
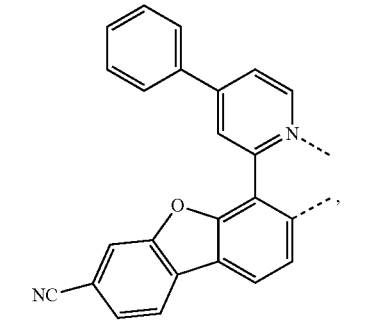
L<sub>a2-21</sub>

L(a2-22)
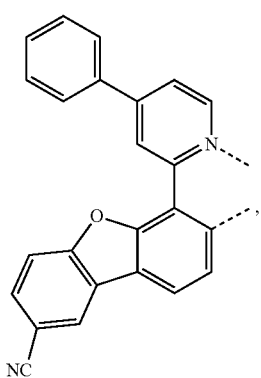
L(a2-23)
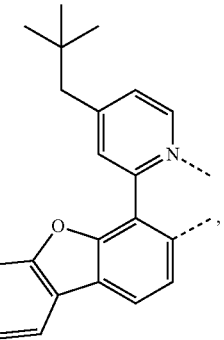
L(a2-26)
L(a2-24)
L(a2-27)
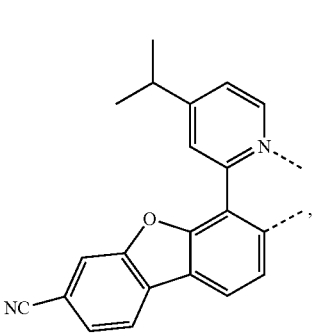
L(a2-25)
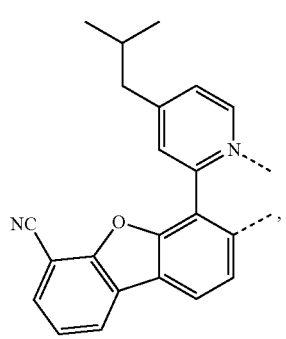
L(a2-28)
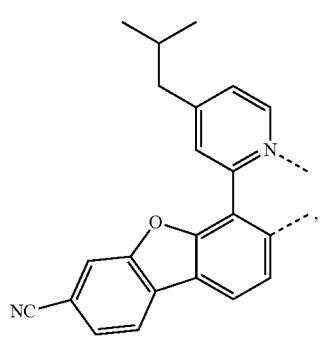
L(a2-29)

L(a2-30)
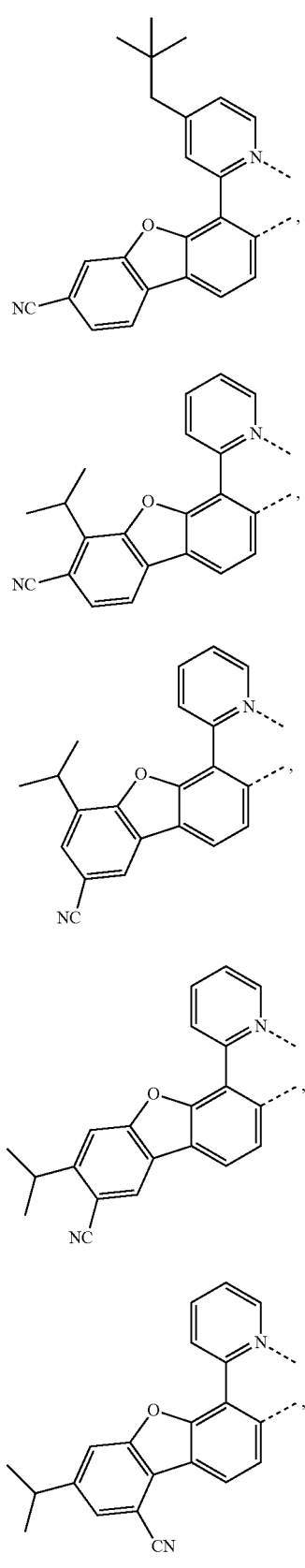
L(a2-31)
L(a2-32)
L(a2-33)
L(a2-34)
L(a2-35)
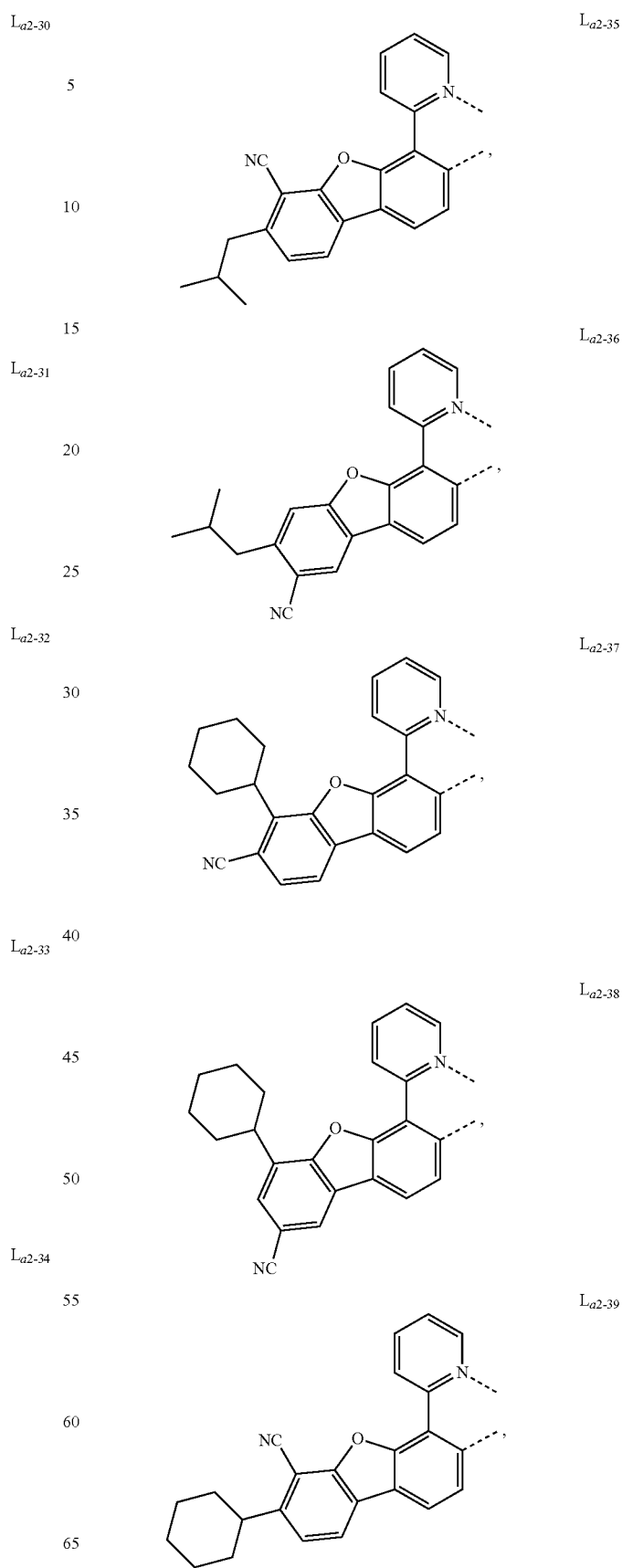
L(a2-36)
L(a2-37)
L(a2-38)
L(a2-39)

-continued
L<sub>a2-40</sub>
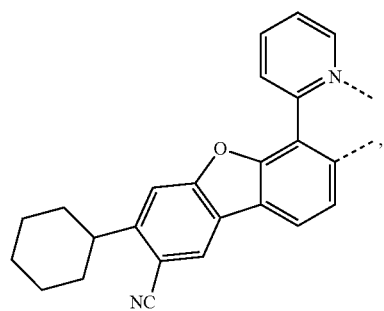
L<sub>a2-41</sub>
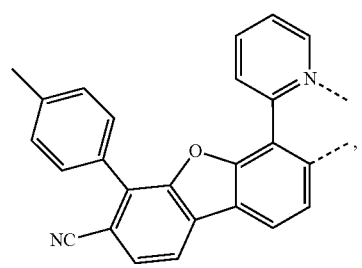
L<sub>a2-42</sub>
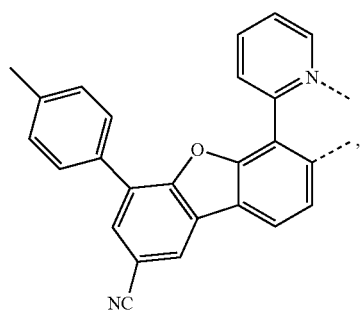
L<sub>a2-43</sub>
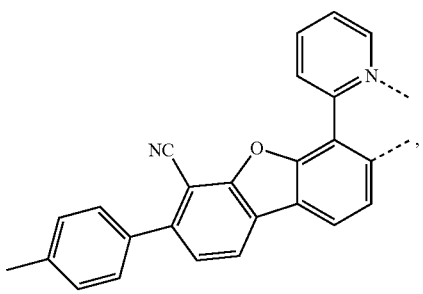
L<sub>a2-44</sub>
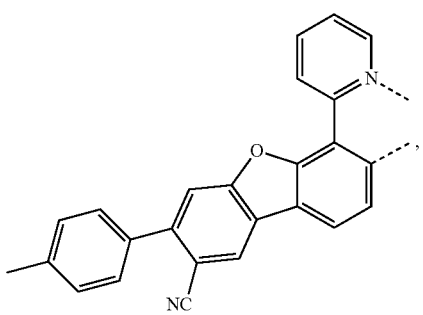
-continued
L<sub>a2-45</sub>
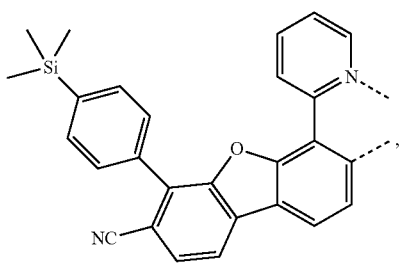
L<sub>a2-46</sub>
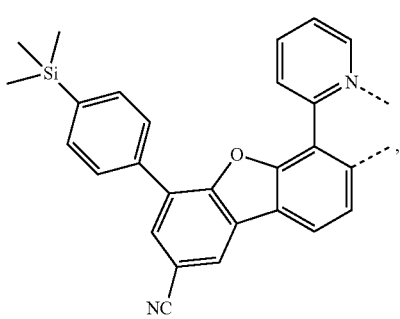
L<sub>a2-47</sub>
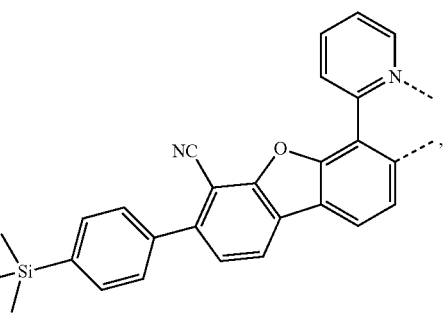
L<sub>a2-48</sub>
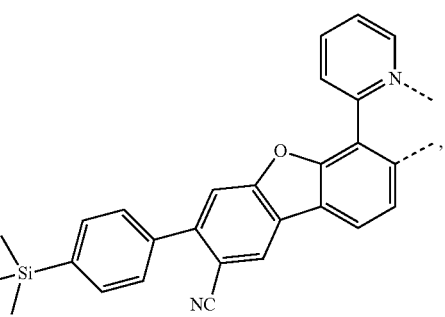
L<sub>a2-49</sub>
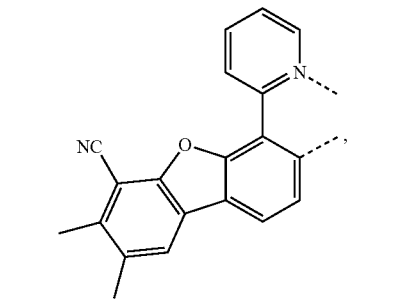

L_{a2-50}
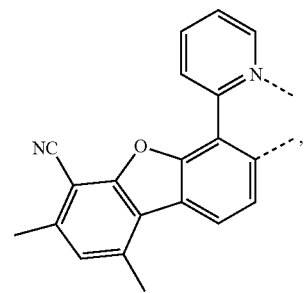
L_{a2-51}
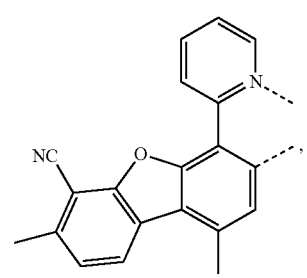
L_{a2-52}
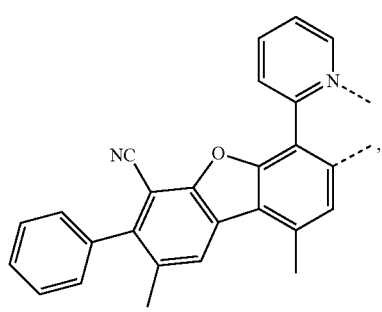
L_{a2-53}
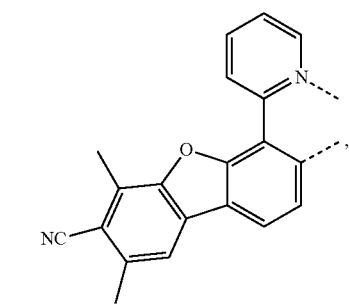
L_{a2-54}
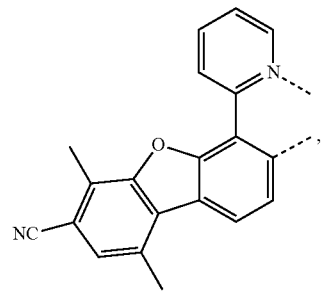
L_{a2-55}
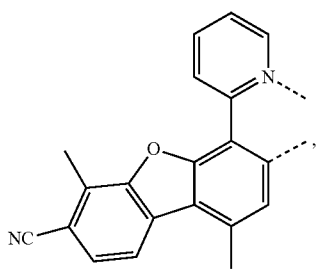
L_{a2-56}
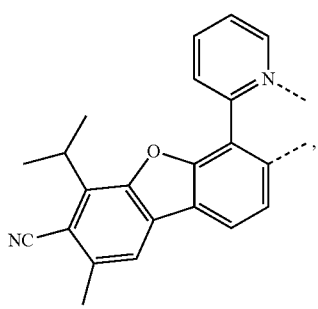
L_{a2-57}
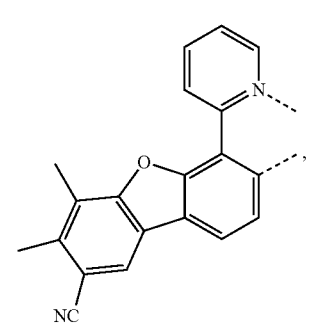
L_{a2-58}
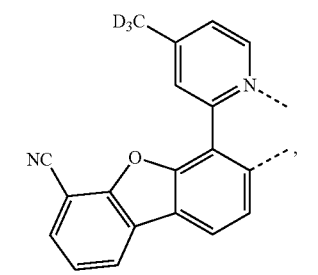
L_{a2-59}
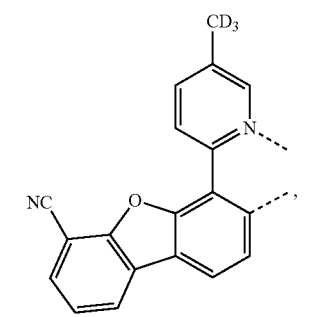

L(a2-60)
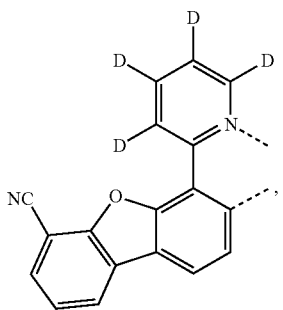
L(a2-61)
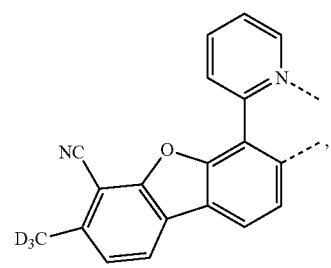
L(a2-62)
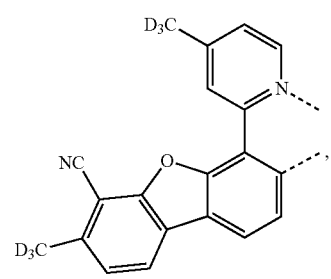
L(a2-63)
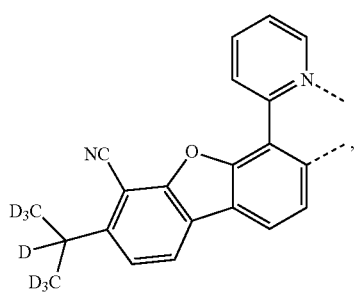
L(a2-64)
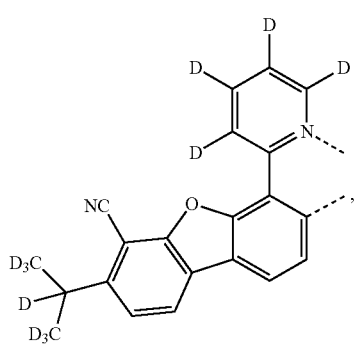
L(a2-65)
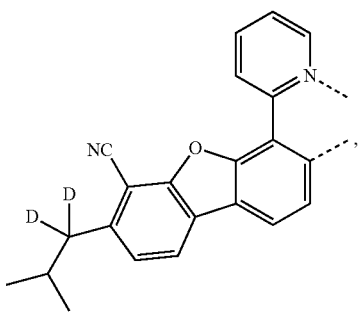
L(a2-66)
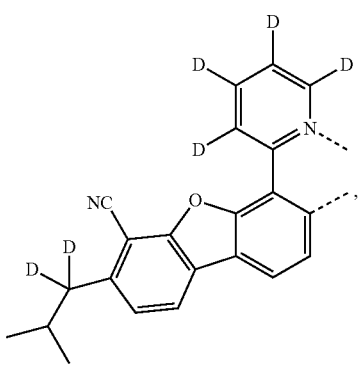
L(a2-67)
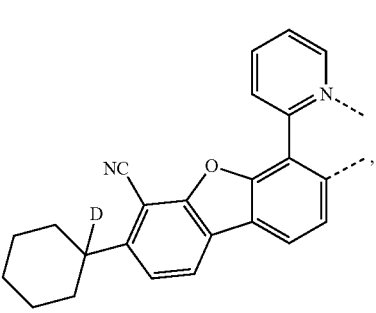
L(a2-68)
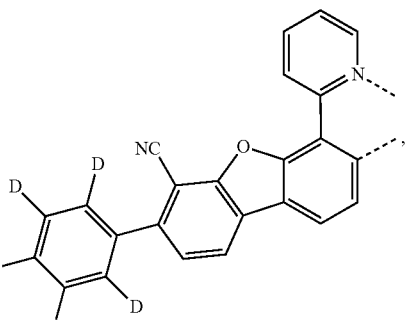
L(a2-69)
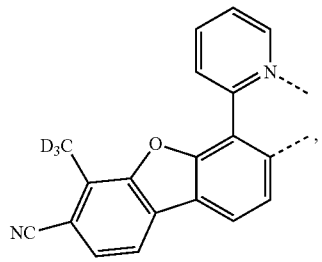

L<sub>a2-70</sub>
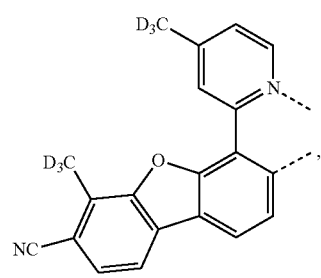
L<sub>a2-71</sub>
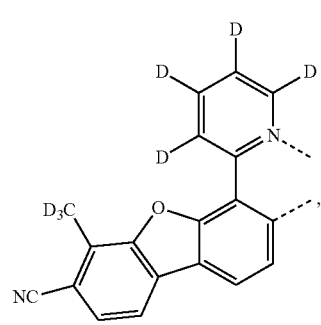
L<sub>a2-72</sub>
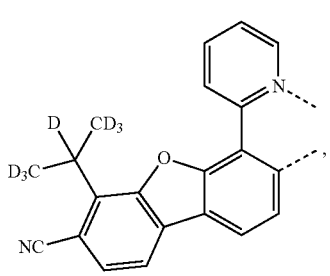
L<sub>a2-73</sub>
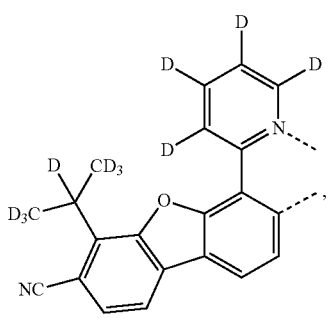
L<sub>a2-74</sub>
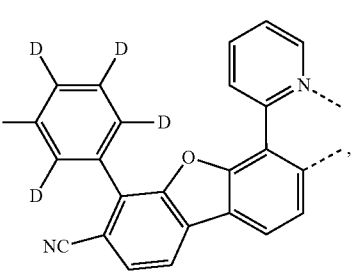
L<sub>a2-75</sub>
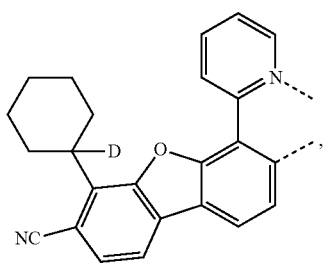
L<sub>a2-76</sub>
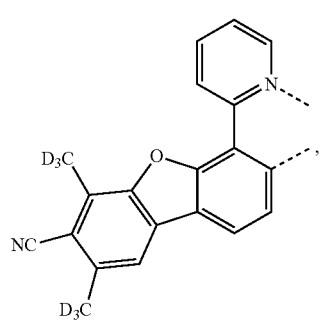
L<sub>a2-77</sub>
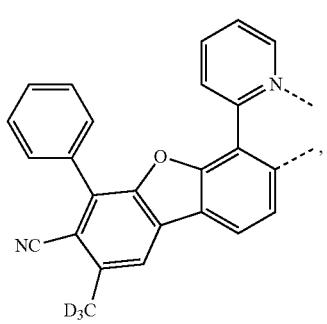
L<sub>a2-78</sub>
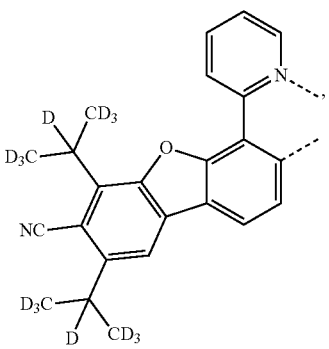

L*a*2-79
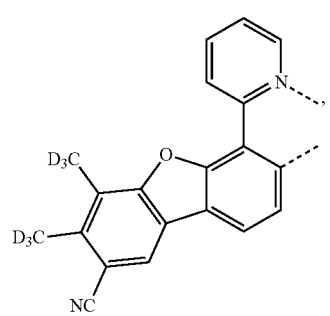
L*a*2-80
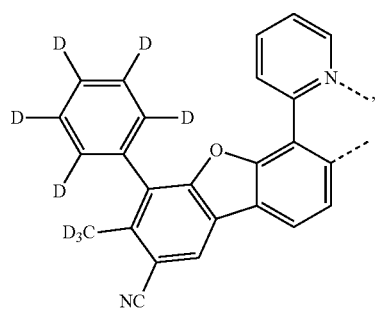
L*a*2-81
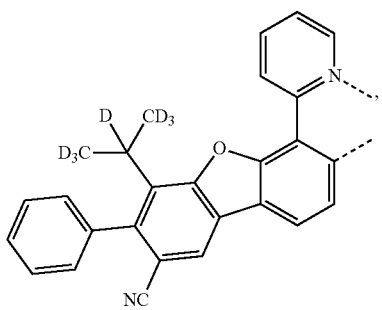
L*a*2-82
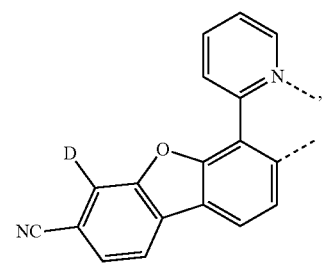
L*a*2-83
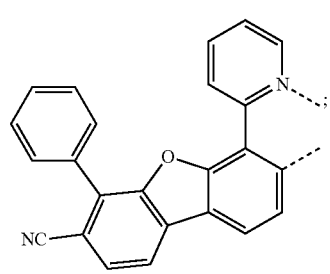
L*a*3-1
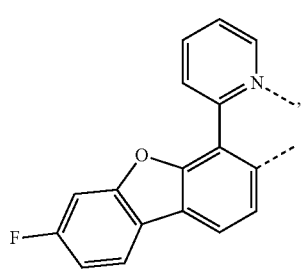
L*a*3-2
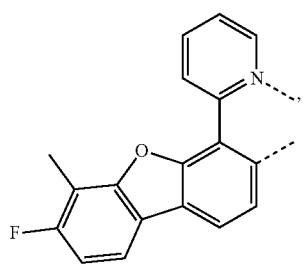
L*a*3-3
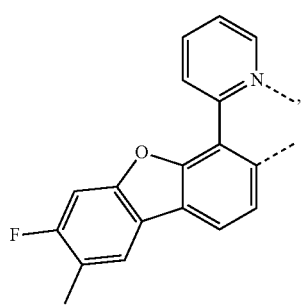
L*a*3-4
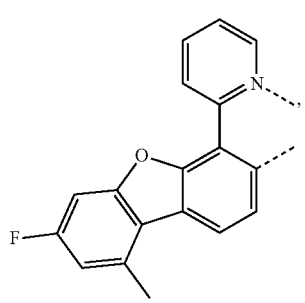
L*a*3-5
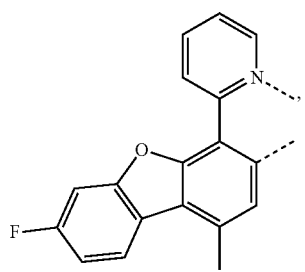

L<sub>a3</sub>-6
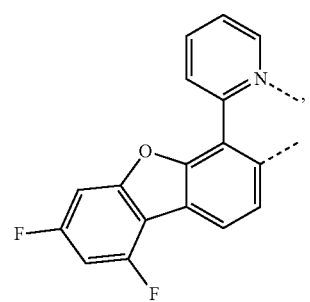
L<sub>a3</sub>-7
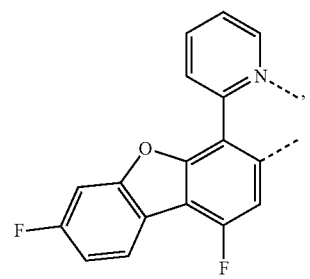
L<sub>a3</sub>-8
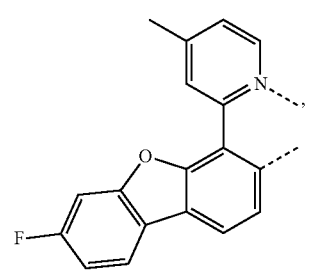
L<sub>a3</sub>-9
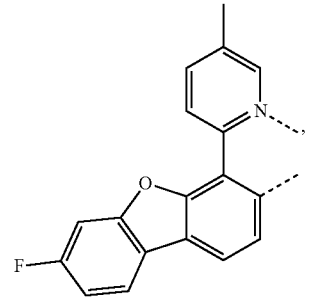
L<sub>a3</sub>-10
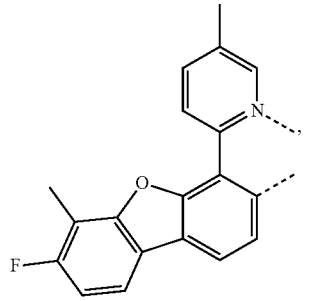
L<sub>a3</sub>-11
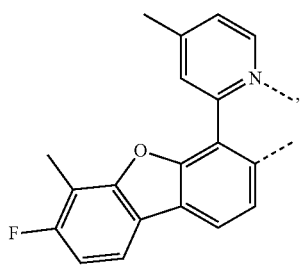
L<sub>a3</sub>-12
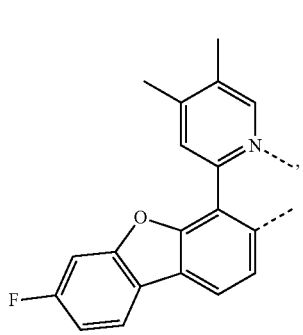
L<sub>a3</sub>-13
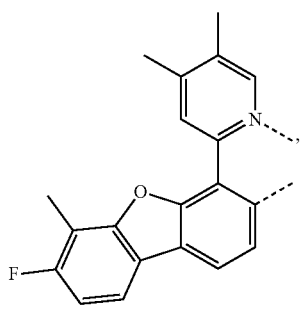
L<sub>a3</sub>-14
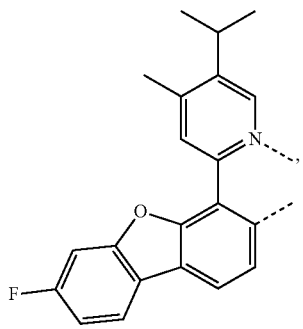
L<sub>a3</sub>-15
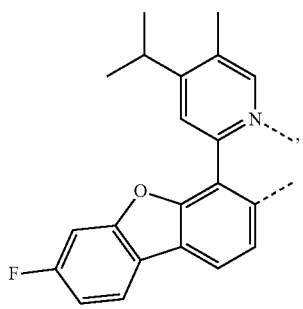

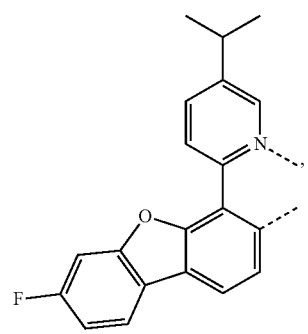 L_{a3-16}
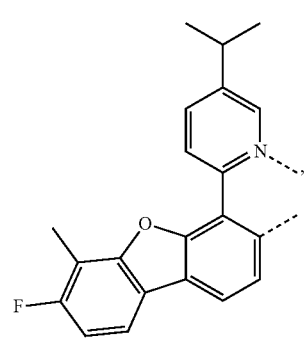 L_{a3-17}
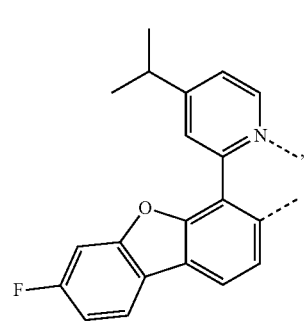 L_{a3-18}
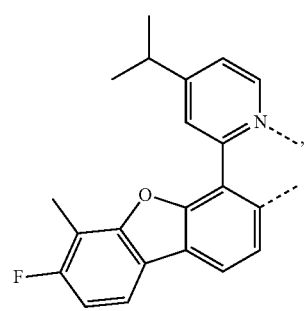 L_{a3-19}
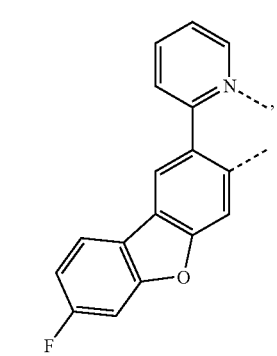 L_{a3-20}
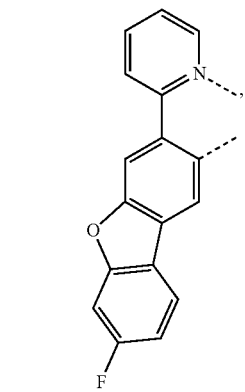 L_{a3-21}
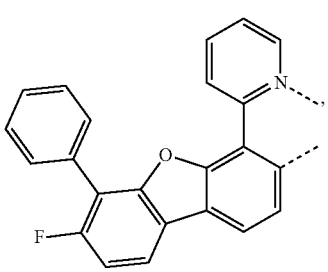 L_{a3-22}
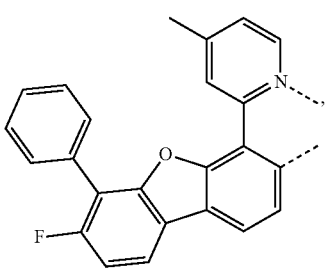 L_{a3-23}
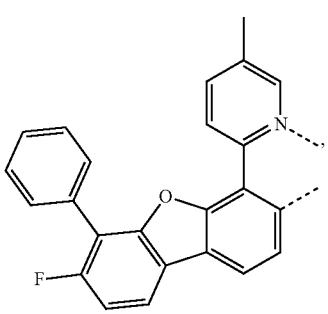 L_{a3-24}
L_{a3-25}

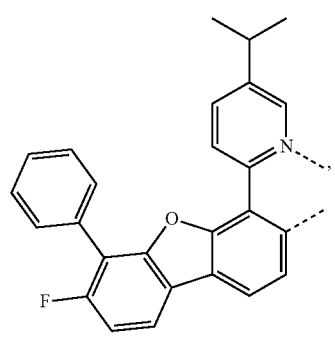 L*a3*-26
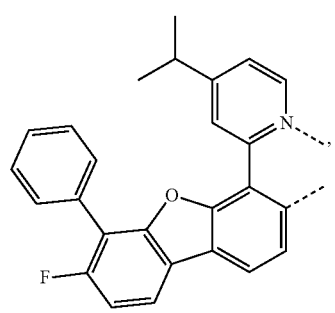 L*a3*-27
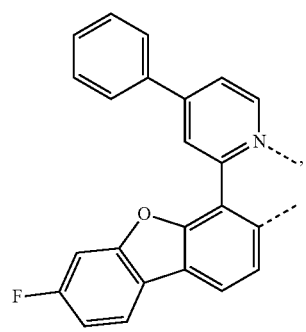 L*a3*-28
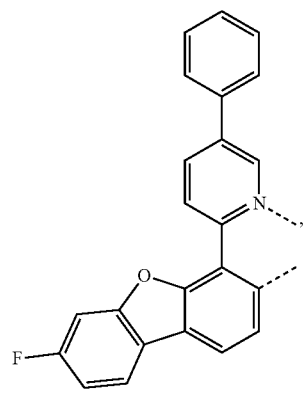 L*a3*-29
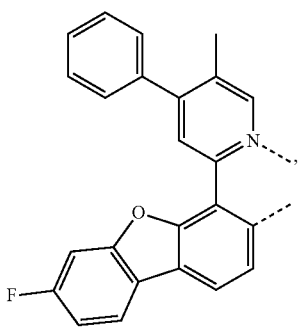 L*a3*-30
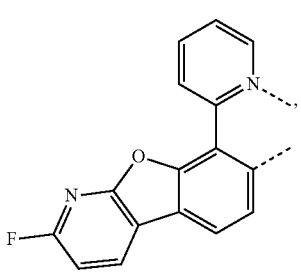 L*a3*-31
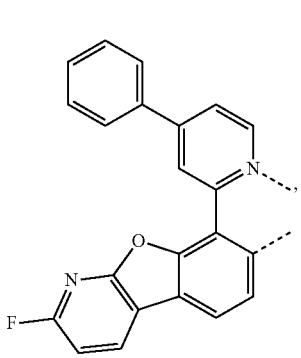 L*a3*-32
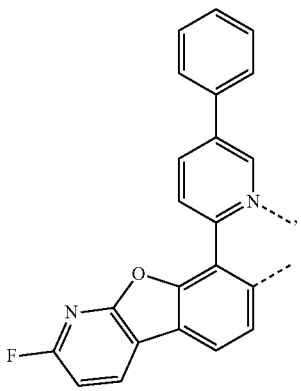 L*a3*-33

-continued
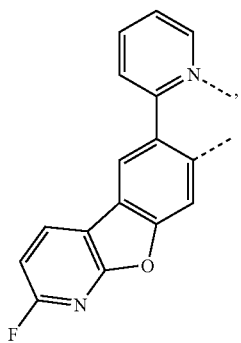 L<sub>a3-34</sub>
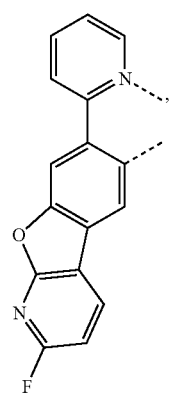 L<sub>a3-35</sub>
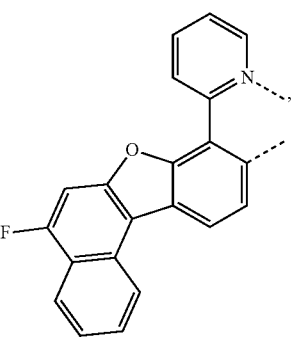 L<sub>a3-36</sub>
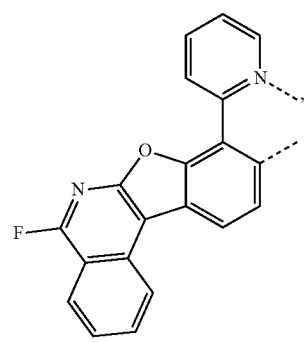 L<sub>a3-37</sub>
-continued
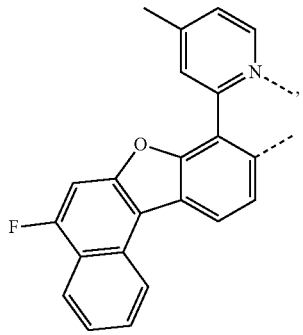 L<sub>a3-38</sub>
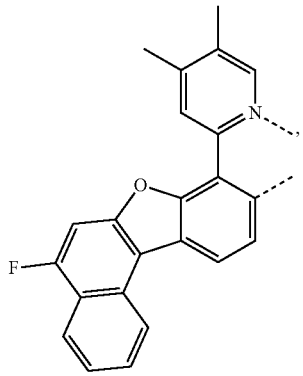 L<sub>a3-39</sub>
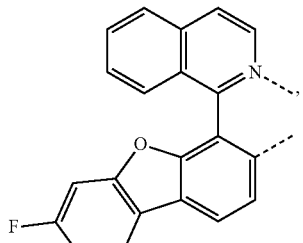 L<sub>a3-40</sub>
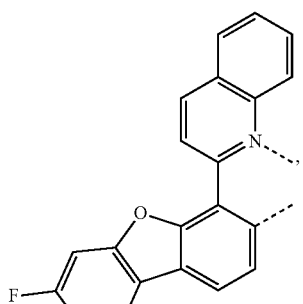 L<sub>a3-41</sub>
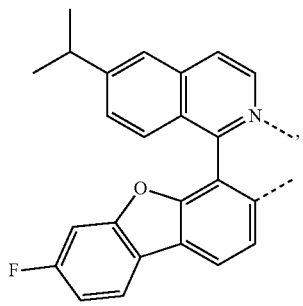 L<sub>a3-42</sub>

L_{a3-43}
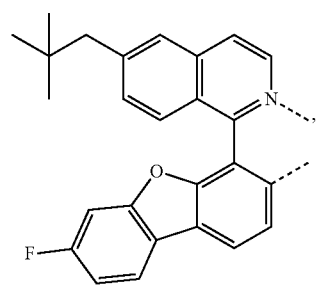
L_{a3-44}
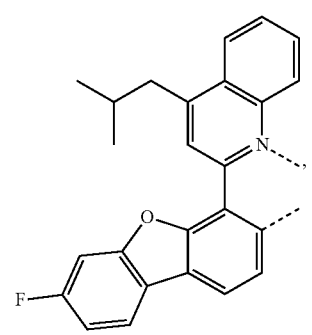
L_{a3-45}
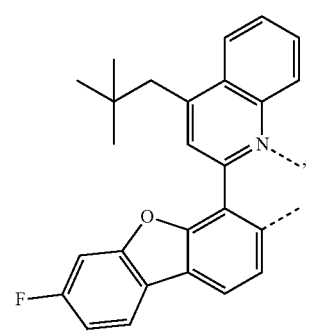
L_{a3-46}
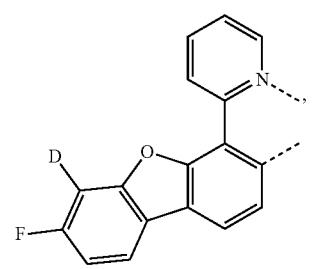
L_{a3-47}
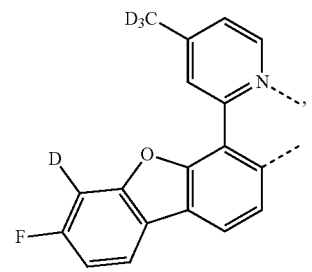
L_{a3-48}
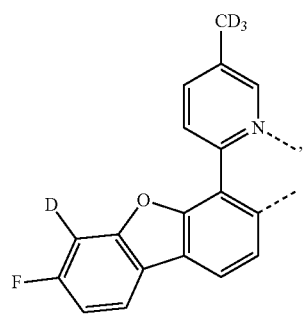
L_{a3-49}
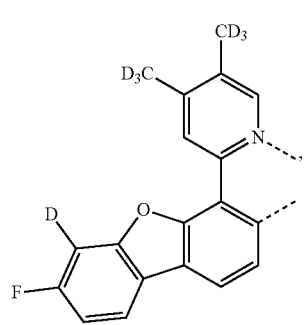
L_{a3-50}
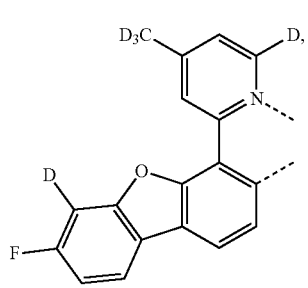
L_{a3-51}
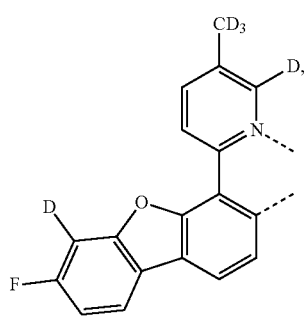
L_{a3-52}
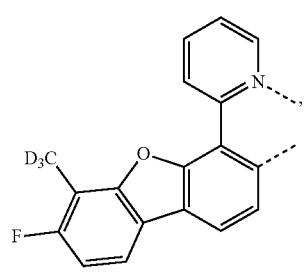

L$_{a3\text{-}53}$
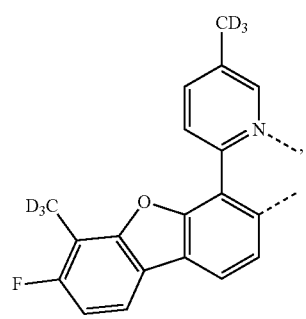
L$_{a3\text{-}54}$
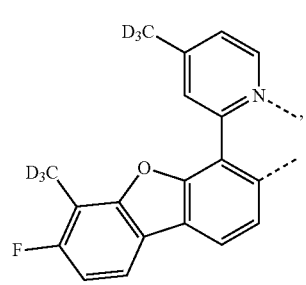
L$_{a3\text{-}55}$
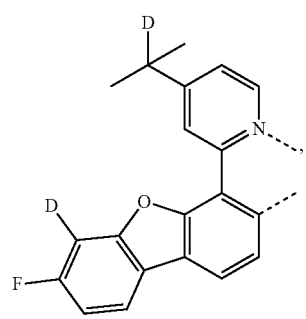
L$_{a3\text{-}56}$
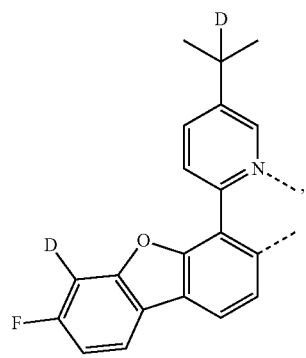
L$_{a3\text{-}57}$
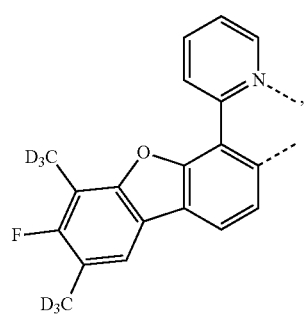
L$_{a3\text{-}58}$
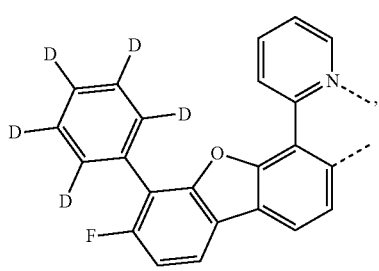
L$_{a3\text{-}59}$
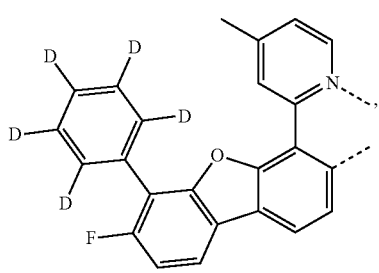
L$_{a3\text{-}60}$
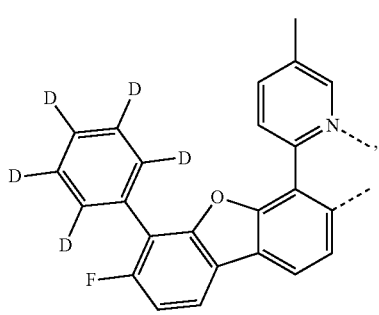
L$_{a3\text{-}61}$
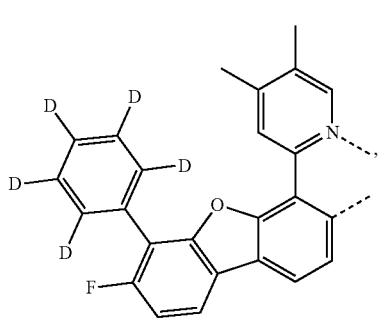
L$_{a3\text{-}62}$
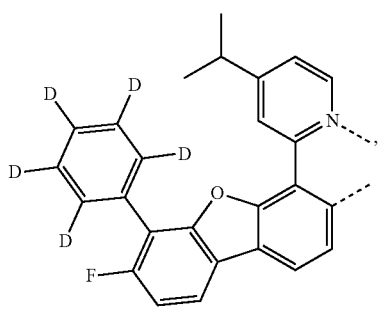

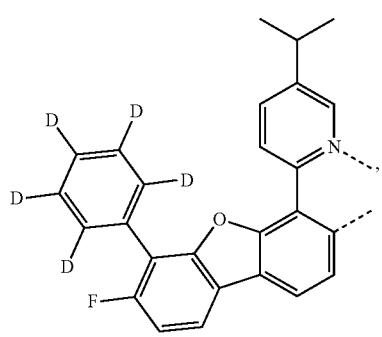 L<sub>a3-63</sub>
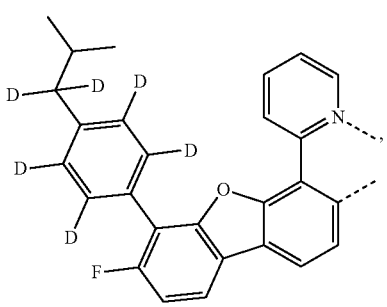 L<sub>a3-64</sub>
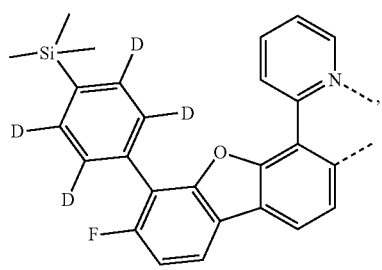 L<sub>a3-65</sub>
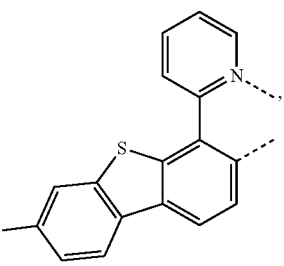 L<sub>a3-66</sub>
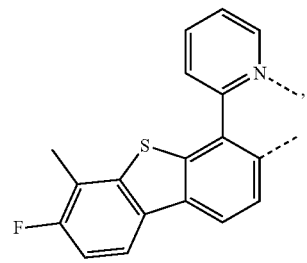 L<sub>a3-67</sub>
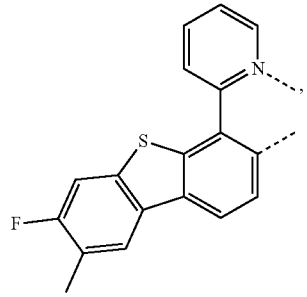 L<sub>a3-68</sub>
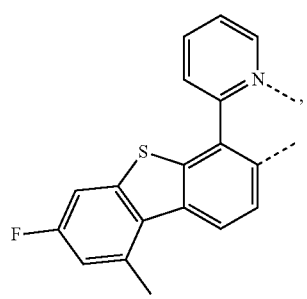 L<sub>a3-69</sub>
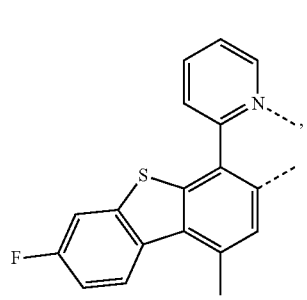 L<sub>a3-70</sub>
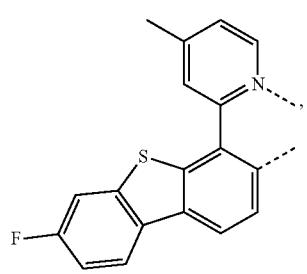 L<sub>a3-71</sub>
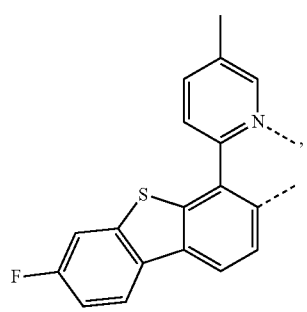 L<sub>a3-72</sub>

L*a*3-73
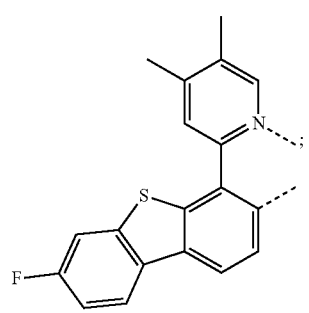
L*a*4-1
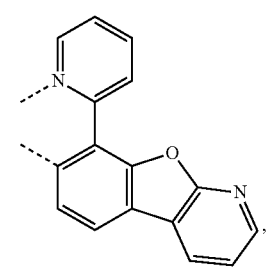
L*a*4-2
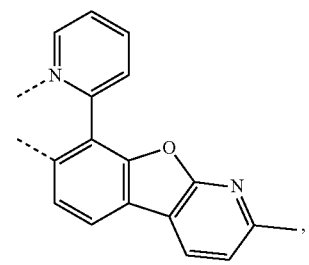
L*a*4-3
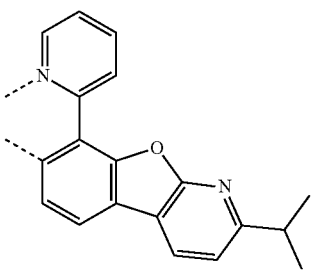
L*a*4-4
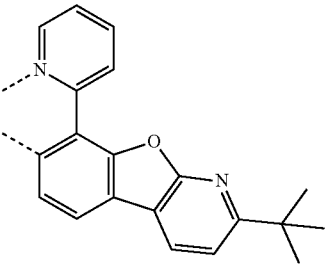
L*a*4-5
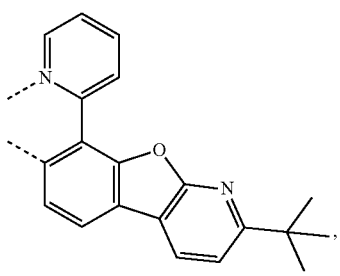
L*a*4-6
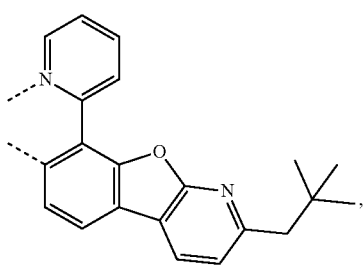
L*a*4-7
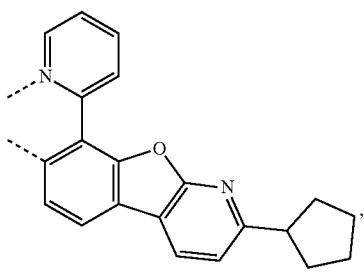
L*a*4-8
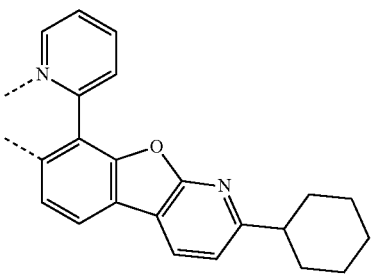
L*a*4-9
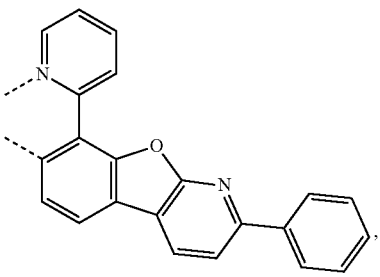

L<sub>a4-10</sub>
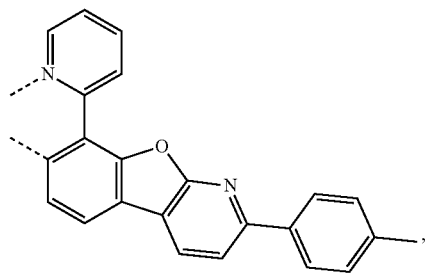
L<sub>a4-11</sub>
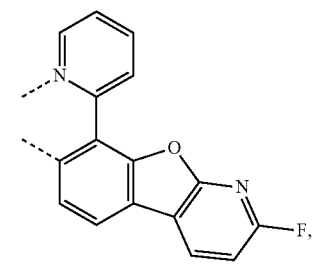
L<sub>a4-12</sub>
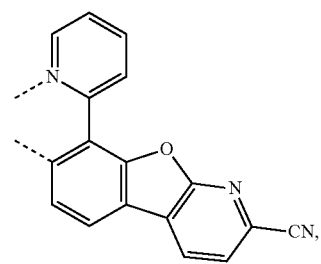
L<sub>a4-13</sub>
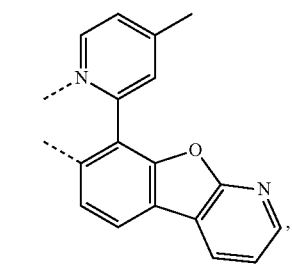
L<sub>a4-14</sub>
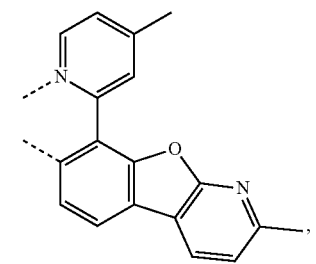
L<sub>a4-15</sub>
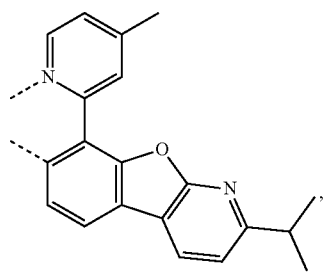
L<sub>a4-16</sub>
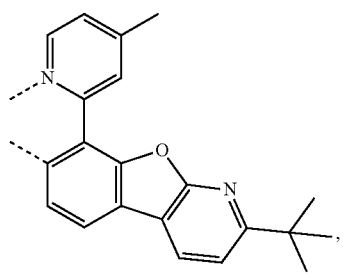
L<sub>a4-17</sub>
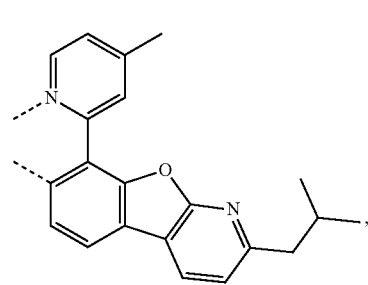
L<sub>a4-18</sub>
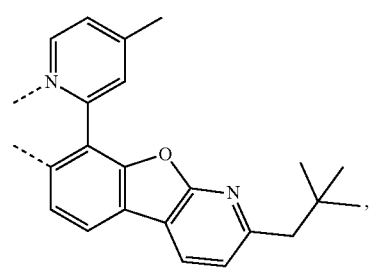
L<sub>a4-19</sub>
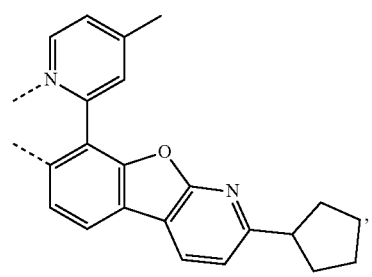
L<sub>a4-20</sub>
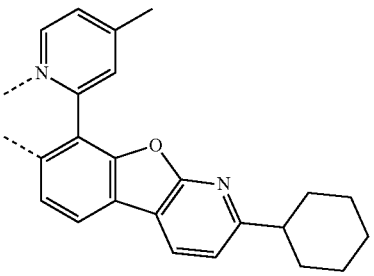

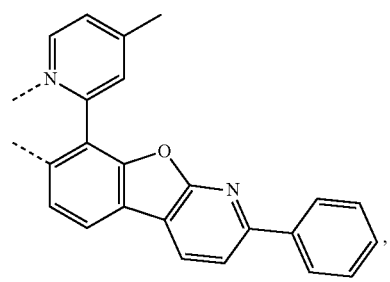
L_{a4-21}
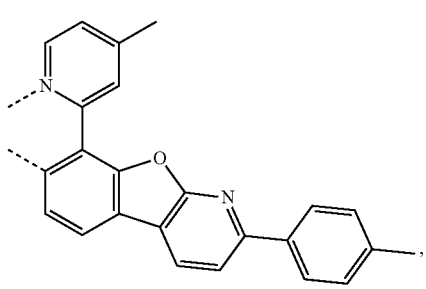
L_{a4-22}
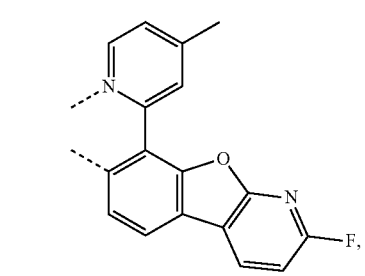
L_{a4-23}
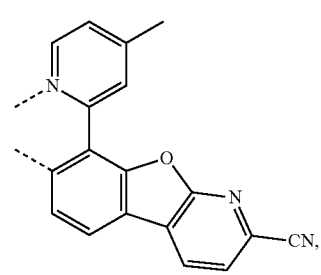
L_{a4-24}
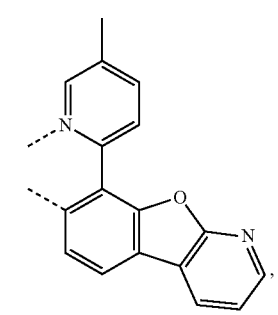
L_{a4-25}
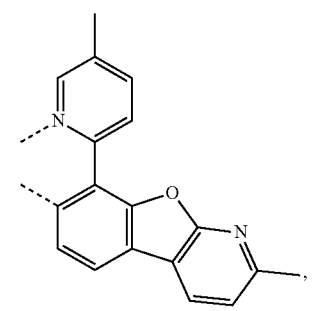
L_{a4-26}
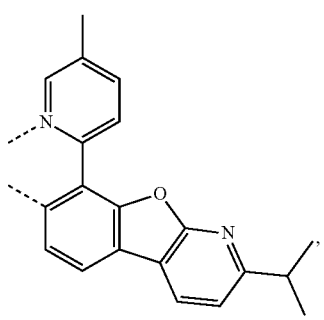
L_{a4-27}
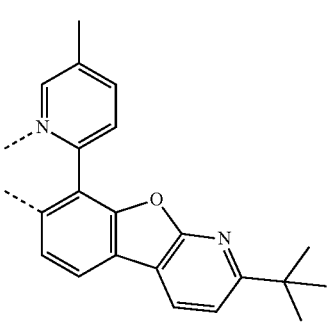
L_{a4-28}
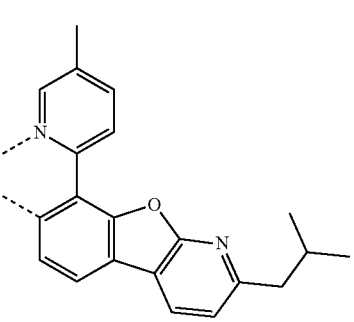
L_{a4-29}
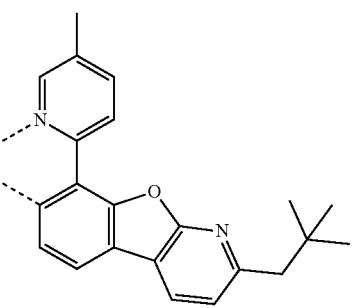
L_{a4-30}

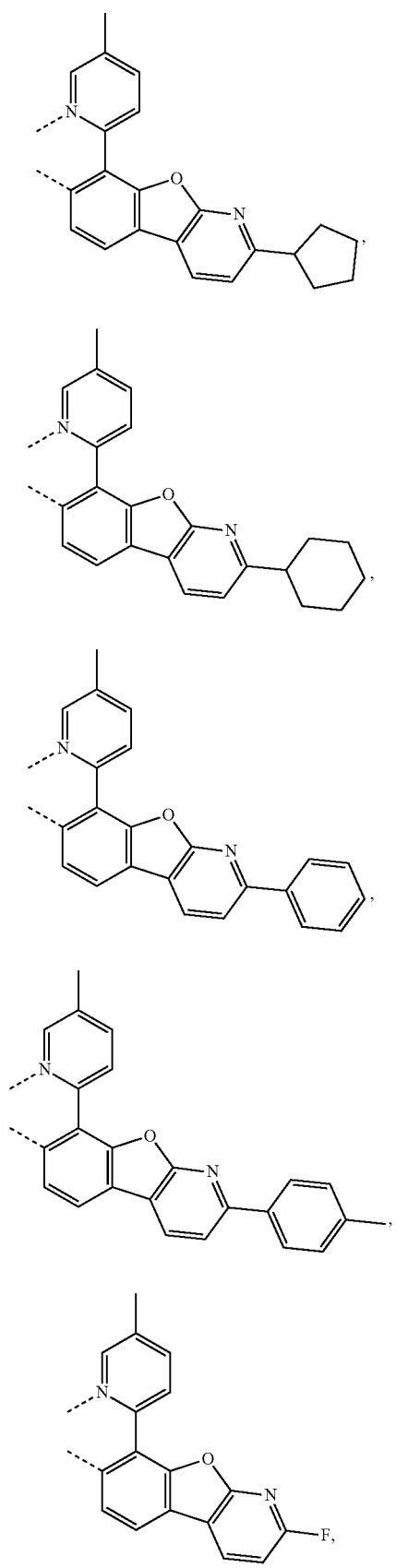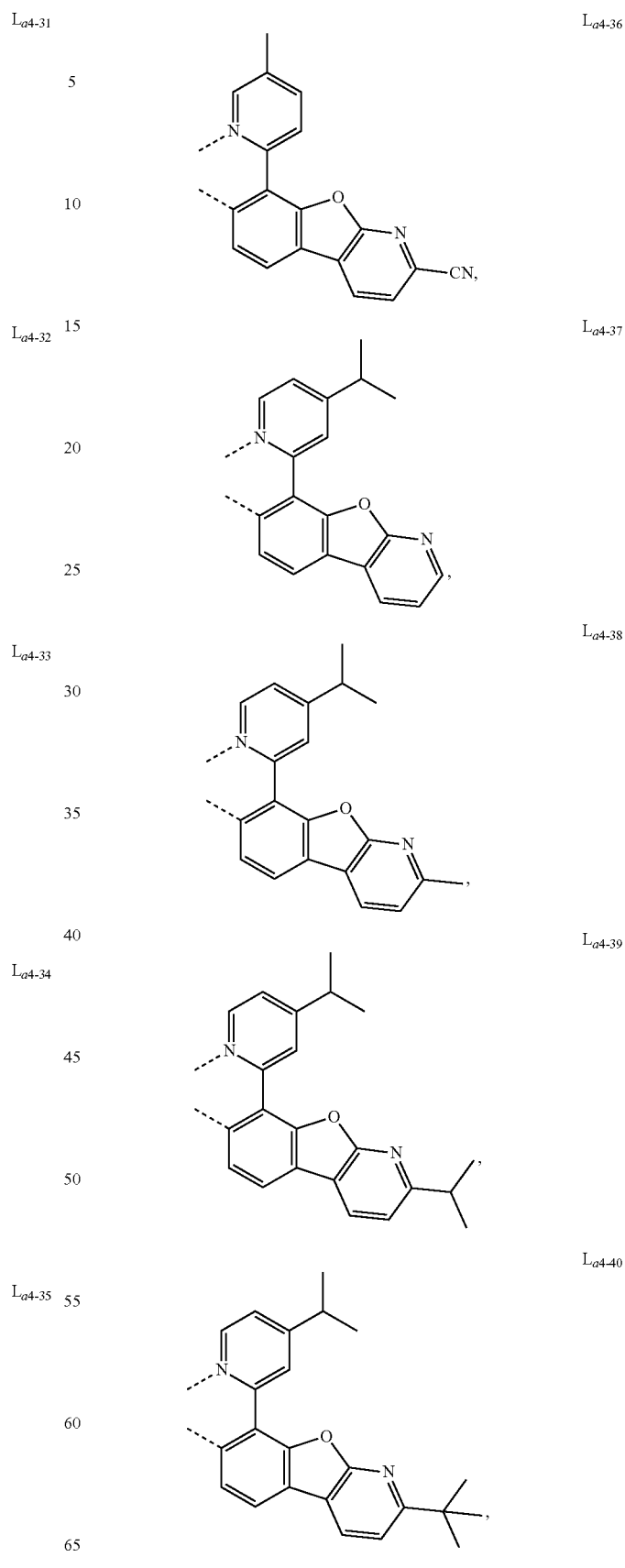

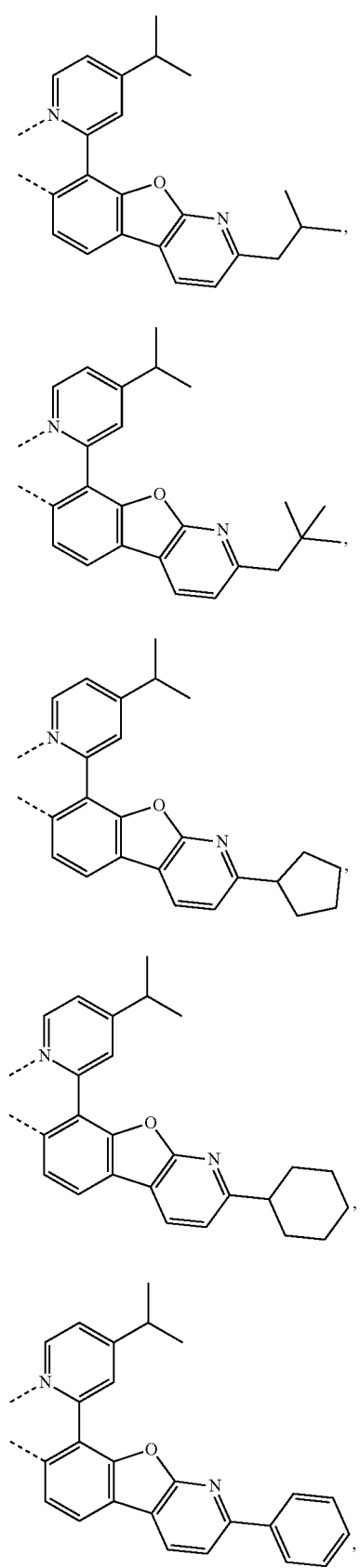
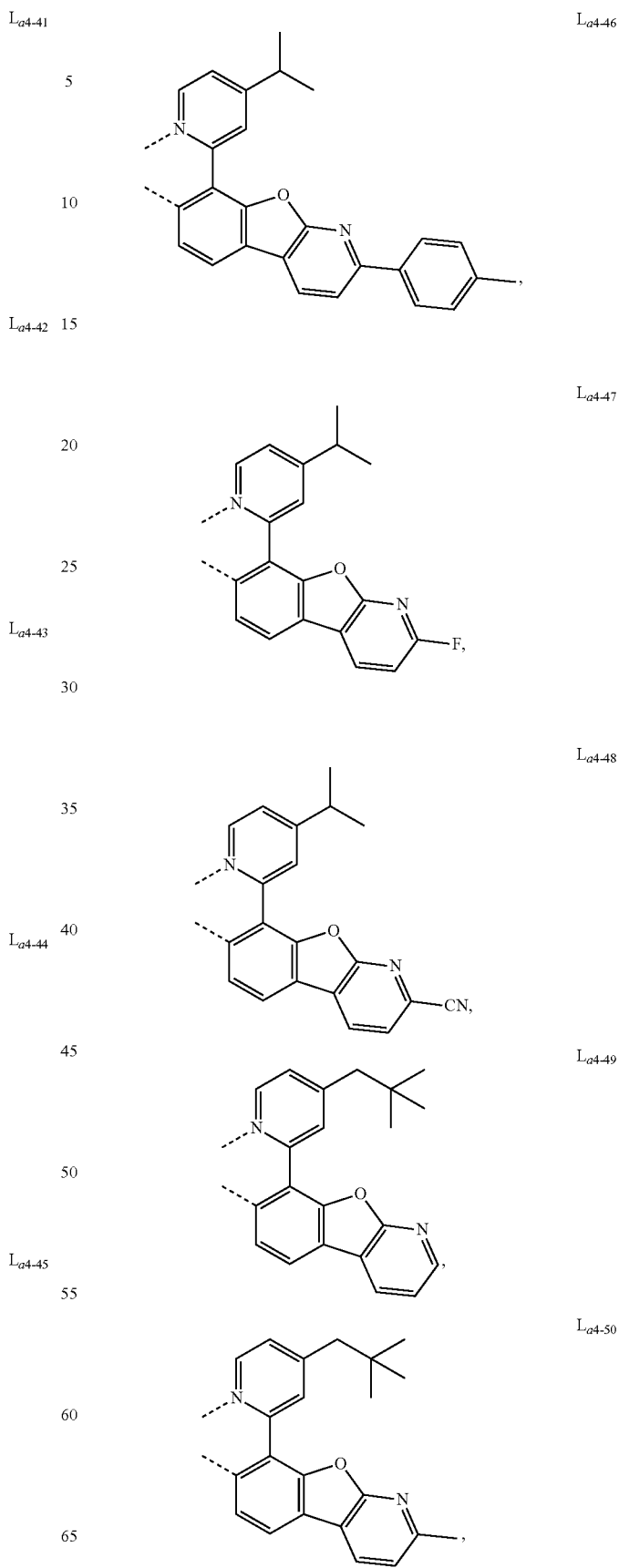

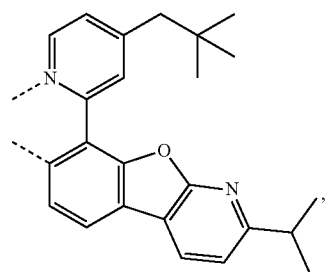
$L_{a4-51}$
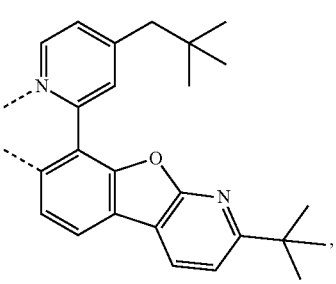
$L_{a4-52}$
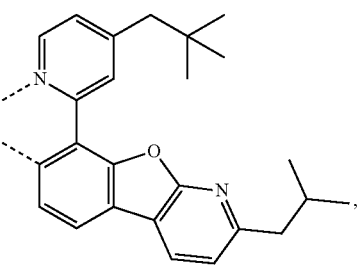
$L_{a4-53}$
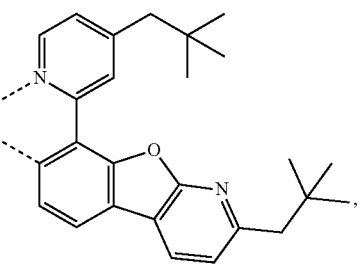
$L_{a4-54}$
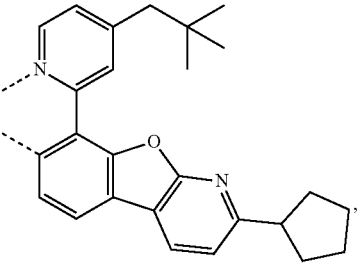
$L_{a4-55}$
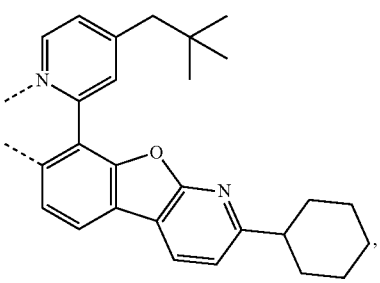
$L_{a4-56}$
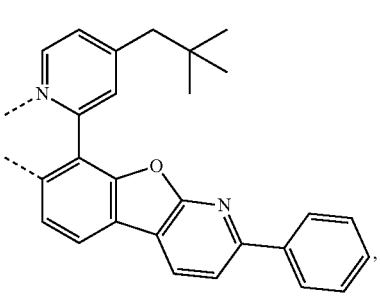
$L_{a4-57}$
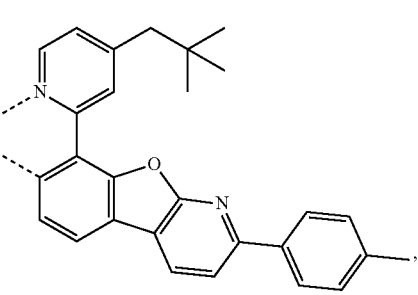
$L_{a4-58}$
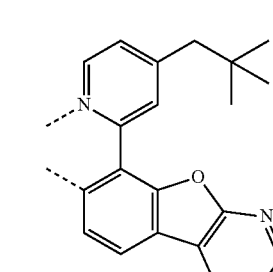
$L_{a4-59}$
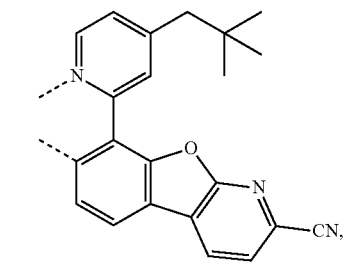
$L_{a4-60}$ L<sub>a4-61</sub>
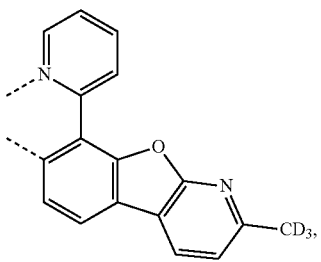
L<sub>a4-62</sub>
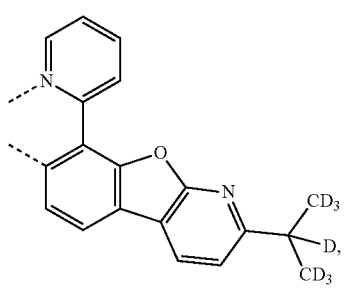
L<sub>a4-63</sub>
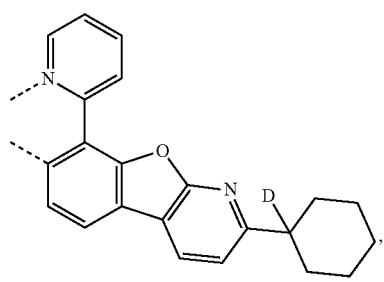
L<sub>a4-64</sub>
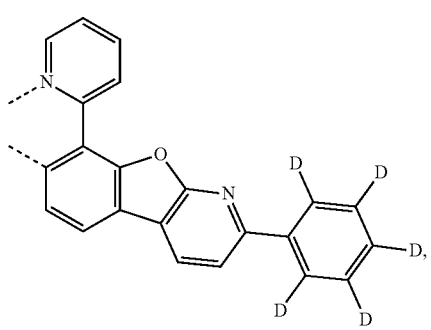
L<sub>a4-65</sub>
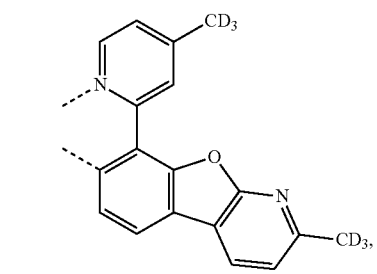
L<sub>a4-66</sub>
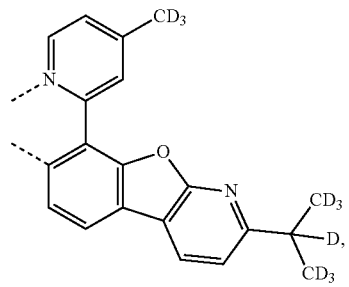
L<sub>a4-67</sub>
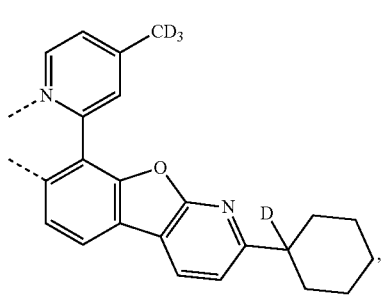
L<sub>a4-68</sub>
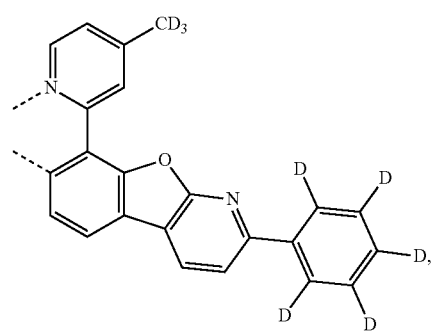
L<sub>a4-69</sub>
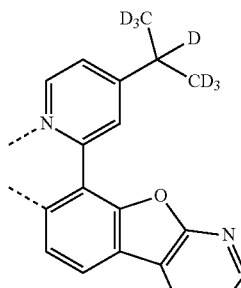
L<sub>a4-70</sub>
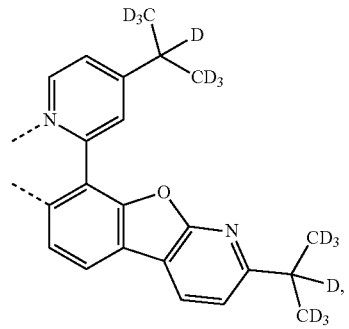

L<sub>a4-71</sub>
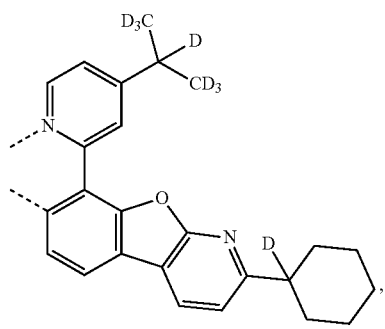
L<sub>a4-72</sub>
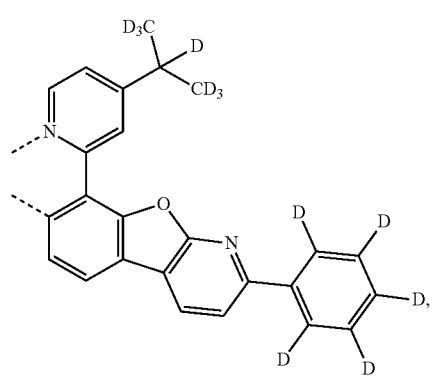
L<sub>a4-73</sub>
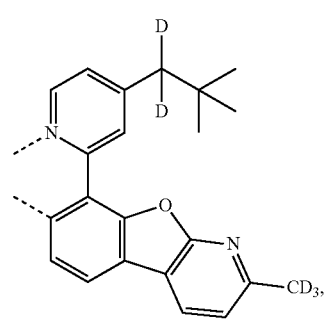
L<sub>a4-74</sub>
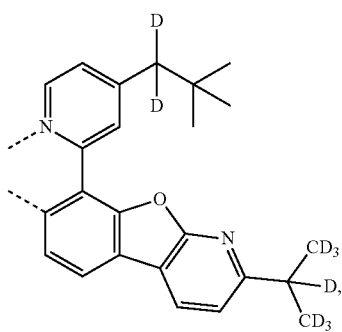
L<sub>a4-75</sub>
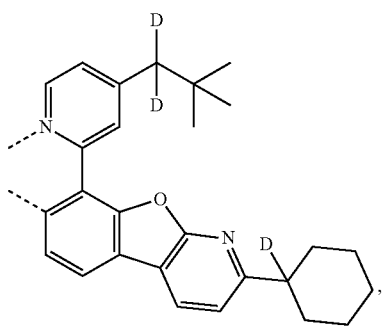
L<sub>a4-76</sub>
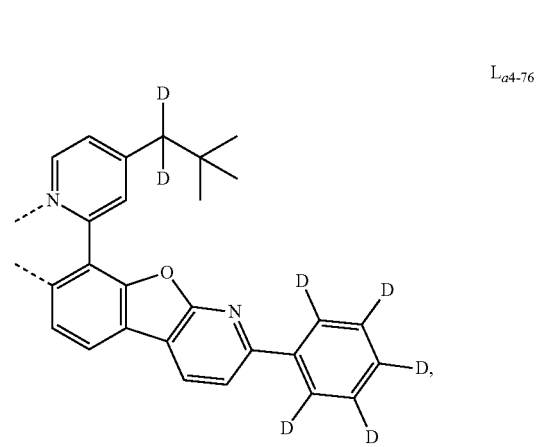
L<sub>a4-77</sub>
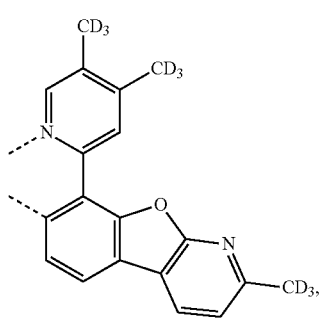
L<sub>a4-78</sub>
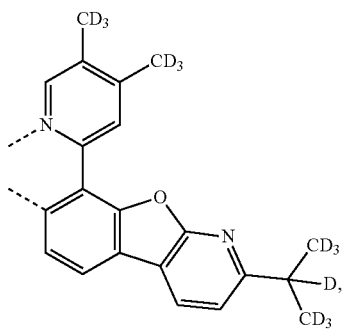

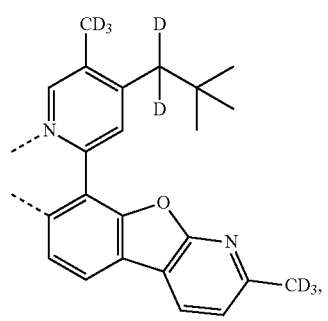
L*a*4-79
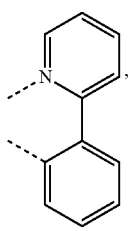
L*b*1
L*a*4-80
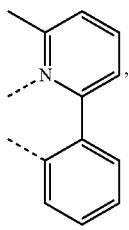
L*b*2
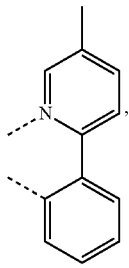
L*b*3
L*a*4-81
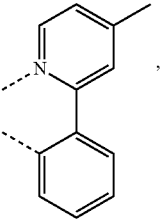
L*b*4
L*a*4-82
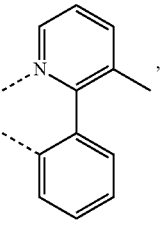
L*b*5
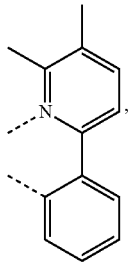
L*b*6
17. The organic electroluminescent device according to claim 11, wherein the ligands L*b* and L*c* are, at each occurrence identically or differently, selected from the group consisting of the following:

-continued
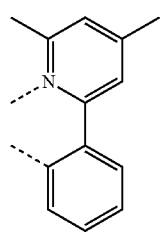, L_{b7}
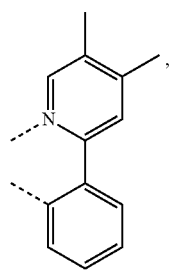, L_{b8}
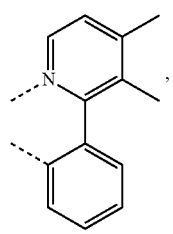, L_{b9}
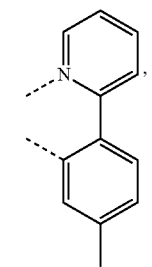, L_{b10}
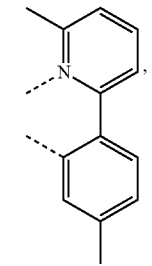, L_{b11}
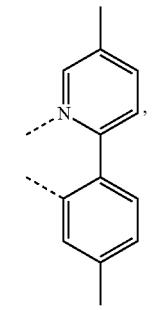, L_{b12}
-continued
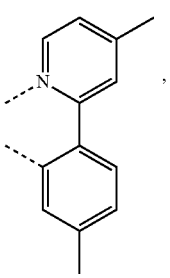, L_{b13}
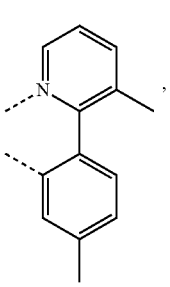, L_{b14}
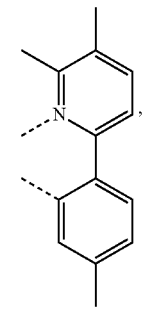, L_{b15}
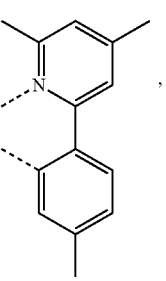, L_{b16}
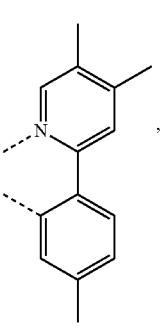, L_{b17}

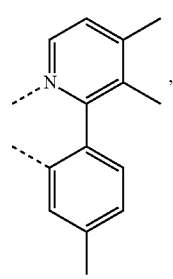 $L_{b18}$,
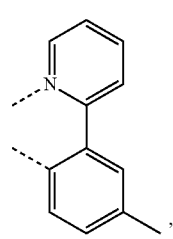 $L_{b19}$,
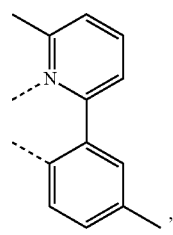 $L_{b20}$,
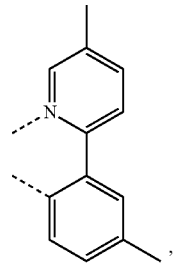 $L_{b21}$,
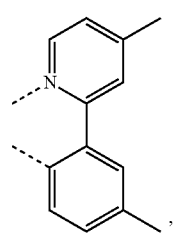 $L_{b22}$,
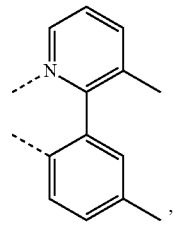 $L_{b23}$,
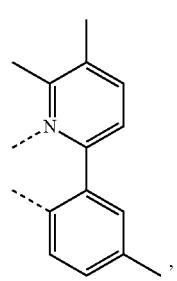 $L_{b24}$,
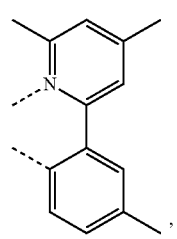 $L_{b25}$,
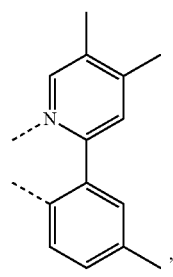 $L_{b26}$,
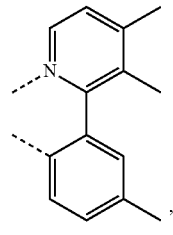 $L_{b27}$,
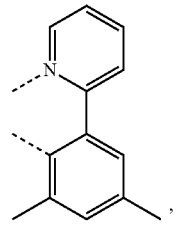 $L_{b28}$,
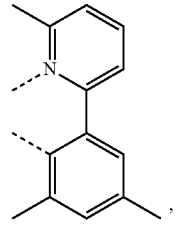 $L_{b29}$,

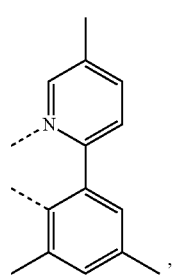 L$_{b30}$,
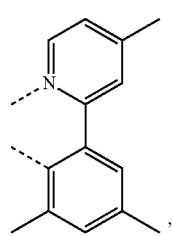 L$_{b31}$,
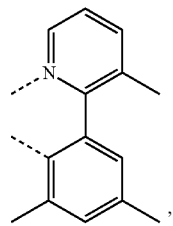 L$_{b32}$,
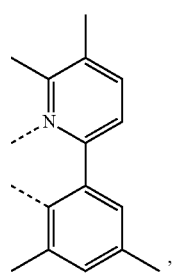 L$_{b33}$,
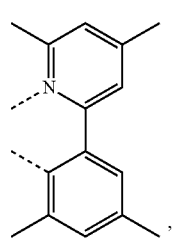 L$_{b34}$,
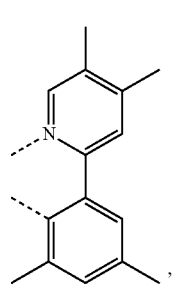 L$_{b35}$,
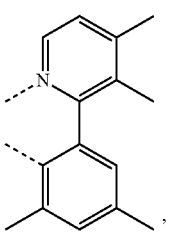 L$_{b36}$,
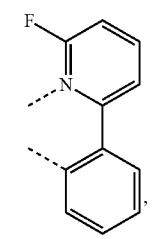 L$_{b37}$,
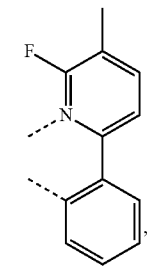 L$_{b38}$,
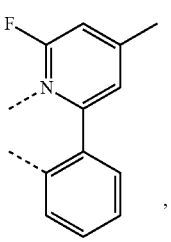 L$_{b39}$,
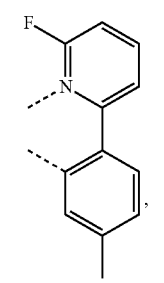 L$_{b40}$,
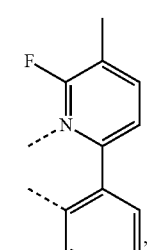 L$_{b41}$

| | |
|---|---|
| 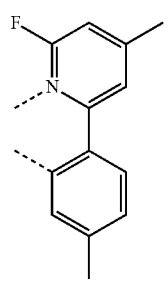 L$_{b42}$ | 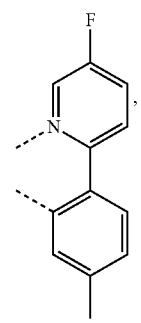 L$_{b47}$ |
| 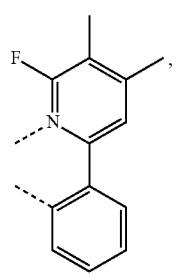 L$_{b43}$ | 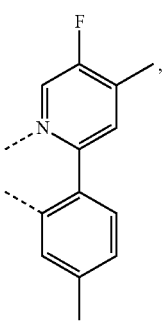 L$_{b48}$ |
| 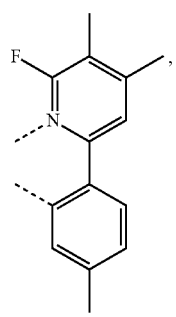 L$_{b44}$ | 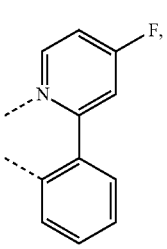 L$_{b49}$ |
| 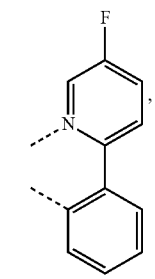 L$_{b45}$ | 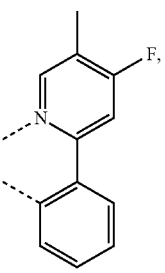 L$_{b50}$ |
| 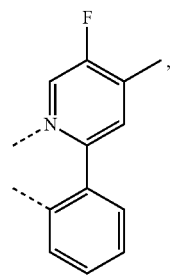 L$_{b46}$ | 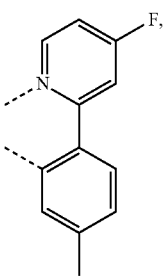 L$_{b51}$ |

| | |
|---|---|
| 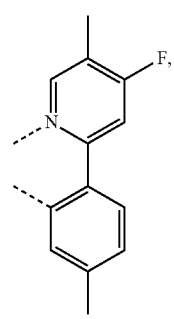 | $L_{b52}$ |
| 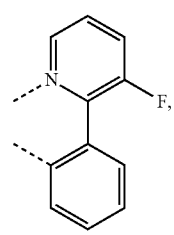 | $L_{b53}$ |
| 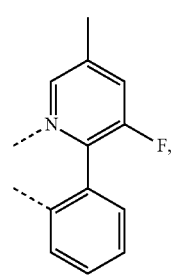 | $L_{b54}$ |
| 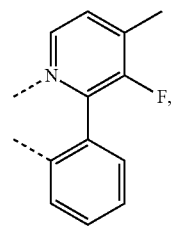 | $L_{b55}$ |
| 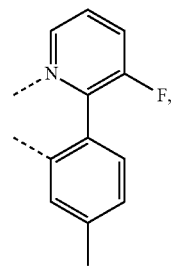 | $L_{b56}$ |
| 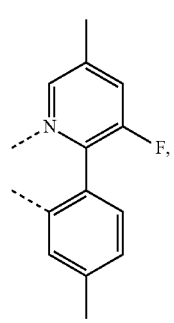 | $L_{b57}$ |
| 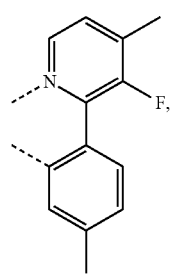 | $L_{b58}$ |
| 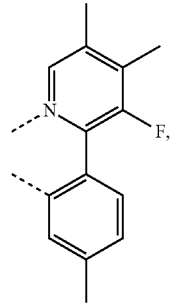 | $L_{b59}$ |
| 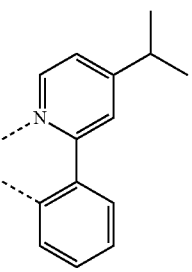 | $L_{b60}$ |
| 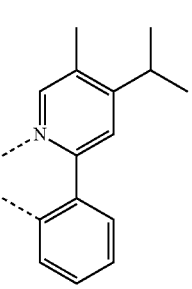 | $L_{b61}$ |

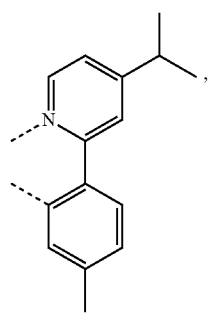 L<sub>b62</sub>
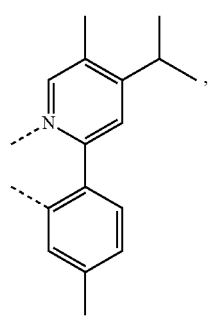 L<sub>b63</sub>
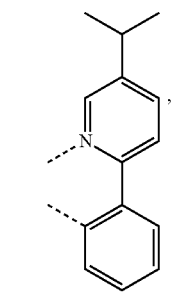 L<sub>b64</sub>
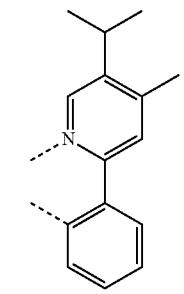 L<sub>b65</sub>
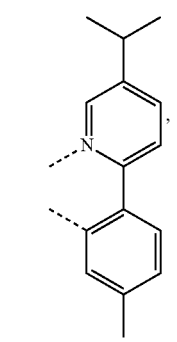 L<sub>b66</sub>
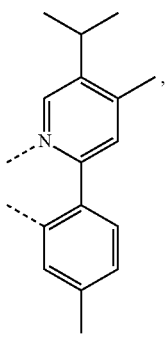 L<sub>b67</sub>
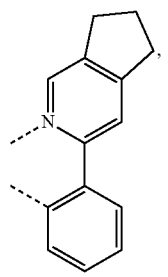 L<sub>b68</sub>
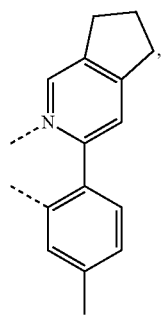 L<sub>b69</sub>
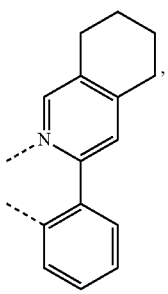 L<sub>b70</sub>
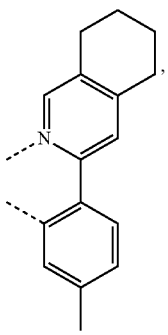 L<sub>b71</sub>

-continued
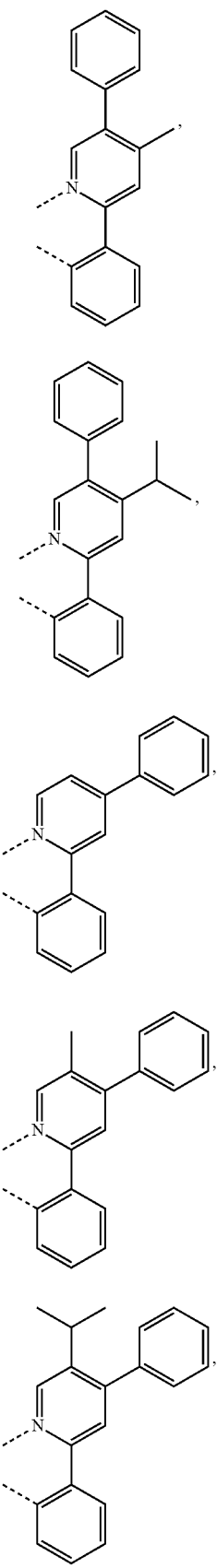
L<sub>b72</sub>
L<sub>b73</sub>
L<sub>b74</sub>
L<sub>b75</sub>
L<sub>b76</sub>
-continued
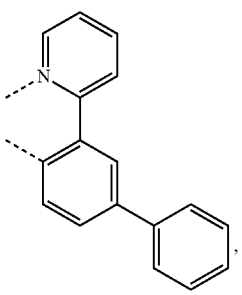
L<sub>b77</sub>
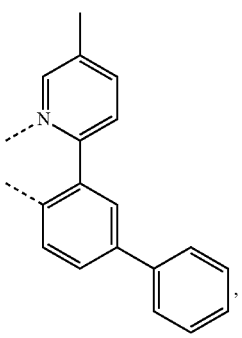
L<sub>b78</sub>
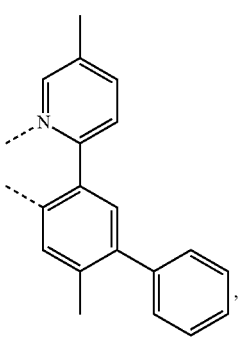
L<sub>b79</sub>
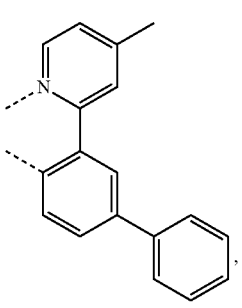
L<sub>b80</sub>
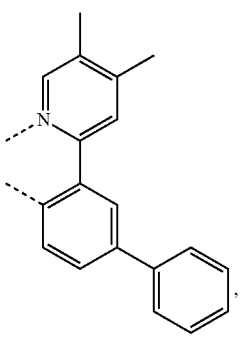
L<sub>b81</sub>

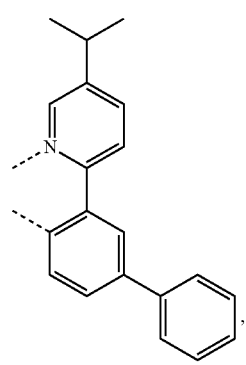
L_{b82}
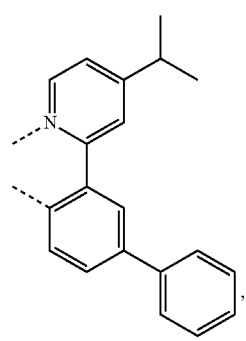
L_{b83}
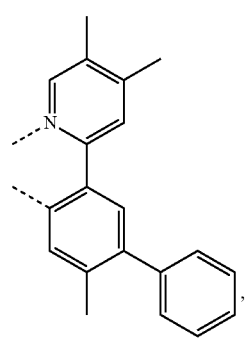
L_{b84}
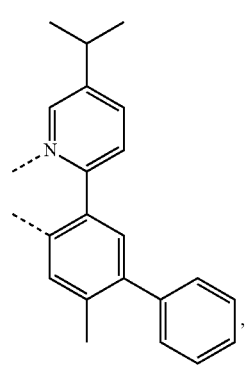
L_{b85}
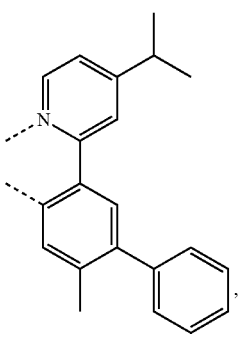
L_{b86}
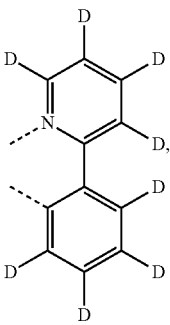
L_{b87}
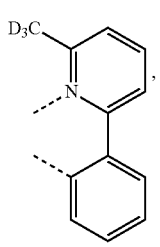
L_{b88}
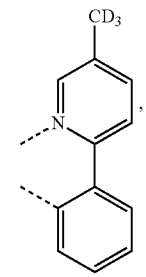
L_{b89}
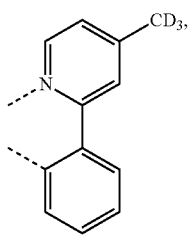
L_{b90}

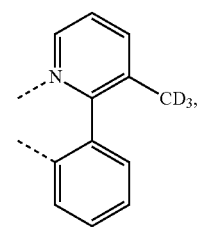 L<sub>b91</sub>
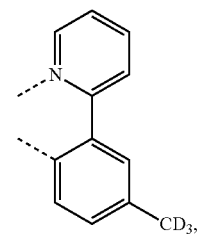 L<sub>b92</sub>
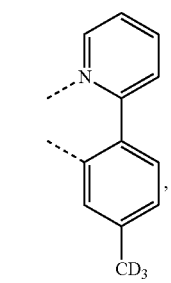 L<sub>b93</sub>
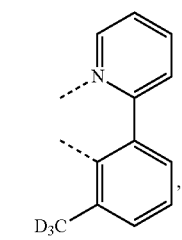 L<sub>b94</sub>
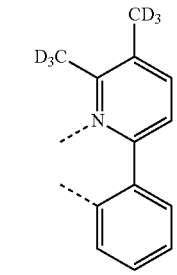 L<sub>b95</sub>
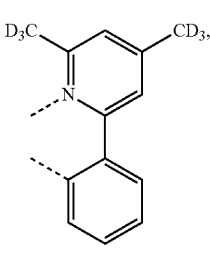 L<sub>b96</sub>
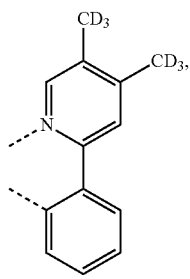 L<sub>b97</sub>
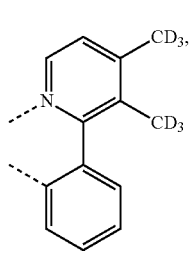 L<sub>b98</sub>
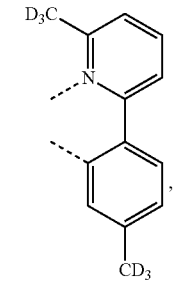 L<sub>b99</sub>
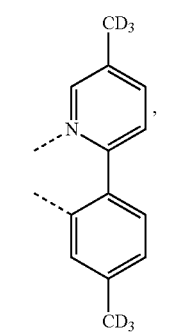 L<sub>b100</sub>
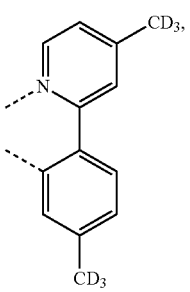 L<sub>b101</sub>

L<sub>b102</sub>
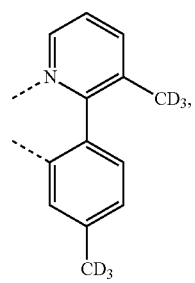
L<sub>b103</sub>
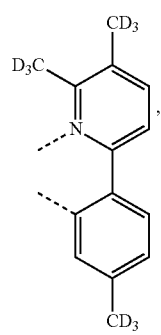
L<sub>b104</sub>
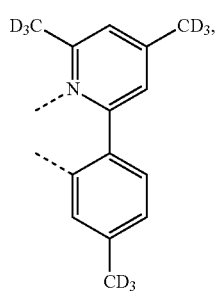
L<sub>b105</sub>
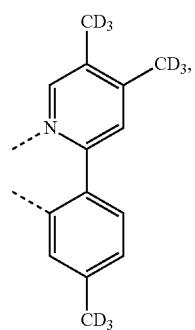
L<sub>b106</sub>
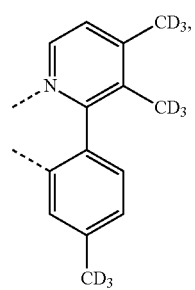

-continued
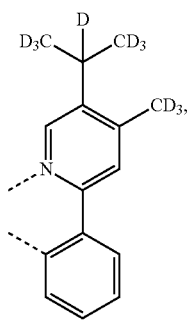 L$_{b112}$
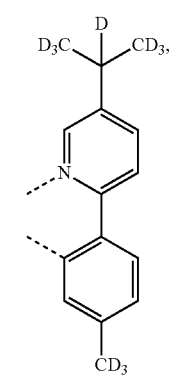 L$_{b113}$
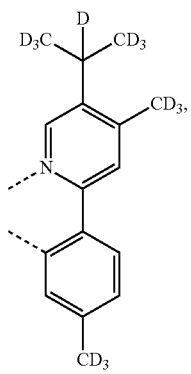 L$_{b114}$
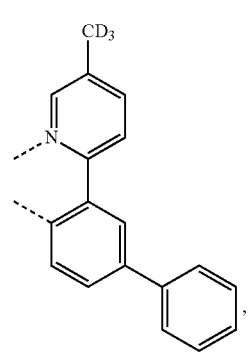 L$_{b115}$
-continued
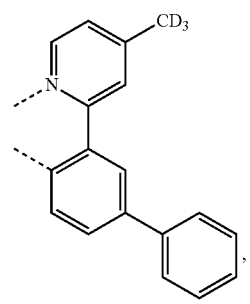 L$_{b116}$
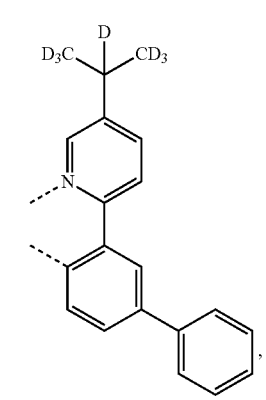 L$_{b117}$
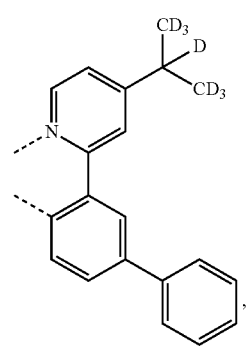 L$_{b118}$
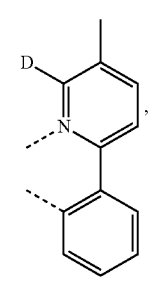 L$_{b119}$
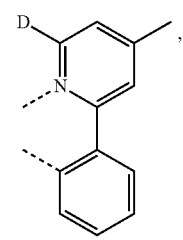 L$_{b120}$

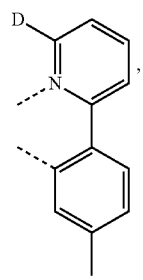 L_{b121}
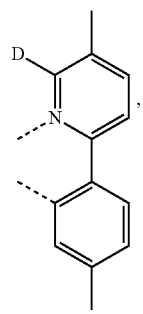 L_{b122}
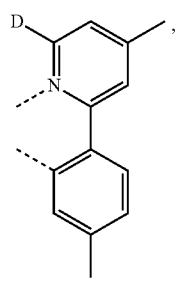 L_{b123}
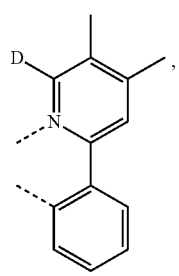 L_{b124}
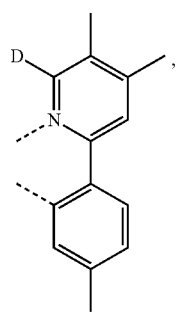 L_{b125}
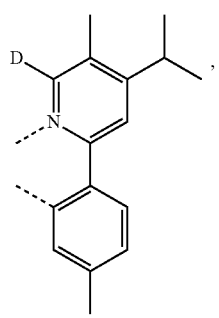 L_{b126}
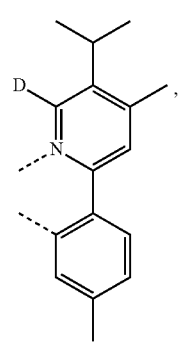 L_{b127}
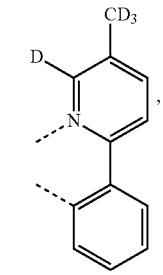 L_{b128}
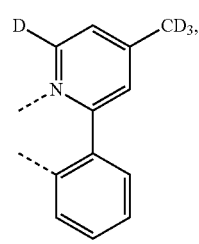 L_{b129}
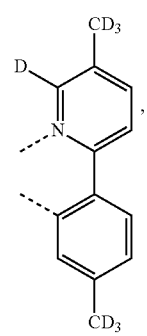 L_{b130}

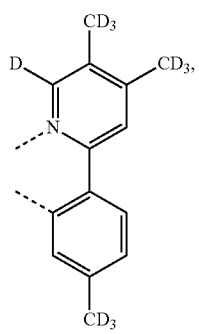 L<sub>b131</sub>
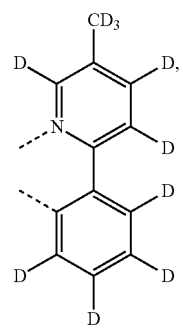 L<sub>b132</sub>
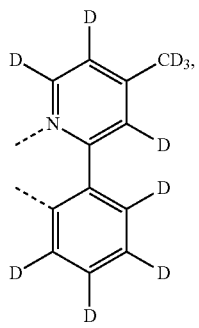 L<sub>b133</sub>
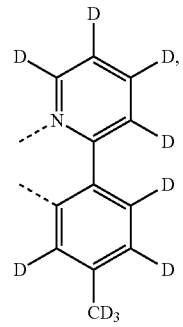 L<sub>b134</sub>
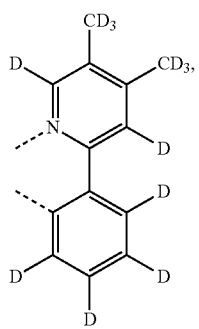 L<sub>b135</sub>
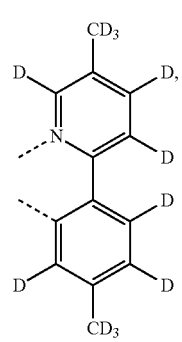 L<sub>b136</sub>
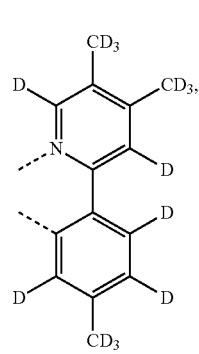 L<sub>b137</sub>
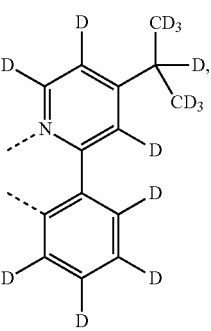 L<sub>b138</sub>
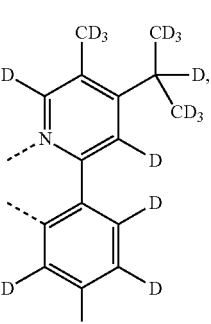 L<sub>b139</sub>
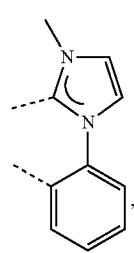 L<sub>b140</sub>

L_b141 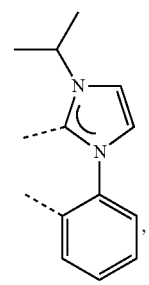
L_b142 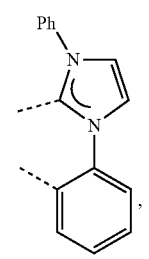
L_b143 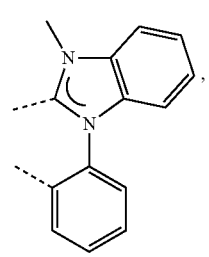
L_b144 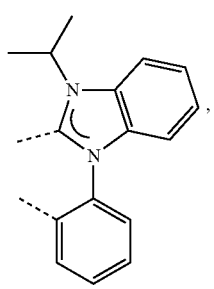
L_b145 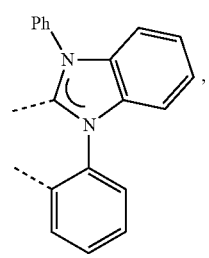
L_b146 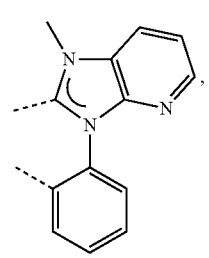
L_b147 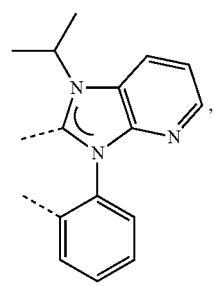
L_b148 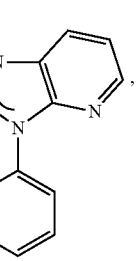
L_b149 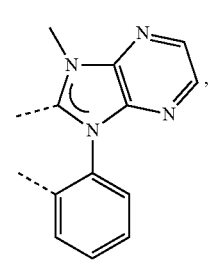
L_b150 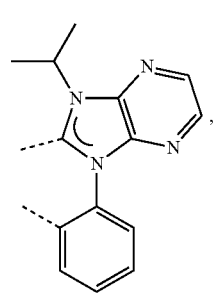
L_b151 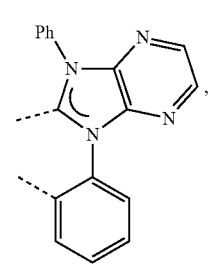
L_b152 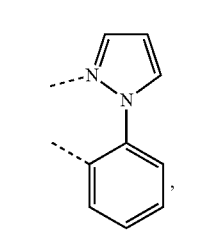

L<sub>b</sub>153 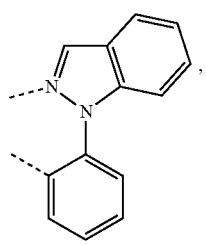
L<sub>b</sub>154 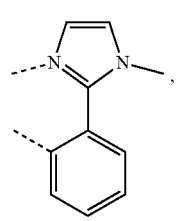
L<sub>b</sub>155 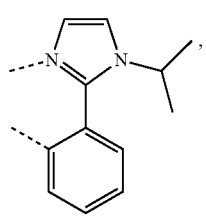
L<sub>b</sub>156 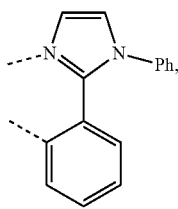
L<sub>b</sub>157 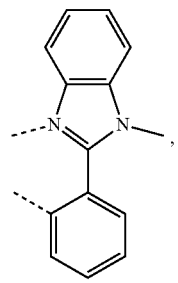
L<sub>b</sub>158 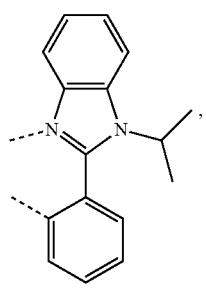
L<sub>b</sub>159 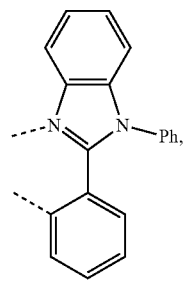
L<sub>b</sub>160 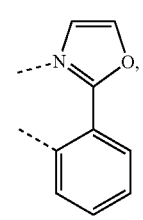
L<sub>b</sub>161 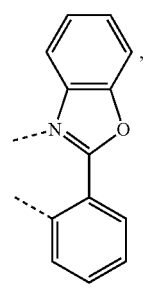
L<sub>b</sub>162 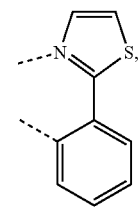
L<sub>b</sub>163 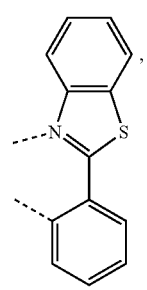
L<sub>b</sub>164 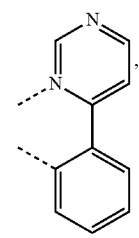

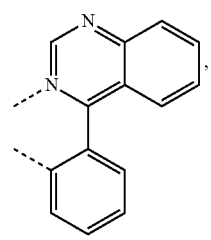 L_{b165}
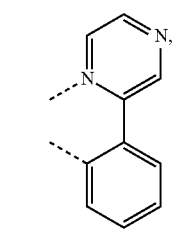 L_{b166}
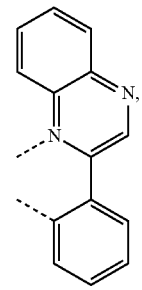 L_{b167}
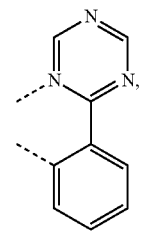 L_{b168}
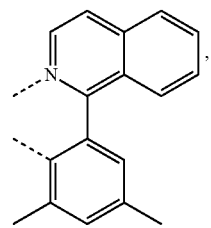 L_{b169}
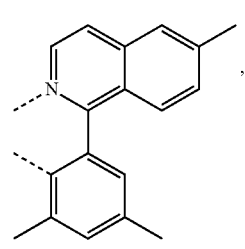 L_{b170}
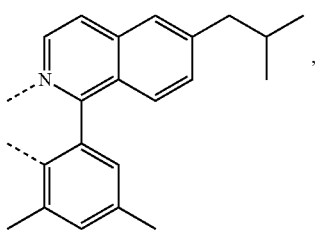 L_{b171}
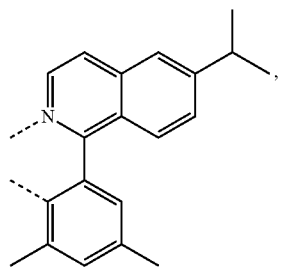 L_{b172}
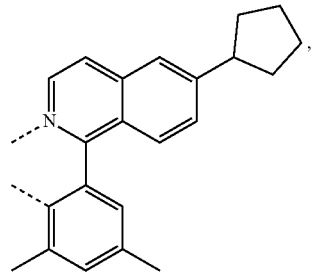 L_{b173}
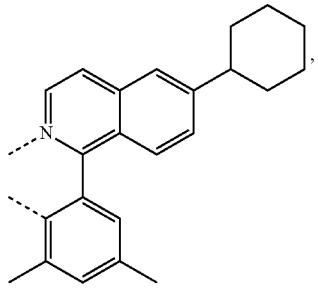 L_{b174}
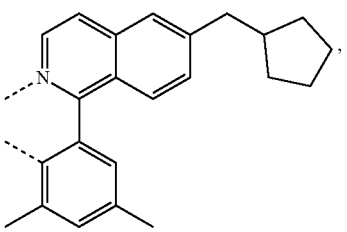 L_{b175}
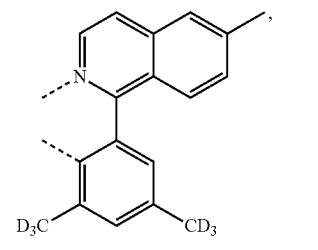 L_{b176}

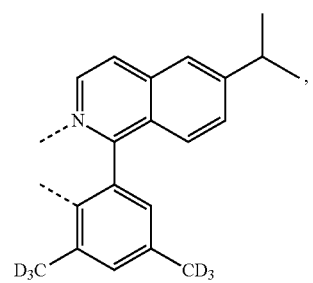  L<sub>b177</sub>
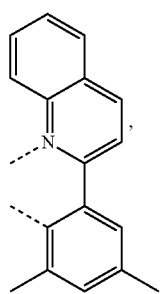  L<sub>b182</sub>
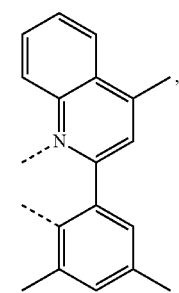  L<sub>b183</sub>
L<sub>b178</sub>
L<sub>b179</sub>
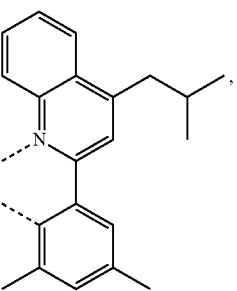  L<sub>b184</sub>
L<sub>b180</sub>
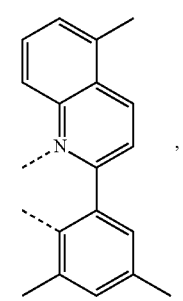  L<sub>b185</sub>
L<sub>b181</sub>
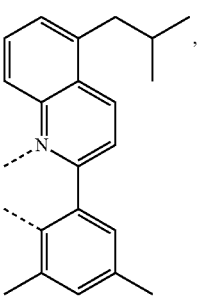  L<sub>b186</sub>

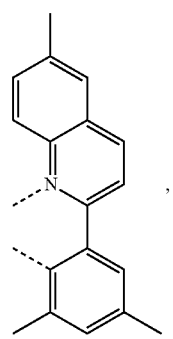
L$_{b187}$,
L$_{b188}$,
L$_{b189}$,
L$_{b190}$,
L$_{b191}$,
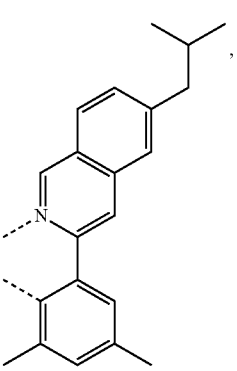
L$_{b192}$,
L$_{b193}$,
L$_{b194}$,
L$_{b195}$,

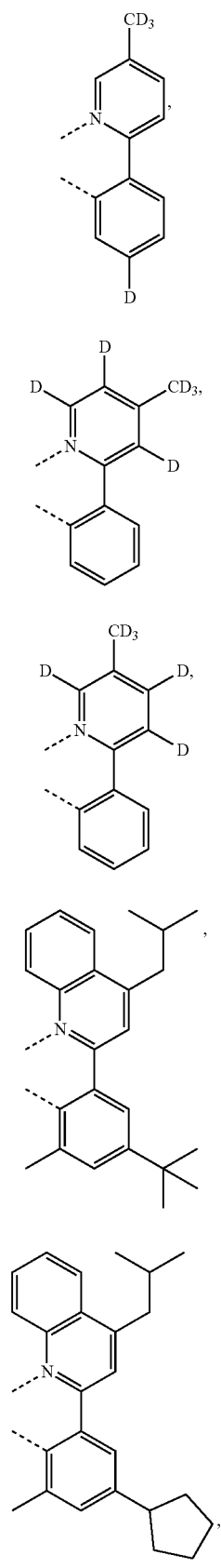
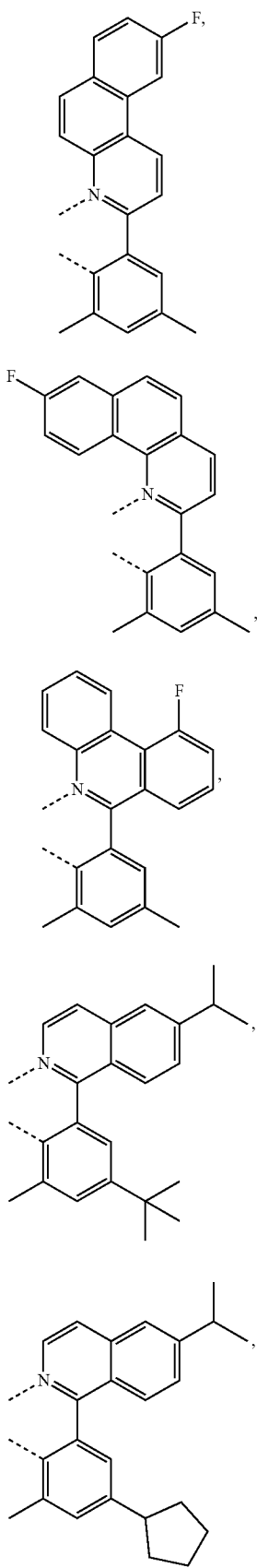

L<sub>b203</sub> 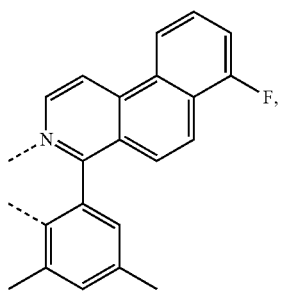
L<sub>b204</sub> 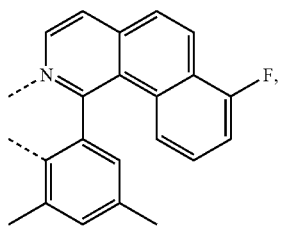
L<sub>b205</sub> 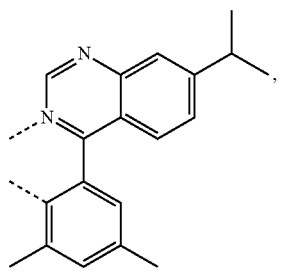
L<sub>b206</sub> 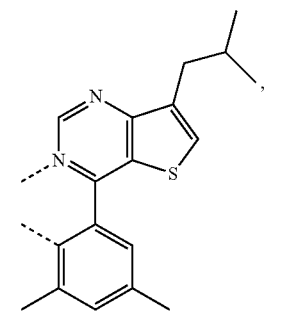
L<sub>b207</sub> 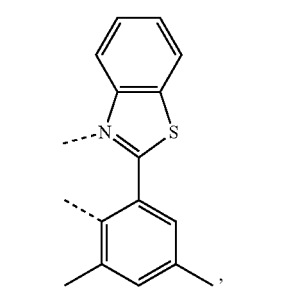
L<sub>b208</sub> 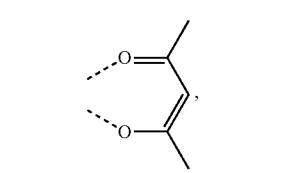
L<sub>b209</sub> 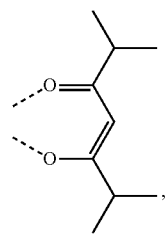
L<sub>b210</sub> 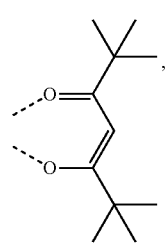
L<sub>b211</sub> 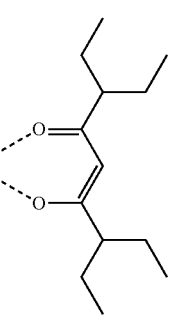
L<sub>b212</sub> 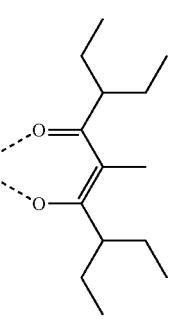
L<sub>b213</sub> 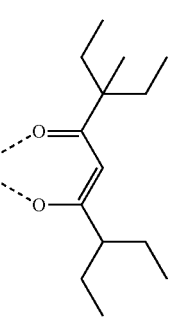

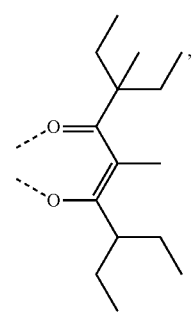
L_{b214}
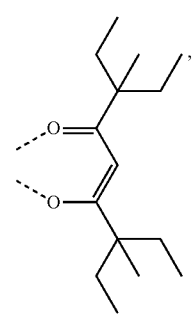
L_{b215}
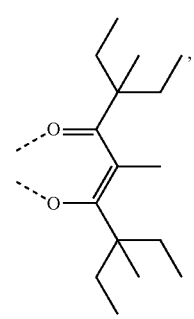
L_{b216}
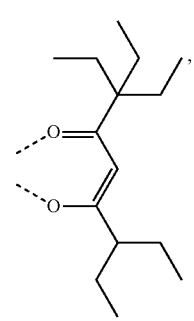
L_{b217}
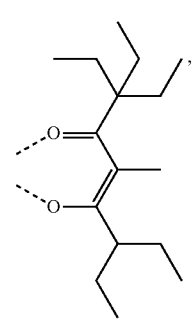
L_{b218}
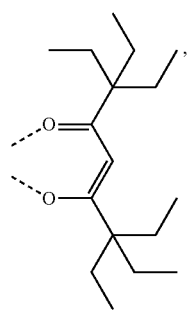
L_{b219}
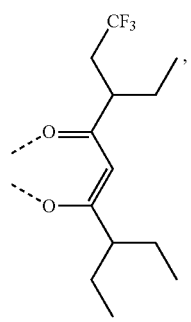
L_{b220}
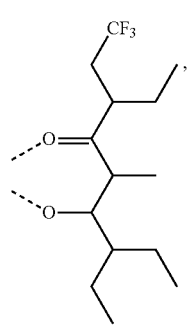
L_{b221}
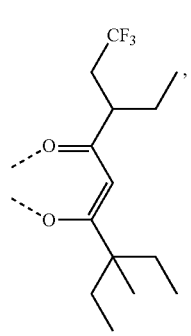
L_{b222}
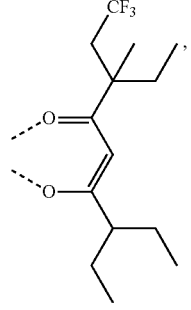
L_{b223}

-continued
L$_{b224}$ 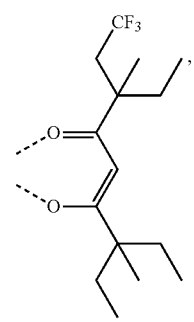
L$_{b225}$ 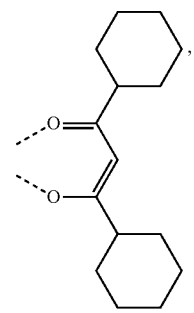
L$_{b226}$ 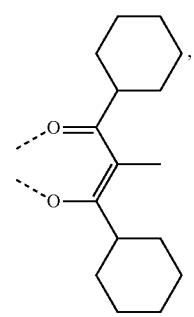
L$_{b227}$ 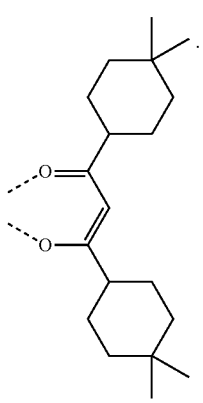
GD1-1 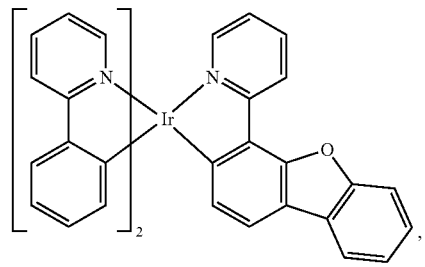
GD1-2 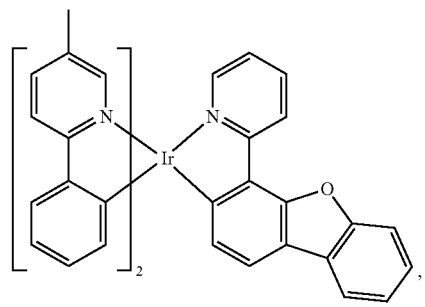
GD1-3 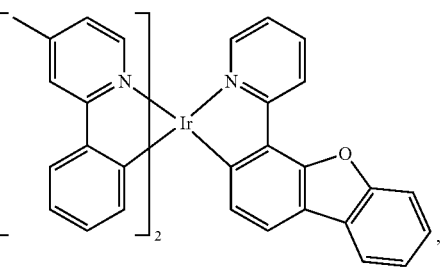
GD1-4 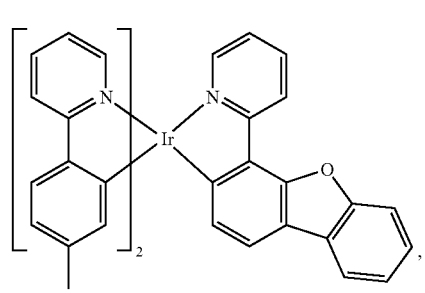
GD1-5 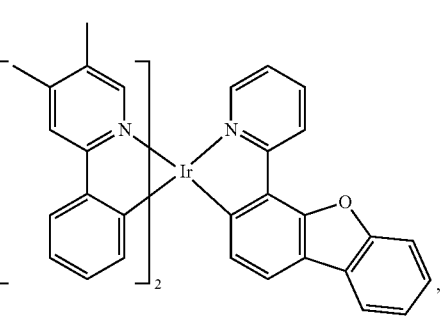
18. The organic electroluminescent device according to claim 9, wherein the first metal complex is selected from the group consisting of the following compounds:

GD1-6
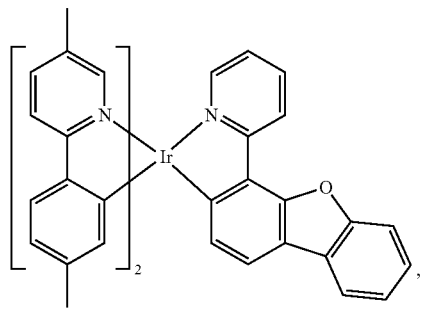
GD1-7
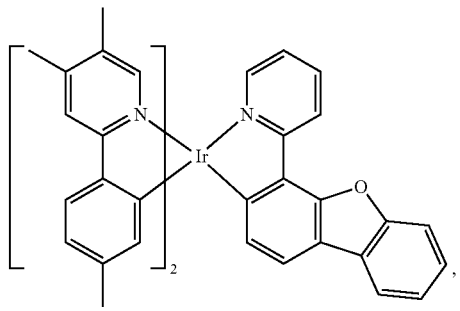
GD1-8
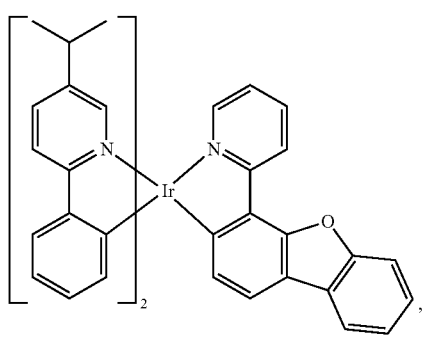
GD1-9
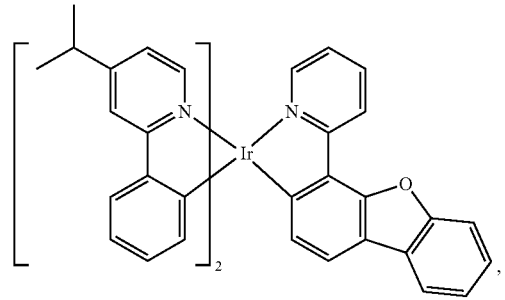
GD1-10
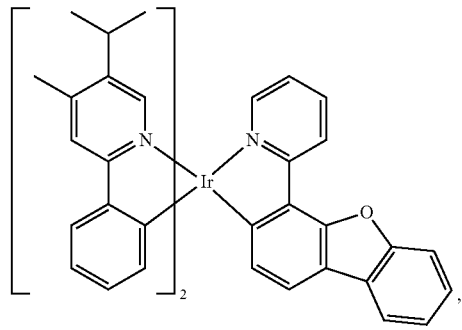
GD1-11
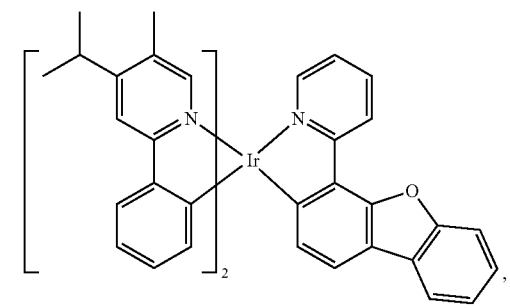
GD1-12
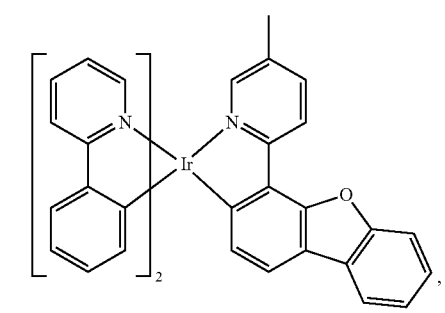
GD1-13
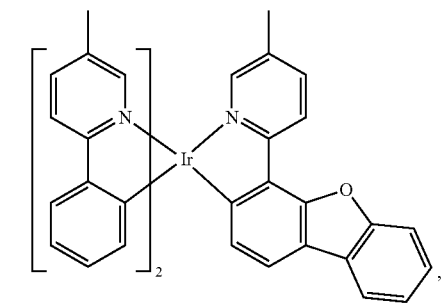
GD1-14
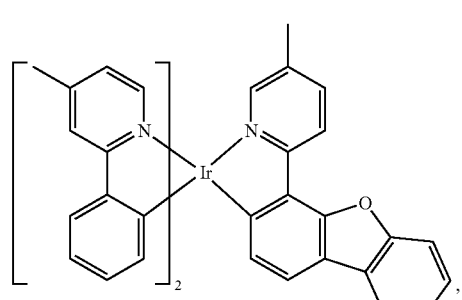

GD1-15
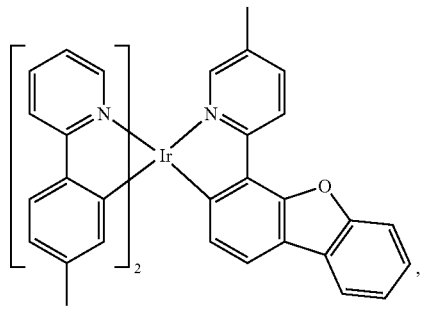
GD1-16
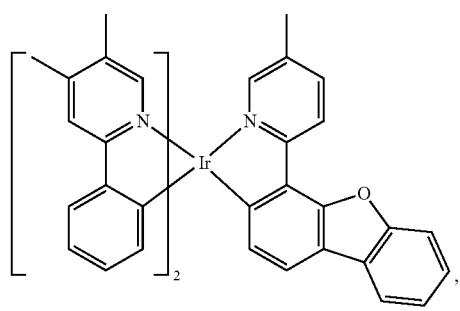
GD1-17
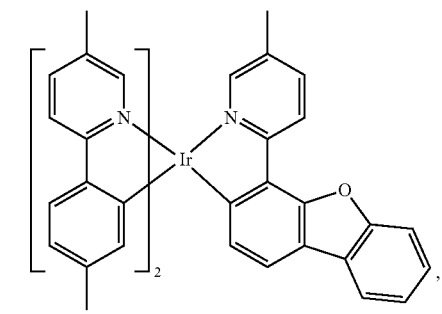
GD1-18
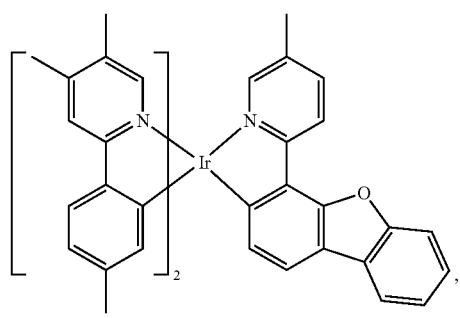
GD1-19
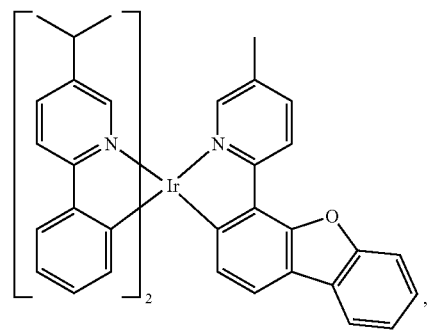
GD1-20
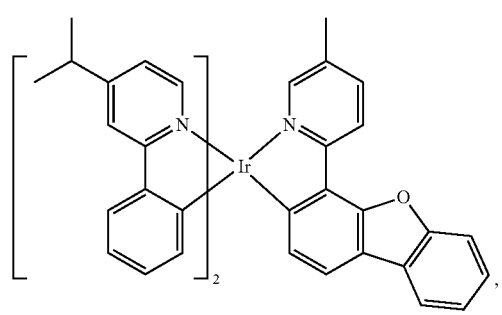
GD1-21
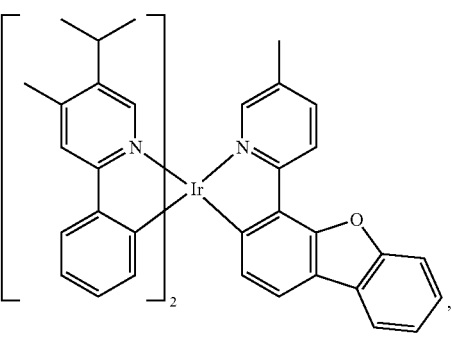
GD1-22
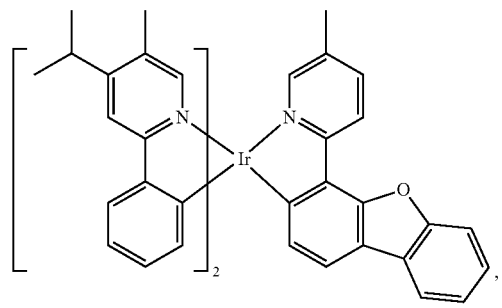
GD1-23
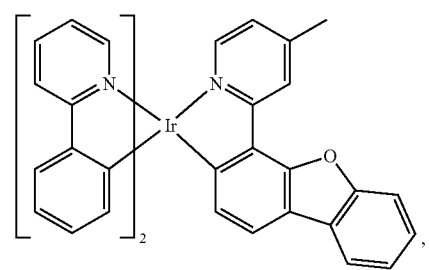

GD1-24
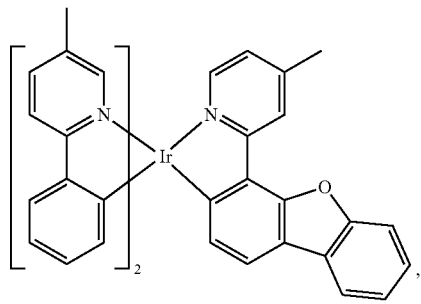
GD1-25
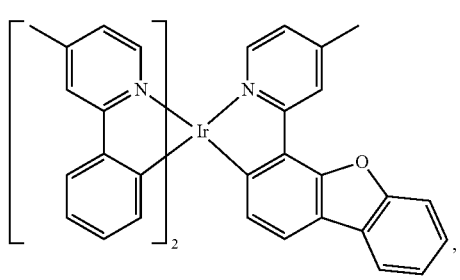
GD1-26
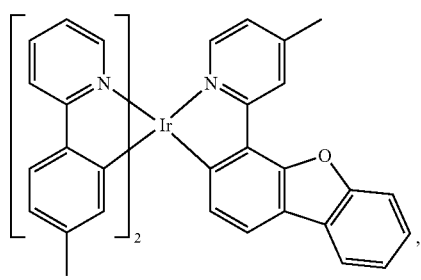
GD1-27
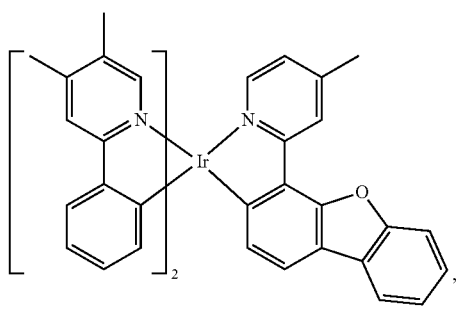
GD1-28
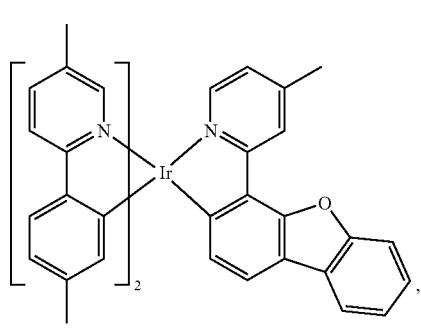
GD1-29
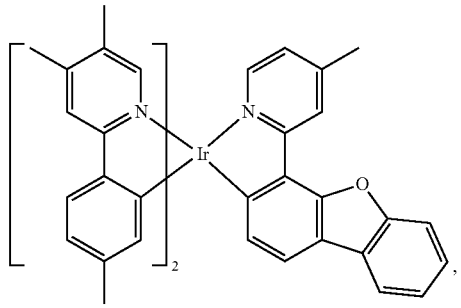
GD1-30
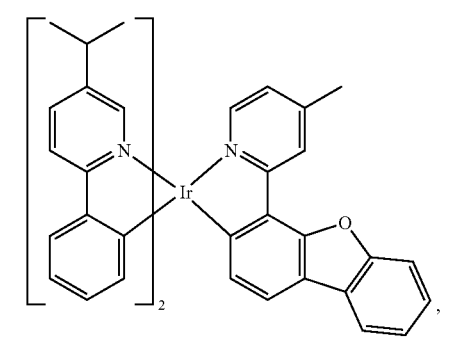
GD1-31
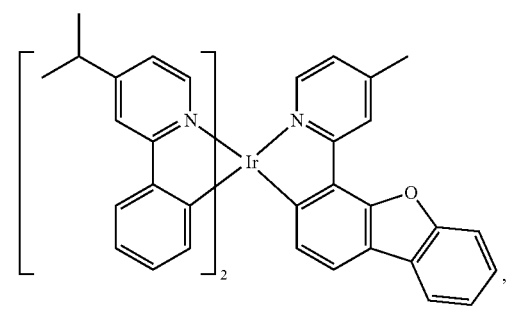
GD1-32
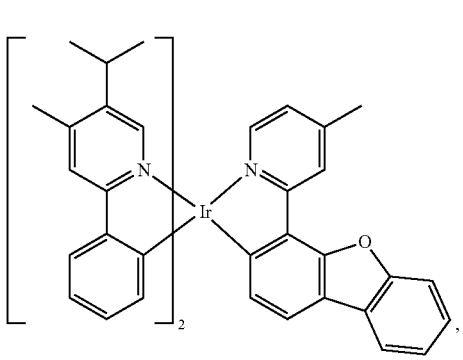

GD1-33
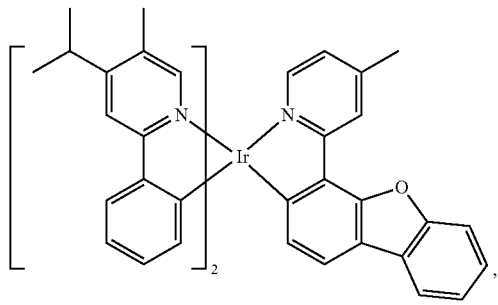
GD1-34
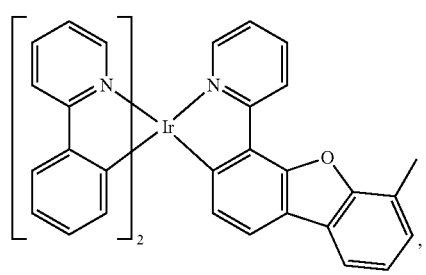
GD1-35
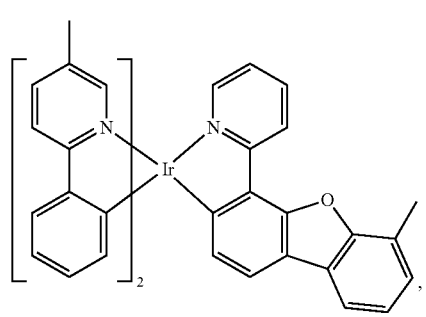
GD1-36
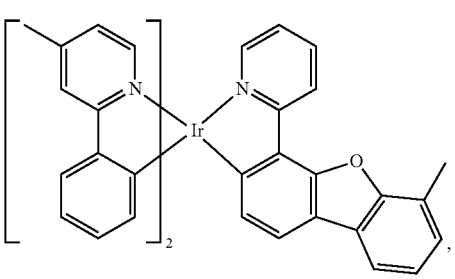
GD1-37
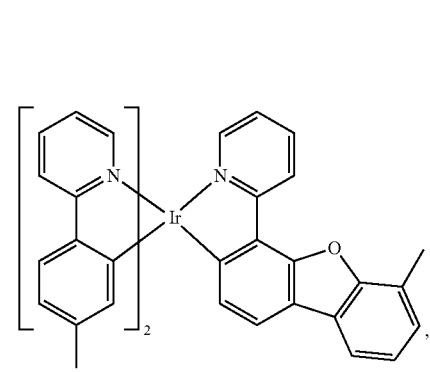
GD1-38
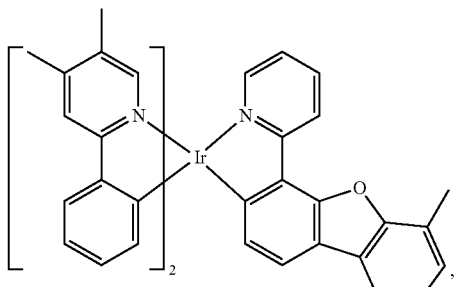
GD1-39
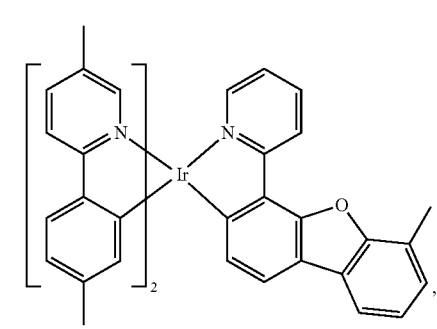
GD1-40
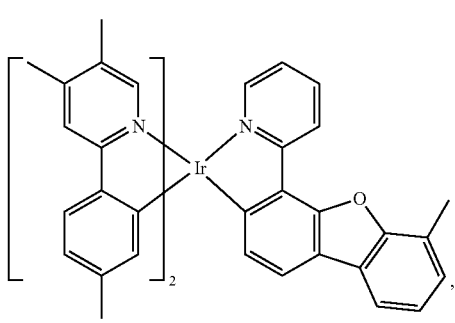
GD1-41
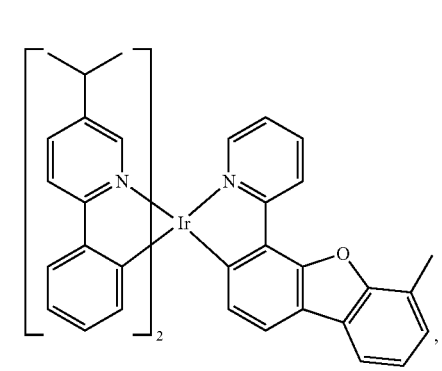

GD1-42
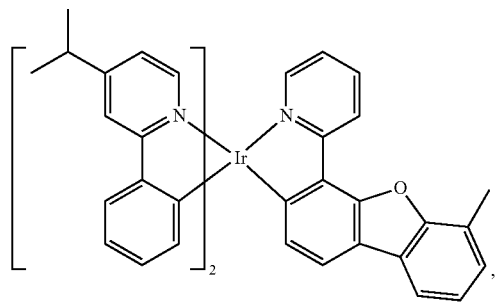
GD1-43
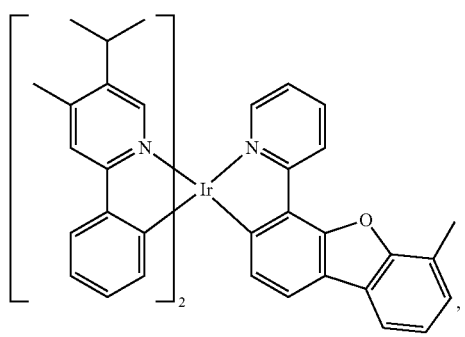
GD1-44
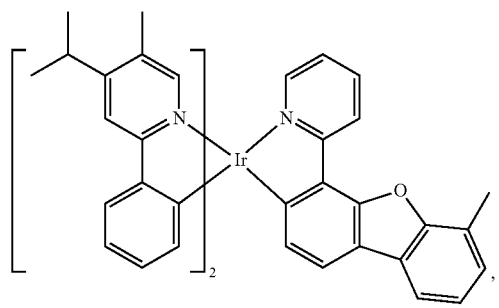
GD1-45
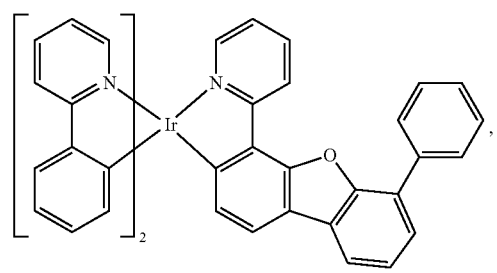
GD1-46
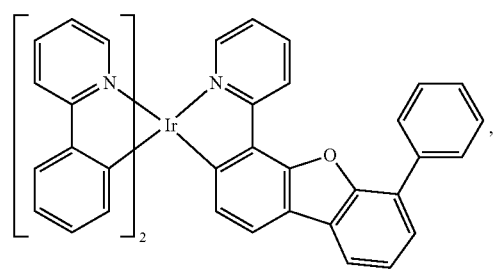
GD1-47
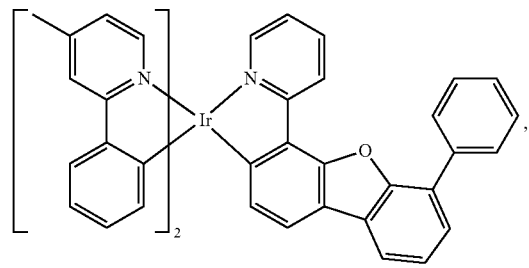
GD1-48
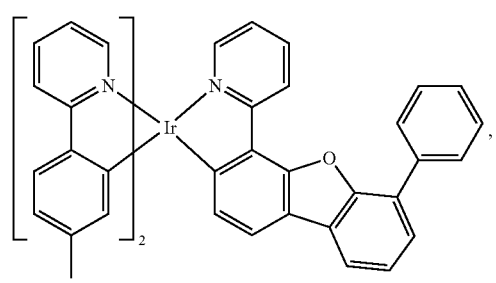
GD1-49
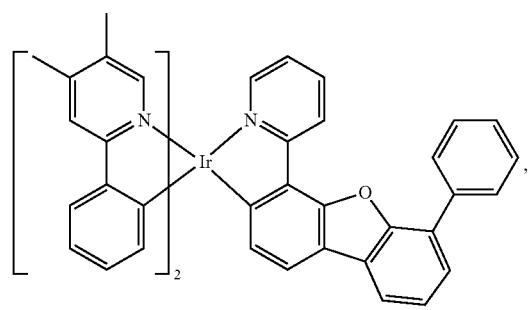
GD1-50
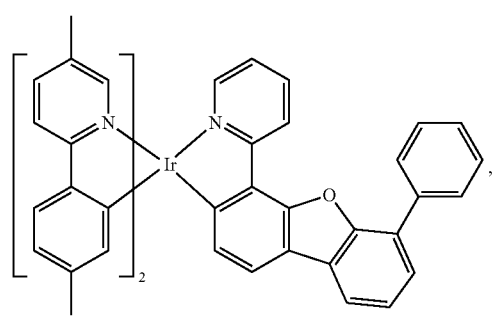
GD1-51
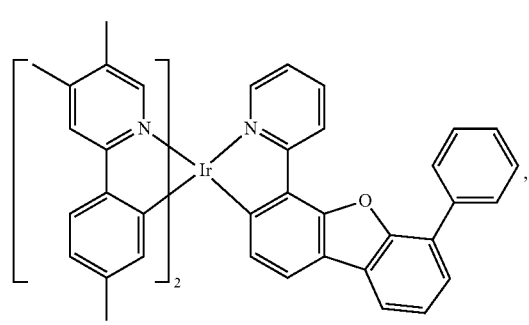

-continued
GD1-52
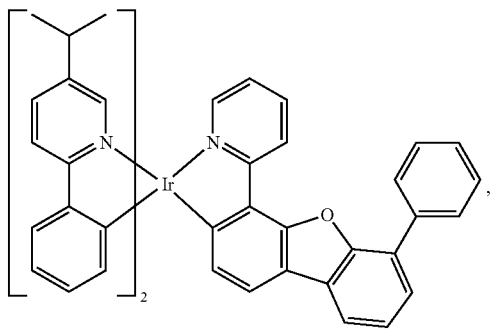
GD1-53
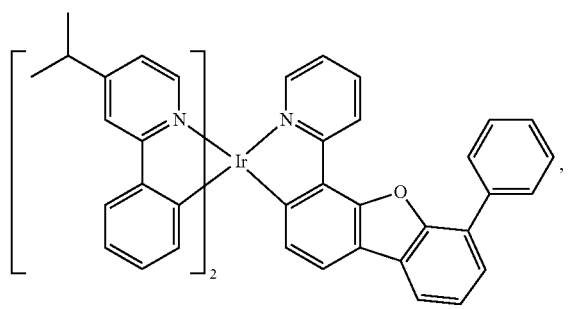
GD1-54
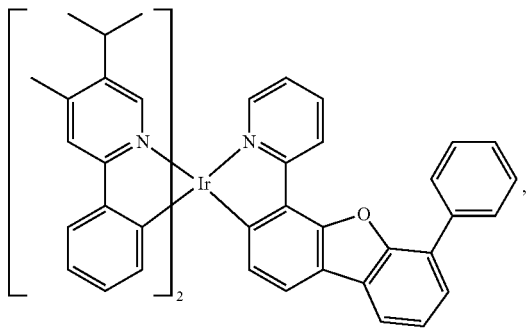
GD1-55
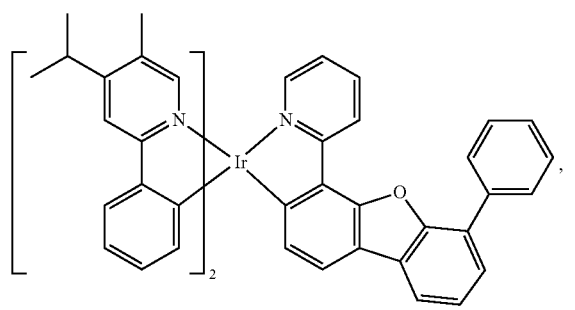
-continued
GD1-56
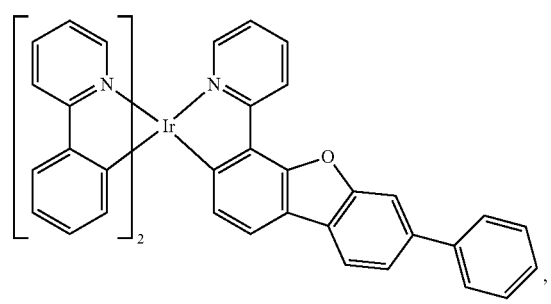
GD1-57
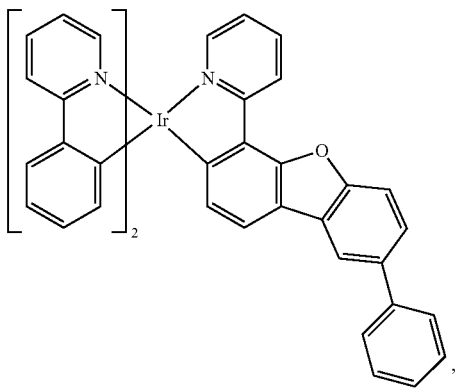
GD1-58
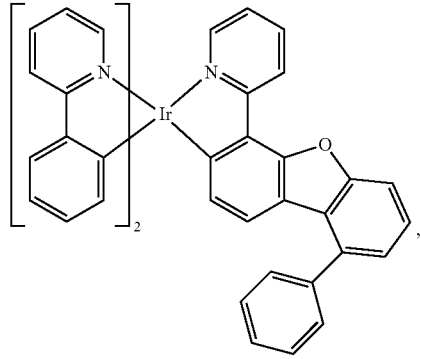
GD1-59
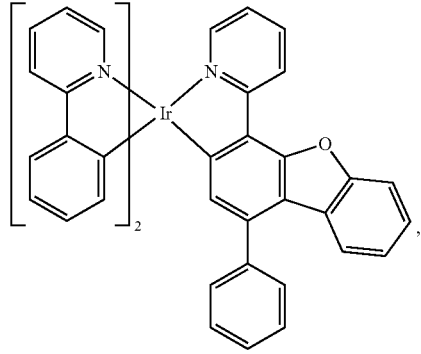

GD1-60
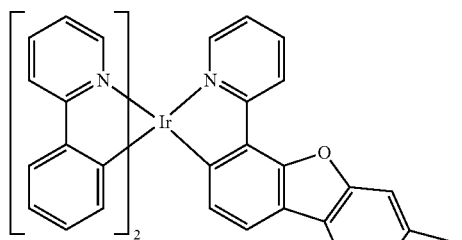
GD1-61
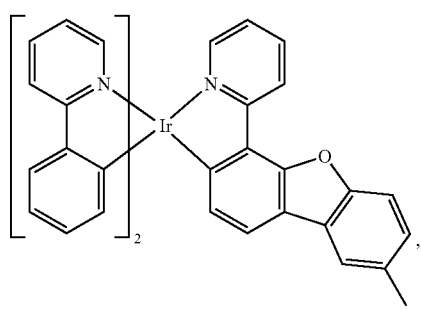
GD1-62
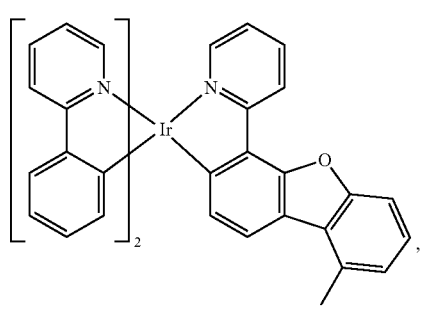
GD1-63
GD1-64
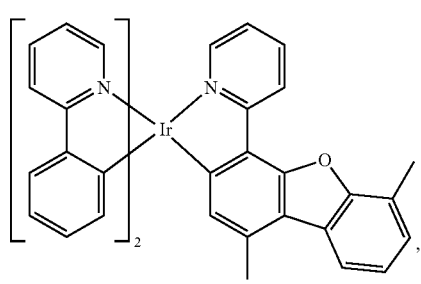
GD1-65
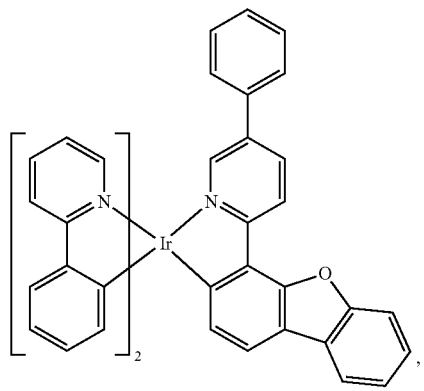
GD1-66
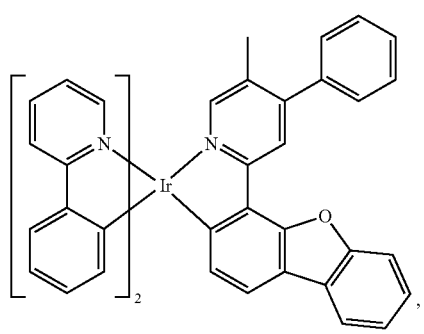
GD1-67
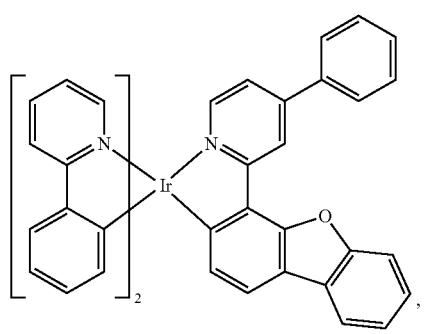
GD1-68
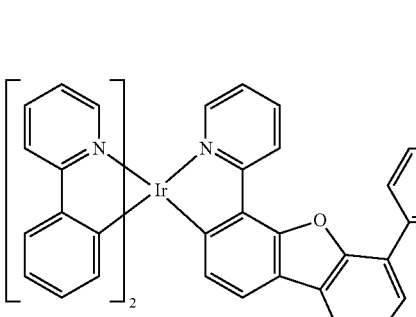

GD1-69
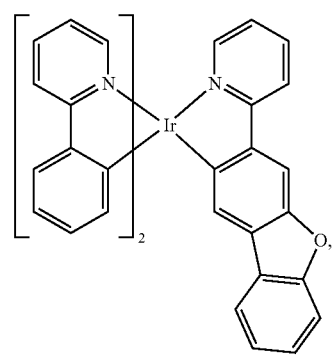
GD1-70
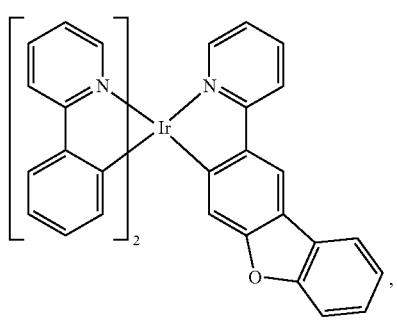
GD1-71
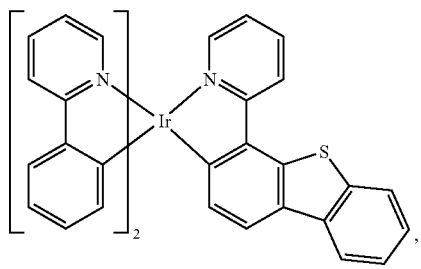
GD1-72
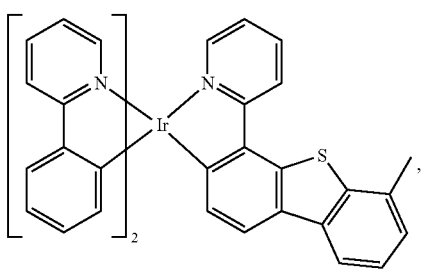
GD1-73
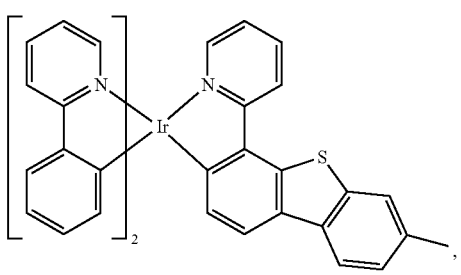
GD1-74
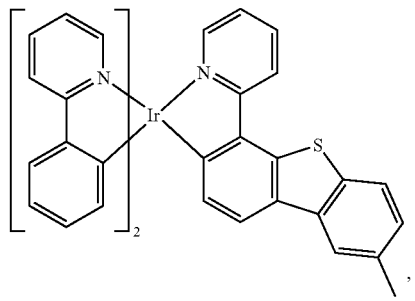
GD1-75
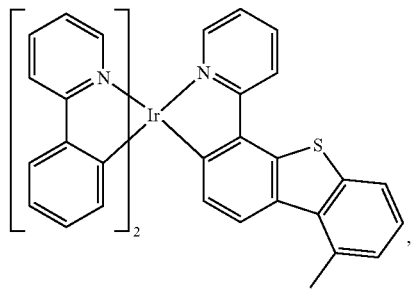
GD1-76
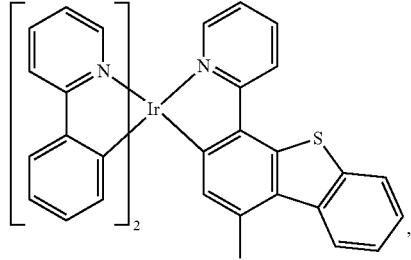
GD1-77
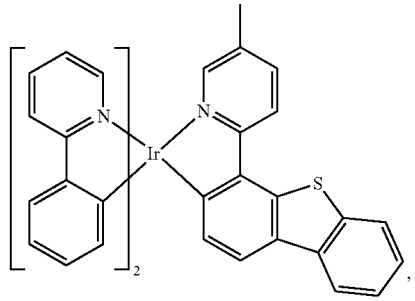
GD1-78
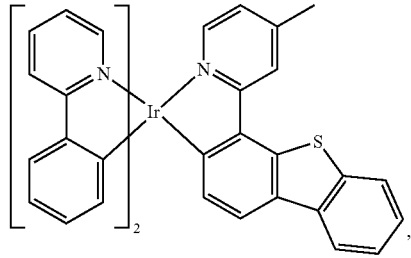

-continued
GD1-79
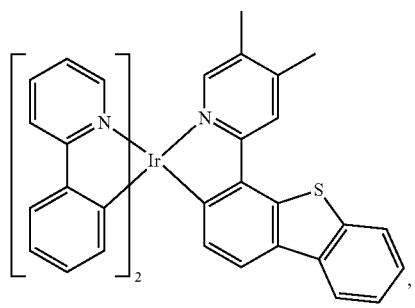
GD1-80
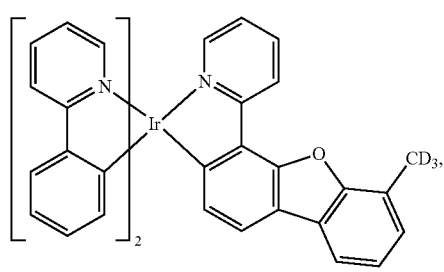
GD1-81
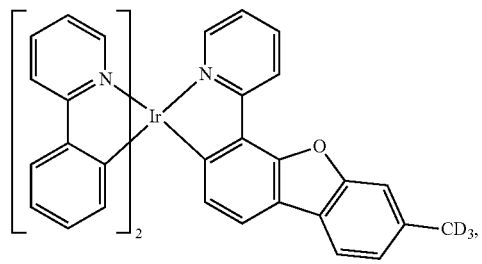
GD1-82
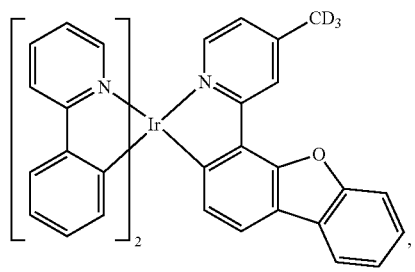
GD1-83
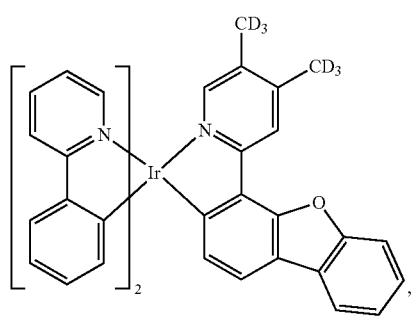
-continued
GD1-84
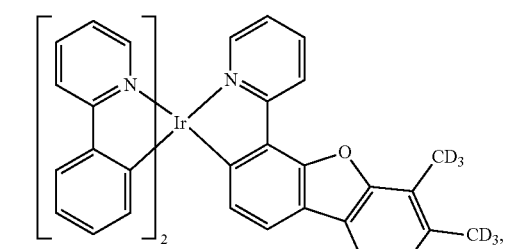
GD1-85
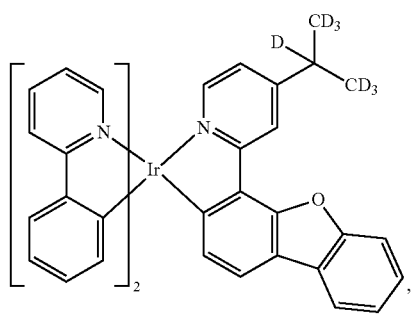
GD1-86
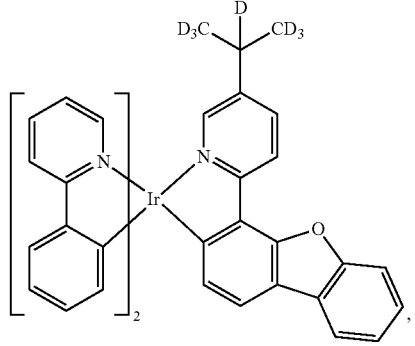
GD1-87
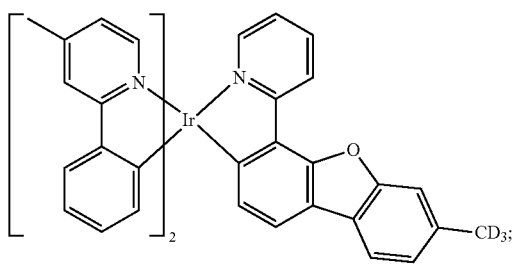
GD2-1
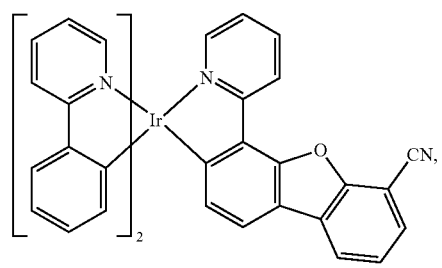

GD2-2
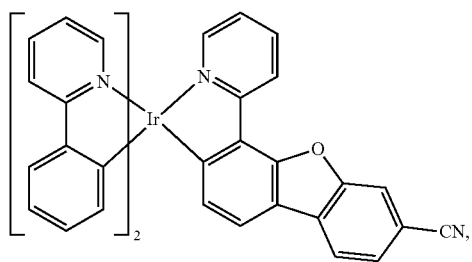
GD2-3
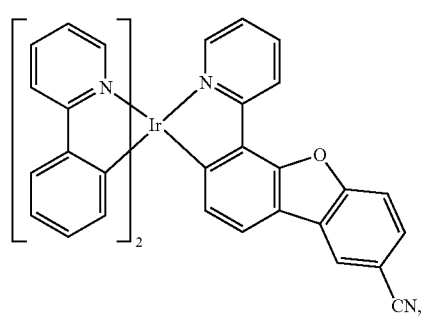
GD2-4
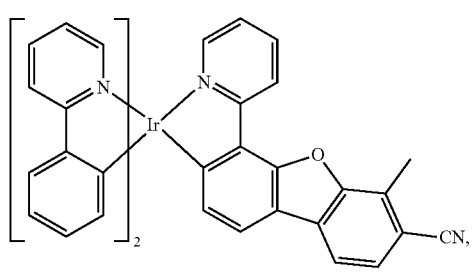
GD2-5
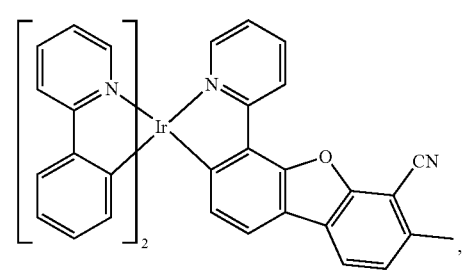
GD2-6
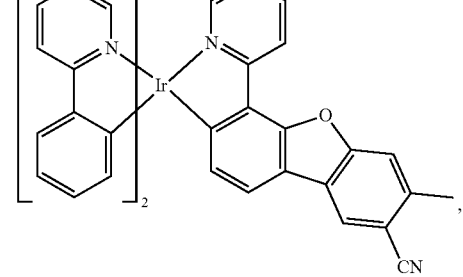
GD2-7
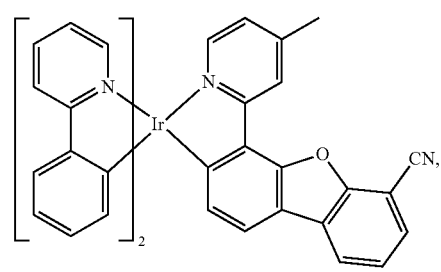
GD2-8
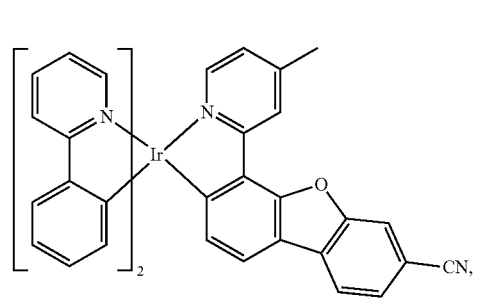
GD2-9
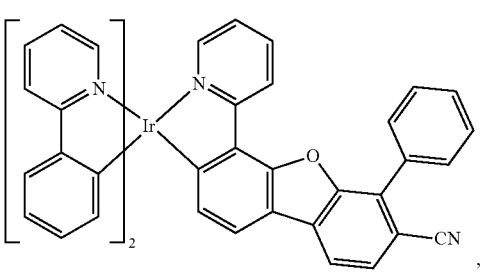
GD2-10
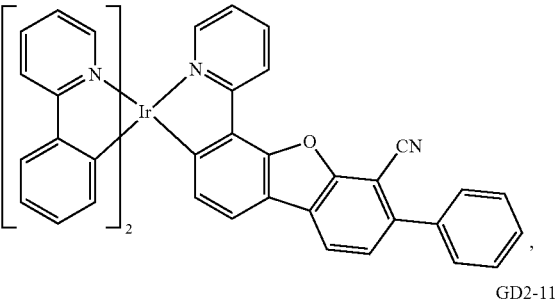
GD2-11
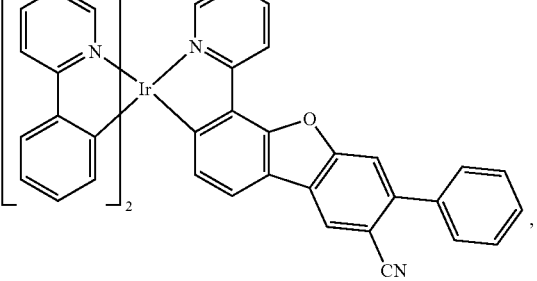

GD2-12
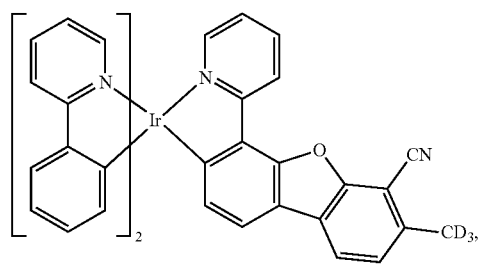
GD2-13
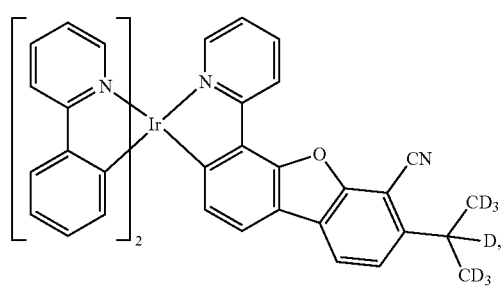
GD2-14
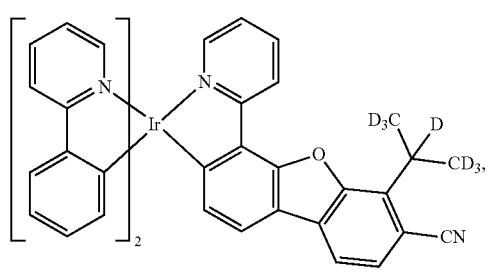
GD2-15
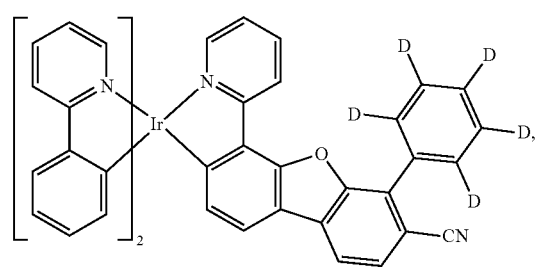
GD2-16
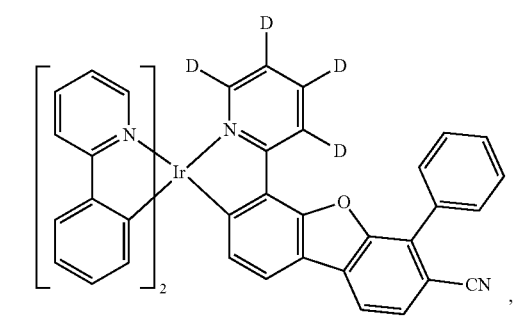
GD2-17
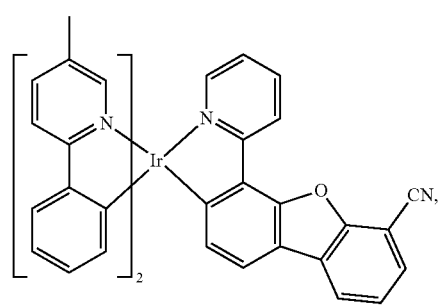
GD2-18
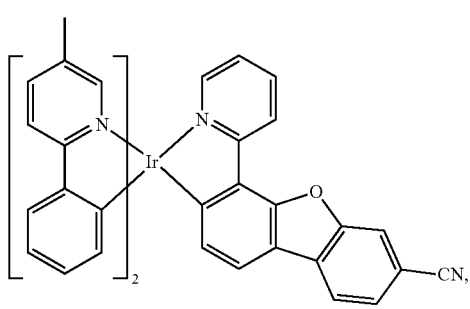
GD2-19
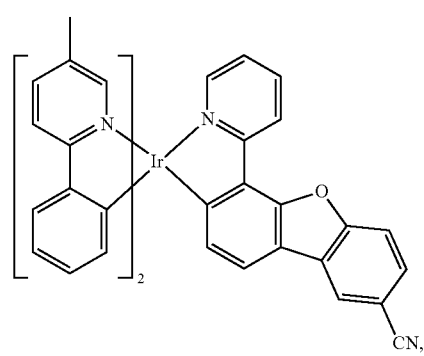
GD2-20
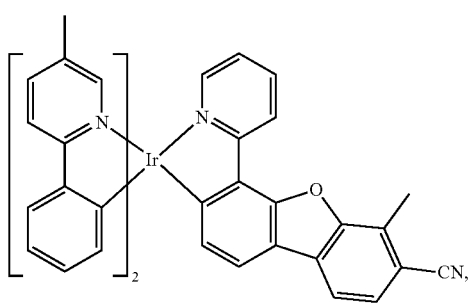
GD2-21
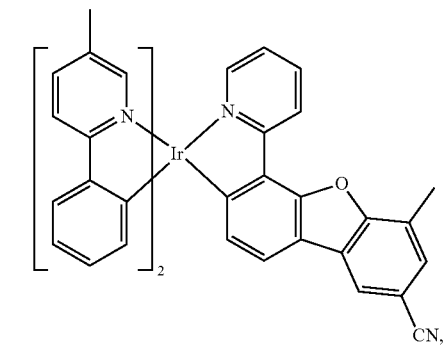

GD2-22
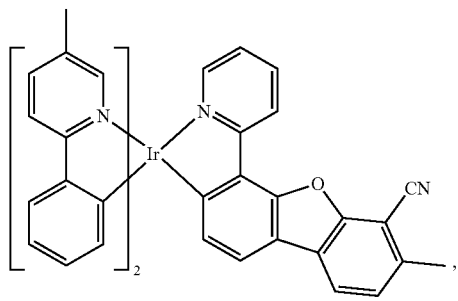
GD2-23
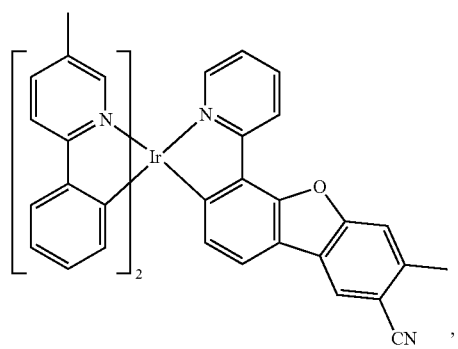
GD2-24
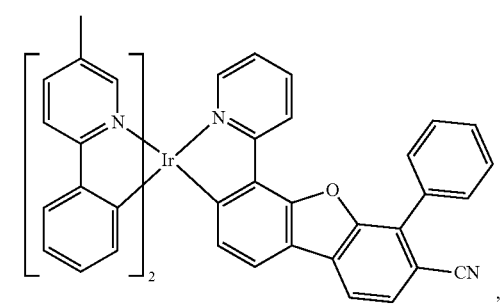
GD2-25
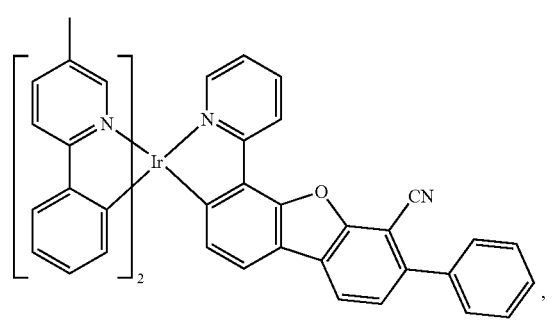
GD2-26
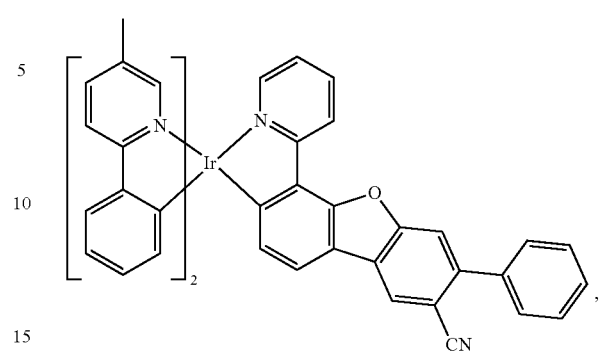
GD2-27
GD2-28
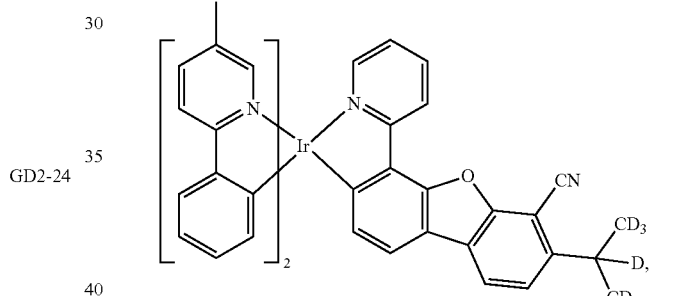
GD2-29
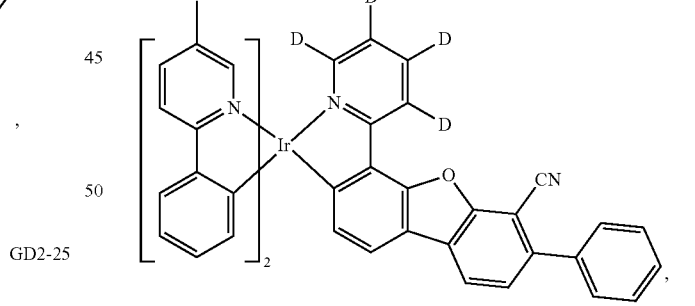
GD2-30
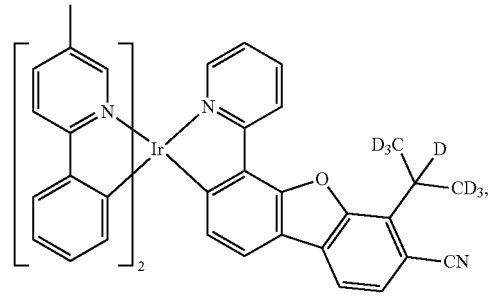

GD2-31
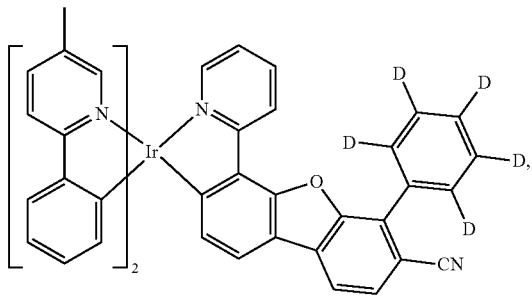
GD2-32
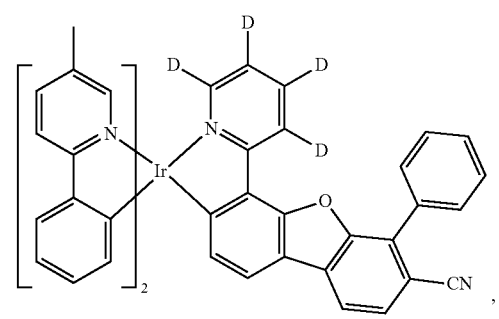
GD2-33
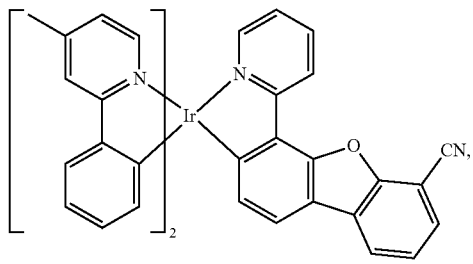
GD2-34
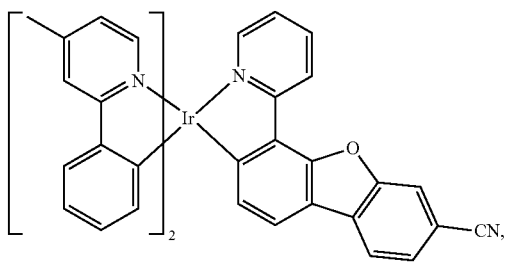
GD2-35
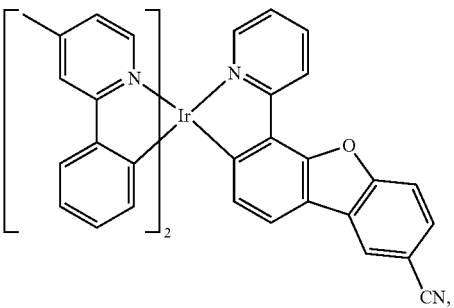
GD2-36
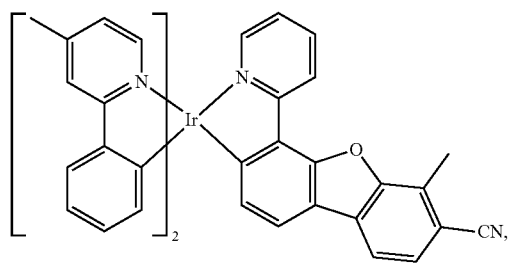
GD2-37
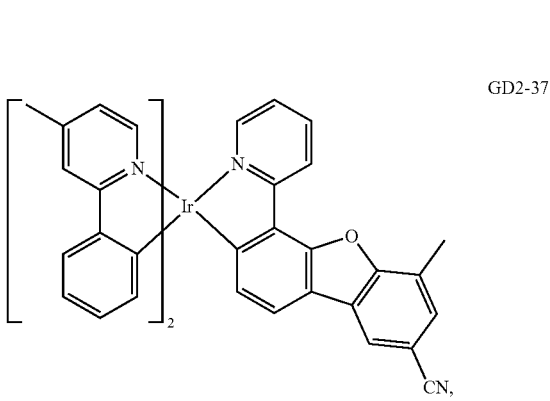
GD2-38
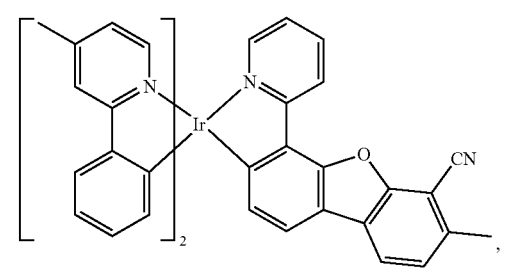
GD2-39
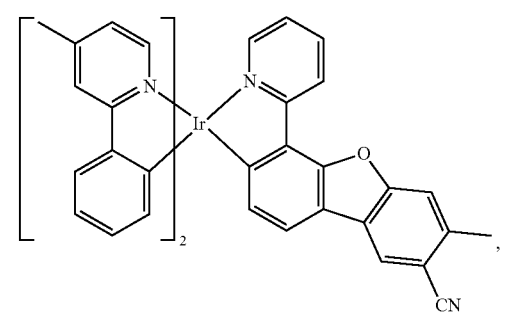
GD2-40
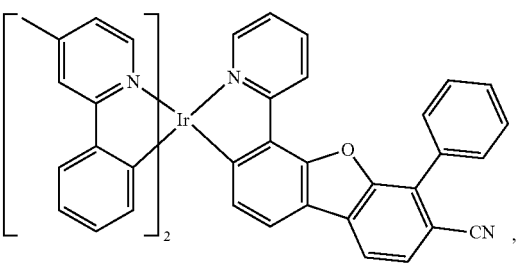

GD2-41
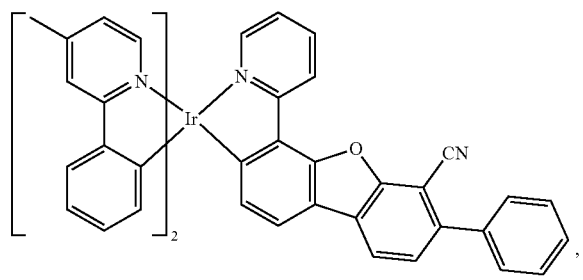
GD2-42
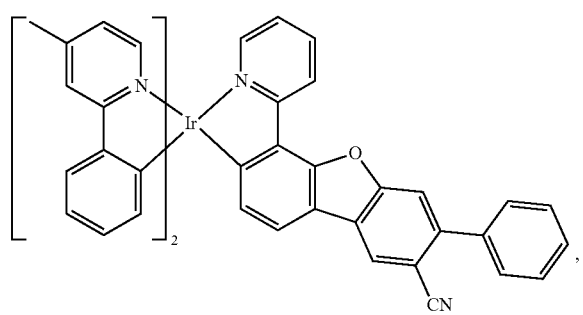
GD2-43
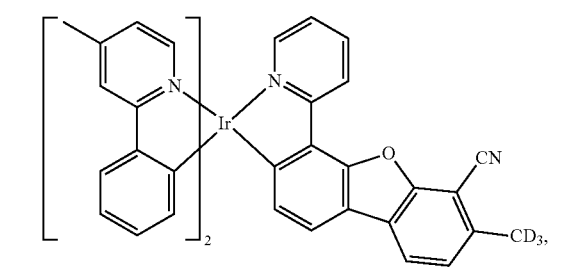
GD2-44
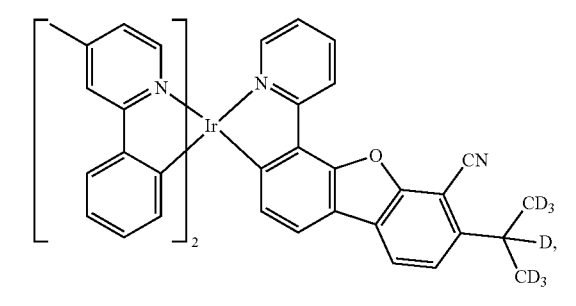
GD2-45
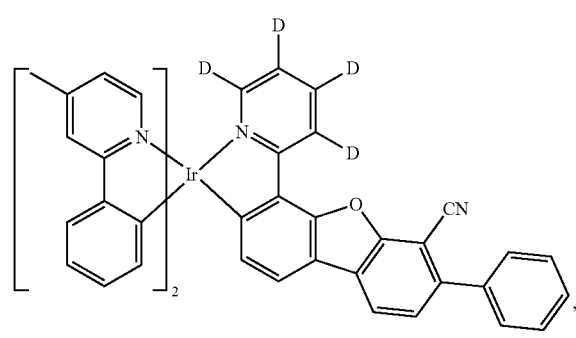
GD2-46
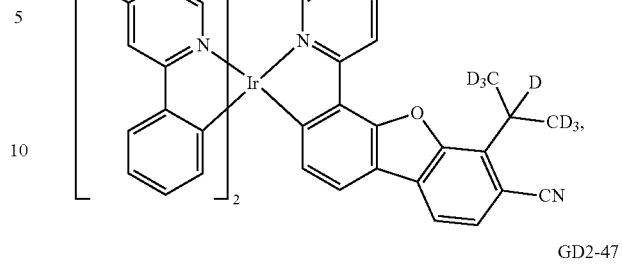
GD2-47
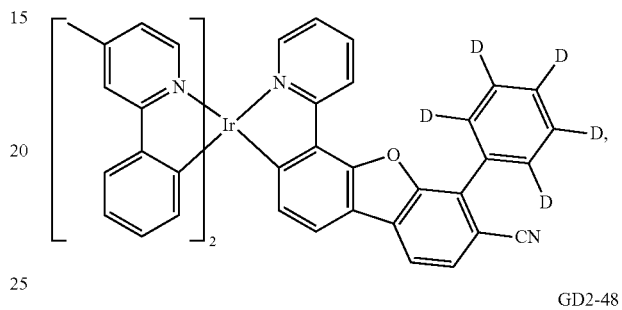
GD2-48
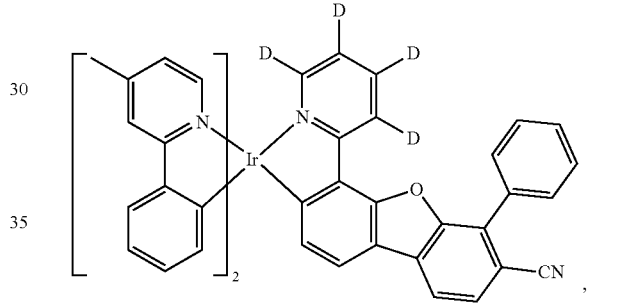
GD2-49
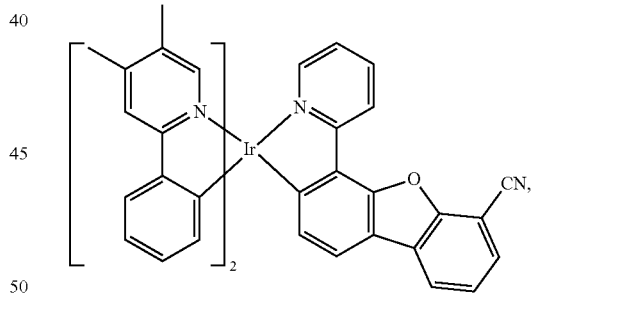
GD2-50
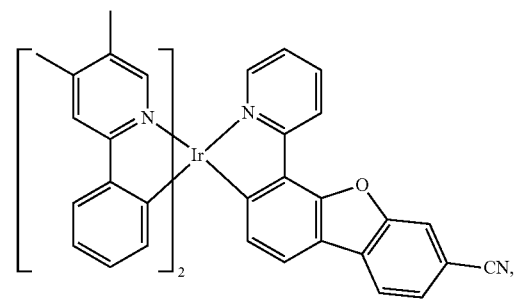

GD2-51
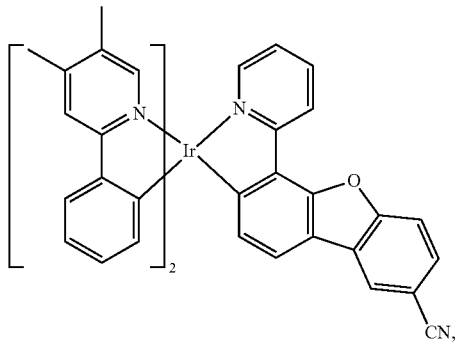
GD2-52
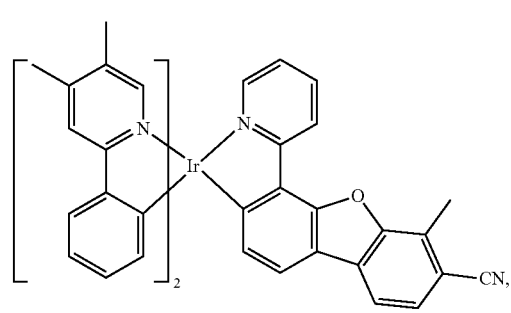
GD2-53
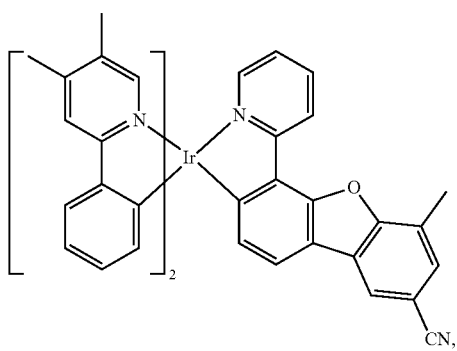
GD2-54
GD2-55
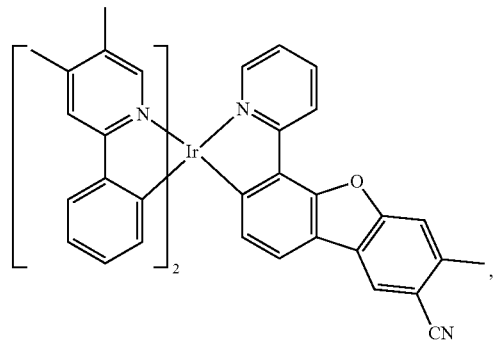
GD2-56
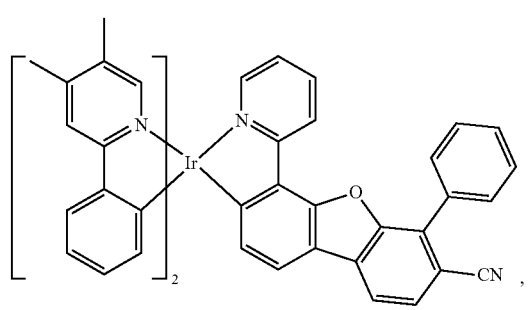
GD2-57
GD2-58
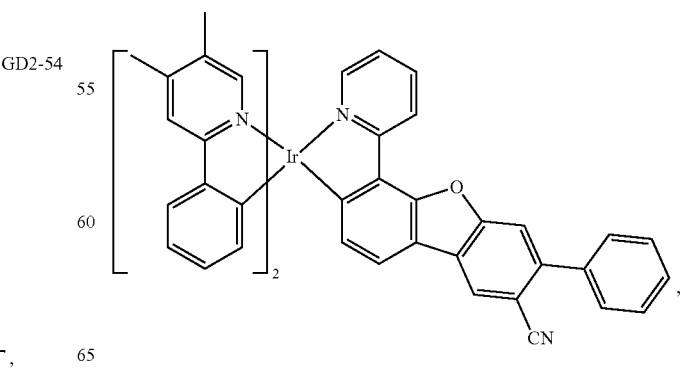

GD2-59
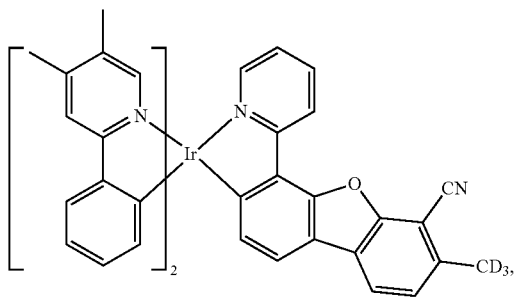
GD2-60
GD2-61
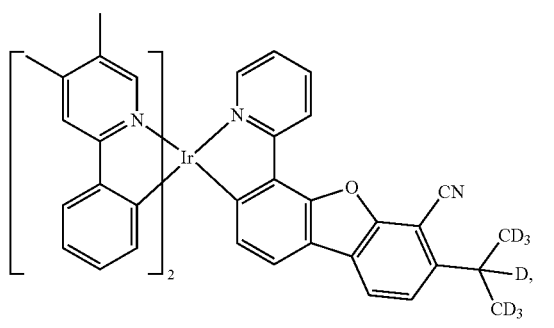
GD2-62
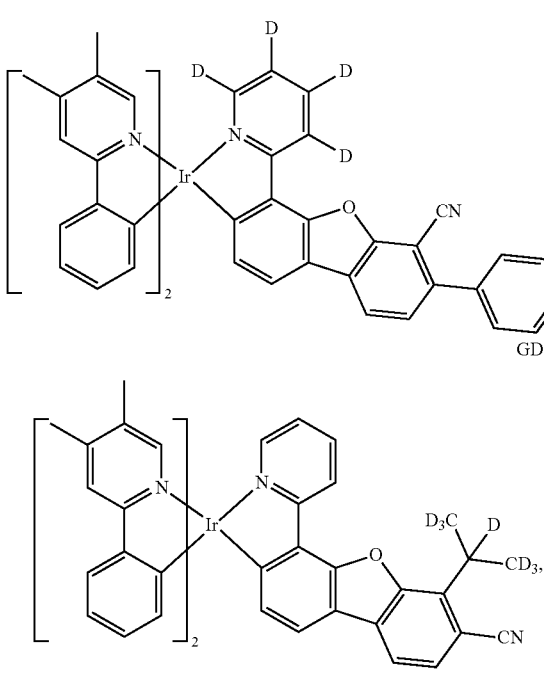
GD2-63
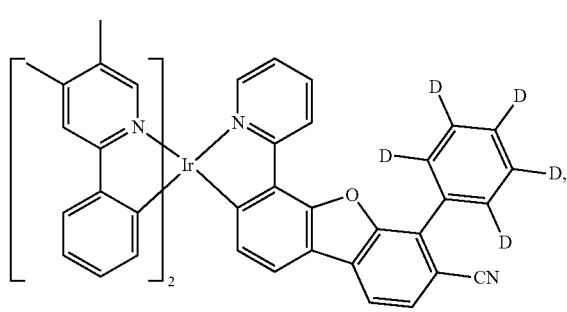
GD2-64
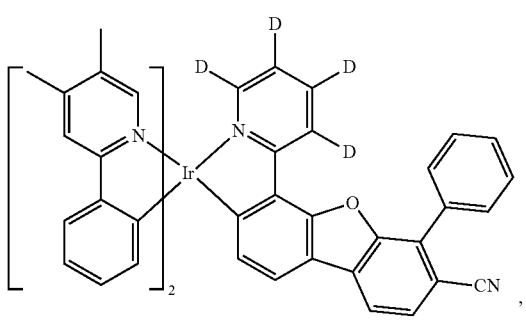
GD2-65
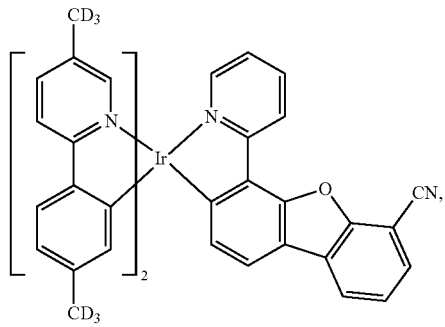
GD2-66
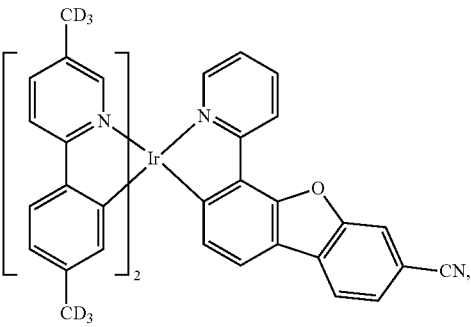
GD2-67
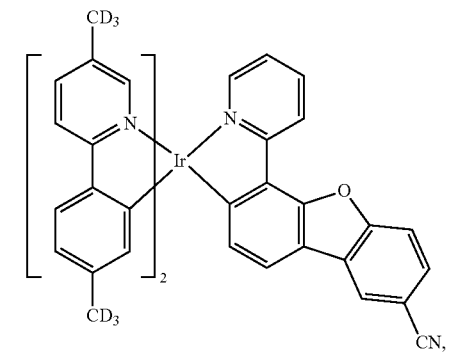

-continued
GD2-68
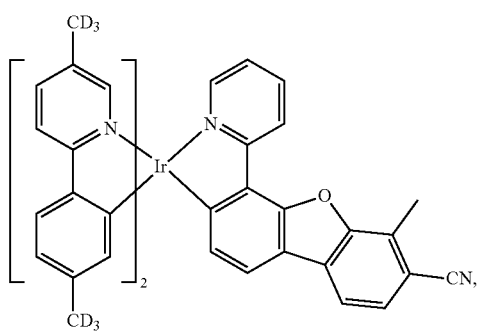
GD2-69
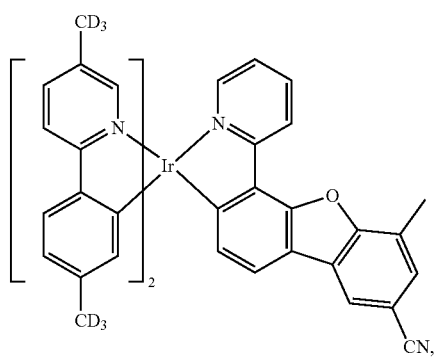
GD2-70
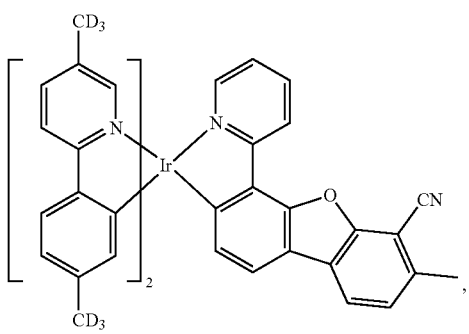
GD2-71
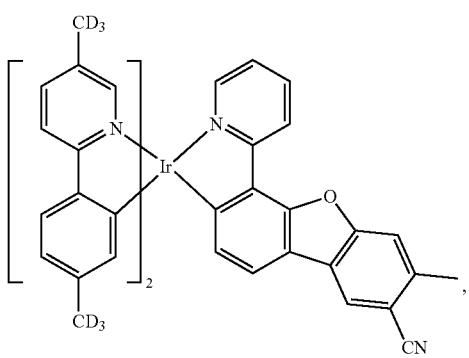
-continued
GD2-72
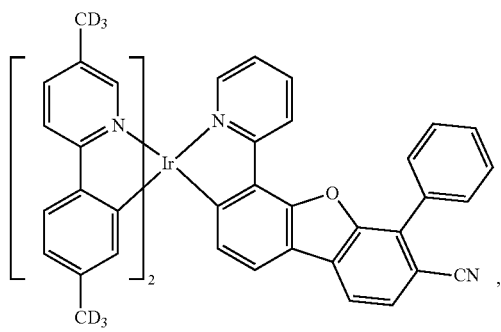
GD2-73
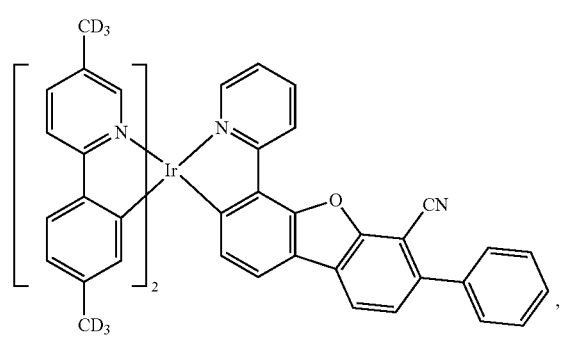
GD2-74
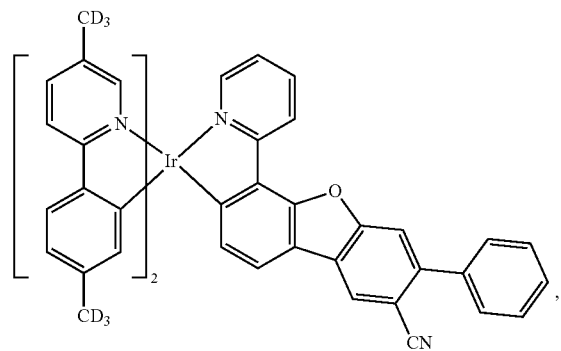
GD2-75
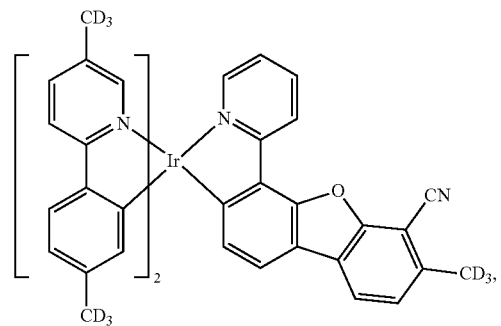

GD2-76
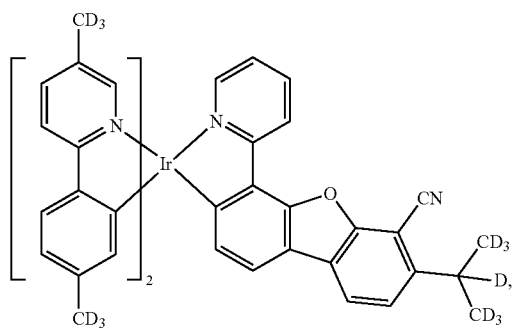
GD2-80
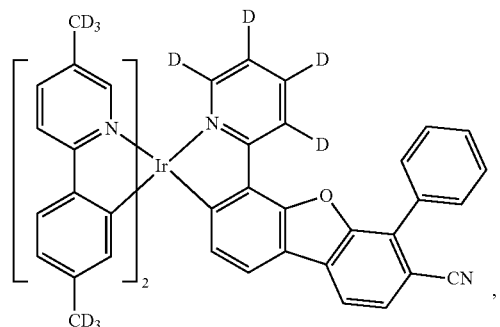
GD2-77
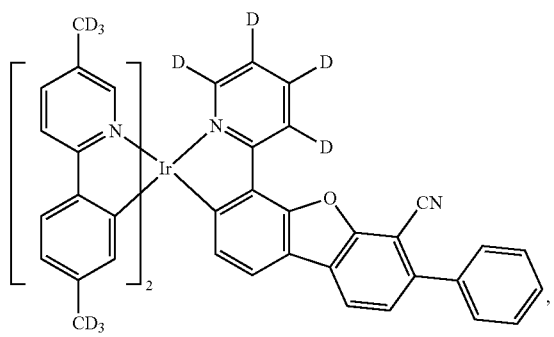
GD2-81
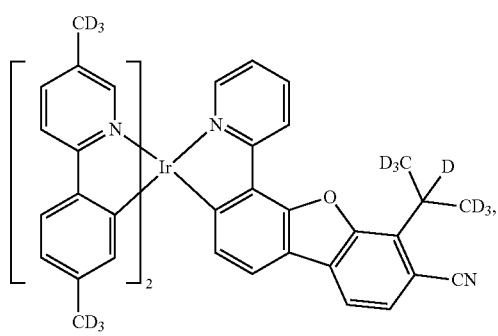
GD2-78
GD2-82
GD2-79
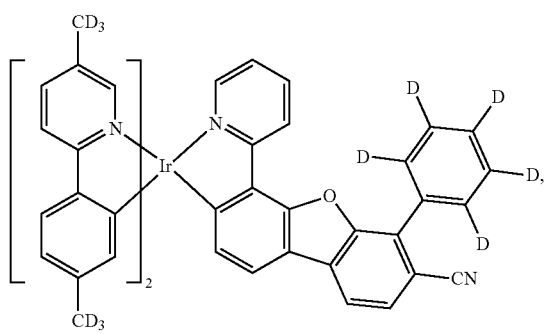
GD2-83
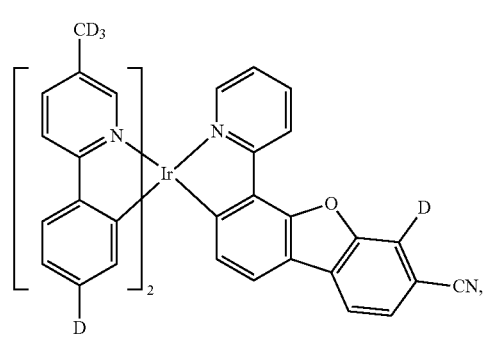

GD2-84
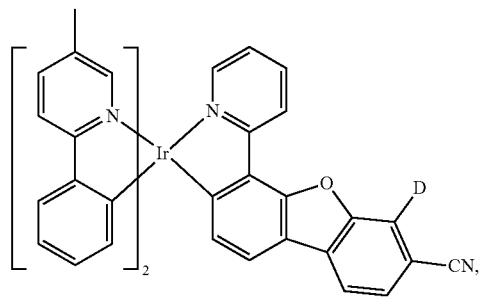
GD3-1
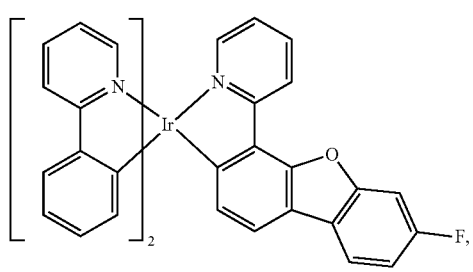
GD3-2
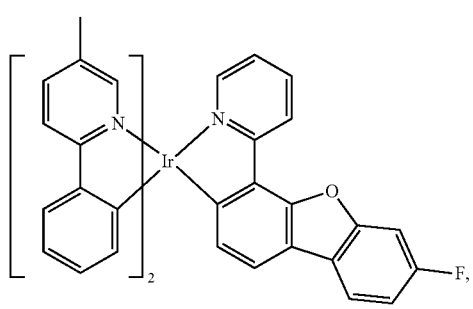
GD3-3
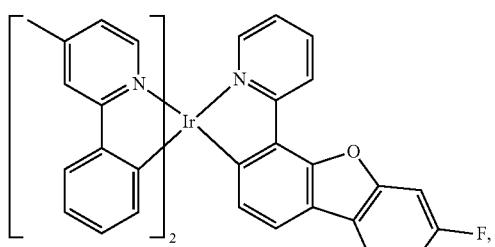
GD3-4
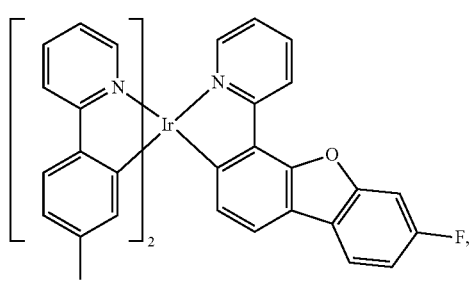
GD3-5
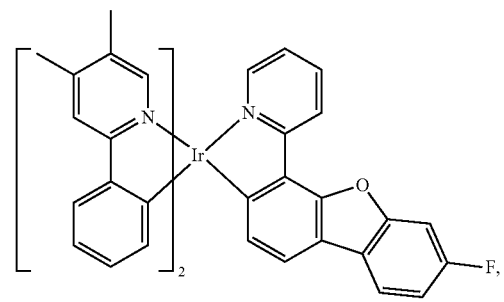
GD3-6
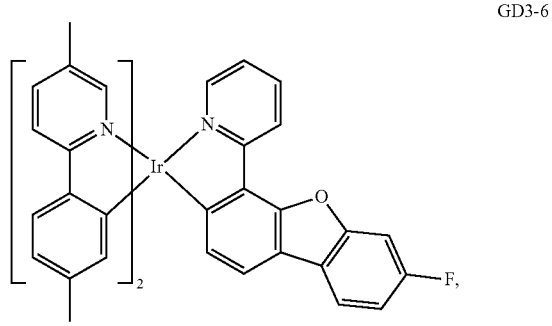
GD3-7
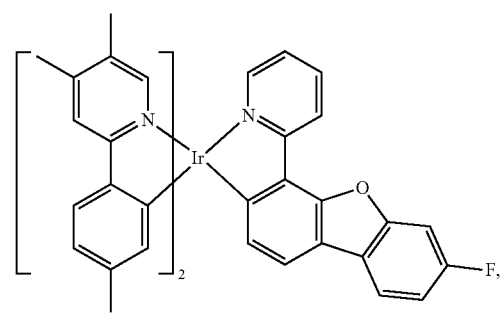
GD3-8
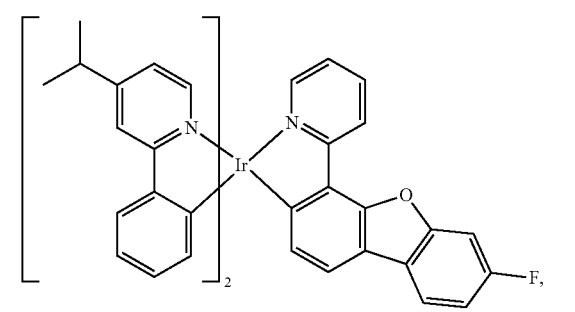
GD3-9
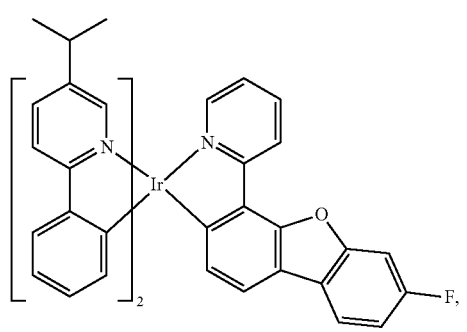

GD3-10
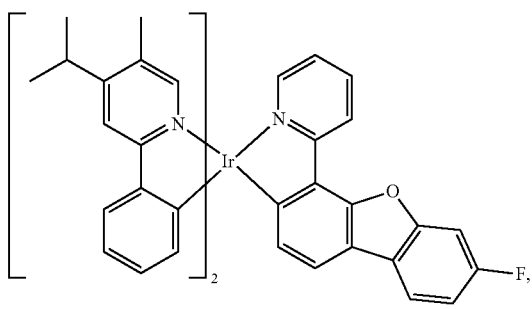
GD3-15
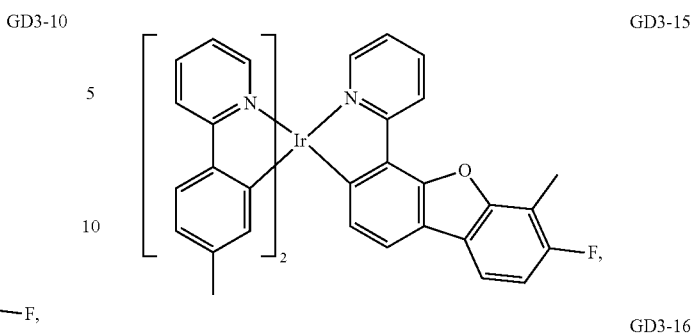
GD3-11
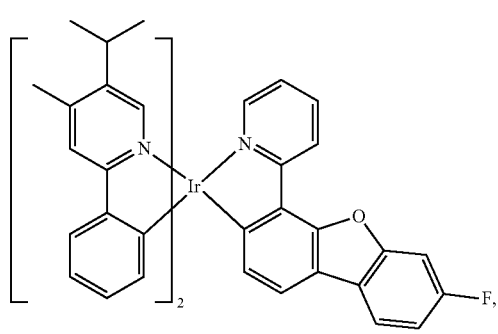
GD3-16
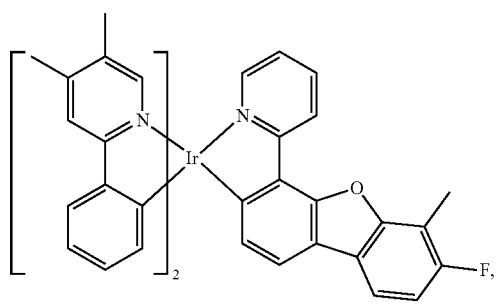
GD3-12
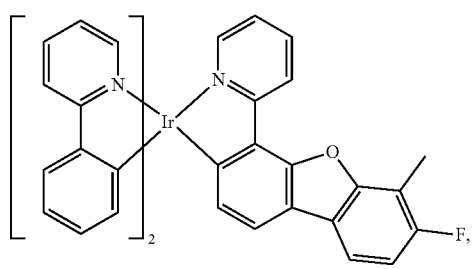
GD3-17
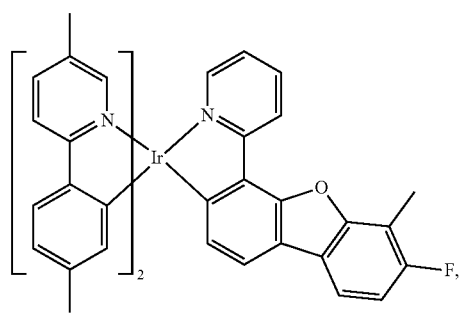
GD3-13
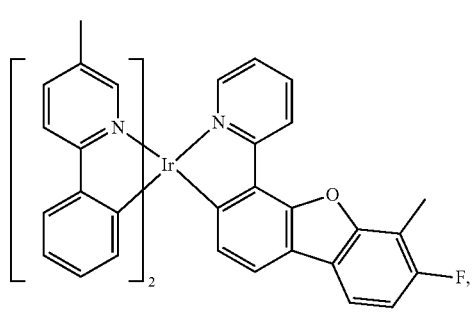
GD3-18
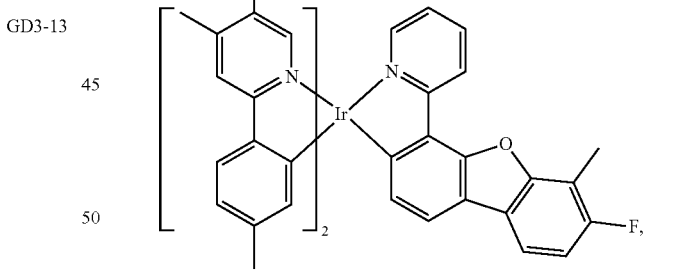
GD3-14
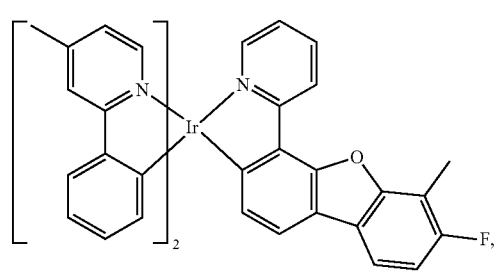
GD3-19
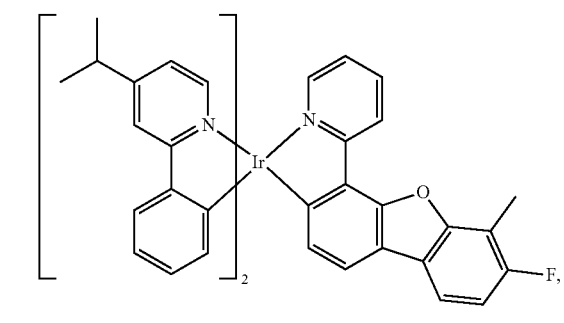

GD3-20
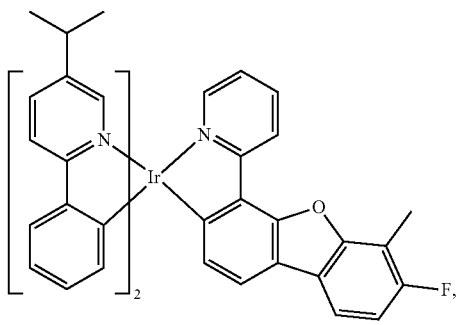
GD3-21
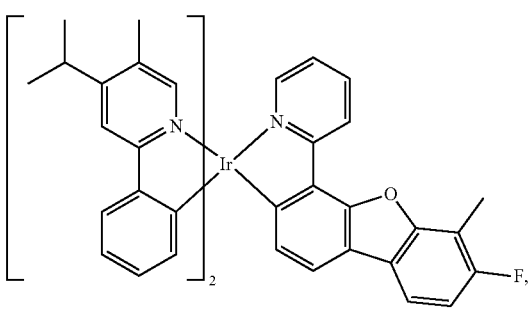
GD3-22
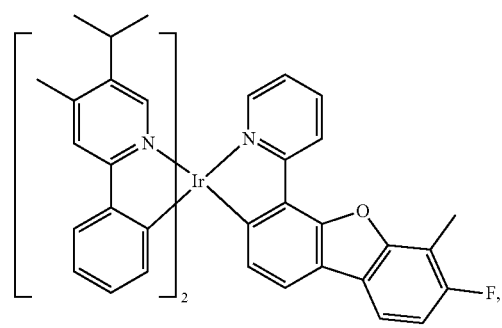
GD3-23
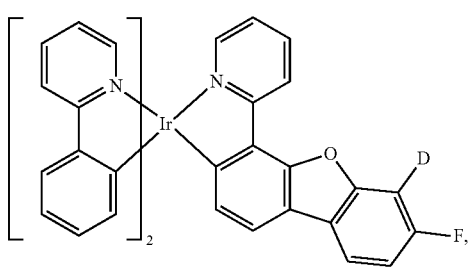
GD3-24
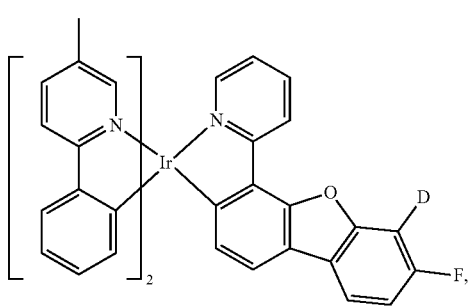
GD3-25
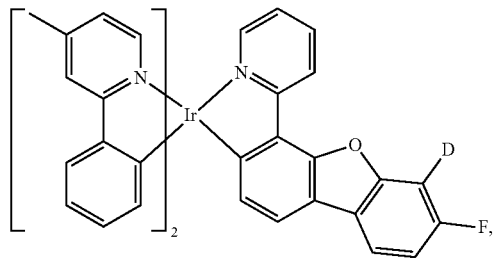
GD3-26
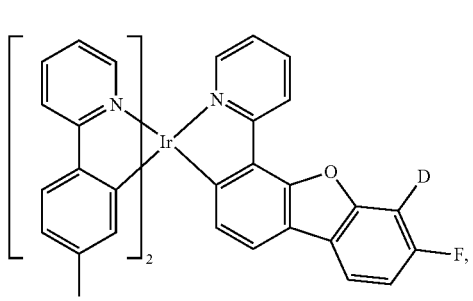
GD3-27
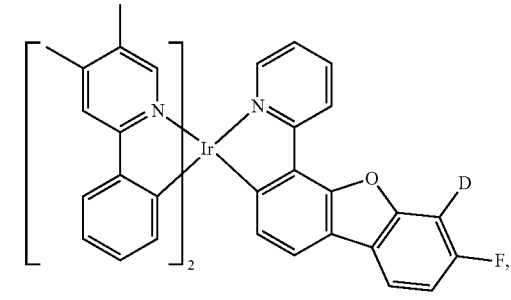
GD3-28
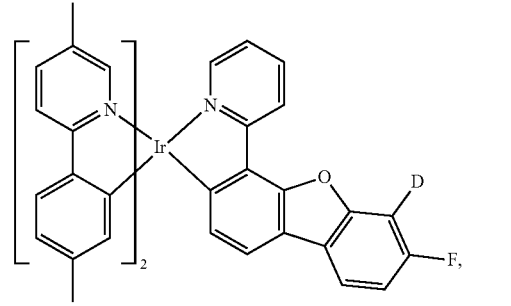
GD3-29
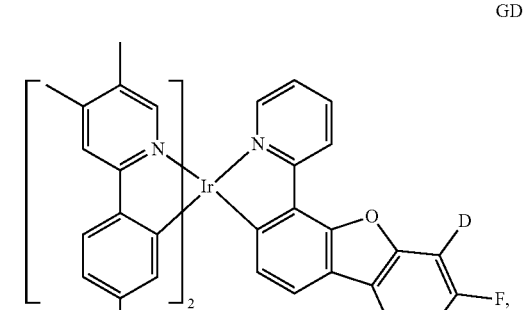

GD3-30
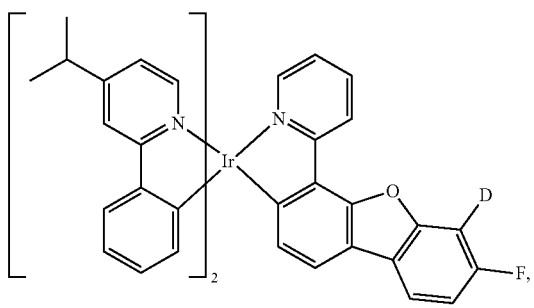
GD3-31
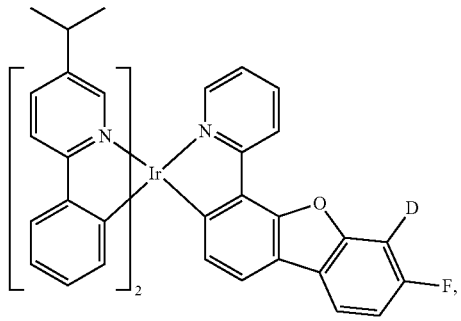
GD3-32
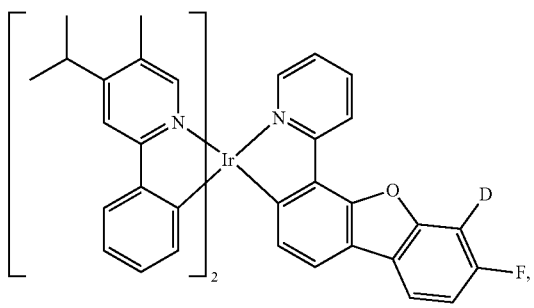
GD3-33
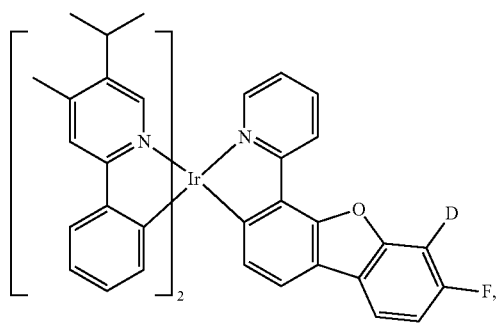
GD3-34
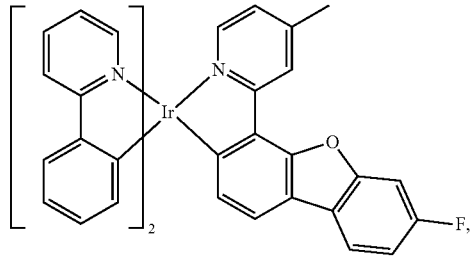
GD3-35
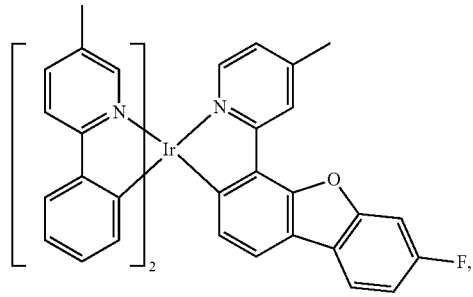
GD3-36
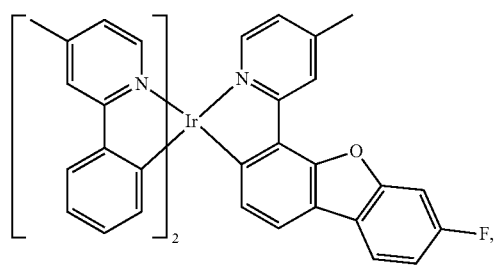
GD3-37
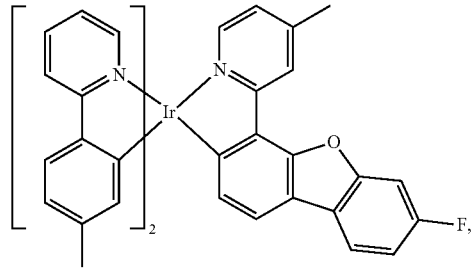
GD3-38
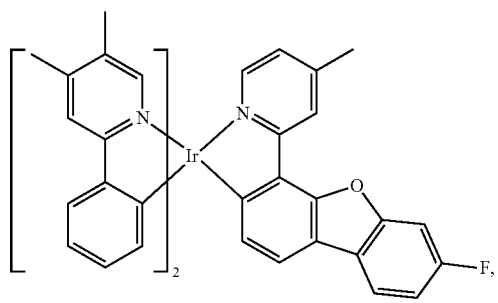
GD3-39
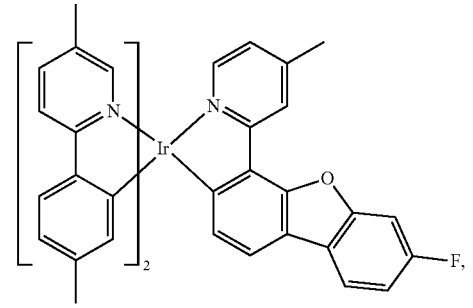

GD3-40
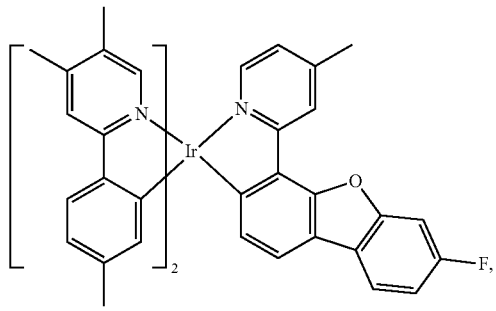
GD3-41
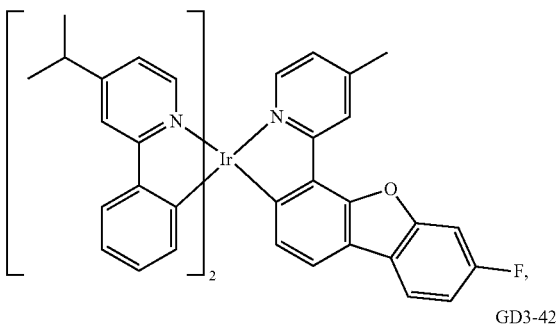
GD3-42
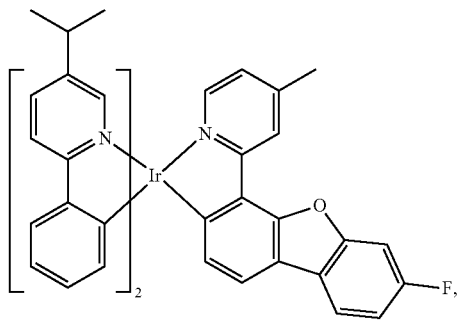
GD3-43
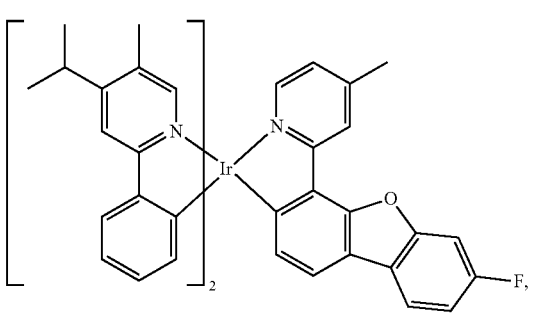
GD3-44
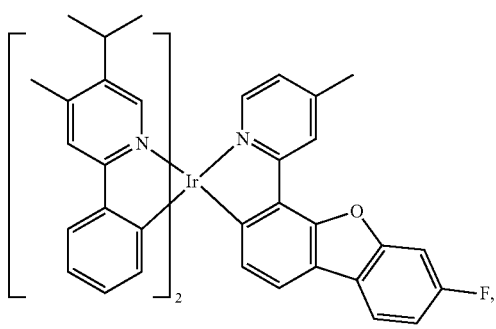
GD3-45
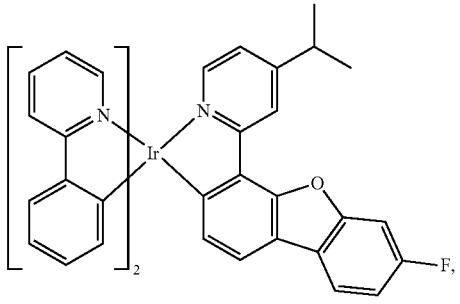
GD3-46
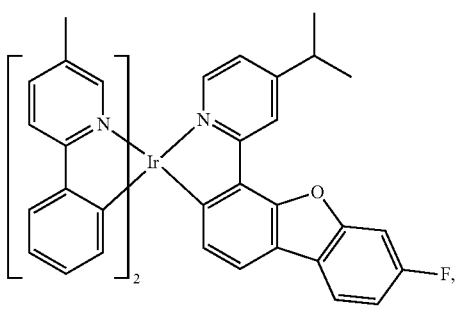
GD3-47
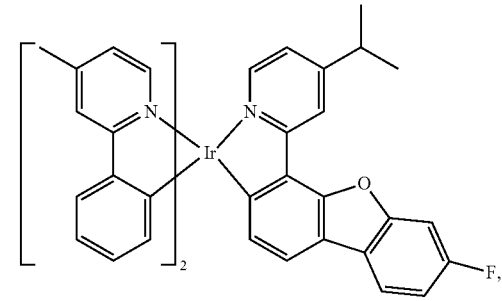
GD3-48
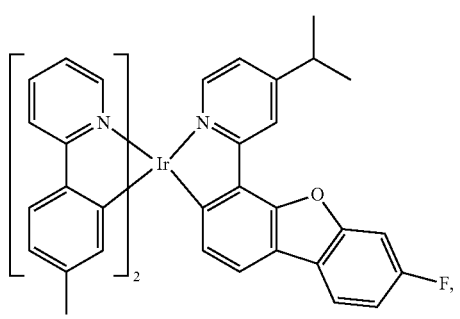

GD3-49
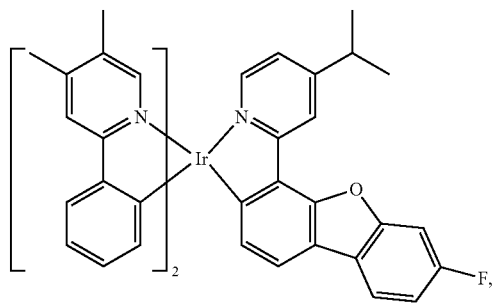
GD3-50
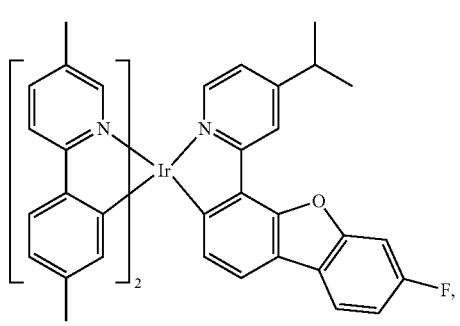
GD3-51
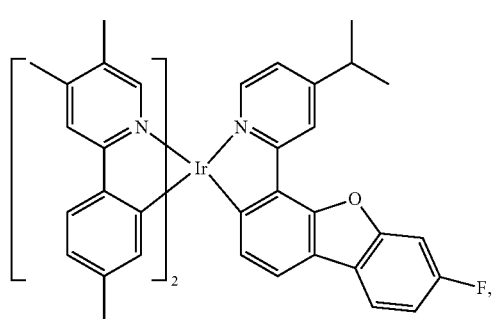
GD3-52
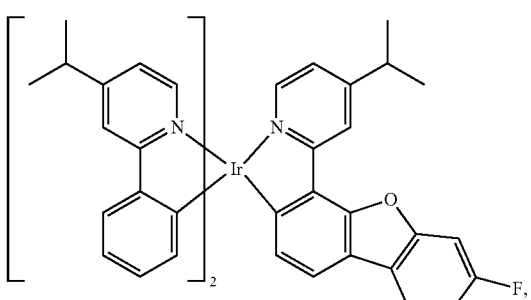
GD3-53
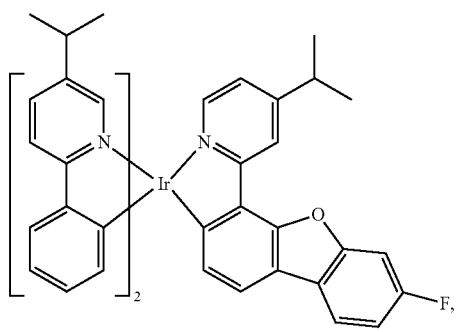
GD3-54
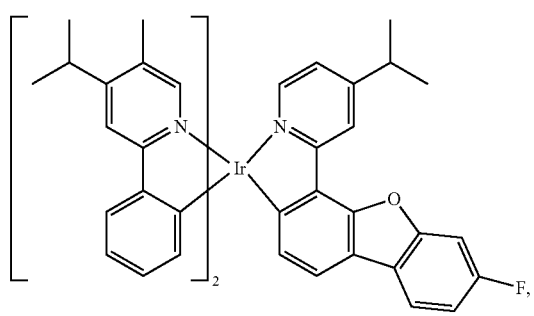
GD3-55
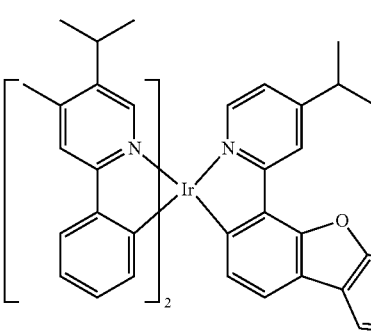
GD3-56
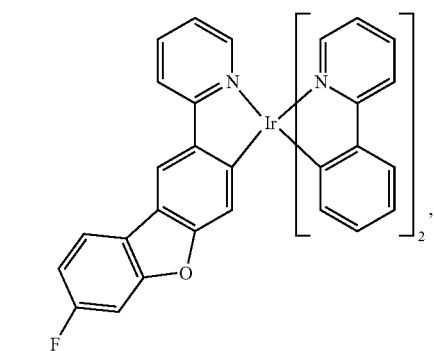
GD3-57
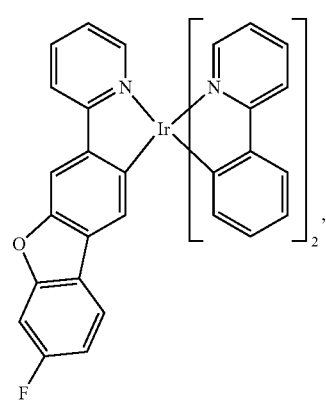

GD3-58
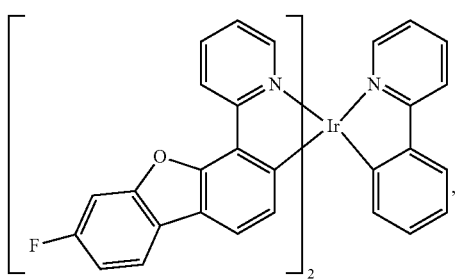
GD3-59
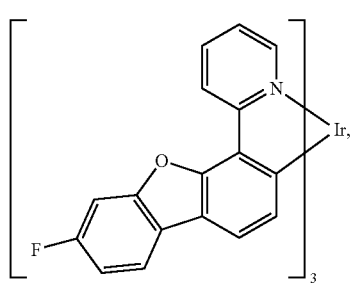
GD3-60
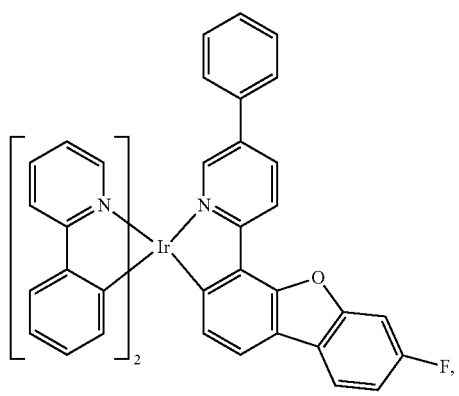
GD3-61
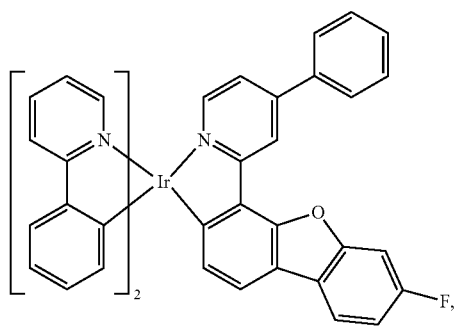
GD3-62
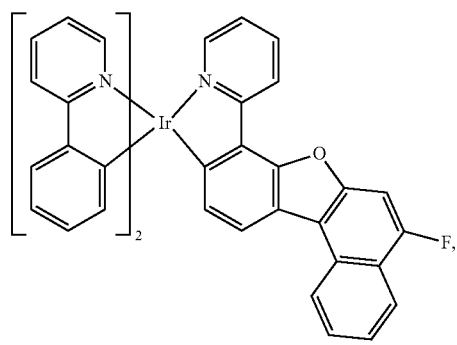
GD3-63
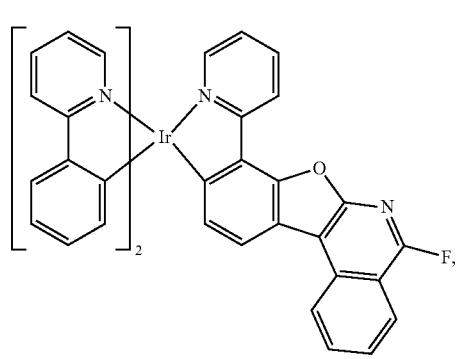
GD3-64
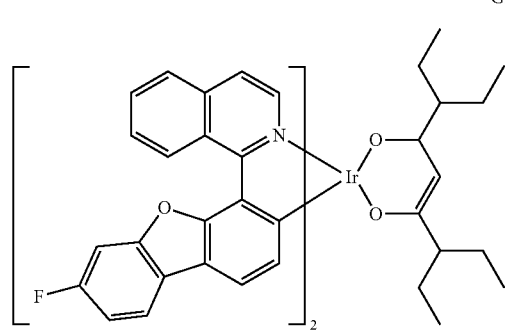
GD3-65
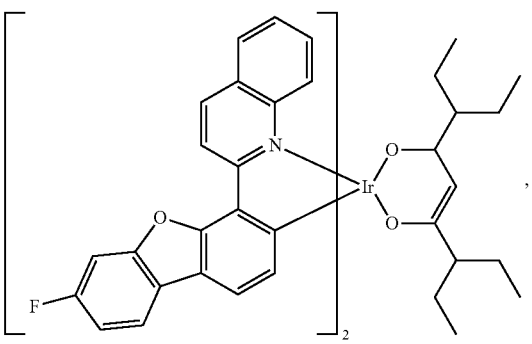

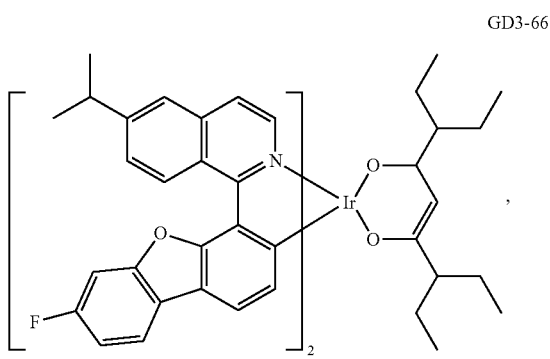
GD3-66
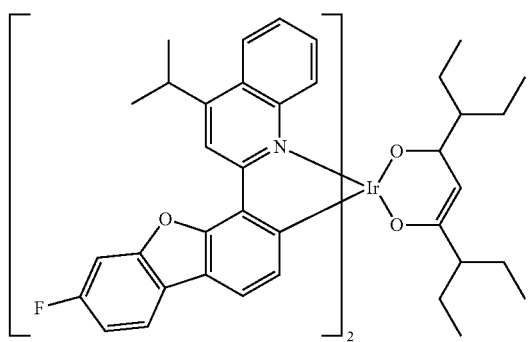
GD3-67
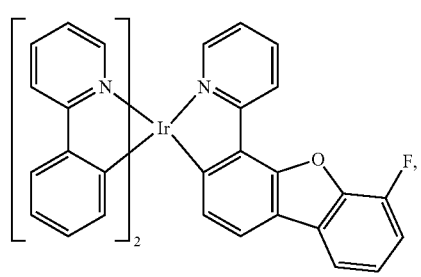
GD3-68
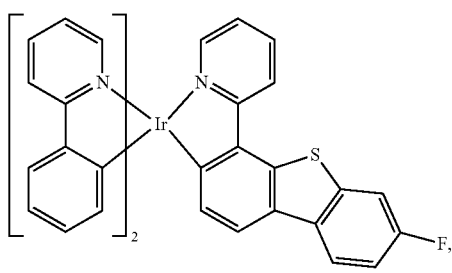
GD3-69
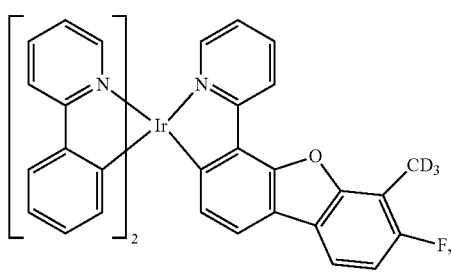
GD3-70
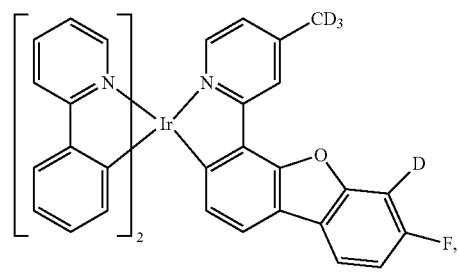
GD3-71
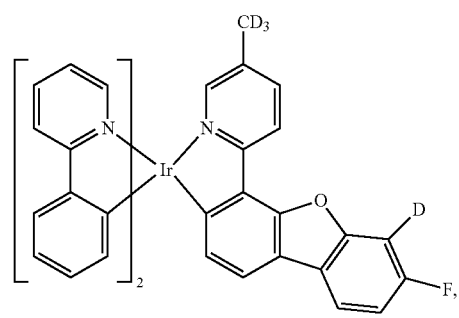
GD3-72
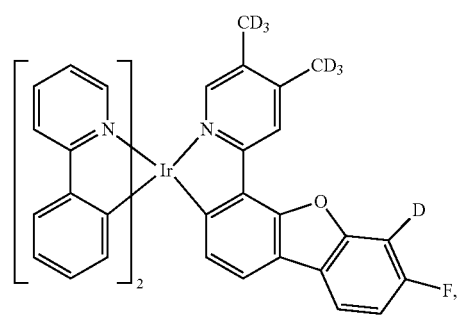
GD3-73
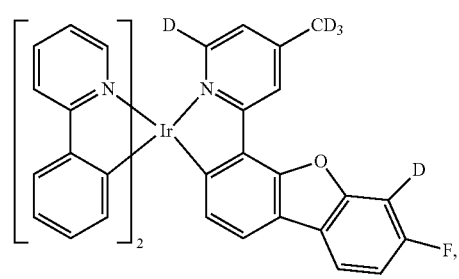
GD3-74
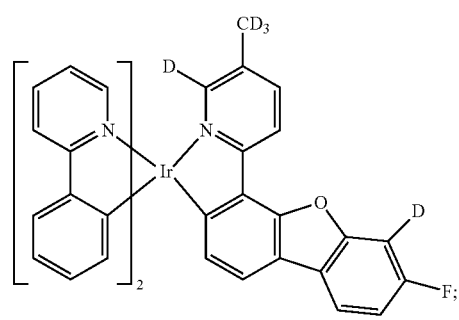
GD3-75

GD4-1
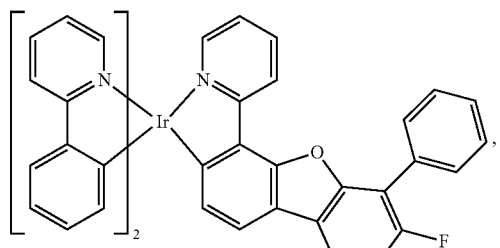
GD4-2
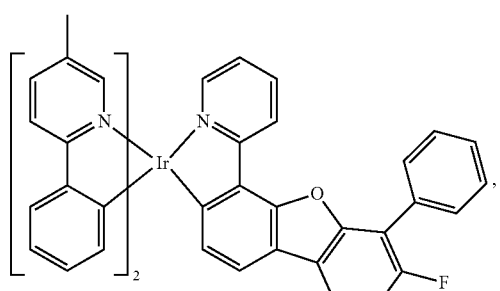
GD4-3
GD4-4
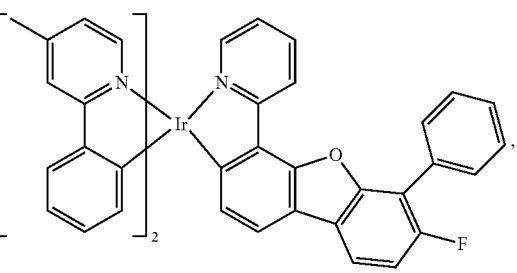
GD4-5
GD4-6
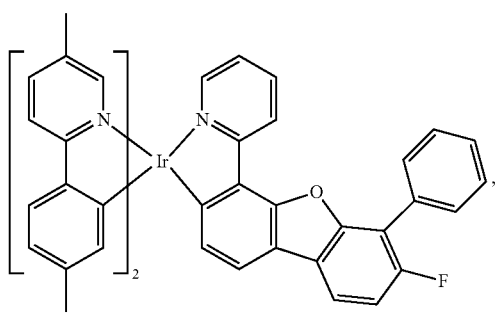
GD4-7
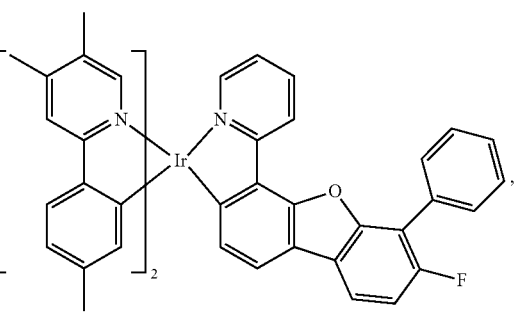
GD4-8
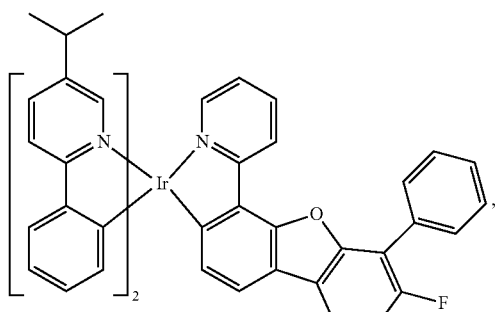
GD4-9
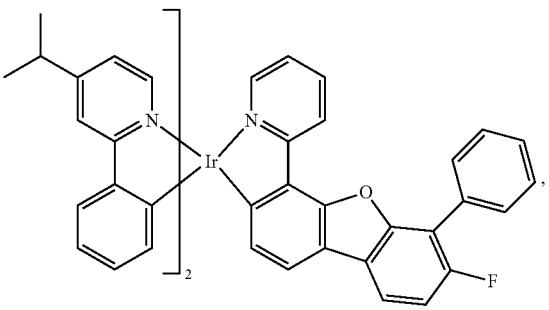

GD4-10
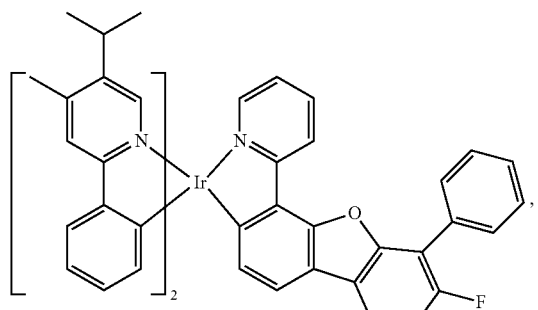
GD4-14
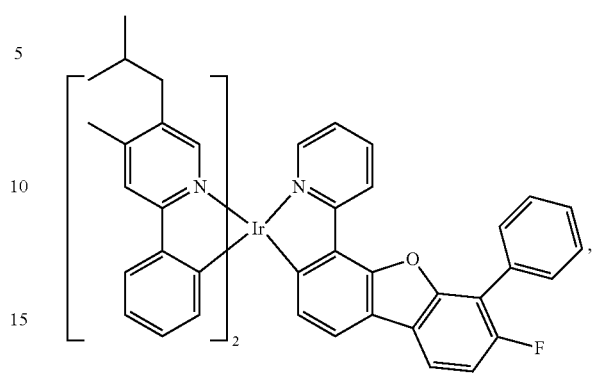
GD4-11
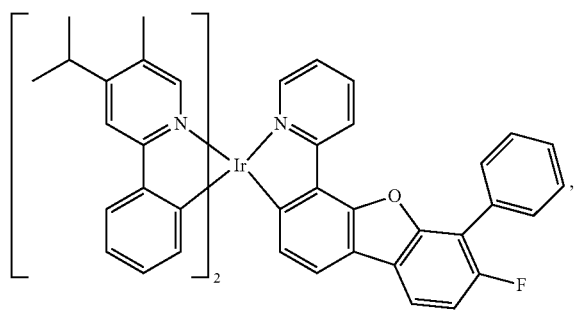
GD4-15
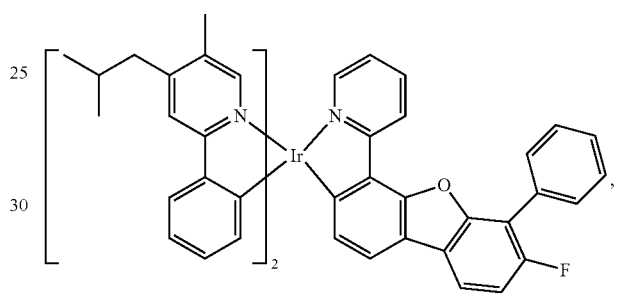
GD4-12
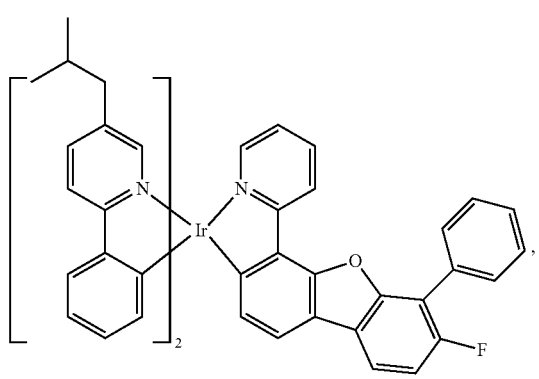
GD4-16
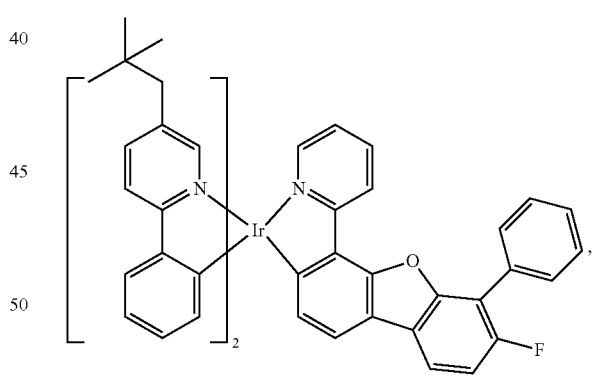
GD4-13
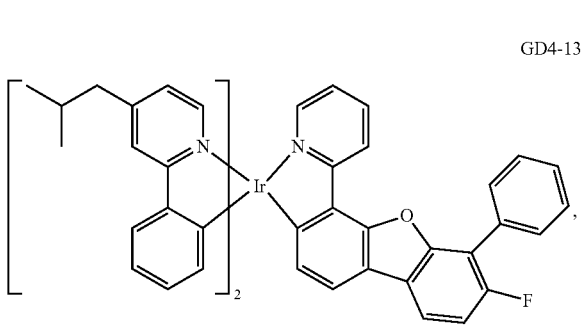
GD4-17
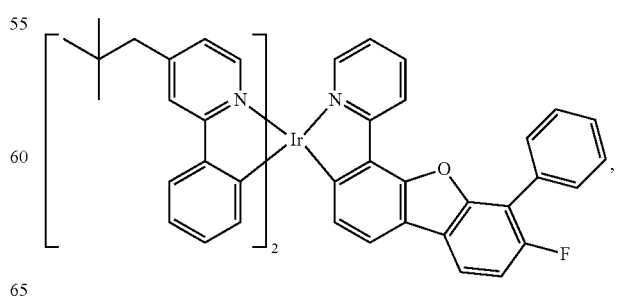

GD4-18
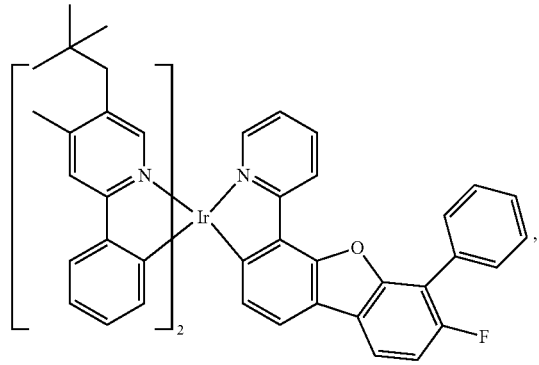
GD4-19
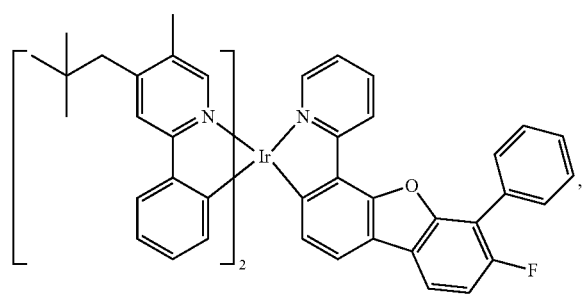
GD4-20
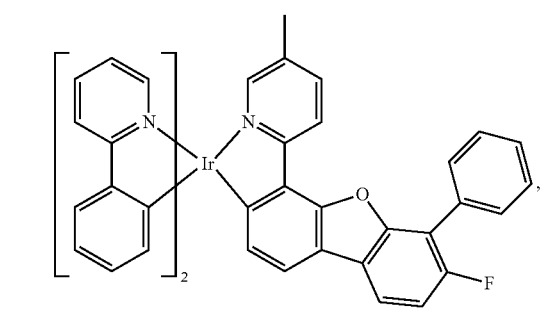
GD4-21
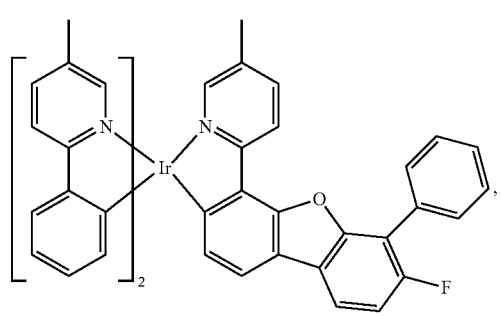
GD4-22
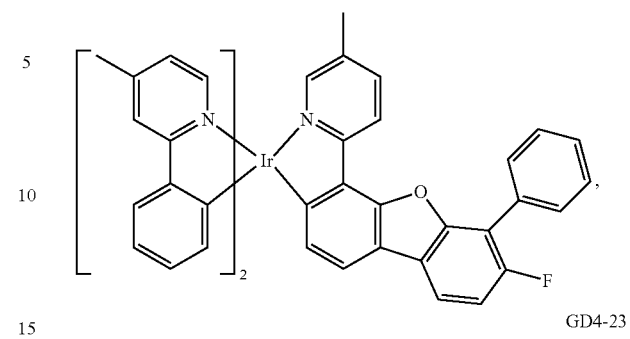
GD4-23
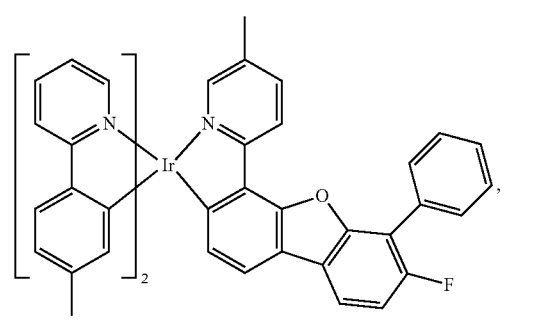
GD4-24
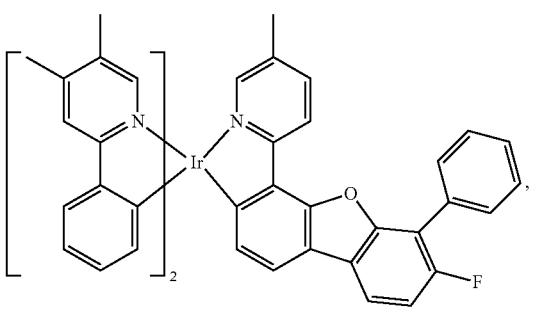
GD4-25
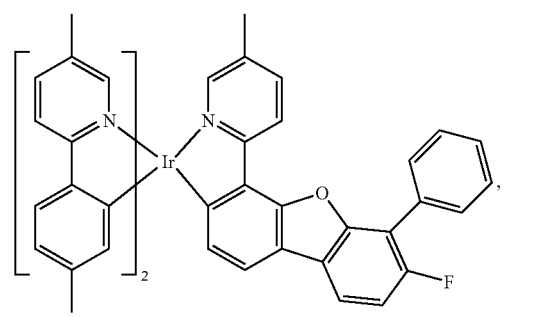
GD4-26
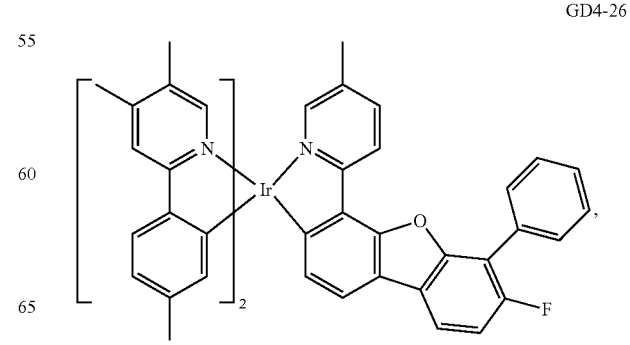

GD4-27
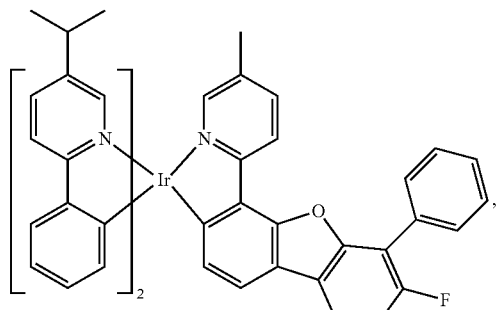
GD4-28
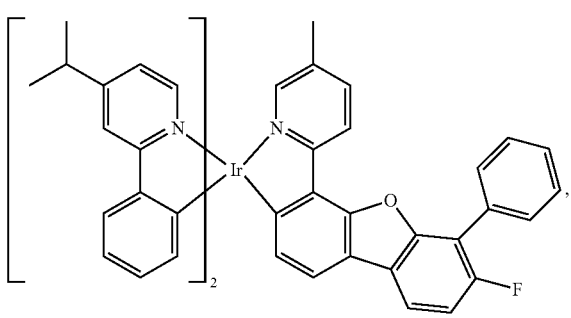
GD4-29
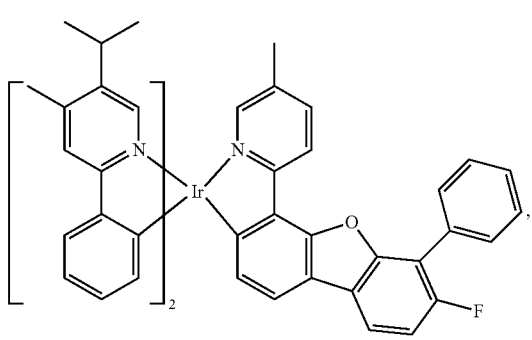
GD4-30
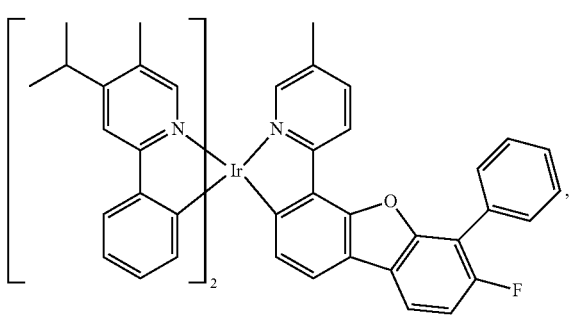
GD4-31
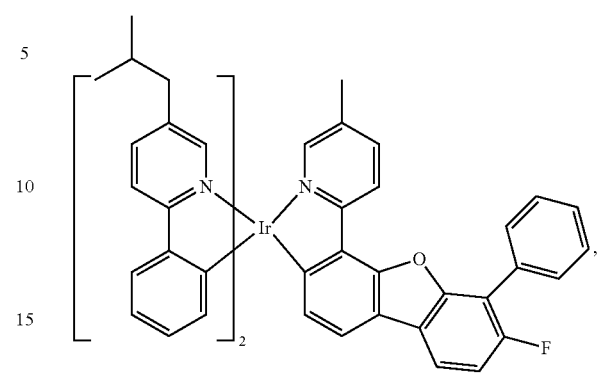
GD4-32
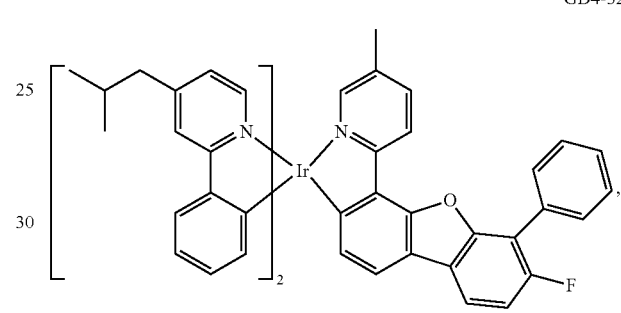
GD4-33
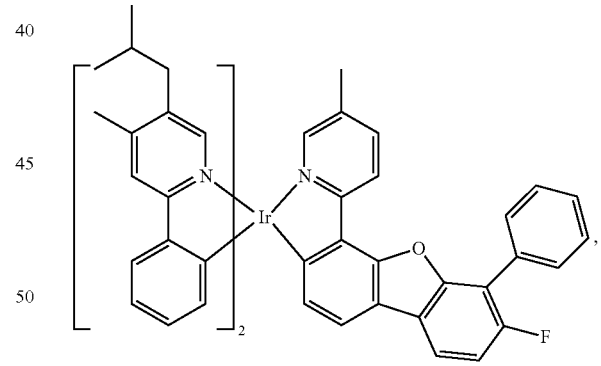
GD4-34
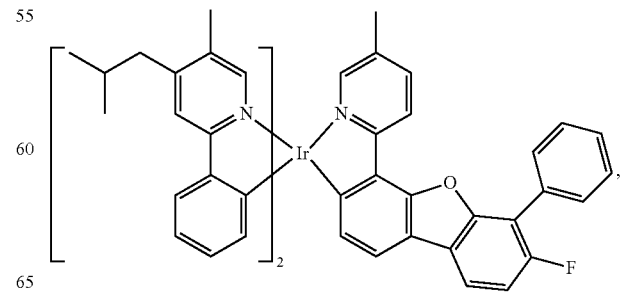

GD4-35
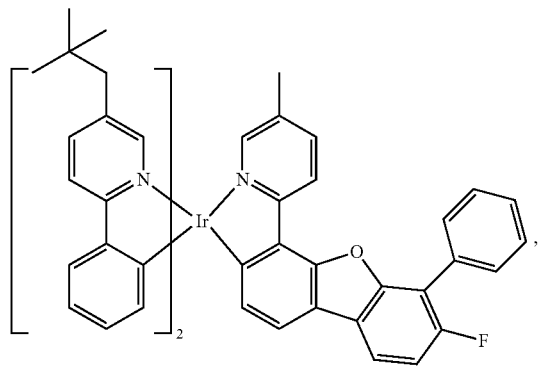
GD4-36
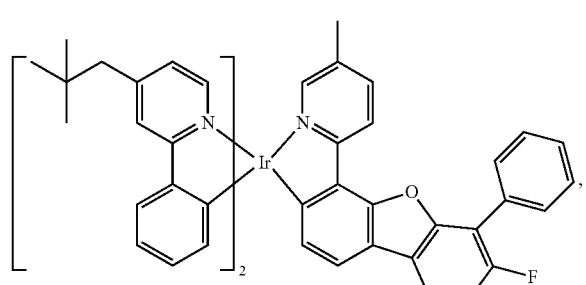
GD4-37
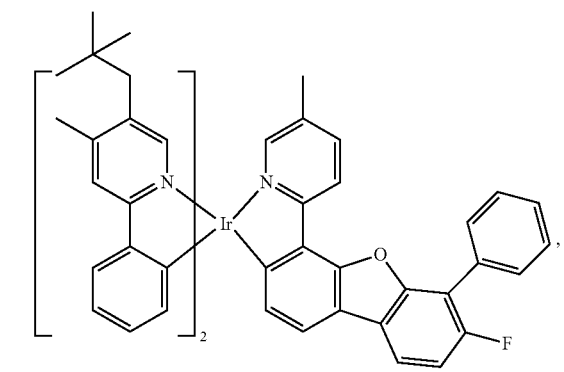
GD4-38
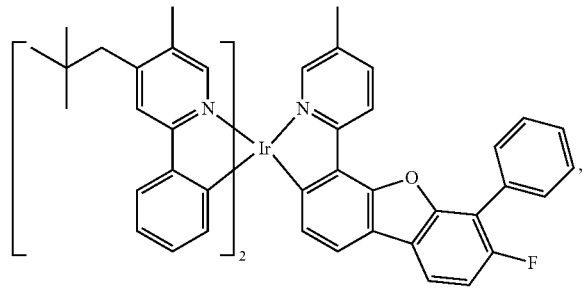
GD4-39
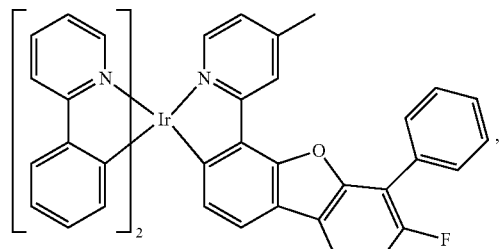
GD4-40
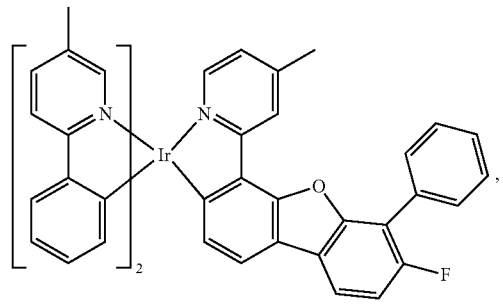
GD4-41
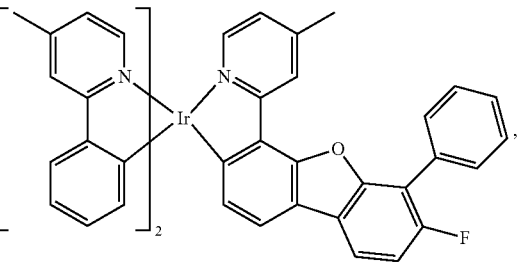
GD4-42
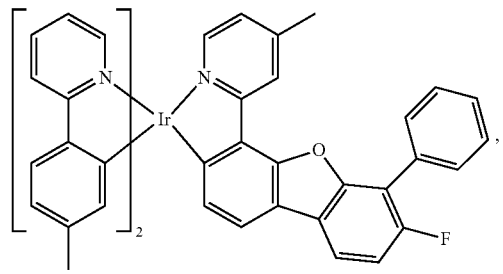
GD4-43
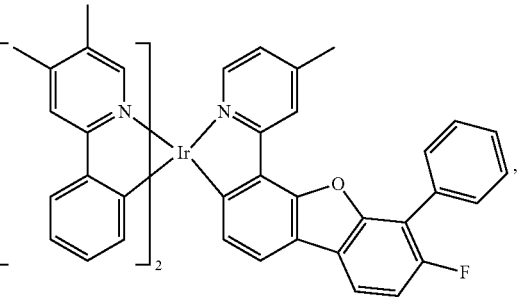

GD4-44
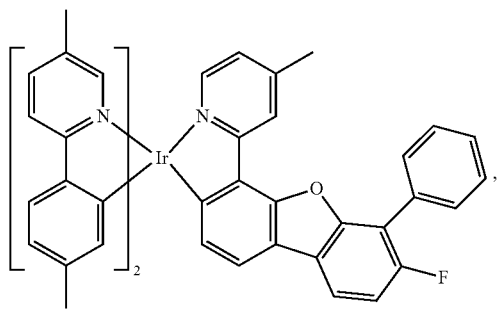
GD4-45
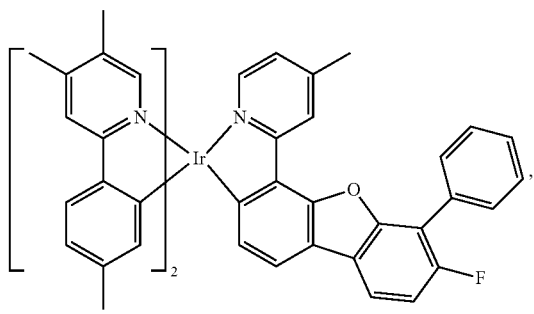
GD4-46
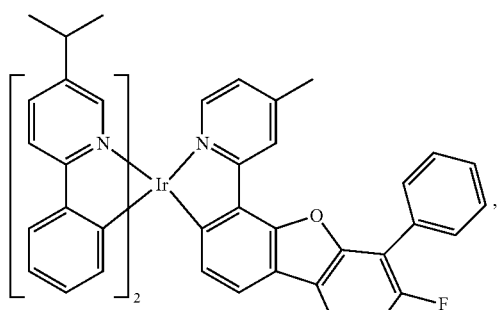
GD4-47
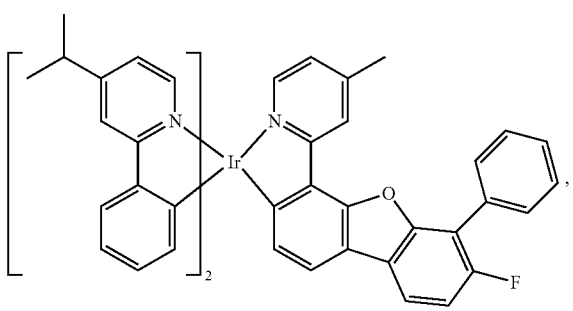
GD4-48
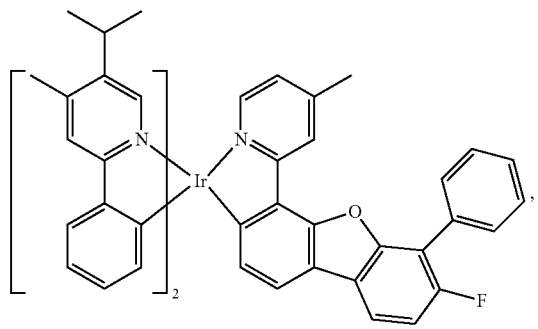
GD4-49
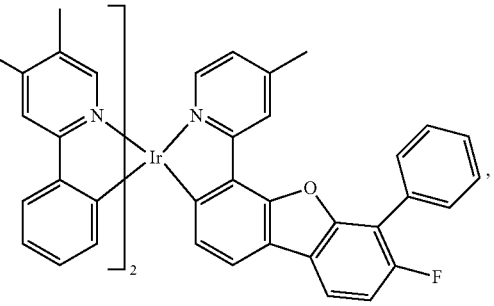
GD4-50
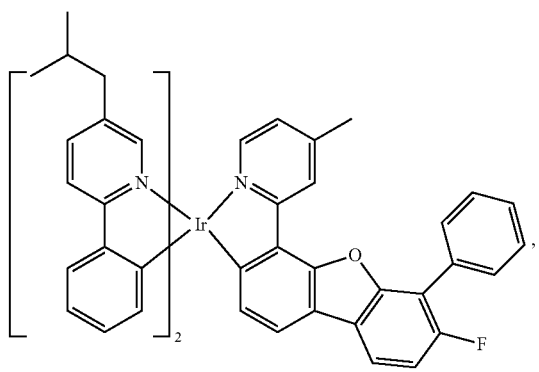
GD4-51
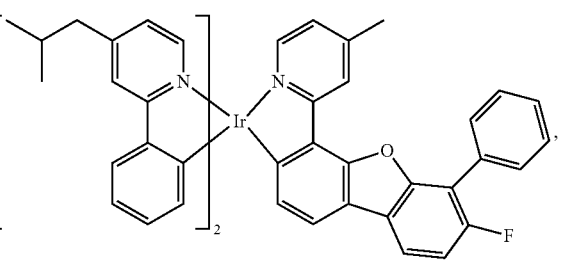

-continued
GD4-52
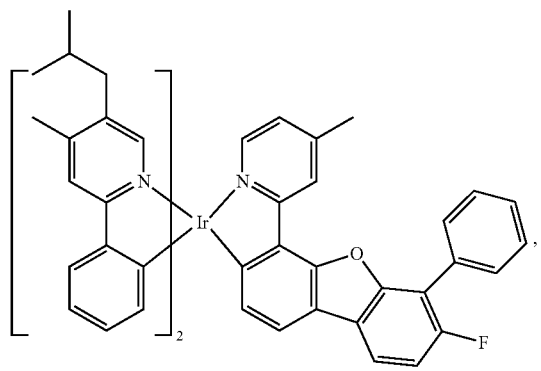
GD4-53
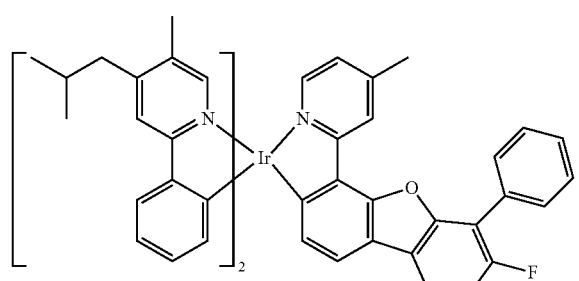
GD4-54
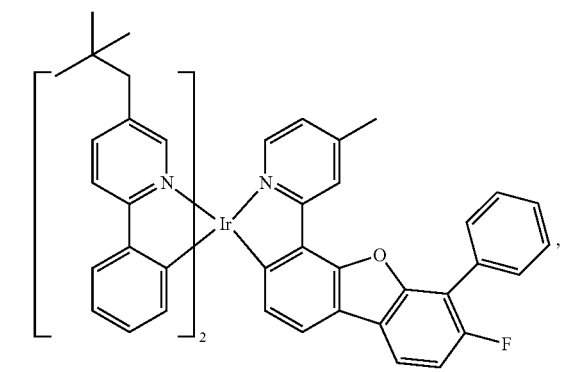
GD4-55
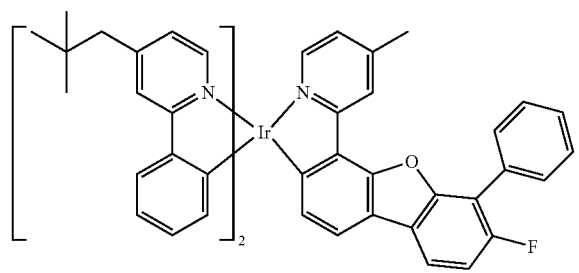
-continued
GD4-56
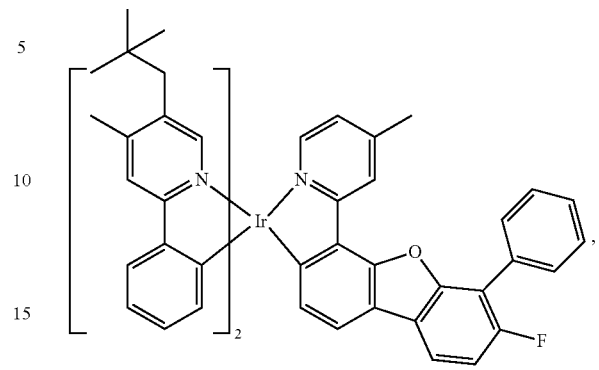
GD4-57
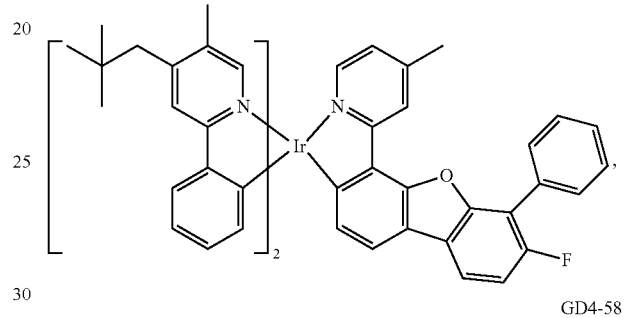
GD4-58
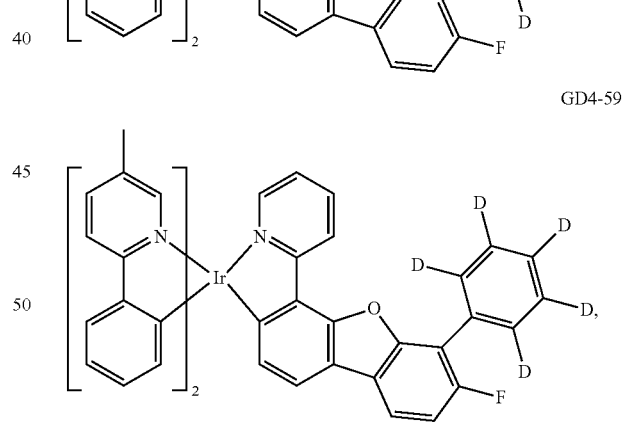
GD4-59
GD4-60
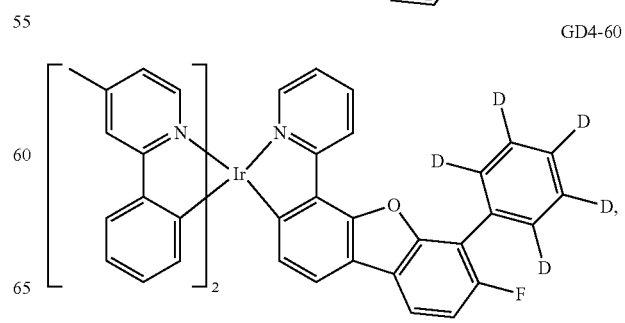

-continued
GD4-61
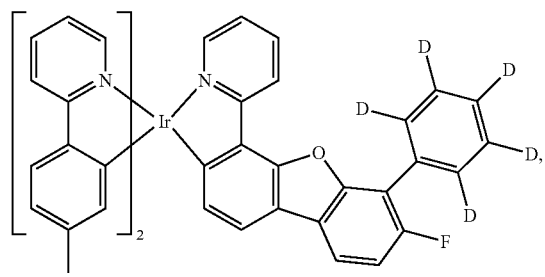
GD4-62
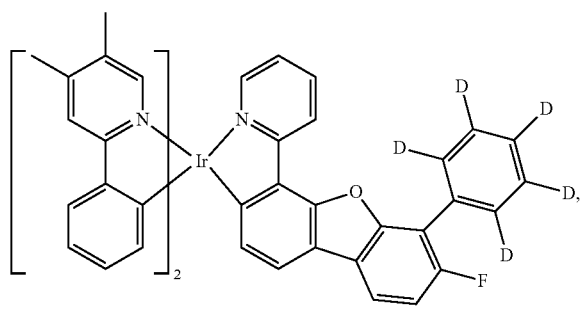
GD4-63
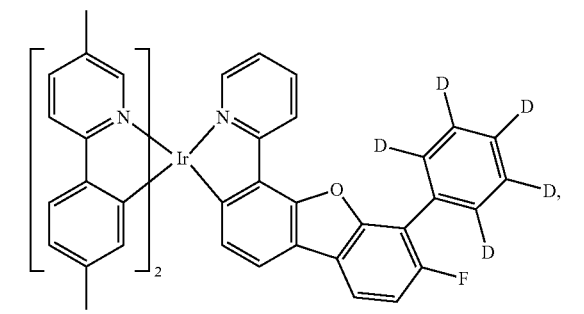
GD4-64
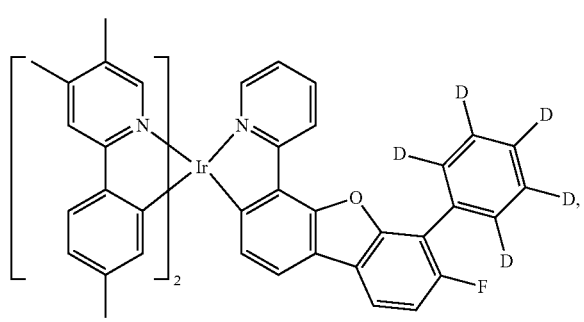
GD4-65
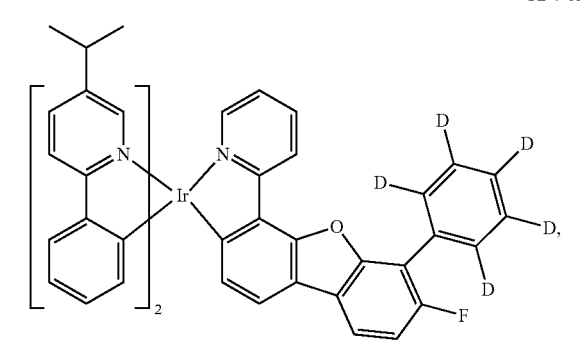
-continued
GD4-66
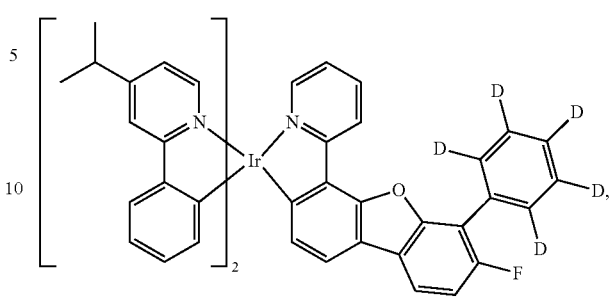
GD4-67
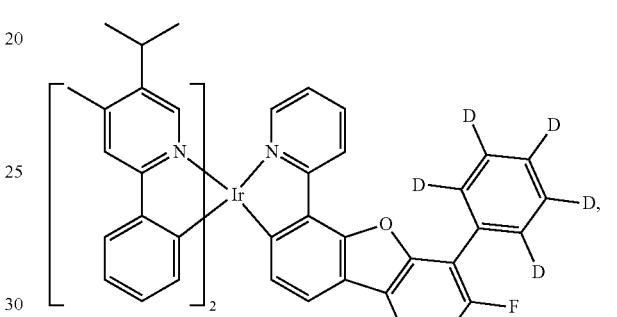
GD4-68
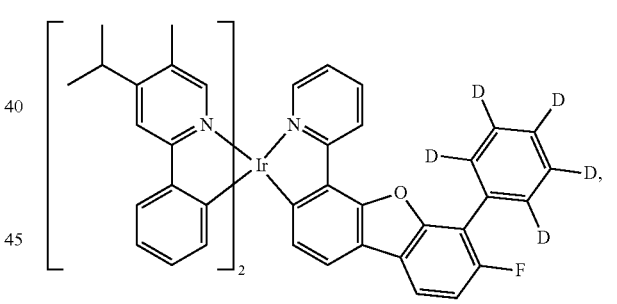
GD4-69
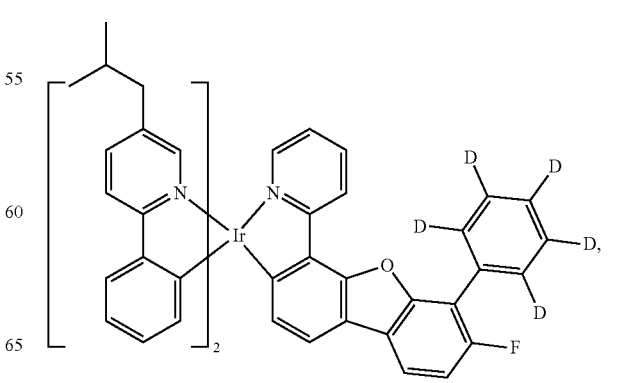

GD4-70
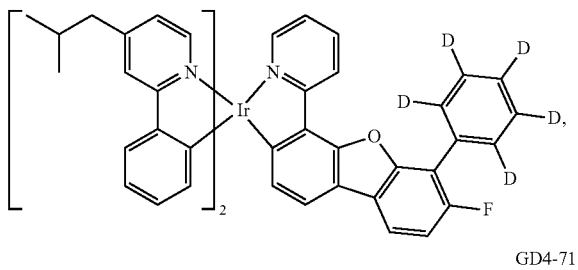
GD4-71
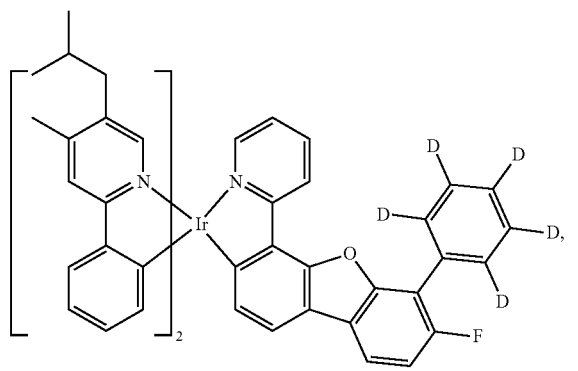
GD4-72
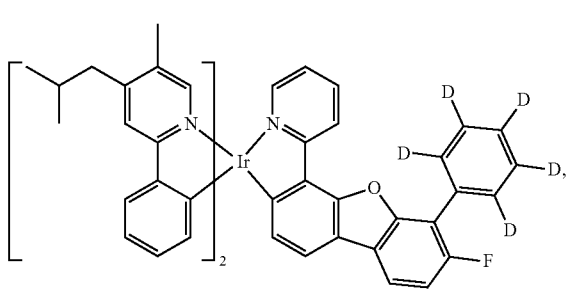
GD4-73
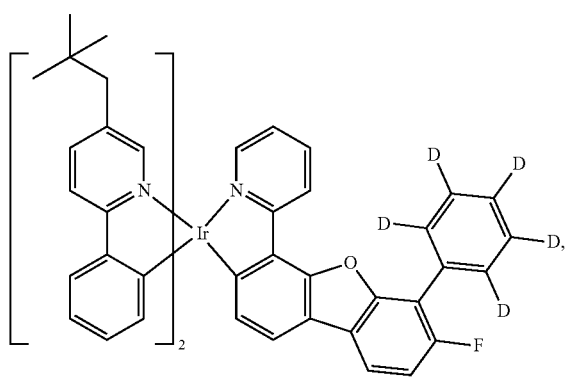
GD4-74
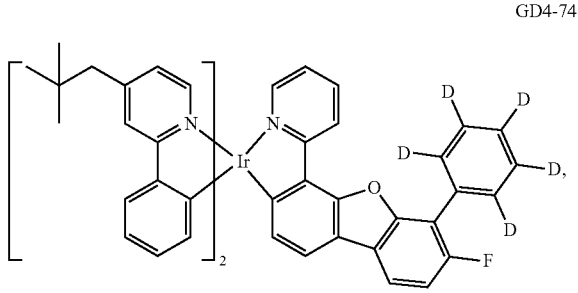
GD4-75
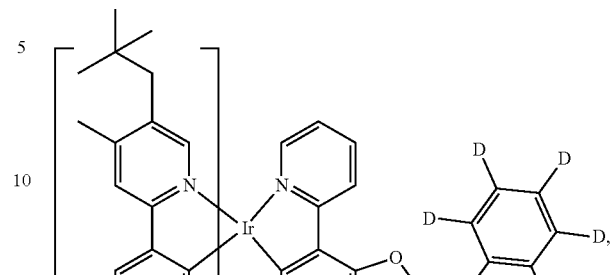
GD4-76
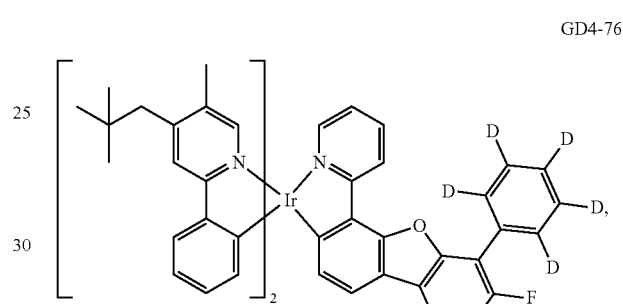
GD4-77
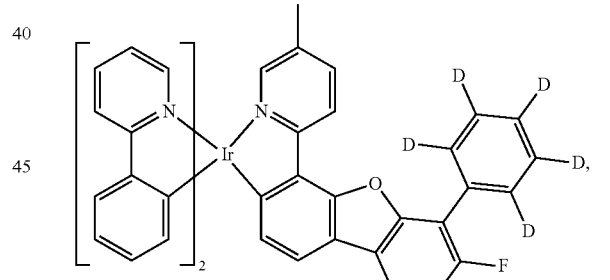
GD4-78

GD4-79
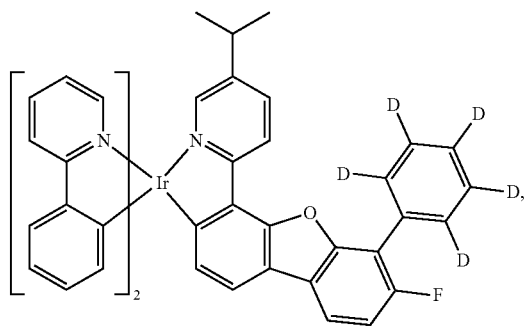
GD4-80
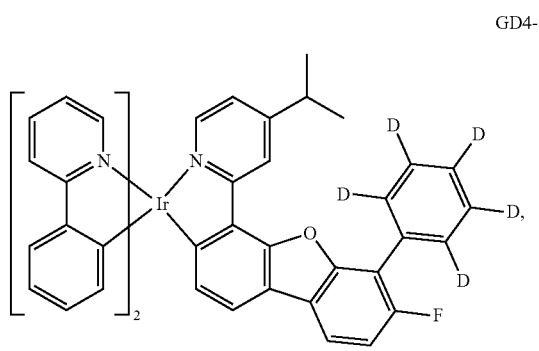
GD4-81
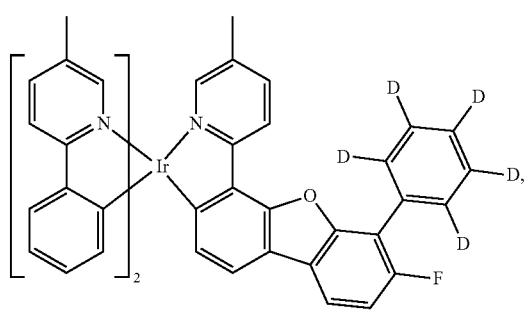
GD4-82
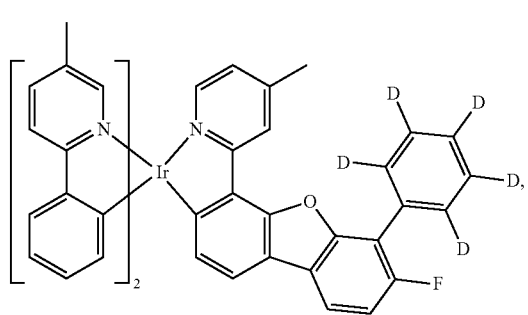
GD4-83
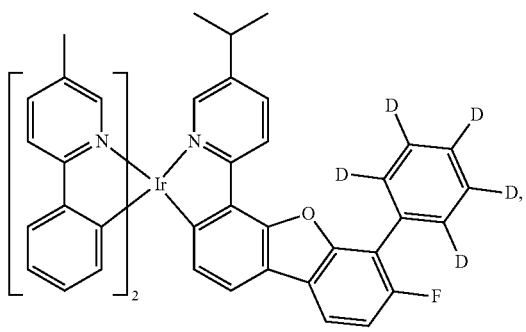
GD4-84
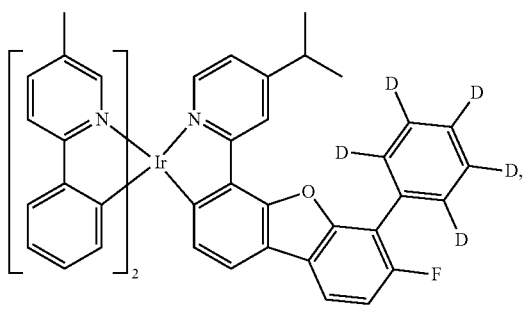
GD4-85
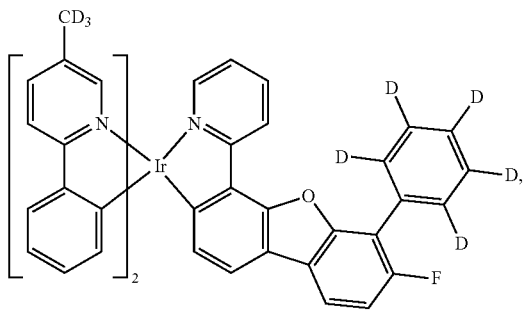
GD4-86
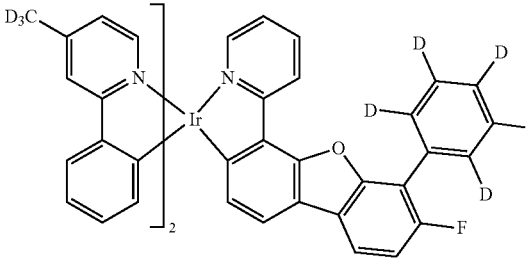
GD5-1
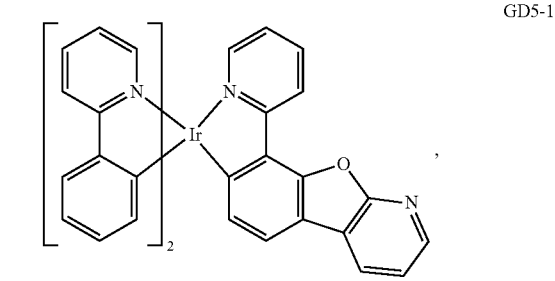

GD5-2
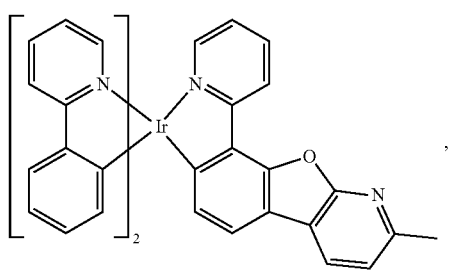
GD5-7
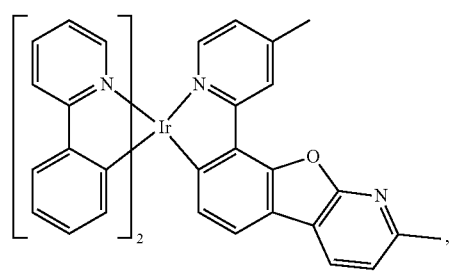
GD5-3
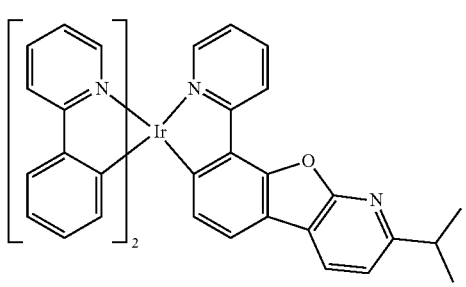
GD5-8
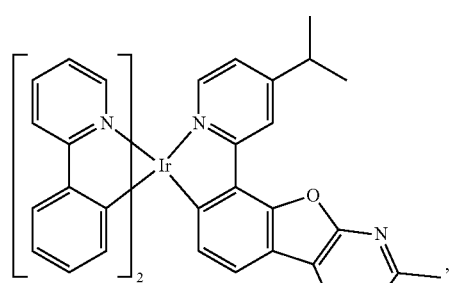
GD5-4
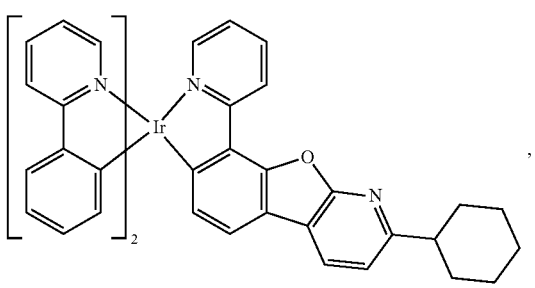
GD5-9
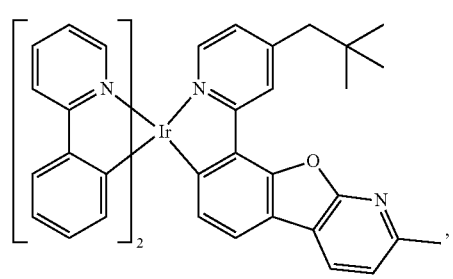
GD5-5
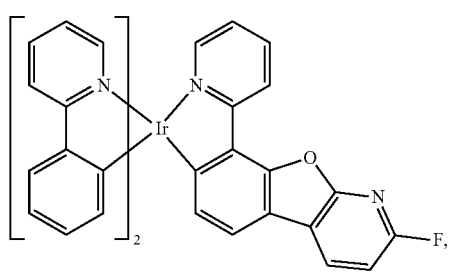
GD5-10
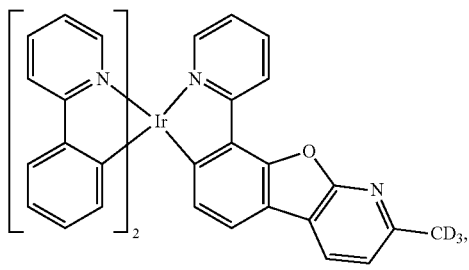
GD5-6
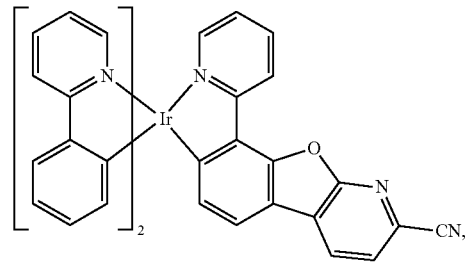
GD5-11
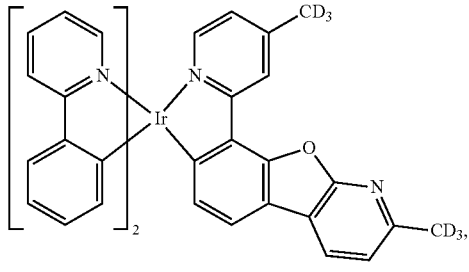

GD5-12
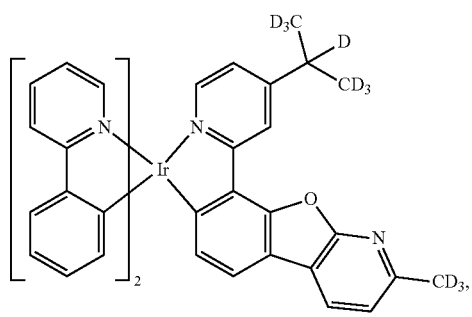
GD5-13
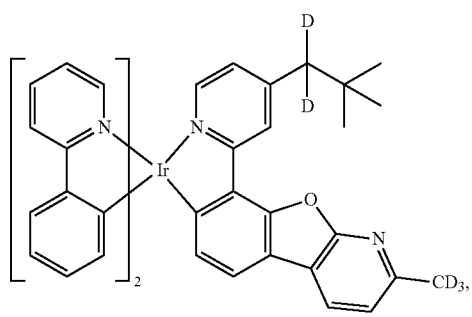
GD5-14
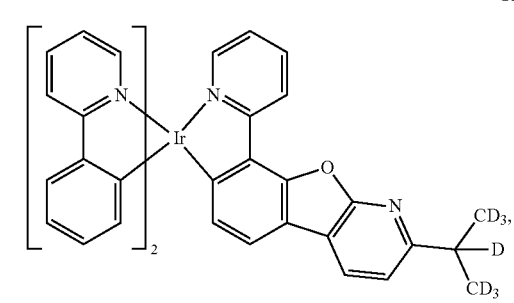
GD5-15
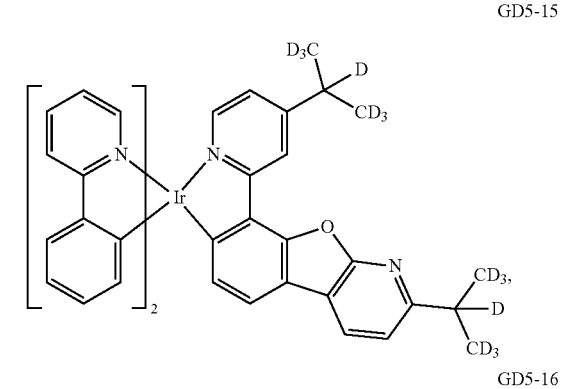
GD5-16
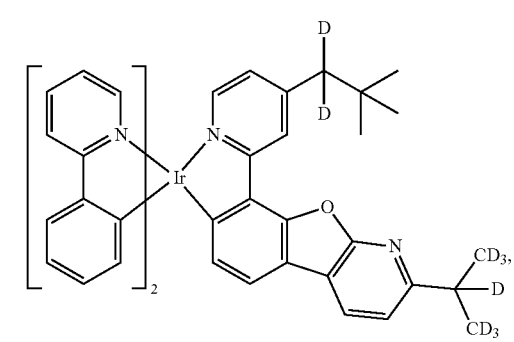
GD5-17
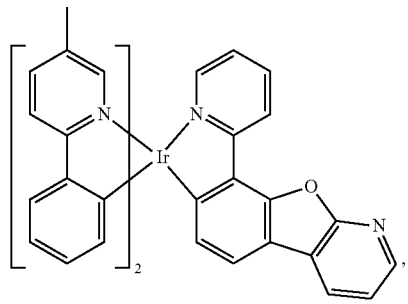
GD5-18
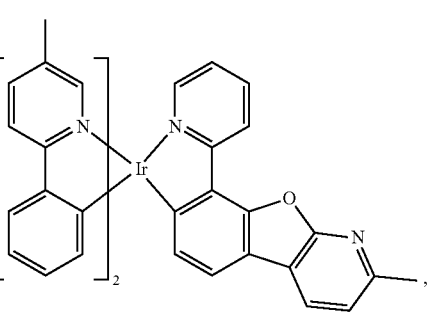
GD5-19
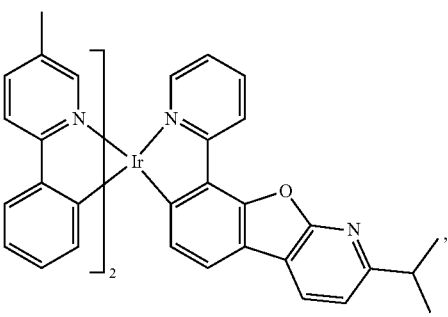
GD5-20
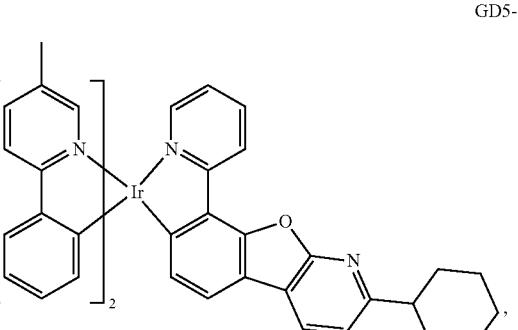
GD5-21
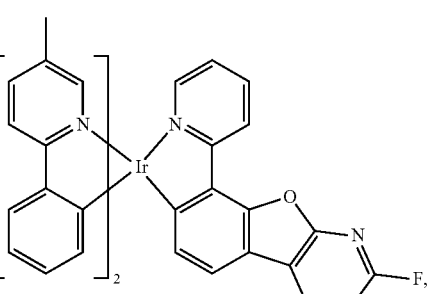

GD5-22
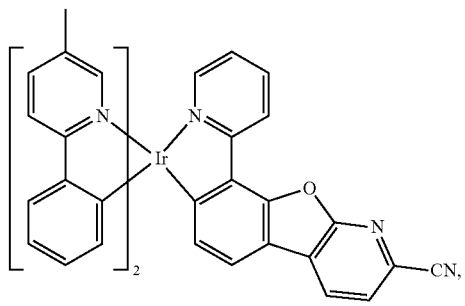
GD5-23
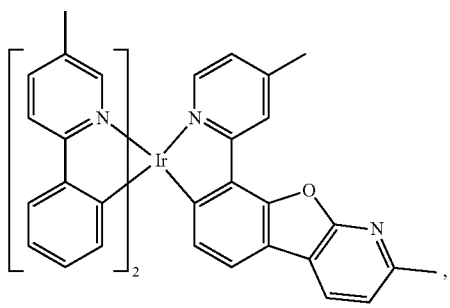
GD5-24
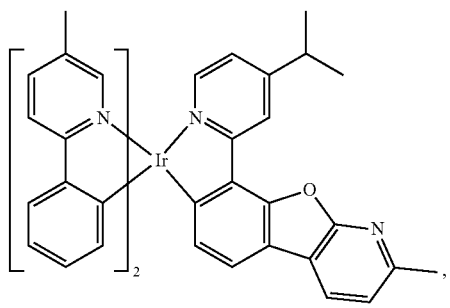
GD5-25
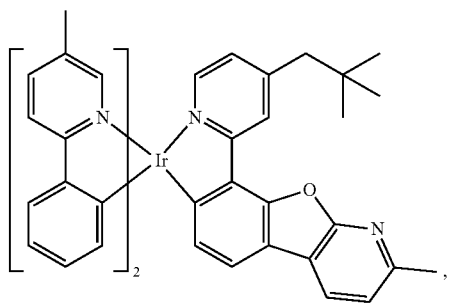
GD5-26
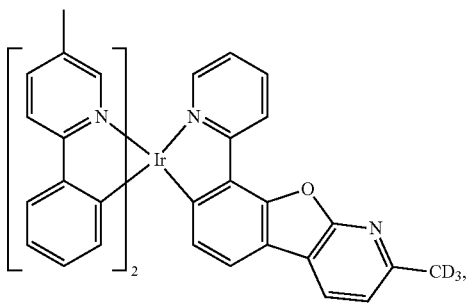
GD5-27
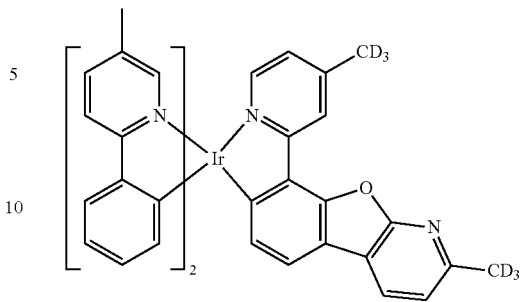
GD5-28
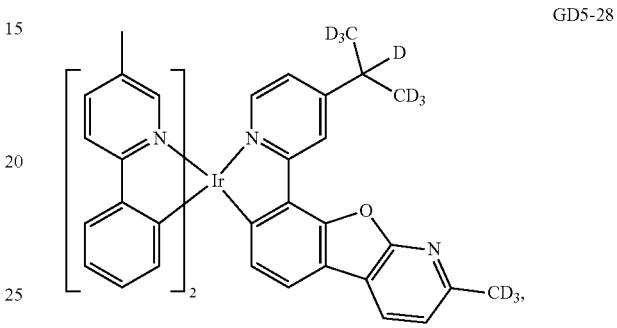
GD5-29
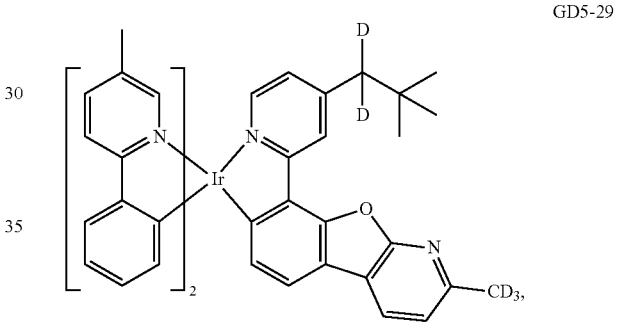
GD5-30
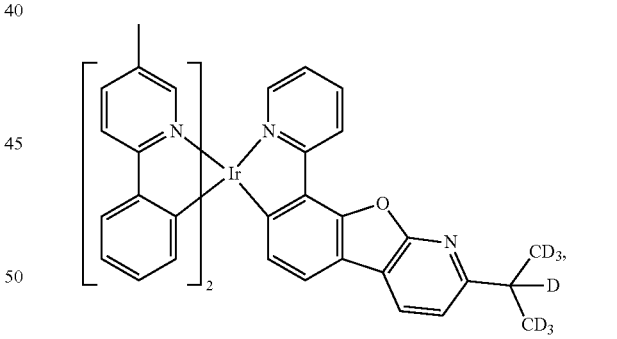
GD5-31
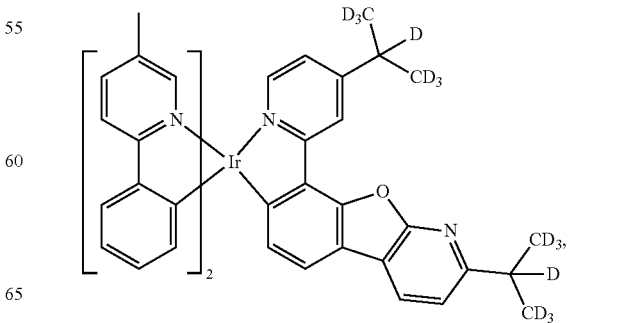

GD5-32
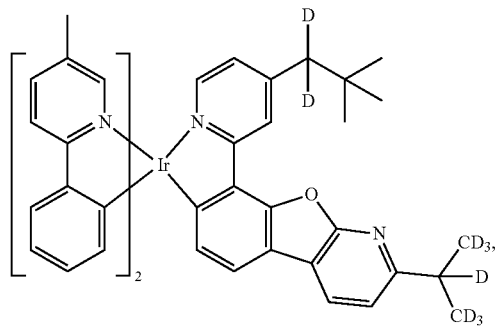
GD5-33
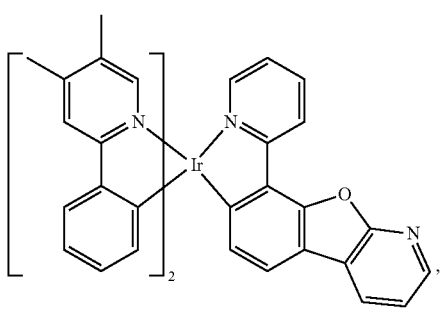
GD5-34
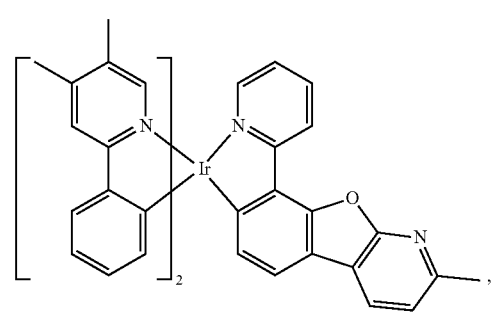
GD5-35
GD5-36
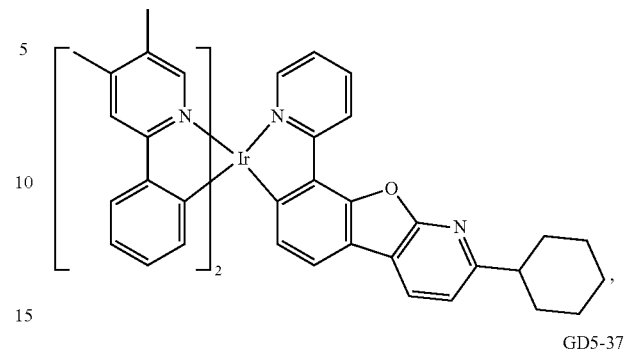
GD5-37
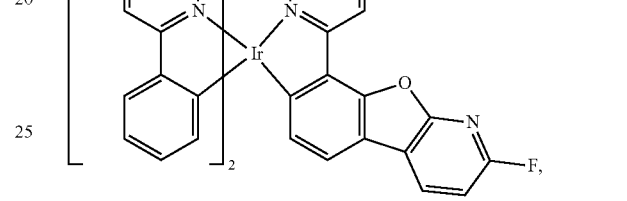
GD5-38
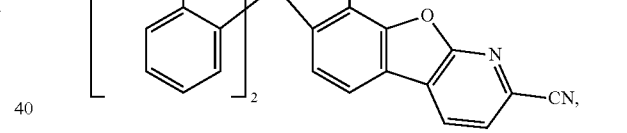
GD5-39
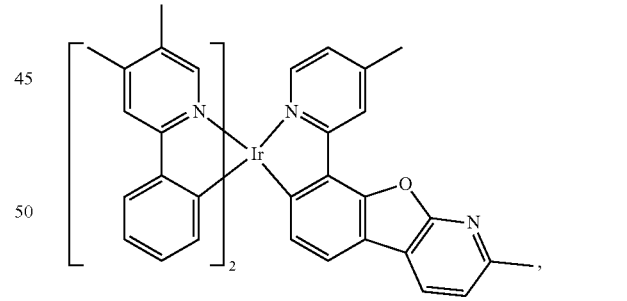
GD5-40
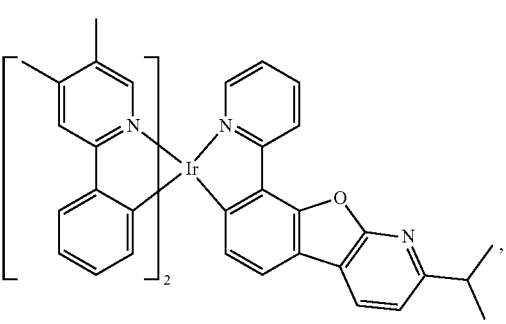
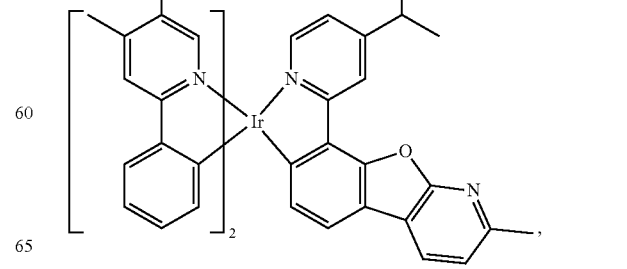

GD5-41
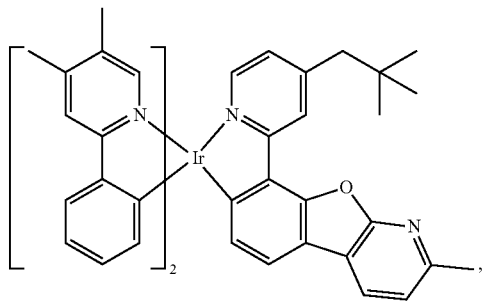
GD5-42
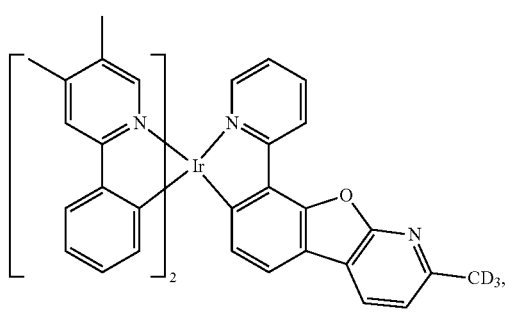
GD5-43
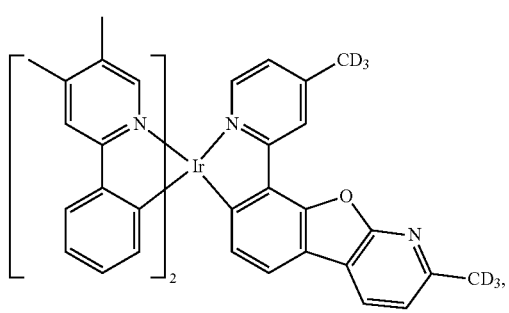
GD5-44
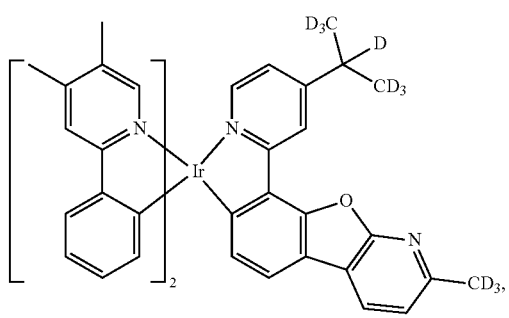
GD5-45
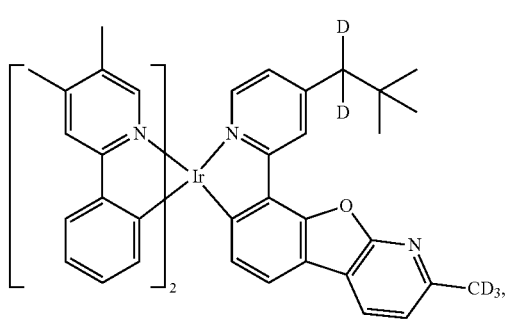
GD5-46
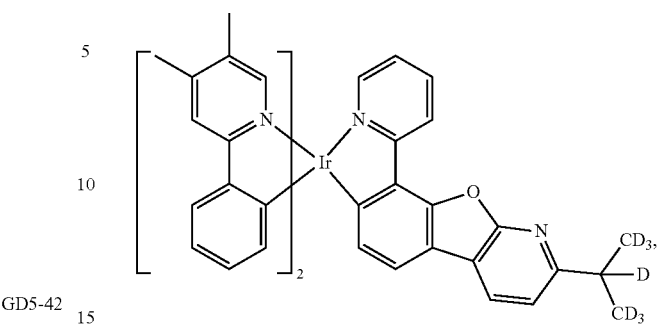
GD5-47
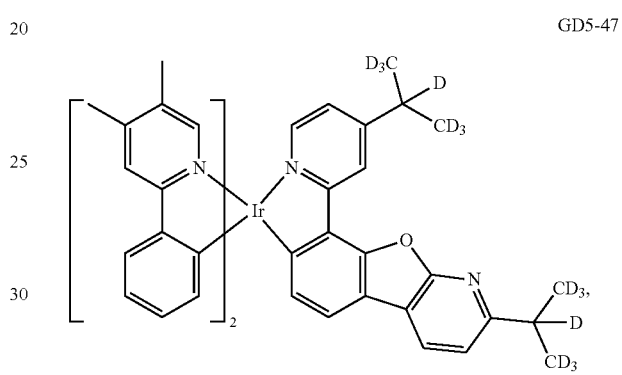
GD5-48
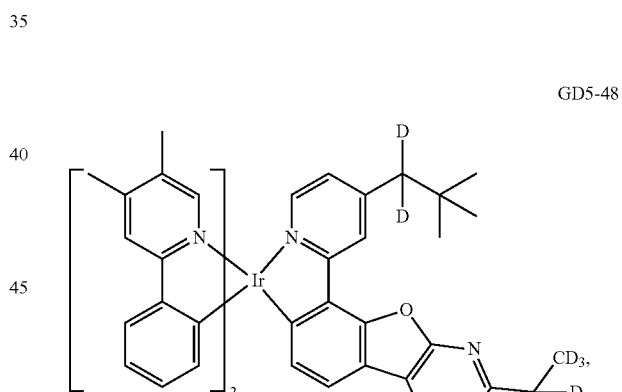
GD5-49
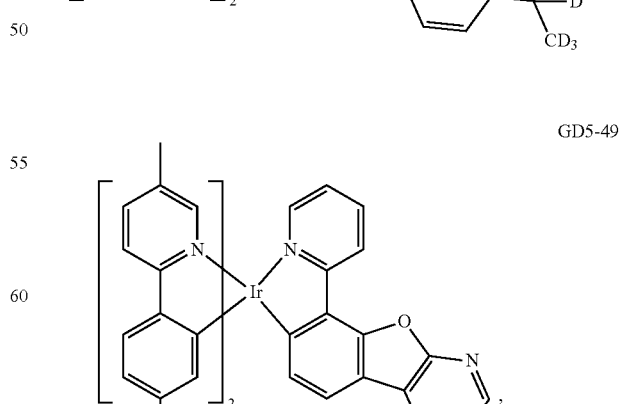

GD5-50
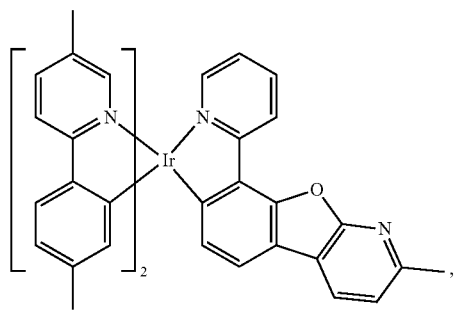
GD5-51
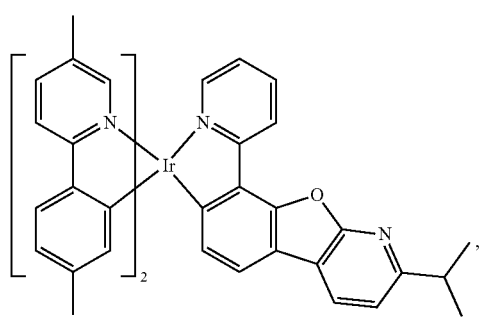
GD5-52
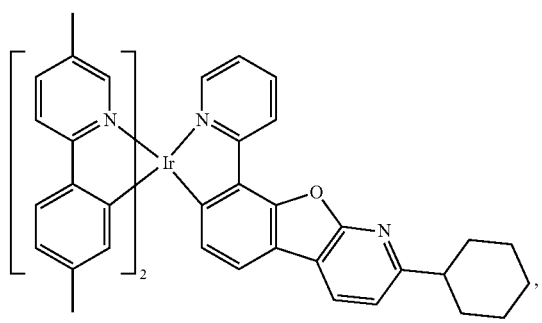
GD5-53
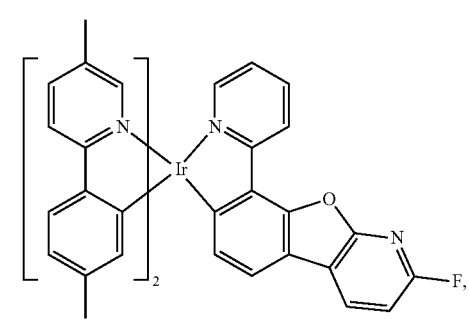
GD5-54
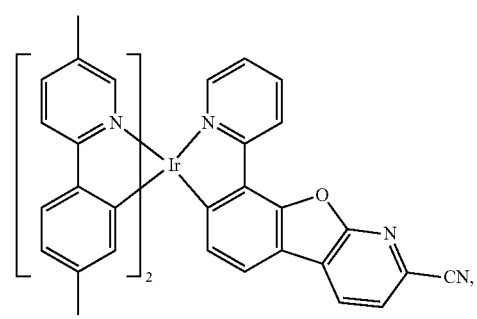
GD5-55
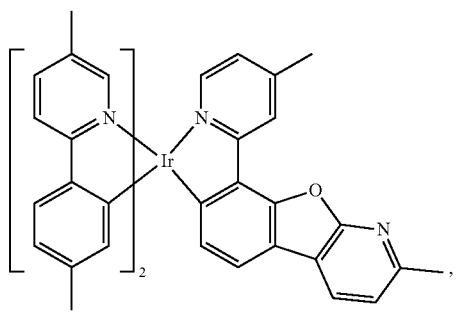
GD5-56
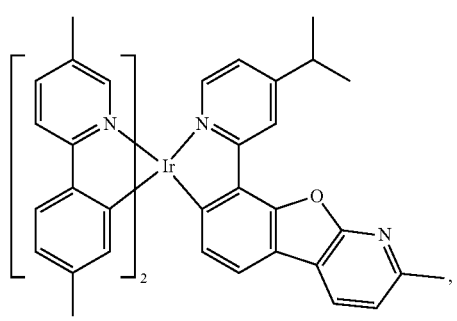
GD5-57
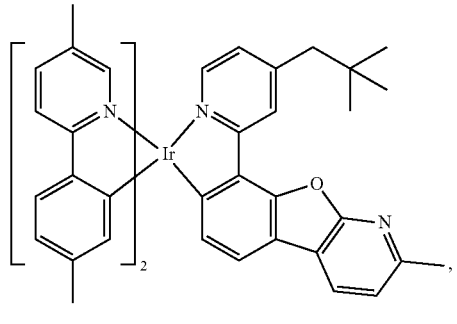
GD5-58
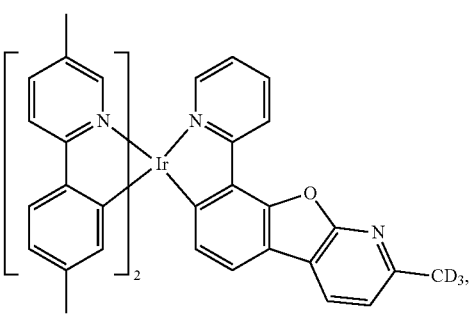
GD5-59
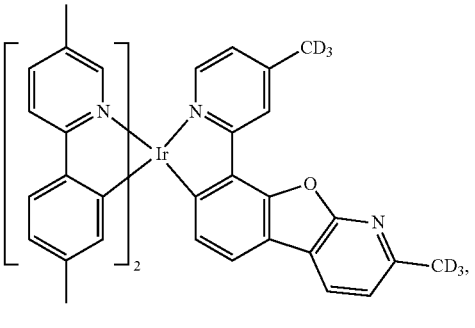

GD5-60
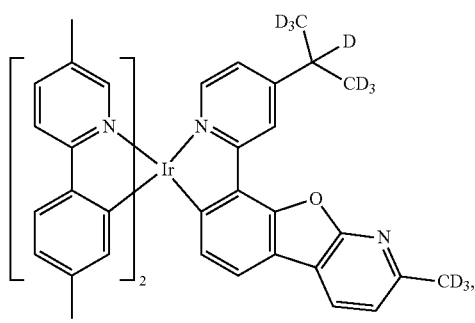
GD5-61
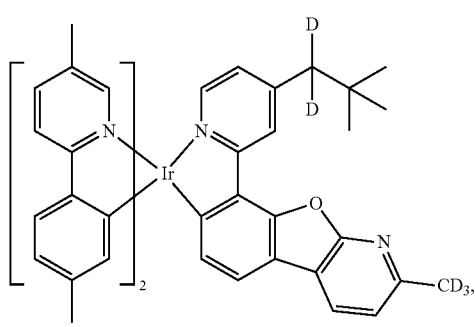
GD5-62
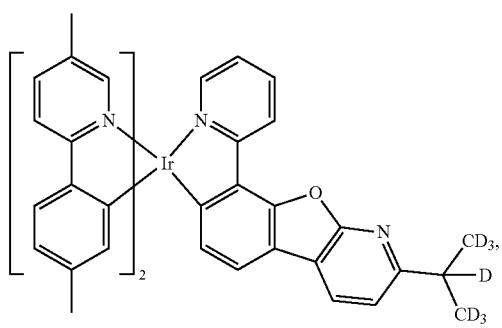
GD5-63
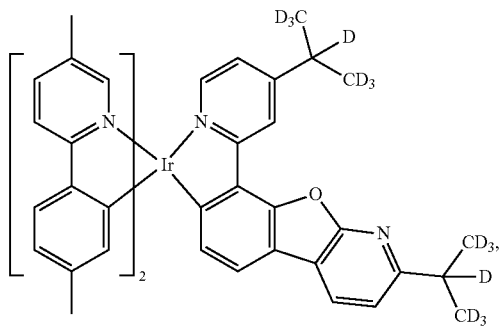
GD5-64
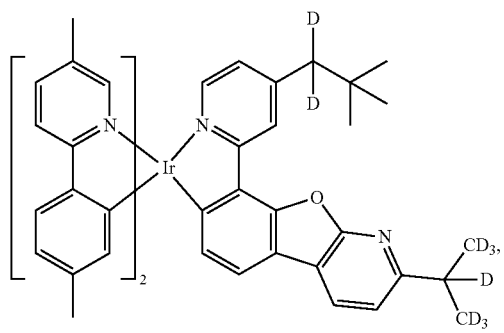
GD5-65
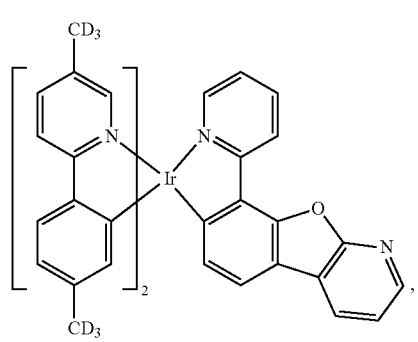
GD5-66
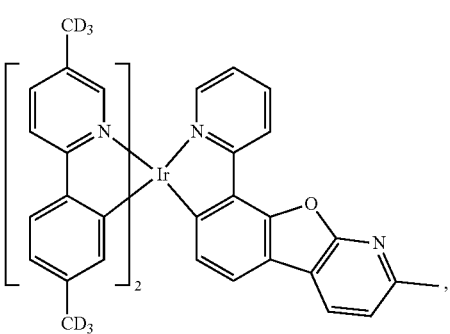
GD5-67
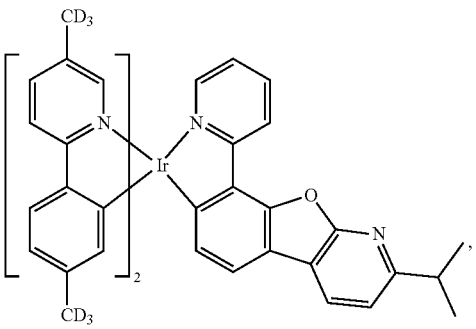

GD5-68
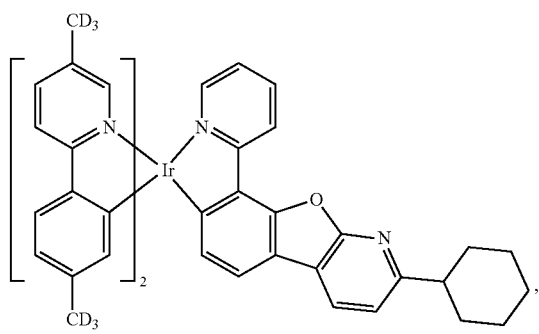
GD5-69
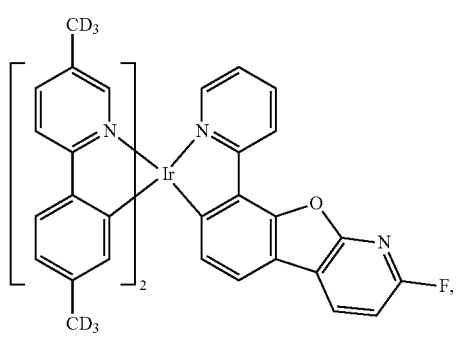
GD5-70
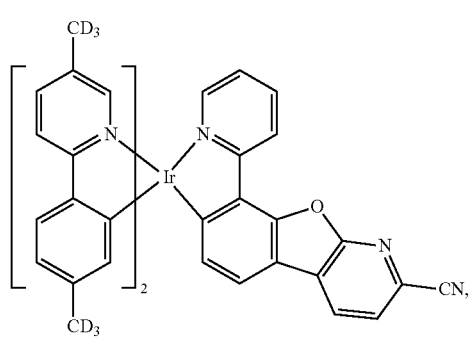
GD5-71
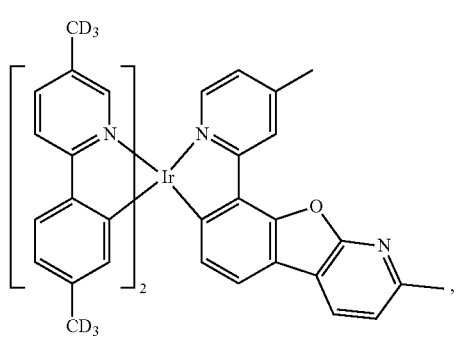
GD5-72
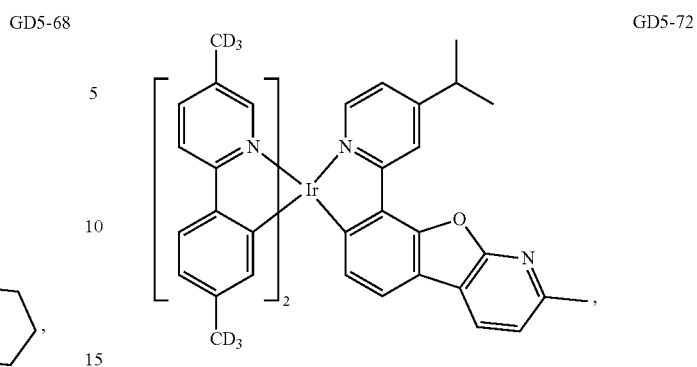
GD5-73
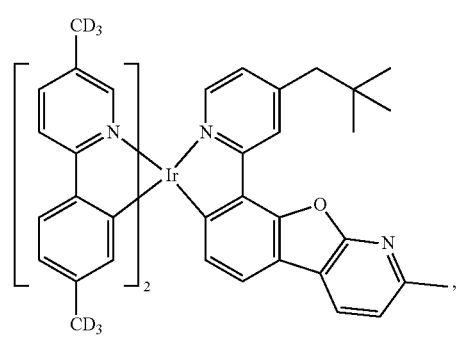
GD5-74
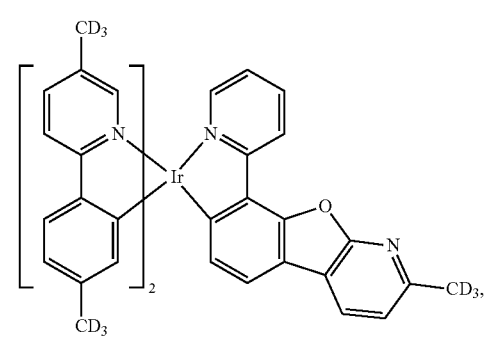
GD5-75
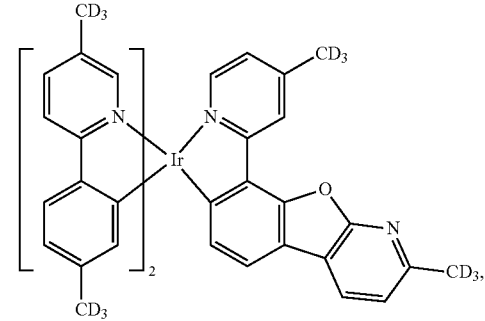

GD5-76
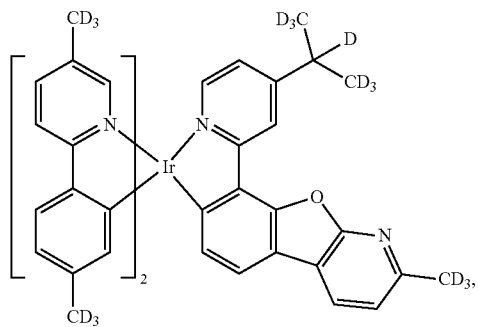
GD5-77
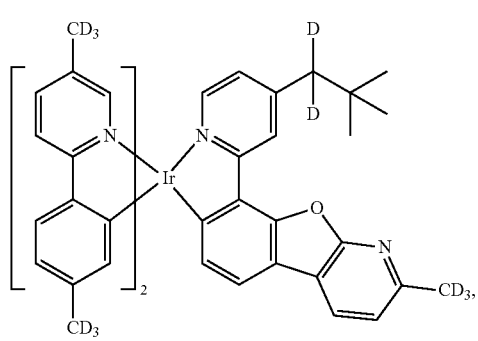
GD5-78
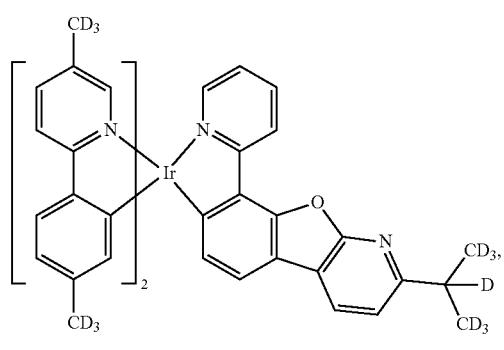
GD5-79
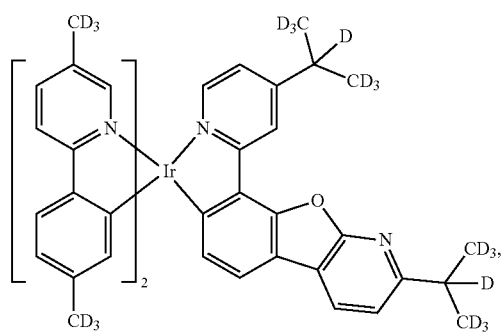
GD5-80
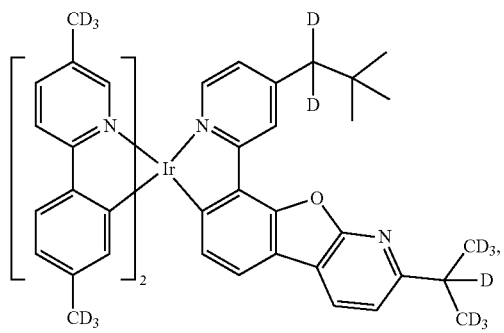
GD5-81
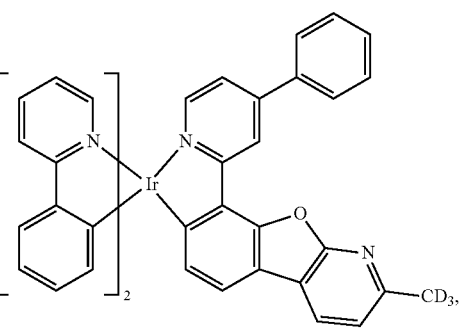
GD5-82
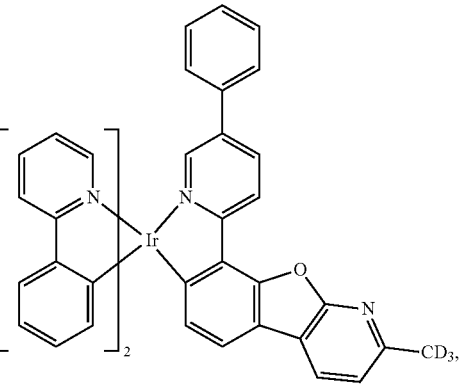
GD5-83
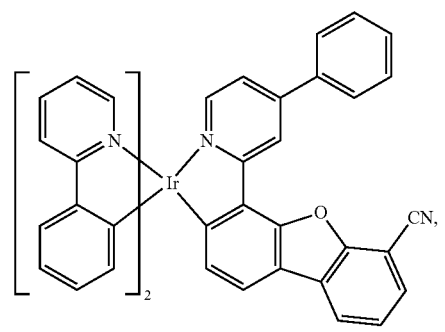

GD5-84
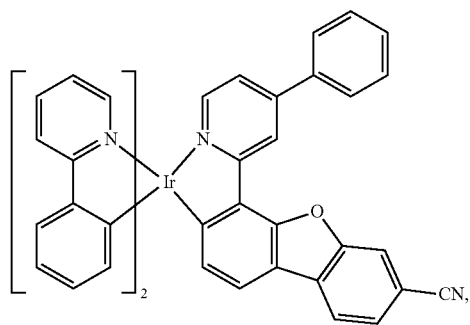
GD5-85
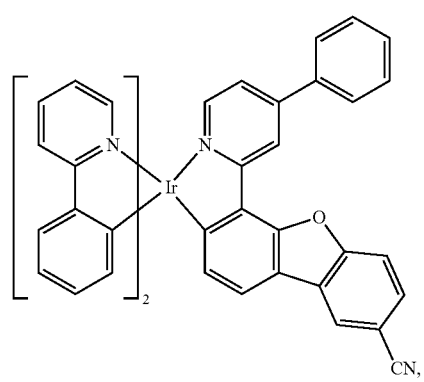
GD6-1
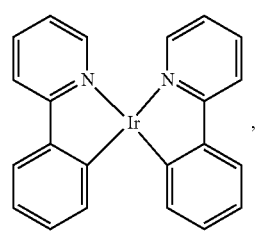
GD6-2
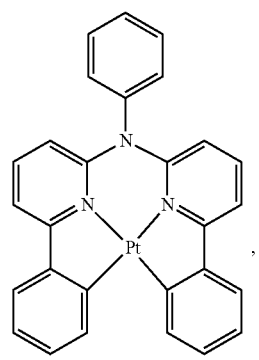
GD6-3
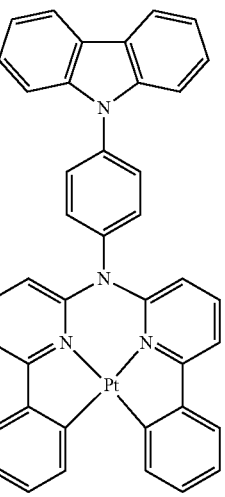
GD6-4
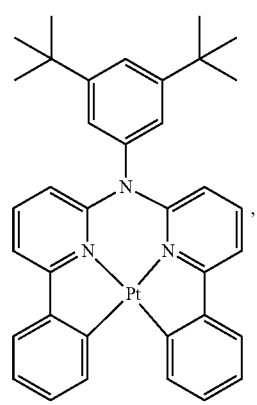
GD6-5
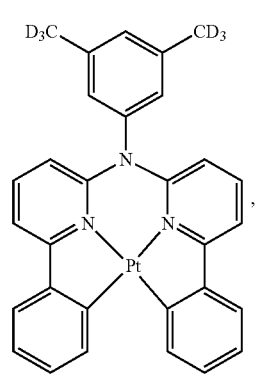
GD6-6
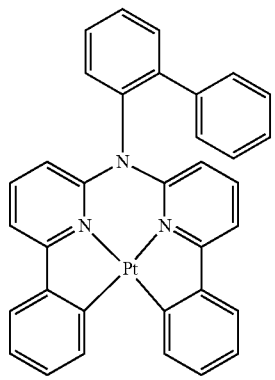

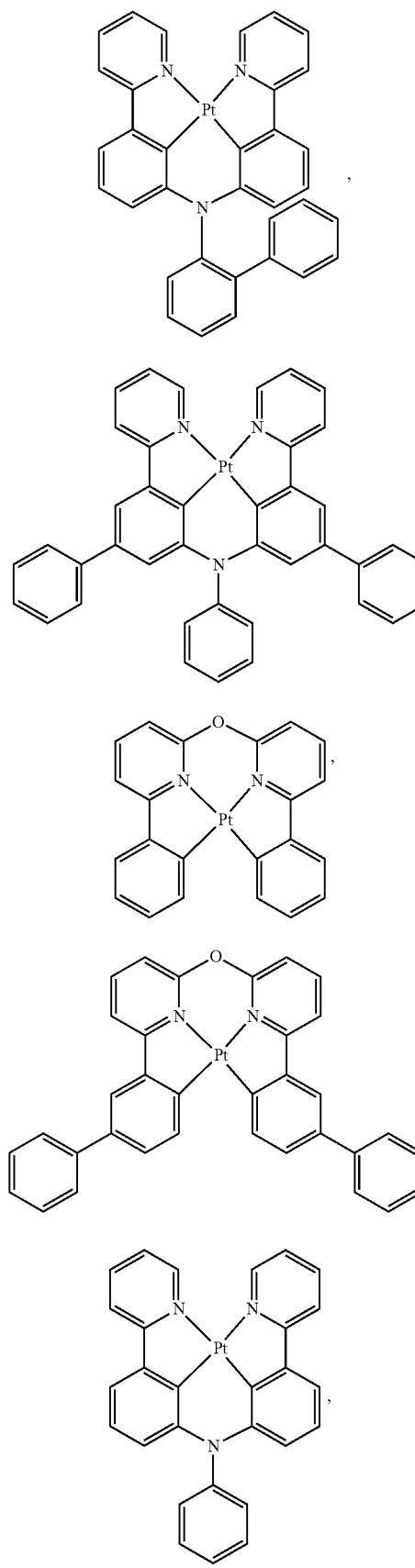

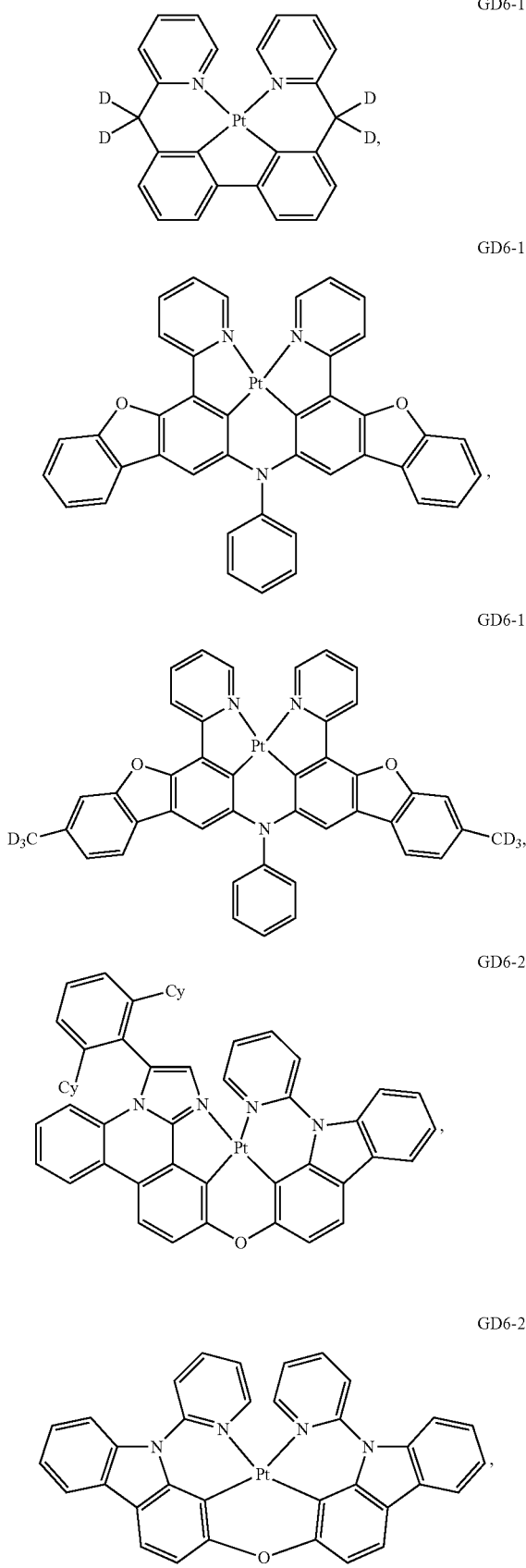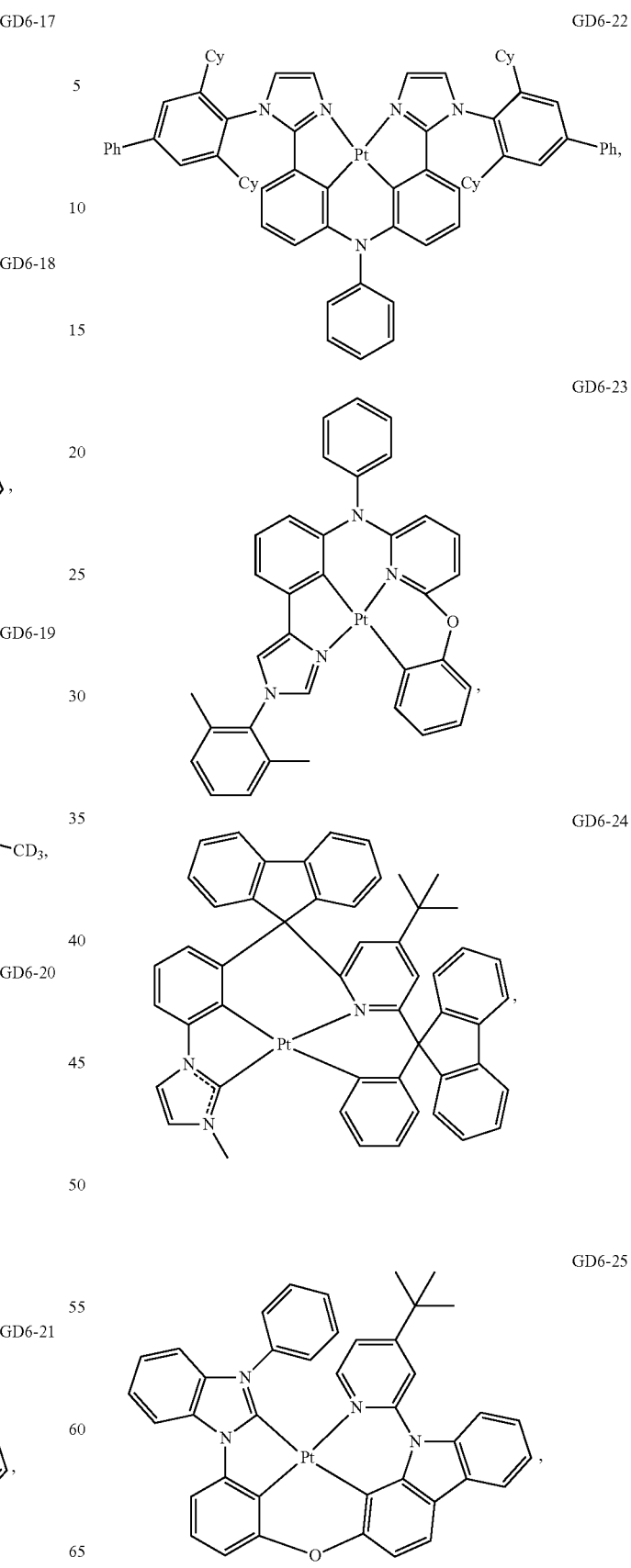

-continued
GD6-26
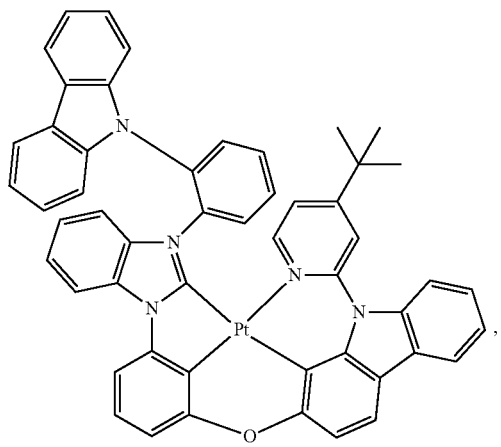
GD6-27
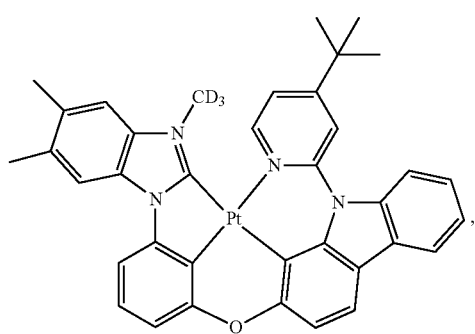
GD6-28
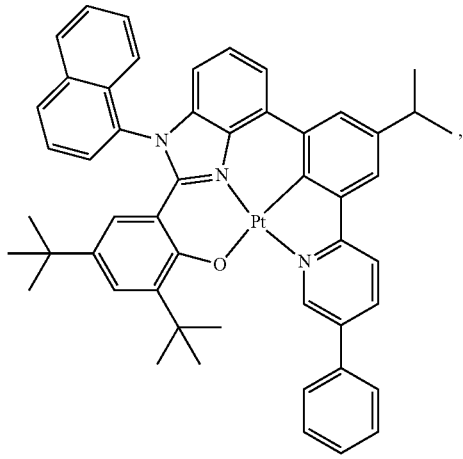
-continued
GD6-29
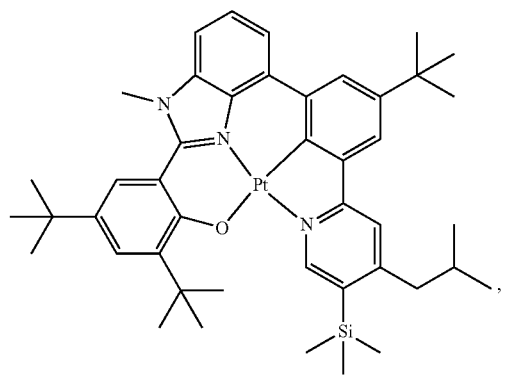
GD6-30
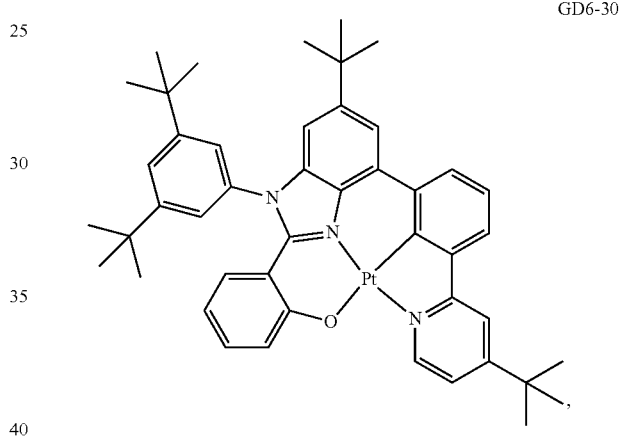
GD6-31
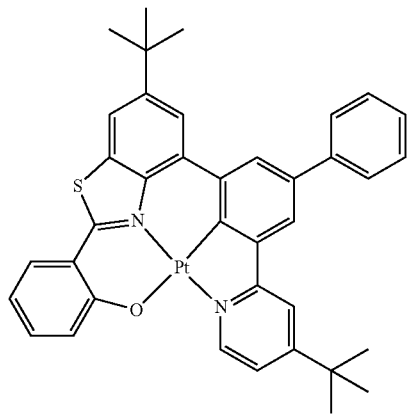

GD6-32
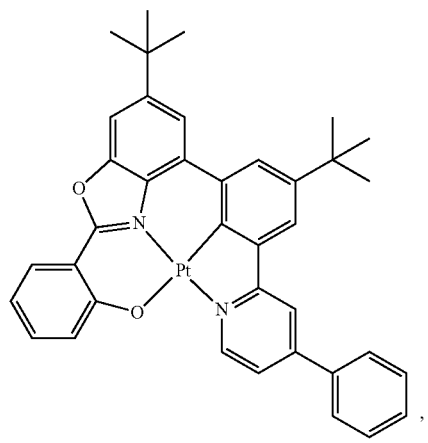
GD6-33
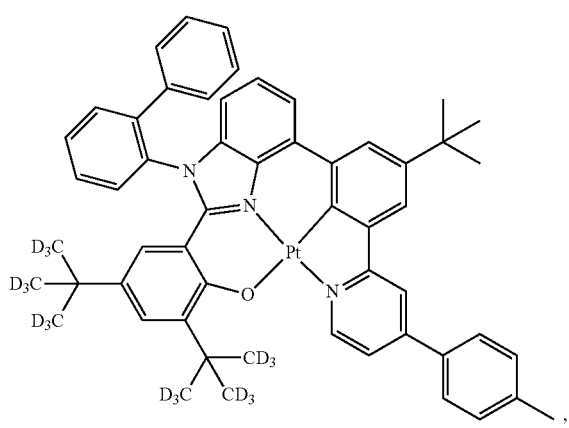
GD6-34
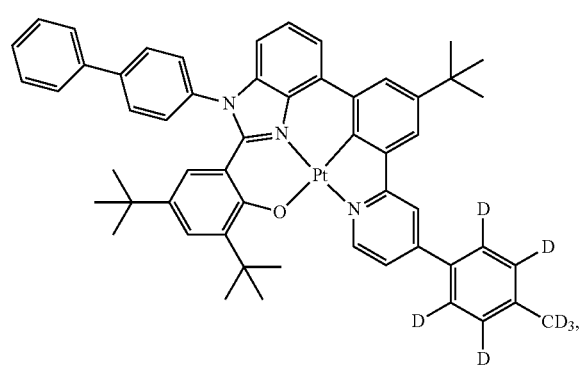
GD6-35
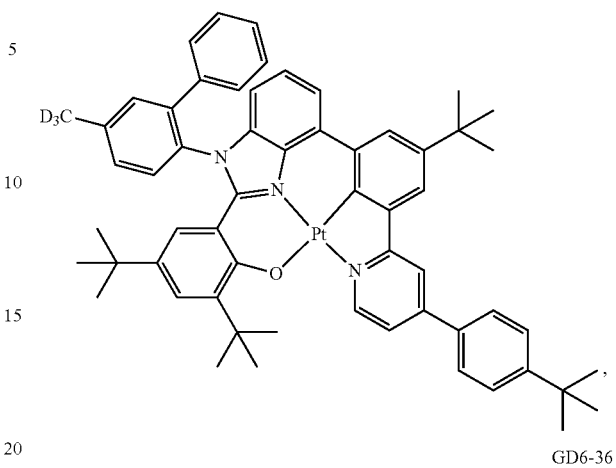
GD6-36
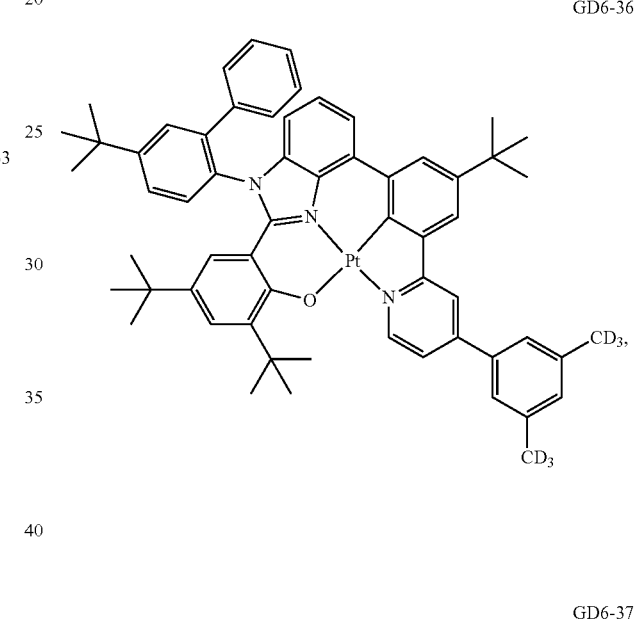
GD6-37
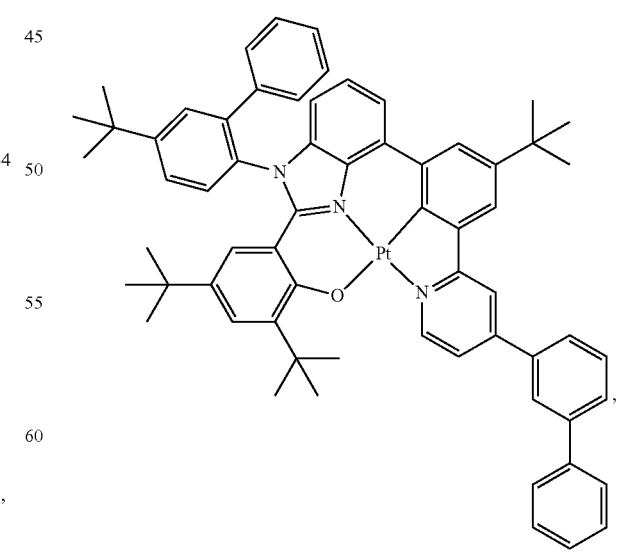

-continued
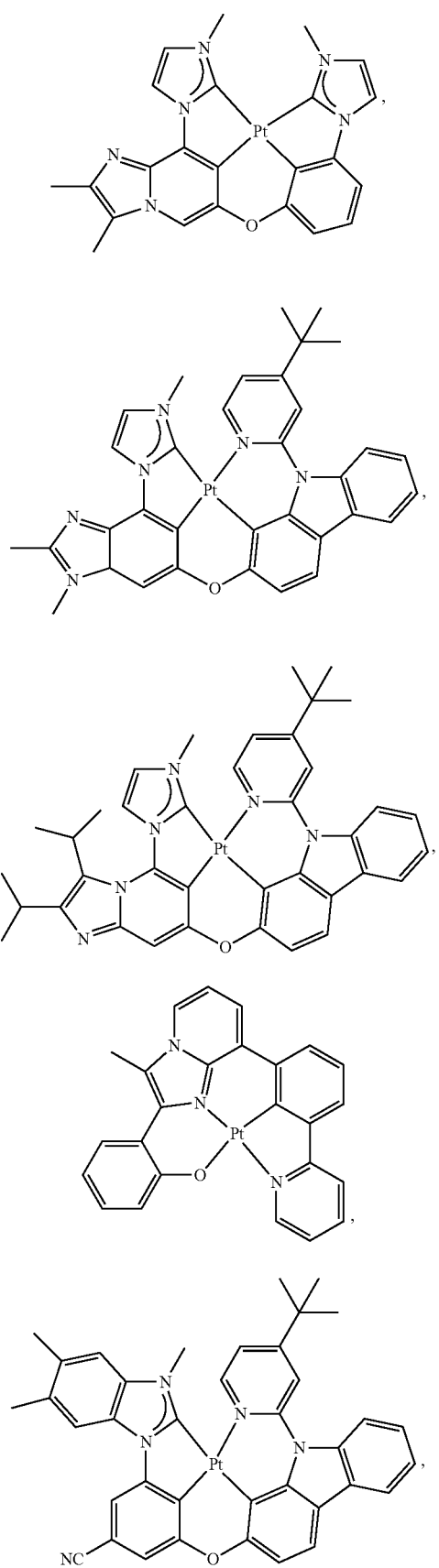
GD6-38
GD6-39
GD6-40
GD6-41
GD6-42
-continued
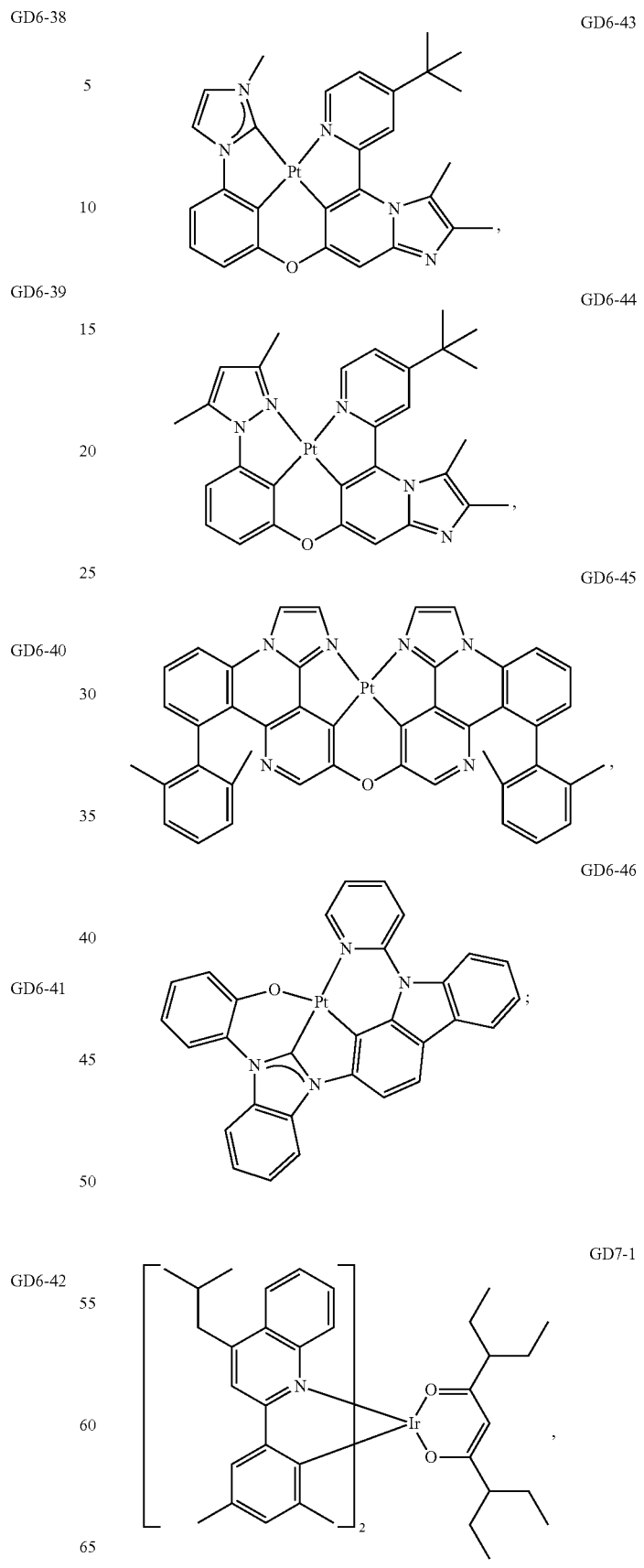
GD6-43
GD6-44
GD6-45
GD6-46
GD7-1

GD7-2
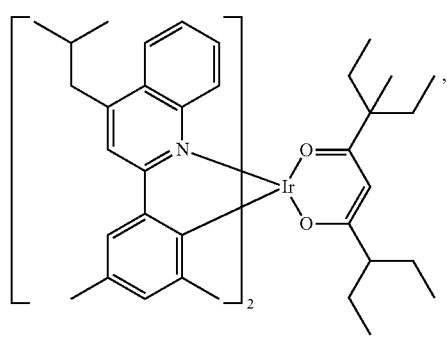
GD7-3
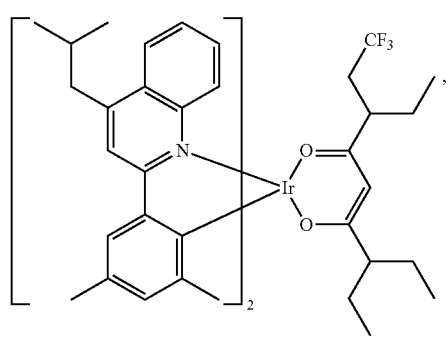
GD7-4
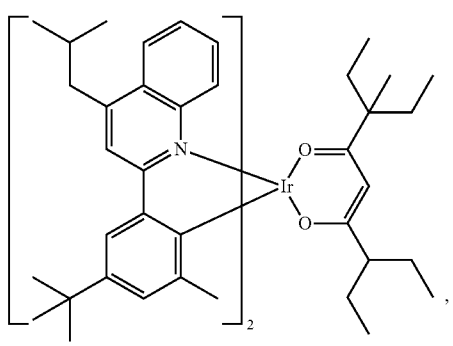
GD7-5
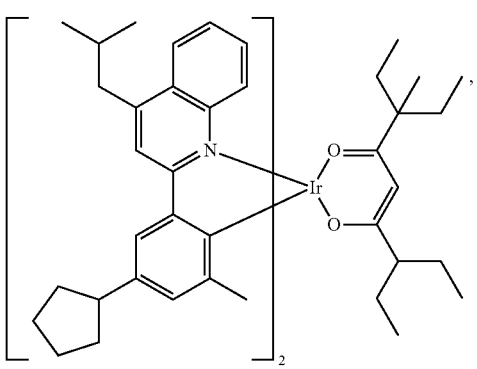
GD7-6
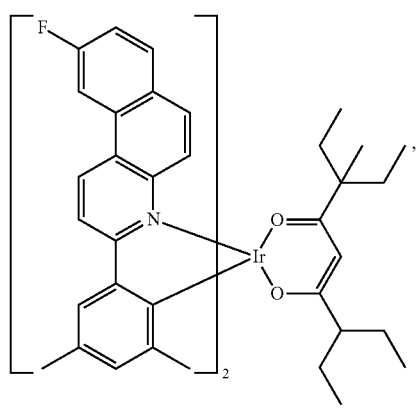
GD7-7
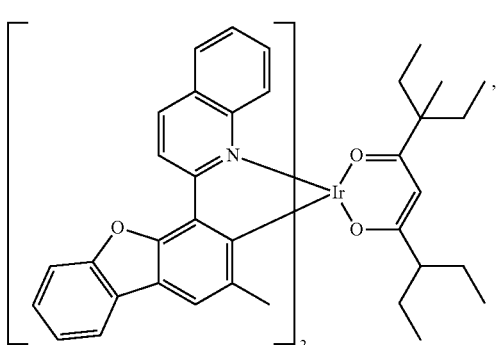
GD7-8
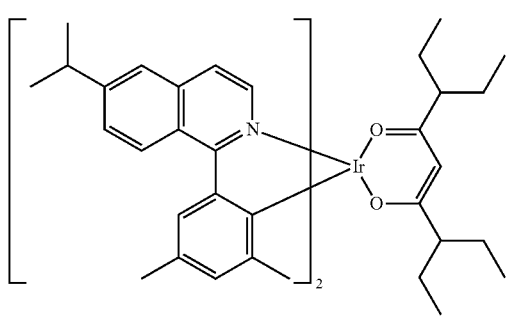
GD7-9
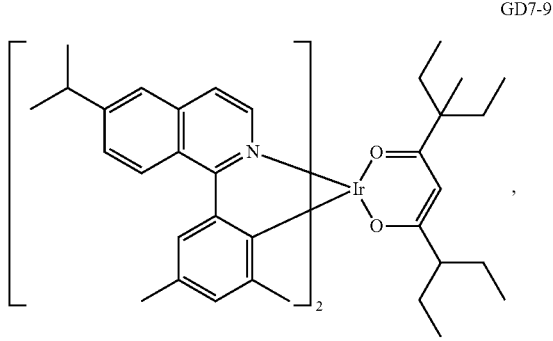

GD7-10
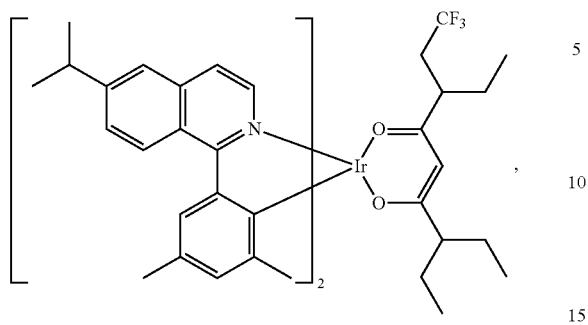
GD7-11
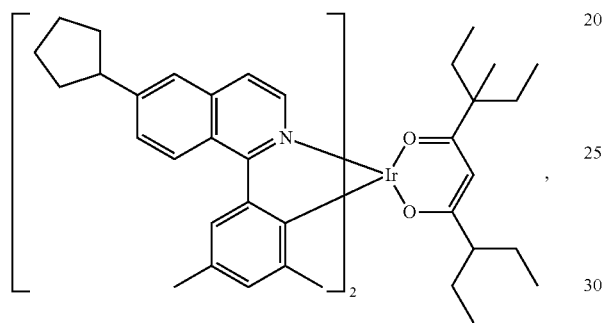
GD7-12
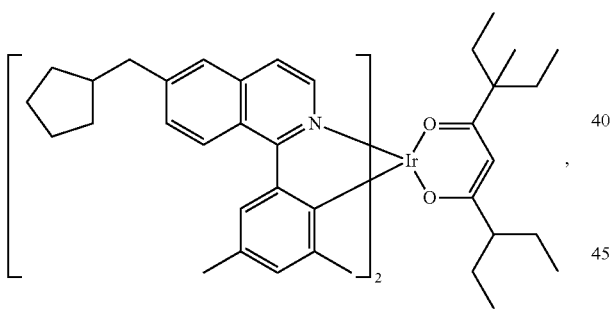
GD7-13
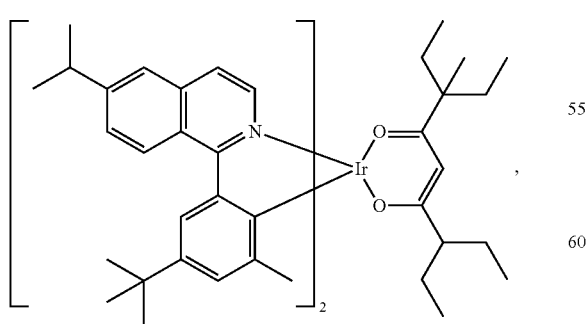
GD7-14
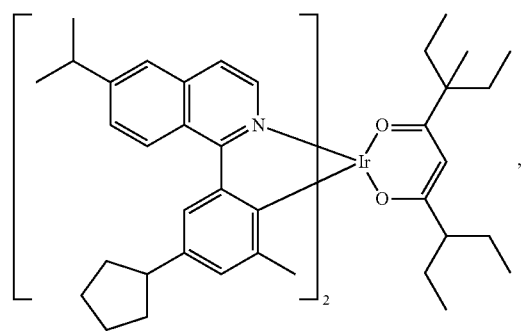
GD7-15
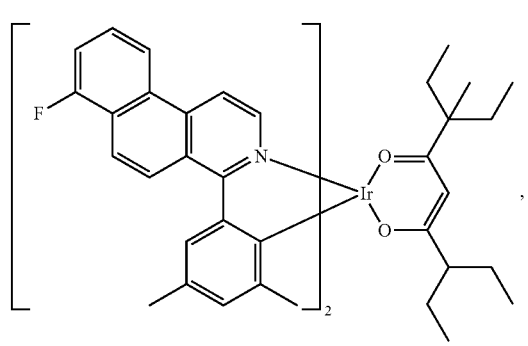
GD7-16
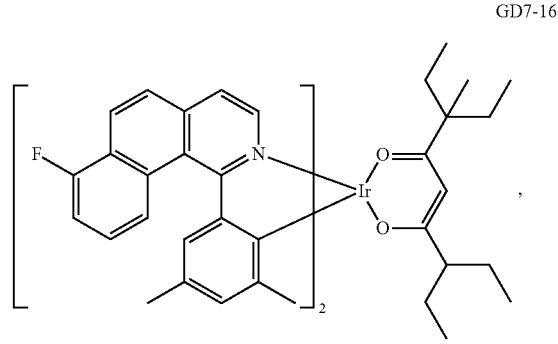
GD7-17
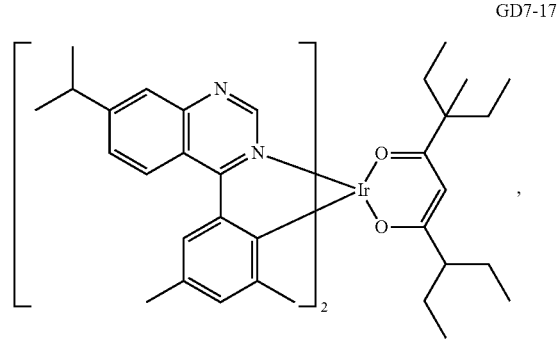

GD7-18
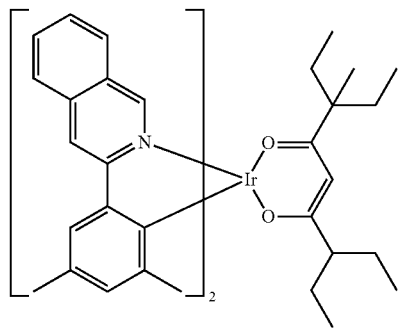
GD7-19
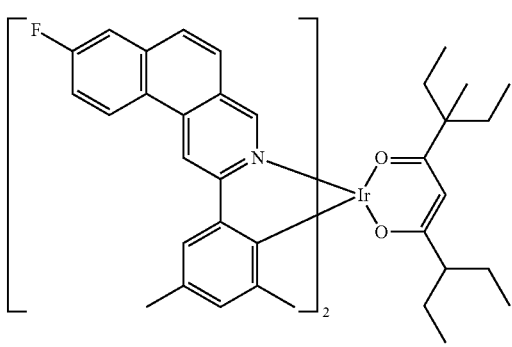
GD7-20
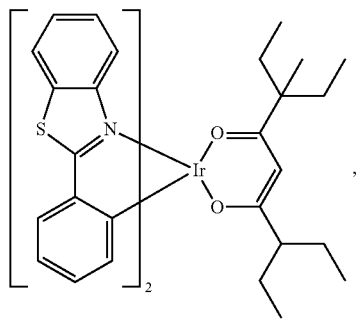
GD7-21
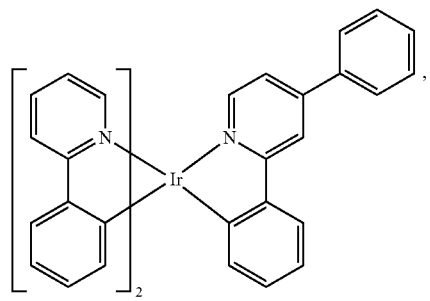
GD7-22
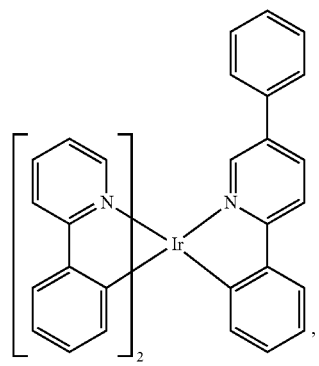
GD7-23
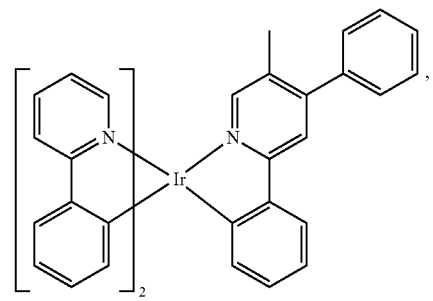
GD7-24
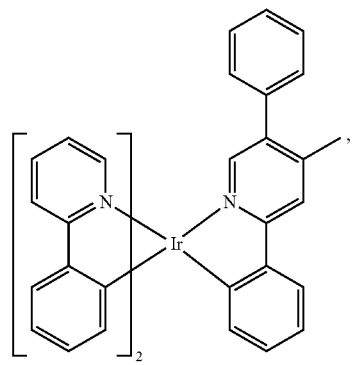
GD7-25
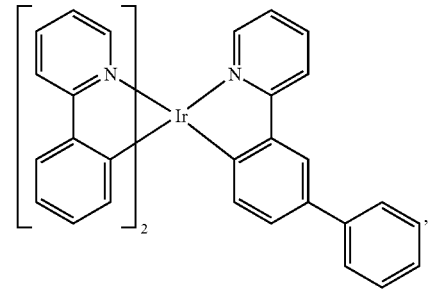

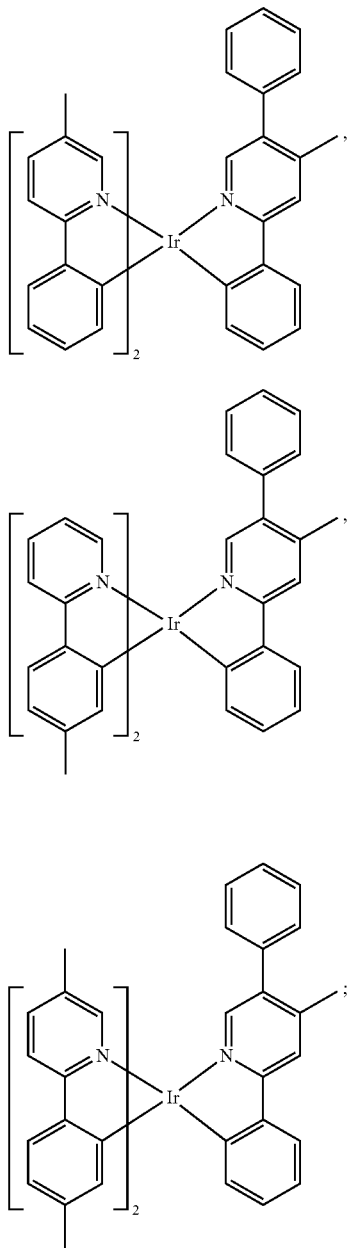

wherein in the above structure, Cy represents cyclohexyl.

19. The organic electroluminescent device according to claim 9, wherein the light-emitting layer further contains a second host compound, wherein the second host compound comprises at least one chemical group selected from the group consisting of: benzene, pyridine, pyrimidine, triazine, carbazole, azacarbazole, indolocarbazole, dibenzothiophene, aza-dibenzothiophene, dibenzofuran, azadibenzofuran, dibenzoselenophene, triphenylene, azatriphenylene, fluorene, silafluorene, naphthalene, quinoline, isoquinoline, quinazoline, quinoxaline, phenanthrene, azaphenanthrene and combinations thereof.

20. The organic electroluminescent device according to claim 19, wherein the second host compound has a structure represented by Formula 5 or Formula 6:

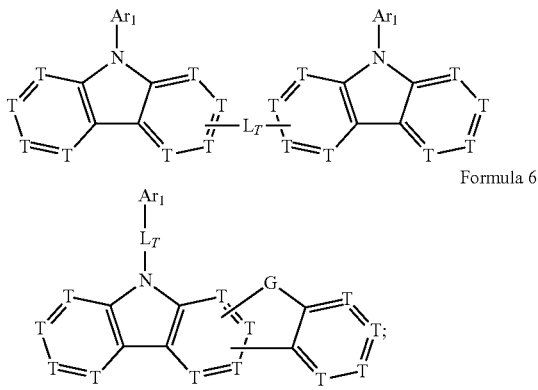

wherein

G is, at each occurrence identically or differently, selected from $C(R_g)_2$, $NR_g$, O or S;

$L_T$ is, at each occurrence identically or differently, selected from a single bond, substituted or unsubstituted alkylene having 1 to 20 carbon atoms, substituted or unsubstituted cycloalkylene having 3 to 20 carbon atoms, substituted or unsubstituted arylene having 6 to 20 carbon atoms, substituted or unsubstituted heteroarylene having 3 to 20 carbon atoms or a combination thereof;

T is, at each occurrence identically or differently, selected from C, $CR_t$ or N;

$R_t$ and $R_g$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof;

$Ar_1$ is, at each occurrence identically or differently, selected from substituted or unsubstituted aryl having 6 to 30 carbon atoms, substituted or unsubstituted heteroaryl having 3 to 30 carbon atoms or a combination thereof;

adjacent substituents $R_t$ can be optionally joined to form a ring; and adjacent substituents $R_t$, $R_g$ can be optionally joined to form a ring.

21. The organic electroluminescent device according to claim 8, wherein the organic layer is an electron transporting layer and the compound is an electron transporting compound.

22. A compound composition containing the compound according to claim 1.

23. The compound according to claim 3, wherein Rx and Rz are, at each occurrence identically or differently, selected from the group consisting of: hydrogen, deuterium, fluorine, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms and combinations thereof.

24. The compound according to claim 3, wherein Rx and Rz are, at each occurrence identically or differently, selected from hydrogen, deuterium, fluorine, substituted or unsubstituted phenyl, substituted or unsubstituted naphthyl, substituted or unsubstituted biphenyl or a combination thereof.

25. The compound according to claim 4, wherein Rw, R and Ry are, at each occurrence identically or differently, selected from the group consisting of: hydrogen, deuterium, fluorine, substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms and combinations thereof.

26. The compound according to claim 4, wherein Rw, R and Ry are, at each occurrence identically or differently, selected from hydrogen, deuterium, fluorine, substituted or unsubstituted vinyl, substituted or unsubstituted phenyl, substituted or unsubstituted naphthyl, substituted or unsubstituted biphenyl, substituted or unsubstituted terphenyl, substituted or unsubstituted phenanthryl or a combination thereof.

\* \* \* \* \*